(12) United States Patent
Wang et al.

(10) Patent No.: US 7,629,375 B2
(45) Date of Patent: *Dec. 8, 2009

(54) CYTOPROTECTIVE COMPOUNDS, PHARMACEUTICAL AND COSMETIC FORMULATIONS, AND METHODS

(75) Inventors: Bing Wang, Cupertino, CA (US); Yong-Kang Zhang, San Jose, CA (US); Jian Chen, Sunnyvale, CA (US); Wei Zhang, Santa Clara, CA (US); Jiangao Song, Cupertino, CA (US); Ughetta Del Balzo, Morgan Hill, CA (US); Lesley Brown, Reno, NV (US); Sekhar Boddupalli, San Jose, CA (US); Steven Bobzin, San Jose, CA (US); Sylvain Gilat, San Francisco, CA (US); Guy Miller, San Jose, CA (US)

(73) Assignee: Johnson & Johnson Consumer Companies, Inc., Skillman, NJ (US)

( * ) Notice: Subject to any disclaimer, the term of this patent is extended or adjusted under 35 U.S.C. 154(b) by 802 days.

This patent is subject to a terminal disclaimer.

(21) Appl. No.: 11/015,198

(22) Filed: Dec. 16, 2004

(65) Prior Publication Data

US 2005/0113416 A1 May 26, 2005

Related U.S. Application Data

(62) Division of application No. 10/202,670, filed on Jul. 23, 2002, now abandoned.

(60) Provisional application No. 60/307,439, filed on Jul. 23, 2001, provisional application No. 60/353,702, filed on Jan. 31, 2002.

(51) Int. Cl.
*A61K 31/415* (2006.01)
*A01N 43/56* (2006.01)
(52) U.S. Cl. ............... 514/407; 514/406; 514/403
(58) Field of Classification Search ............ 514/403, 514/406, 407
See application file for complete search history.

(56) References Cited

U.S. PATENT DOCUMENTS

| | | | |
|---|---|---|---|
| 4,743,606 A | 5/1988 | Lazer | |
| 4,812,460 A | 3/1989 | Lazer | |
| 4,877,881 A | 10/1989 | Belliotti et al. | |
| 4,992,468 A | 2/1991 | Chandraratna | |
| 5,068,252 A | 11/1991 | Chandraratna | |
| 5,208,250 A | 5/1993 | Cetenko et al. | |
| 5,302,606 A | 4/1994 | Spada et al. | |
| 5,306,822 A | 4/1994 | Cetenko et al. | |
| 5,326,898 A | 7/1994 | Chandraratna | |
| 5,356,917 A | 10/1994 | Paneta | |
| 5,360,924 A | 11/1994 | Beller et al. | |
| 5,378,705 A | 1/1995 | Klaus et al. | |
| 5,416,112 A | 5/1995 | Kuo | |
| 5,418,245 A | 5/1995 | Spada et al. | |
| 5,430,062 A | 7/1995 | Cushman et al. | |
| 5,464,856 A | 11/1995 | Cetenko et al. | |
| 5,489,614 A | 2/1996 | Korkolainen et al. | |
| 5,530,157 A | 6/1996 | Mewshaw et al. | |
| 5,547,983 A | 8/1996 | Charpentier | |
| 5,565,191 A | 10/1996 | Raspanti | |
| 5,614,541 A | 3/1997 | Backstrom et al. | |
| 5,827,898 A | 10/1998 | Khandwala et al. | |
| 5,844,004 A | 12/1998 | Muller et al. | |
| 5,854,285 A | 12/1998 | Sriram et al. | |
| 5,889,037 A | 3/1999 | Backstrom et al. | |
| 5,952,390 A | 9/1999 | Muller et al. | |
| 6,117,911 A | 9/2000 | Grainger et al. | |
| 6,121,303 A | 9/2000 | Backstrom et al. | |
| 6,127,426 A | 10/2000 | Muller et al. | |
| 6,147,121 A | 11/2000 | Breton et al. | |
| 6,165,998 A | 12/2000 | Wobbe et al. | |
| 6,194,453 B1 | 2/2001 | Sriram et al. | |
| 6,224,854 B1 | 5/2001 | Robinson | |
| 6,245,774 B1 | 6/2001 | Warrellow et al. | |
| 6,407,142 B1 | 6/2002 | Courbriere et al. | |
| 6,462,075 B1 | 10/2002 | Bowen et al. | |
| 6,552,085 B2 | 4/2003 | Inman et al. | |
| 6,610,877 B1 | 8/2003 | Klaus et al. | |
| 6,624,182 B1 | 9/2003 | Haap et al. | |
| 2002/0025975 A1 | 2/2002 | Nag et al. | |
| 2002/0032225 A1 | 3/2002 | Nag et al. | |
| 2002/0045620 A1 | 4/2002 | Druzgala et al. | |

(Continued)

FOREIGN PATENT DOCUMENTS

DE            10 38 050           9/1958

(Continued)

OTHER PUBLICATIONS

Trusevich et al. (1980) "Synthesis And Spectrometric Study Of 2,4,5-Substituted Pyrazol-3-One" Urk. Khin. Kh. (Russ. Ed.) 46(6):642-645 (abstract only).

(Continued)

*Primary Examiner*—Yong S. Chong

(57) ABSTRACT

Cytoprotective compounds, many of which are phenolic derivatives characterized by a substituted phenol having certain conjugated bonds, are useful in the treatment of certain ischemic or inflammatory conditions, including but not limited to stroke, myocardial infarction, congestive heart failure, and skin disorders characterized by inflammation or oxidative damage. They are also useful in the manufacture of pharmaceutical and cosmetic formulations for the treatment of such conditions.

9 Claims, No Drawings

U.S. PATENT DOCUMENTS

| | | |
|---|---|---|
| 2002/0051799 A1 | 5/2002 | Pruche et al. |
| 2003/0118617 A1 | 6/2003 | Soby et al. |
| 2003/0144363 A1 | 7/2003 | Liviero et al. |
| 2003/0144525 A1 | 7/2003 | Alanine et al. |
| 2003/0149003 A1 | 8/2003 | Chaplin et al. |
| 2003/0171429 A1 | 9/2003 | Chen et al. |

FOREIGN PATENT DOCUMENTS

| | | |
|---|---|---|
| EP | 0 322 738 | 7/1989 |
| EP | 0334119 | 9/1989 |
| EP | 0 391 644 | 10/1990 |
| EP | 1016654 | 7/2000 |
| FR | 2169334 | 9/1973 |
| JP | 52005751 | 1/1977 |
| JP | 52083360 | 7/1977 |
| JP | 52083361 | 7/1977 |
| JP | 10175854 | 6/1988 |
| JP | 04089436 | 3/1992 |
| JP | 05032587 | 2/1993 |
| JP | 06072866 | 3/1994 |
| JP | 07053359 | 2/1995 |
| JP | 10017455 | 1/1998 |
| JP | 10072330 | 3/1998 |
| JP | 10087641 | 4/1998 |
| JP | 10175852 | 6/1998 |
| JP | 10017455 | 1/1999 |
| JP | 11060537 | 3/1999 |
| JP | 10335472 | 12/2001 |
| WO | WO/96/20936 | 7/1996 |
| WO | WO/98/46588 | 10/1998 |
| WO | WO/99/01148 | 1/1999 |
| WO | WO/99/04747 | 2/1999 |
| WO | WO/99/58127 | 11/1999 |
| WO | WO/00/04889 | 2/2000 |
| WO | WO/00/19989 | 4/2000 |
| WO | WO/00/21368 | 4/2000 |
| WO | WO/00/45782 | 8/2000 |
| WO | WO/01/42231 | 6/2001 |
| WO | WO/01/43705 | 6/2001 |
| WO | WO/02/057219 | 7/2002 |

OTHER PUBLICATIONS

Li et al. (2002) "Syntesis of Water-Soluble Optically Nonlinear Materials Based On Trans-Distyrylbenzene" Youji Huaxue 22(2):141-144 (abstract only).

Bonina et al. (1987) "Synthesis and Analgesic Anti-Inflammatory Activities of 2-Arylethenyl-4-Arylthiazole-5-Acetic Acids" Farmaco. Ed. Sci. 42(12)905-913.

Bonina et al. (1985) "Synthesis and Pharmacological Activities of 2-Arylethenyl-thiazole-4-Acetic and 4-carboxylic Acids" Farmaco. Ed. Sci. 40(11):875-884 (abstract only).

Walter et al. (1966) "Synthesis and Cyclization Reactions of 3-(2-Hydroxybenzylidene)-2(3H0-Coumarones" Journal of Organic Chemistry 31(11):3854-3857.

Lazer et al. (1989) "Antiinflammatory 2.6-Di-tert-butyl-4-(2-arylthenyl)phenois" J. Med. Chem. 32:100-104.

Aihara et al. (1990) "Increasing 5-Lipoxygenase Inhibitory Activities By Oxidative Conversion of 0-Methoxyphenois To Catechols Using a Cu2+ -Ascorbic Acid-O2 System" Chem. Pharm. Bull. 38(3):842-844.

Flynn et al. (1991) "Styrylpyrazoles, Styryloxazoles, Styrylisothiazoles. Novel 5-Lipoxygenase and Cyclooxygenase Inhibitors" J. Med. Chem. 34:518-525.

Cushman et al. (1991) "Synthesis and evaluation of Stilbene and Dihydrostibene Derivatives as Potential Anticancer Agents That Inhibit Tubulin Polymerization" J. Med. Chem. 34:2579-2588.

Unangst et al. (1992) "Synthesis and Transformations of 2,6-Bis(1,1-dimethylethyl)-4-[2-(thiazolyl)ethenyl]phenois" J. Heterocyclic Chem. 29:1097-1100.

Farina et al. (1993) "A Prodrug of a 2,6-Disubstituted 4-(2-Arylethenyl)phenol is a Selective and Orally Active 5-Lipoxygenase Inhibitor", The Journal of Pharmacology and Experimental Therapeutics 265(2):483-489.

Treadwell et al. (1999) "Synthesis of Schweinfurthin C, a Geranylated Stilbene from Macaranga schweinfurthii" J. Org. chem. 64:8718-8723.

Shukla et al. (1999) "Dinuclear Complexes of a New Bridging Ligand Containing 2,2-Bipyridyl and Dioxolene Binding Sites; Syntheses, Electrochemical and Electronic Spectroscopic Properties" Inorganica Chemica Acta. 285:89-96.

Hung et al. (2001) "Beneficial Effects of Astringinin, a Resveratrol Analogue, on the Ischemia and Reperfusion Damage in Rat Heart" Free Radical Biology and Medicine 30(8):877-883.

Cotias et al. Longistyline C, antibiotic isolated from *Lonchocarpus longistyllus*.Preliminary results of its pharmacological properties. (1979) Revista ed Quimica Industrial (Rio de Janeiro) 48(564):12-15 (abstract/no translation).

Christensen et al. "Excelsaoctaphenol, a stilbene dimer from *Chlorophora excelsa*" (1989) Phytochemistry 28(3):917-918.

Marta et al. "Synthesis of longistylin A, B, C, D and other new prenylated stilbenes" (1979) Gazzetta Chemica Italiana 109(6-7) 323-324.

Gierer et al. Acta Chemica Scandinavica, Series B: Organic Chemistry and Biochemistry (1974) 28(7):717-729 (abstract).

Minn et al. J. of Agricultural and Food Chem (1996) 44(1):2946-2947 (abstract).

CYTOPROTECTIVE COMPOUNDS, PHARMACEUTICAL AND COSMETIC FORMULATIONS, AND METHODS

CROSS-REFERENCE TO RELATED APPLICATIONS

This application is a divisional of the co-pending application U.S. Ser. No. 10/202,670, filed Jul. 23, 2002 which application claims priority of provisional applications U.S. Ser. No. 60/307,439, filed Jul. 23, 2001, and U.S. Ser. No. 60/353,702, filed Jan. 31, 2002, incorporated herein by reference in their entirety.

FIELD OF THE INVENTION

The present invention relates to certain compounds having cytoprotective activity, and particularly to a series of phenolic derivatives. The invention is also directed to formulations and methods for treating stroke, myocardial infarction and chronic heart failure, as well as other oxidative stress-related conditions that are typically responsive to cellular enzyme modulation.

BACKGROUND INFORMATION

The present invention is concerned with cytoprotective compounds, many of which are phenolic derivatives characterized by a substituted phenol having certain conjugated bonds, also referred to herein as a "conjugated phenol."

Compositions of the invention are active in certain experimental models that predict efficacy in, for example, certain ischemic or inflammatory conditions, including but not limited to stroke, myocardial infarction, congestive heart failure, and skin disorders characterized by inflammation or oxidative damage. The invention is therefore related to the use of the cytoprotective derivatives in such conditions.

Various agents have heretofore been provided for such conditions. In one group of compounds, the substituted stilbenes (e.g., including resveratrol and its derivatives), many if not all of the possible positions have been disclosed as substituted with various moieties for use as cosmetics, antioxidants, fungicides and as pharmaceutical active agents for the treatment of dermatological conditions, inflammation, menopause, diabetes, cell growth inhibition, protection against UV damage, antimicrobial agents and the like (see, e.g., U.S. Pat. Nos. 4,992,468; 5,547,983; 5,565,191; and 6,147,121). It has, however, remained desired to provide new, improved and more specifically targeted therapies for conditions characterized by oxidative stress, and particularly, for providing protection in the event of cerebral ischemia or ultraviolet exposure; especially desired are agents that are effective even if first administered after a significant period of time (e.g., about 5 or more hours) following an ischemic or oxidative insult.

SUMMARY OF THE INVENTION

The present invention is concerned with certain novel and related cytoprotective compounds that are particularly active in restoring or preserving metabolic integrity in oxidatively competent cells that have been subjected to oxygen deprivation. Such compounds, predominantly conjugated phenols (both synthetic and naturally occurring), are useful in the manufacture of pharmaceutical and cosmetic compositions for treating a number of conditions characterized by oxidative stress, and particularly, in providing protection in the event of cerebral ischemia or ultraviolet exposure, even when administered a significant time interval after an ischemic or oxidative insult. In particular, the compositions of the present invention are useful in the treatment of stroke, as demonstrated by providing neuroprotection in a standard experimental model of focal cerebral ischemia. They are also useful in the treatment of myocardial ischemia (myocardial infarction), as well as other indications characterized by oxidative stress and/or inflammation, including, but not limited to, neurodegenerative disorders such as Alzheimer's, dementia, and Parkinson's disease; diabetes, renal disease, pre-menstrual syndrome, asthma, cardiopulmonary inflammatory disorders, chronic heart failure, rheumatoid arthritis, inflammatory bowel syndrome, muscle fatigue, intermittent claudication and for the preservation of allograft tissue for transplantation. Particularly with regard to dermatological conditions, the compounds, formulations and methods of the present invention are useful in regulating skin condition, regulating the signs of skin aging and in treating a number of conditions, including, but not limited to contact dermatitis, acne, psoriasis, and in the prevention and protection of skin tissue against age-related damage or damage resulting from insults such as harmful (UV) radiation, stress and fatigue.

The present invention concerns the compounds represented by Formulae I to V, particularly compounds embodying certain preferred combinations and permutations of substituent groups, including single stereoisomers, mixtures of stereoisomers, and the pharmaceutically acceptable salts thereof. For example, the substituent group methoxymethoxy has been identified as conferring activity in various methods of treatment of the invention, in addition to serving as a protecting group in the synthesis of hydroxyl-substituted compounds. Another preferred substituent group is alkenyl, represented by the formula H—[CH$_2$—(CH$_3$)C=CH—CH$_2$]$_n$—, where n is an integer from 1 to 4 (most preferably n is 1 or 2, i.e., prenyl and geranyl). The invention further concerns the use of these compounds as active agents in practice of methods of treatment for a mammal suffering from a condition characterized by oxidative stress, their use in the manufacture of the pharmaceutical and/or cosmetic formulations of the invention, and their use as intermediates in the synthesis of active agents.

With regard to Formula I:

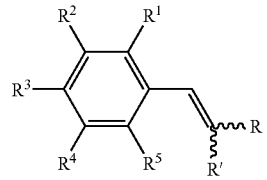

Formula I

R is selected from: substituted alkenyl, optionally substituted aryl, (optionally substituted aryl)carbonyl, optionally substituted heteroaryl (including bipyridinyl metal complexes), optionally substituted heterocyclyl, or nitro;

R' is selected from: hydrogen or (optionally substituted alkoxy)carbonyl;

R$^1$ to R$^5$ are independently selected from: optionally substituted alkoxy, optionally substituted alkenyl, optionally substituted alkyl, optionally substituted aryl, (optionally substituted alkoxy)carbonyl, carboxy, cyano, halo, optionally substituted heteroaryl, hydrogen, hydroxy, nitro, nitrone, sulfonate; or two adjacent members of $R^1$ to $R^5$ are each $O^-$ and together are complexed with carbon or a metal;

provided that at least one of $R^1$ to $R^5$ is not hydrogen.

With regard to Formula II:

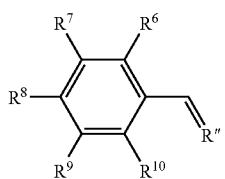

Formula II $R''$ is selected from: optionally substituted anthracenone, substituted alkenyl, di-cyano, optionally substituted heteroaryl, or optionally substituted heterocyclyl;

$R^6$ to $R^{10}$ are independently selected from: optionally substituted alkenyl, optionally substituted alkoxy, optionally substituted alkyl, optionally substituted aryl, (optionally substituted alkoxy)carbonyl, hydrogen, hydroxy and nitrone; or two adjacent members of $R^5$ to $R^8$ are each $O^-$ and together are complexed with carbon or a metal;

provided that at least one of $R^6$ to $R^{10}$ is not hydrogen. Those skilled in the art will appreciate that many compounds analogous to those of Formula II, bearing a single bond to $R''$, can be employed in the methods of treatment of the present invention.

Formula III, IV and V represent compounds of Formula I where two adjacent members of $R^1$ to $R^5$ (preferably $R^3$ with $R^2$ or $R^4$) are each $O^-$ and together are complexed with a metal having one or more apical ligands, where the metal can optionally be further complexed with a second compound of Formula I forming dimers of such complexes:

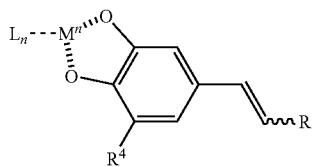

Formula III

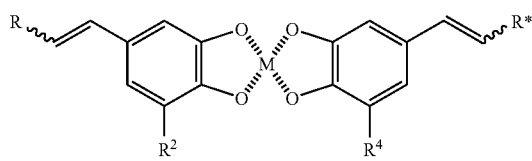

Formula IV

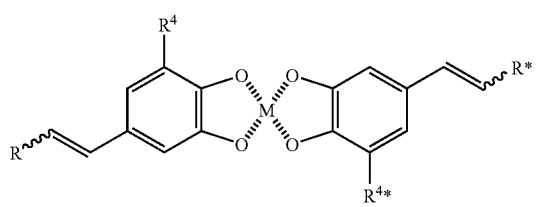

Formula V where:

M is: a metal;

L is: a ligand associated with a remaining free valence on M;

n is: an integer from 1 to 3, corresponding to the remaining free valences on M and the number of associated ligands;

R and R* are independently selected from: optionally substituted anthraquinone, substituted aryl, optionally substituted heteroaryl, optionally substituted heterocyclyl, or nitro; and $R^2$, $R^4$ and $R^{4*}$ are independently selected from: optionally substituted alkoxy, hydrogen, or hydroxy.

Certain naturally occurring conjugated phenols and the like are also useful in the methods and compositions of the invention including: acetoxychavicol acetate, arachidin I, arachadin II, arachidin III, astringin, cis-gnetin, 1-(3,4,5-trimethoxyphenyl)-2-(4-methoxyphenyl)-ethanol, trans-(4,4'-diacetoxy-3,3'-dimethoxy)carboxystilbene, and trans-(4,4'-diacetoxy-3,3'-dimethoxy)stilbene, including single isomers, mixtures of isomers, and the pharmaceutically acceptable salts thereof. Other compounds of interest include (4-methoxyphenyl)-(benzo-1,3-dioxol-5-yl)-ethyne.

As further described below, certain embodiments of the invention provide novel and preferred combinations of the substituents groups pendant from Formulae I to V. Also provided are methods of treatment for cardiovascular, cerebrovascular and neurologic, inflammatory and/or autoimmune, and dermatologic conditions characterized as involving oxidative stress, and certain preferred combinations of the substituent groups pendant from Formulae I to V for their respective treatment.

In another aspect, the invention relates to a pharmaceutical and/or cosmetic compositions containing a therapeutically effective amount of a compound of any of Formulae I to V, an above-described naturally occurring conjugated phenol, or a pharmaceutically acceptable salt thereof admixed with at least one pharmaceutically acceptable excipient. Particularly preferred are those pharmaceutical or cosmetic compositions wherein a compound of Formulae I to V is selected from the Preferred Compounds.

In still another aspect, the invention relates to a method of treating stroke and other oxidative stress-related conditions that are responsive to cellular enzyme modulation such as cerebral ischemia, myocardial infarction, chronic heart failure and exposure to UV radiation in a mammal by administering to a mammal in need of such treatment (even a significant period of time following an ischemic or oxidative insult, such as about 5 or more hours) a therapeutically effective amount of a compound of any of Formulae I to V, an above-described naturally occurring conjugated phenol, or a pharmaceutically acceptable salt thereof. In a method for regulating skin condition, regulating the signs of skin aging, or for treating contact dermatitis, acne, psoriasis, age-related damage or damage resulting from harmful (UV) radiation, stress or fatigue, the invention entails topically administering to a mammal in need of such treatment a therapeutically effective amount of a compound of any of Formulae I to V, an above-described naturally occurring conjugated phenol, or a pharmaceutically acceptable salt thereof. Particularly preferred are those methods of treatment and uses in the manufacture of pharmaceutical and/or cosmetic compositions therefor, wherein a compound of Formulae I to V is selected from the Preferred Compounds.

In yet another aspect, the invention relates to a method of promoting a product by directing a user to apply to the skin a pharmaceutical or cosmetic composition incorporating a compound of any of Formulae I to V, an above-described naturally occurring conjugated phenol, or a pharmaceutically acceptable salt thereof, for regulating skin condition, regulating the signs of skin aging, or for treating contact dermatitis, acne, psoriasis, age-related damage or damage resulting from harmful (UV) radiation, stress or fatigue. The invention also entails a product including instructions directing the user to apply a composition of the invention to the skin for regulating skin condition, regulating the signs of skin aging, or for treating contact dermatitis, acne, psoriasis, age-related damage or damage resulting from harmful (UV) radiation, stress or fatigue, where the composition incorporates a compound of any of Formulae I to V, an above-described naturally occurring conjugated phenol, or a pharmaceutically acceptable salt thereof.

DETAILED DESCRIPTION OF THE INVENTION

Definitions

As used in the present specification, the following words and phrases are generally intended to have the meanings as set forth below, except to the extent that the context in which they are used indicates otherwise.

The term "optional" or "optionally" means that the subsequently described event or circumstance may or may not occur, and that the description includes instances where said event or circumstance occurs and instances in which it does not. For example, "optionally substituted alkyl" means either "alkyl" or "substituted alkyl," as defined below. It will be understood by those skilled in the art with respect to any group containing one or more substituents that such groups are not intended to introduce any substitution or substitution patterns that are sterically impractical and/or synthetically non-feasible.

Certain compound, reactant, or reaction parameter abbreviations are defined as follows:

"DCM" refers to dichloromethane or methylene chloride
"t-Bu" refers to t-butyl
"DIC" refers to N,N-diisopropylcarbodiimide
"DIPEA" refers to diisopropyl ethylamine
"DMAP" refers to 4-N,N-dimethylamino pyridine
"DMF" refers to N,N-dimethyl formamide
"Eq." refers to equivalent
"MeOH" refers to methanol
"MOM" refers to methoxymethyl
"OMOM" refers to methoxymethoxy
"EtOH" refers to ethanol
"PCC" refers to pyridinium chlorochromate
"TBDMS" refers to t-butyl di-methyl silyl
"THF" refers to tetrahydrofuran
"TBAF" refers to tetrabutyl ammonium fluoride
"TMEDA" refers to N,N,N',N'-tetramethylethylenediamine
"CSA" refers to camphorsulfonic acid, and
"EtOAc" refers to ethyl acetate.

The term "acyl" refers to the groups —C(O)—H, —C(O)-(optionally substituted alkyl), —C(O)-(optionally substituted cycloalkyl), —C(O)-(optionally substituted alkenyl), —C(O)-(optionally substituted cycloalkenyl), —C(O)-(optionally substituted aryl), —C(O)-(optionally substituted heteroaryl) and —C(O)-(optionally substituted heterocyclyl).

The term "alkenyl" refers to a monoradical branched or unbranched, unsaturated or polyunsaturated hydrocarbon chain, having from about 2 to 20 carbon atoms, more preferably about 2 to 10 carbon atoms. This term is exemplified by groups such as ethenyl, but-2-enyl, 3-methyl-but-2-enyl (also referred to as "prenyl"), octa-2,6-dienyl, 3,7-dimethyl-octa-2,6-dienyl (also referred to as "geranyl"), and the like.

The term "substituted alkenyl" refers to an alkenyl group in which 1 or more (up to about 5, preferably up to about 3) hydrogen atoms is replaced by a substituent independently selected from the group: optionally substituted anthraquinone, optionally substituted aryl, (optionally substituted aryl)carbonyl, optionally substituted heteroaryl, optionally substituted heterocyclyl, or nitro. Preferred optional substituents for alkenyl are substituted aryl and substituted heteroaryl, exemplified by groups, such as p-nitrobenzyl, 5-methyl-2-phenyl-2,4-dihydro-pyrazol-3-one, and thiazolidine-2,4-dione.

The term "alkoxy" refers to the groups —O-alkyl, —O-alkenyl, —O-cycloalkyl, —O-cycloalkenyl, and —O-alkynyl. Preferred alkoxy groups are —O-alkyl and —O-alkenyl and include, by way of example, methoxy, ethoxy, n-propoxy, iso-propoxy, n-butoxy, tert-butoxy, sec-butoxy, n-pentoxy, n-hexoxy, 1,2-dimethylbutoxy, 3,7-dimethyl-octa-2,6-dienyloxy and the like.

The term "substituted alkoxy" refers to the groups —O-(substituted alkyl), —O-(substituted alkenyl), —O-(substituted cycloalkyl), —O-(substituted cycloalkenyl), —O-(substituted alkynyl) and —O-(optionally substituted alkylene)-alkoxy. One preferred substituted alkoxy group is "polyalkoxy" or —O-(substituted alkylene)-alkoxy, and includes groups such as —OCH$_2$OCH$_3$, —OCH$_2$CH$_2$OCH$_3$, and (or PEG) groups such as —O(CH$_2$CH$_2$O)$_x$CH$_3$ and —O(CH$_2$CH$_2$O)$_x$H where x is an integer of about 2-20, preferably about 2-10, and more preferably about 2-5.

The term "alkyl" refers to a monoradical branched or unbranched saturated hydrocarbon chain preferably having from about 1 to 20 carbon atoms, more preferably about 1 to 10 carbon atoms, and even more preferably about 1 to 6 carbon atoms. This term is exemplified by groups such as methyl, ethyl, n-propyl, iso-propyl, n-butyl, iso-butyl, n-hexyl, n-decyl, tetradecyl, and the like.

The term "substituted alkyl" refers to an alkyl group in which 1 or more (up to about 5, preferably up to about 3) hydrogen atoms is replaced by a substituent independently selected from the group: =O, =S, acyl, acyloxy, optionally substituted alkoxy, optionally substituted amino, azido, carboxyl, (optionally substituted alkoxy)carbonyl, (optionally substituted amino)carbonyl, cyano, optionally substituted cycloalkyl, optionally substituted cycloalkenyl, halogen, hydroxyl, nitro, sulfanyl, sulfinyl, and sulfonyl. One of the preferred optional substituents for alkyl is hydroxy, exemplified by hydroxyalkyl groups, such as 2-hydroxyethyl, 3-hydroxypropyl, 3-hydroxybutyl, 4-hydroxybutyl, and the like; dihydroxyalkyl groups (glycols), such as 2,3-dihydroxypropyl, 3,4-dihydroxybutyl, 2,4-dihydroxybutyl, and the like; mixed hydroxy and carboxy substituted alkyl groups, such as pyruvates; and those compounds known as polyethylene glycols, polypropylene glycols and polybutylene glycols, and the like.

The term "alkylene" refers to a diradical derived from the above-defined monoradical, alkyl. This term is exemplified by groups such as methylene (—CH$_2$—), ethylene (—CH$_2$CH$_2$—), the propylene isomers [e.g., —CH$_2$CH$_2$CH$_2$— and —CH(CH$_3$)CH$_2$—] and the like.

The term "substituted alkylene" refers to a diradical derived from the above-defined monoradical, substituted alkyl. Examples of substituted alkylenes are chloromethylene (—CH(Cl)—), aminoethylene (—CH(NH$_2$)CH$_2$—), methylaminoethylene (—CH(NHMe)CH$_2$—), 2-carboxypropylene isomers (—CH$_2$CH(CO$_2$H)CH$_2$—), ethoxyethylene (—CH$_2$CH$_2$O—CH$_2$CH$_2$—), ethyl(N-methyl)aminoethylene (—CH$_2$CH$_2$N(CH$_3$)CH$_2$CH$_2$—), 1-ethoxy-2-(2-ethoxyethoxy)ethylene (—CH$_2$CH$_2$O—CH$_2$CH$_2$—OCH$_2$CH$_2$—OCH$_2$CH$_2$—), and the like.

The term "amino" refers to the group —NH$_2$.

The term "substituted amino" refers to the group —NHR or —NRR where each R is independently selected from the group: optionally substituted alkyl, optionally substituted cycloalkyl, optionally substituted alkenyl, optionally substituted cycloalkenyl, optionally substituted alkynyl, optionally substituted aryl, optionally substituted heteroaryl, optionally substituted heterocyclyl, acyl, optionally substituted alkoxy, carboxy and alkoxycarbonyl.

The term "aromatic" refers to a cyclic or polycyclic moiety having a conjugated unsaturated (4n+2) π electron system (where n is a positive integer), sometimes referred to as a delocalized π electron system.

The term "aryl" refers to an aromatic cyclic hydrocarbon group of from 6 to 20 carbon atoms having a single ring (e.g., phenyl) or multiple condensed (fused) rings (e.g., naphthyl or anthryl). Preferred aryls include phenyl, naphthyl and the like.

The term "substituted aryl" refers to an aryl group as defined above, which unless otherwise constrained by the definition for the aryl substituent, is substituted with from 1 to 5 substituents, and preferably 1 to 3 substituents, independently selected from the group consisting of: =O, =S, acyl, acyloxy, optionally substituted alkenyl, optionally substituted alkoxy, optionally substituted alkyl (such as tri-halomethyl), optionally substituted alkynyl, optionally substituted amino, optionally substituted aryl, optionally substituted aryloxy, azido, carboxyl, (optionally substituted alkoxy)carbonyl, (optionally substituted amino)carbonyl, cyano, optionally substituted cycloalkyl, optionally substituted cycloalkenyl, halogen, optionally substituted heteroaryl, optionally substituted heteroaryloxy, optionally substituted heterocyclyl, optionally substituted heterocyclooxy, hydroxyl, hydroxylamino, nitro, nitroso, phosphoryl, sulfanyl, sulfinyl, and sulfonyl. Preferred aryl substituents include: =O (e.g., anthracenone and anthraquinone), optionally substituted alkenyl, optionally substituted alkyl, alkoxy, substituted amino, halo, hydroxyl, alkoxycarbonyl, carboxy, cyano, nitro, phosphoryl, 2,4-dihydro-pyrazol-3-one, thiazolidine-2,4-dione, trihalomethyl, sulfinyl, sulfonamide, methyl-sulfonamide.

The term "carbonyl" refers to the di-radical "—C(=O)—", which is also illustrated as "—C(O)—".

The term "(optionally substituted alkoxy)carbonyl" refers to the groups: —C(O)O-(optionally substituted alkyl), —C(O)O-(optionally substituted cycloalkyl), —C(O)O-(optionally substituted alkenyl), —C(O)O-(optionally substituted alkynyl), —C(O)O-(optionally substituted aryl), —C(O)O-(optionally substituted heteroaryl), and —C(O)O-(optionally substituted heterocyclyl). These moieties are also referred to as esters.

The term "(optionally substituted amino)carbonyl" refers to the group —C(O)-(optionally substituted amino). This moiety is also referred to as a primary, secondary or tertiary carboxamide.

The term "carboxy" or "carboxyl" refers to the moiety "—C(O)OH", which is also illustrated as "—COOH".

The term "compound of Formula" is intended to encompass the derivatives of the invention as disclosed, and/or the pharmaceutically acceptable salts of such compounds. In addition, the compounds employed in this invention include the individual stereochemical isomers (arising from the selection of substituent groups) and mixtures of isomers. For the sake of brevity, particularly in the dependent claims, except where specifically indicated to the contrary (e.g., by designation of a single salt, isomer or mixture) the term should be understood to include single stereoisomers, mixtures of stereoisomers, and the pharmaceutically acceptable salts thereof.

The term "cycloalkyl" refers to non-aromatic cyclic hydrocarbon groups of having 3 to about 20 (preferably about 4 to 10) carbon atoms having a single ring or multiple condensed rings. Such cycloalkyl groups include, by way of example, single ring structures such as cyclopropyl, cyclobutyl, cyclopentyl, cyclooctyl, and the like, or multiple ring structures such as adamantanyl, and the like.

The term "cosmetics" includes make-up, foundation, and skin care products. "Cosmetic formulation" entails an active component and the excipients (typically dermatologically-acceptable) employed in cosmetics. The term "make-up" refers to products that leave color on the face, including foundations, blacks and browns, i.e., mascara, concealers, eye liners, brow colors, eye shadows, blushers, lip colors, and so forth. The term "foundation" refers to liquid, creme, mousse, pancake, compact, concealer or like products that even out the overall coloring of the skin. Foundation is typically manufactured to work better over moisturized and/or oiled skin. The term "skin care products" refers to products used to treat or otherwise care for, moisturize, improve, or clean the skin. Products contemplated by the phrase "skin care products" include, but are not limited to, adhesives, bandages, toothpaste, moisturizers, lotions, antiperspirants, deodorants, occlusive drug delivery patches, nail polish, powders, tissues, wipes, solid emulsion compact, hair conditioners, medicated shampoos, scalp treatments and the like. The term "personal care products" refer to health and cosmetic beauty aid products generally recognized as being formulated for beautifying and grooming the skin and hair. For example, personal care products include sunscreen products (e.g., lotions, skin creams, etc.), cosmetics, toiletries, and over-the-counter pharmaceutical products intended for topical usage. The term "dermatologically-acceptable," as used herein, means that the compositions or excipient components thereof are suitable for use in contact with human skin without undue toxicity, incompatibility, instability, allergic response, or the like.

The term "excipient" refers to a cosmetic excipient or a pharmaceutically acceptable excipient.

The term "halo" or "halogen" refers to fluoro, chloro, bromo and iodo.

The term "heteroaryl" refers to an aromatic cyclic hydrocarbon group having about 1 to 40 (preferably from about 3 to 15) carbon atoms and about 1 to 10 hetero atoms (preferably about 1 to 4 heteroatoms, selected from nitrogen, sulfur, phosphorus, and/or oxygen) within at least one ring. Such heteroaryl groups can have a single ring (e.g., pyridyl or furyl) or multiple condensed rings (e.g., indolizinyl, benzothienyl, and benzo[1,3]dioxo-5-yl). Preferred heteroaryis include pyridyl, [2,2']bipyridinyl, pyrrolyl and furyl.

The term "substituted heteroaryl" refers to a heteroaryl group as defined above, which unless otherwise constrained by the definition for the heteroaryl substituent, is substituted with from 1 to 5 substituents, and preferably 1 to 3 substituents, independently selected from the group consisting of: =O, =S, acyl, acyloxy, optionally substituted alkenyl, optionally substituted alkoxy, optionally substituted alkyl (such as tri-halomethyl), optionally substituted alkynyl, optionally substituted amino, optionally substituted aryl, optionally substituted aryloxy, azido, carboxyl, (optionally substituted alkoxy)carbonyl, (optionally substituted amino) carbonyl, cyano, optionally substituted cycloalkyl, optionally substituted cycloalkenyl, halogen, optionally substituted heteroaryl, optionally substituted heteroaryloxy, optionally substituted heterocyclyl, optionally substituted heterocyclooxy, hydroxyl, nitro, sulfanyl, sulfinyl, and sulfonyl. Preferred substituted heteroaryls include [2,2']bipyridinyl metal complexes, especially with Zn(II), Cu(II), Mn(III), Ru(II), Fe, Fe(II) or Fe(III).

The term "heteroaralkyl" refers to the moiety "-alkylene-heteroaryl" each having the meaning as defined herein.

The term "substituted heteroaralkyl" refers to the moiety "-(optionally substituted aklylene)- (optionally substituted heteroaryl)", each having the meaning as defined herein.

The term "heteroarylene" refers to the diradical group derived from heteroaryl (including substituted heteroaryl), as defined above, and is exemplified by the groups 2,6-pyridylene, 2,4-pyridiylene, 1,2-quinolinylene, 1,8-quinolinylene, 1,4-benzofuranylene, 2,5-pyridnylene, 2,5-indolenyl and the like.

The terms "heterocycle", "heterocyclic" and "heterocyclyl" refer to a monoradical, saturated or unsaturated, non-aromatic cyclic hydrocarbon group having about 1 to 40 (preferably from about 3 to 15) carbon atoms and about 1 to 10 hetero atoms (preferably about 1 to 4 heteroatoms, selected from nitrogen, sulfur, phosphorus, and/or oxygen) within the ring. Such heterocyclic groups can have a single ring or multiple condensed rings. Preferred heterocyclics include morpholino, piperidinyl, and the like.

The terms "substituted heterocycle", "substituted heterocyclic" and "substituted heterocyclyl" refer to a heterocyclyl group as defined above, which unless otherwise constrained by the definition for the heterocycle, is substituted with from 1 to 5 substituents, and preferably 1 to 3 substituents, independently selected from the group consisting of: =O, =S, acyl, acyloxy, optionally substituted alkenyl, optionally substituted alkoxy, optionally substituted alkyl (such as tri-halomethyl), optionally substituted alkynyl, optionally substituted amino, optionally substituted aryl, optionally substituted aryloxy, azido, carboxyl, (optionally substituted alkoxy)carbonyl, (optionally substituted amino)carbonyl, cyano, optionally substituted cycloalkyl, optionally substituted cycloalkenyl, halogen, optionally substituted heteroaryl, optionally substituted heteroaryloxy, optionally substituted heterocyclyl, optionally substituted heterocyclooxy, hydroxyl, nitro, sulfanyl, sulfinyl, and sulfonyl. Preferred substituted heterocycles include 2-thioxo-thiazolidin-4-one and thiazolidine-2,4-dione.

The term "heterocycloalkyl" refers to the moiety "-alkylene-heterocycle" each having the meaning as defined herein.

The term "substituted heterocycloalkyl" refers to the moiety "-(optionally substituted aklylene)- (optionally substituted heterocycle)", each having the meaning as defined herein.

As used herein, "pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

The term "pharmaceutically acceptable salt" refers to salts which retain the biological effectiveness and properties of the compounds of this invention and which are not biologically or otherwise undesirable. In many cases, the compounds of this invention are capable of forming acid and/or base salts by virtue of the presence of amino and/or carboxyl groups or groups similar thereto. Pharmaceutically acceptable base addition salts can be prepared from inorganic and organic bases. Salts derived from inorganic bases, include by way of example only, sodium, potassium, lithium, ammonium, calcium and magnesium salts. Salts derived from organic bases include, but are not limited to, salts of primary, secondary and tertiary amines, such as alkyl amines, dialkyl amines, trialkyl amines, substituted alkyl amines, di(substituted alkyl) amines, tri(substituted alkyl) amines, alkenyl amines, dialkenyl amines, trialkenyl amines, substituted alkenyl amines, di(substituted alkenyl) amines, tri(substituted alkenyl) amines, cycloalkyl amines, di(cycloalkyl) amines, tri(cycloalkyl) amines, substituted cycloalkyl amines, disubstituted cycloalkyl amine, trisubstituted cycloalkyl amines, cycloalkenyl amines, di(cycloalkenyl) amines, tri(cycloalkenyl) amines, substituted cycloalkenyl amines, disubstituted cycloalkenyl amine, trisubstituted cycloalkenyl amines, aryl amines, diaryl amines, triaryl amines, heteroaryl amines, diheteroaryl amines, triheteroaryl amines, heterocyclic amines, diheterocyclic amines, triheterocyclic amines, mixed di- and tri-amines where at least two of the substituents on the amine are different and are selected from the group consisting of alkyl, substituted alkyl, alkenyl, substituted alkenyl, cycloalkyl, substituted cycloalkyl, cycloalkenyl, substituted cycloalkenyl, aryl, heteroaryl, heterocyclic, and the like. Also included are amines where the two or three substituents, together with the amino nitrogen, form a heterocyclic or heteroaryl group.

Specific examples of suitable amines include, by way of example only, isopropylamine, trimethyl amine, diethyl amine, tri(iso-propyl) amine, tri(n-propyl) amine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, morpholine, N-ethylpiperidine, and the like.

Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like.

The term "phosphoryl" refers to the group —P(O)(OR")$_2$, where R" is independently selected from hydrogen or alkyl and aryl, which group is sometimes also referred to as "phosphono" or as a "phosphate" or "phosphonic acid."

"Regulating skin condition" includes prophylactically regulating and/or therapeutically regulating skin condition, including visible and/or tactile discontinuities in skin such as, but not limited to, regulating visible and/or tactile discontinuities in the texture of skin, reducing post-inflammatory hyperpigmentation, regulating non-melanin discoloration of skin, regulating moisturization and barrier properties of skin, regulating epidermal differentiation of skin, regulating exfoliation of skin, thickening of skin to reduce skin atrophy, regulating the elasticity of skin, reducing oily skin, regulating cellulite in skin, regulating pruritus in skin, and promoting wound healing in skin. As used herein, prophylactically regulating skin condition includes delaying, minimizing and/or preventing visible and/or tactile discontinuities in skin. As used herein, therapeutically regulating skin condition includes ameliorating, e.g., diminishing, minimizing and/or effacing, discontinuities in skin. Regulating skin condition involves improving skin appearance and/or feel.

"Regulating the signs of skin aging" includes prophylactically regulating and/or therapeutically regulating one or more of such signs (similarly, regulating a given sign of skin aging, e.g., lines, wrinkles or pores, includes prophylactically regulating and/or therapeutically regulating that sign). As used herein, prophylactically regulating such signs includes delaying, minimizing and/or preventing signs of skin aging. As used herein, therapeutically regulating such signs includes ameliorating, e.g., diminishing, minimizing and/or effacing signs of skin aging.

"Signs of skin aging" include, but are not limited to, all outward visibly and tactilely perceptible manifestations as well as any other macro or micro effects due to skin aging. Such signs may be induced or caused by intrinsic factors or extrinsic factors, e.g., chronological aging and/or environmental damage (e.g., sunlight, UV, smoke, ozone, pollutants, stress, etc.). These signs may result from processes which include, but are not limited to, the development of textural discontinuities such as wrinkles, including both fine superficial wrinkles and coarse deep wrinkles, skin lines, facial frown lines, expression lines, rhytides, dermatoheliosis, photodamage, premature skin aging, crevices, bumps, pits, large pores (e.g., associated with adnexal structures such as sweat gland ducts, sebaceous glands, or hair follicles), "orange-peel" skin appearance, dryness, scaliness, flakiness and/or other forms of skin unevenness or roughness; blemishes such as acne, pimples, breakouts; excess skin oil problems such as over production of sebum, oiliness, facial shine, foundation breakthrough; abnormal desquamation (or exfoliation) or abnormal epidermal differentiation (e.g., abnormal skin turnover) such as scaliness, flakiness, keratoses, hyperkeratinization; inadequate skin moisturization (or hydration) such as caused by skin barrier damage, environmental dryness; loss of skin elasticity (loss and/or inactivation of functional skin elastin) such as elastosis, sagging (including puffiness in the eye area and jowls), loss of skin firmness, loss of skin tightness, loss of skin recoil from deformation; non-melanin skin discoloration such as undereye circles, blotching (e.g., uneven red coloration due to, e.g., rosacea), sallowness (pale color), discoloration caused by telangiectasia or spider vessels; melanin-related hyperpigmented (or unevenly pigmented) skin regions such as age spots (liver spots, brown spots) and freckles; post-inflammatory hyperpigmentation such as that which occurs following an inflammatory event (e.g., as an acne lesion, in-grown hair, insect/spider bite or sting, scratch, cut, wound, abrasion, and the like); atrophy such as, but not limited to, that associated with aging or steroid use; other histological or microscopic alterations in skin components such as ground substance (e.g., hyaluronic acid, glycosaminoglycans, etc.), collagen breakdown and structural alterations or abnormalities (e.g., changes in the stratum corneum, dermis, epidermis, the skin vascular system such as telangiectasia or spider vessels); tissue responses to insult such as itch or pruritus; and alterations to underlying tissues (e.g., subcutaneous fat, cellulite, muscles, trabeculae, septae, and the like), especially those proximate to the skin.

The term "sulfonyl" refers to the groups: —S(O$_2$)-(optionally substituted alkyl), —S(O$_2$)-(optionally substituted amino), —S(O$_2$)-optionally substituted aryl), —S(O$_2$)-(optionally substituted heteroaryl), —S(O$_2$)-(optionally substituted heterocyclyl). Preferred sulfonyl groups include, by way of example, methylsulfonyl, ethylsulfonyl, aminosulfonyl, piperidin-1-sulfonyl and morpholine-4-sulfonyl.

The term "therapeutically effective amount" or "effective amount" refers to that amount of a compound of any of Formulae I to V that is sufficient to effect treatment, as defined below, when administered to a mammal in need of such treatment. The therapeutically effective amount will vary depending upon the subject and disease condition being treated, the weight and age of the subject, the severity of the disease condition, the particular compound chosen, the dosing regimen to be followed, timing of administration, the manner of administration and the like, all of which can readily be determined by one of ordinary skill in the art.

The term "treatment" or "treating" means any treatment of a disease or disorder in a mammal, including:
preventing or protecting against the disease or disorder, that is, causing the clinical symptoms not to develop;
inhibiting the disease or disorder, that is, arresting or suppressing the development of clinical symptoms; and/or
relieving the disease or disorder, that is, causing the regression of clinical symptoms.

It will be understood by those skilled in the art that in human medicine, it is not always possible to distinguish between "preventing" and "suppressing" since the ultimate inductive event or events may be unknown, latent, or the patient is not ascertained until well after the occurrence of the event or events. Therefore, as used herein the term "prophylaxis" is intended as an element of "treatment" to encompass both "preventing" and "suppressing" as defined herein. The term "protection," as used herein, is meant to include "prophylaxis."

The term "topical application," as used herein, means to apply or spread the compositions of the present invention onto the surface of the skin.

Nomenclature

The compounds employed in the present invention are named and numbered herein as described below.

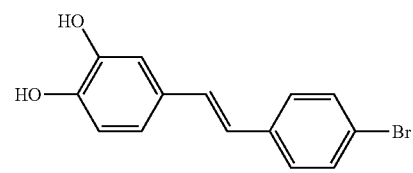

Formula Ia

Formula Ia represents the compound according to Formula I where $R^1$, $R^4$ and $R^5$ are H, $R^2$ and $R^3$ are OH, and R is p-bromo-phenyl, and can be named 4-[2-(4-bromo-phenyl)-vinyl]-benzene-1,2-diol.

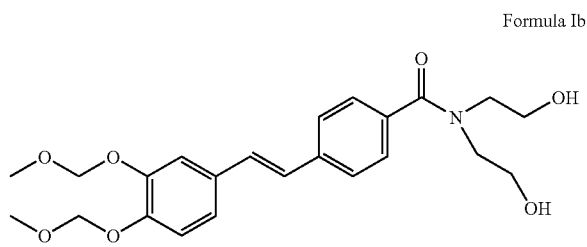

Formula Ib

Formula Ib represents the compound according to Formula I where $R^1$, $R^4$ and $R^5$ are H, $R^2$ and $R^3$ are OMOM (i.e., the group —O—CH$_2$—O—CH$_3$, which can also be named "methoxymethoxy"), and R is N,N-bis-(2-hydroxy-ethyl)-benzamide, and can be named 4-[2-(3,4-bis-methoxymethoxy-phenyl)-vinyl]-N,N-bis-(2-hydroxy-ethyl)-benzamide.

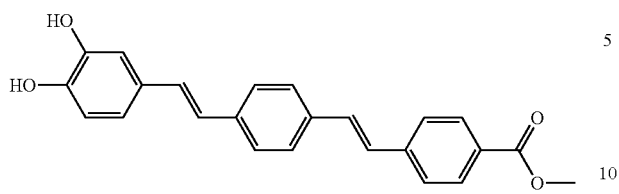

Formula Ic

Formula Ic represents the compound according to Formula I where R¹, R⁴ and R⁵ are H, R² and R³ are OH, and R is p-phenyl-vinyl benzoic acid methyl ester, and can be named 4-(2-{4-[2-(3,4-dihydroxy-phenyl)-vinyl]-phenyl}-vinyl)-benzoic acid methyl ester.

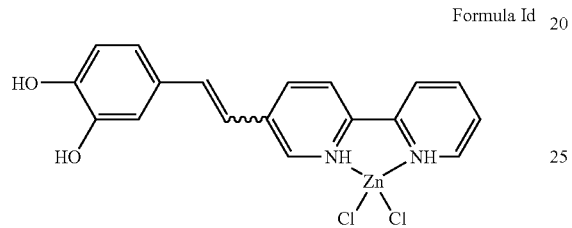

Formula Id

Formula Id represents the compound according to Formula I where R¹, R² and R⁵ are H, R³ and R⁴ are OH, and R is a [2,2']bipyridinyl-5-yl Zn(II) chloride complex, and can be named 4-(2-[2,2']bipyridinyl-5-yl-vinyl)benzene-1,2-diol, Zn(II) chloride.

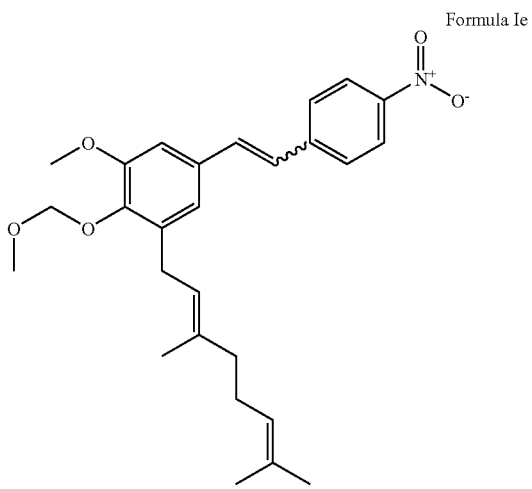

Formula Ie

Formula Ie represents the compound according to Formula I where R¹ and R⁵ are H, R² is methoxy, R³ is methoxymethoxy, R⁴ is geranyl (i.e., 3,7-dimethyl-octa-2,6-dienyl), and R is nitro-benzene, and can be named 4-{2-[3-(3,7-dimethyl-octa-2,6-dienyl)-5-methoxy-4-methoxymethoxy-phenyl]-vinyl}-1-nitro-benzene.

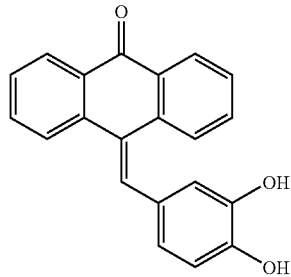

Formula IIa

Formula IIa represents the compound according to Formula II where R⁶, R⁷ and R¹⁰ are H, R⁸ and R⁹ are OH, and R" is 10H-anthracen-9-one, and can be named 10-(3,4-dihydroxy-benzylidene)10H-anthracen-9-one.

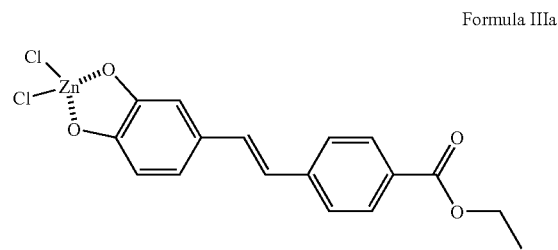

Formula IIIa

Formula IIIa represents the compound according to Formula III where R² and R³ are each O⁻ and together are complexed to a metal M" (in which M is zinc and n is two), L is chloro, R⁴ is H, and R is p-benzoic acid ethyl ester, and can be named 4-[2-(phenyl-1,2-diol)-vinyl]-benzoic acid ethyl ester, zinc(II) chloride.

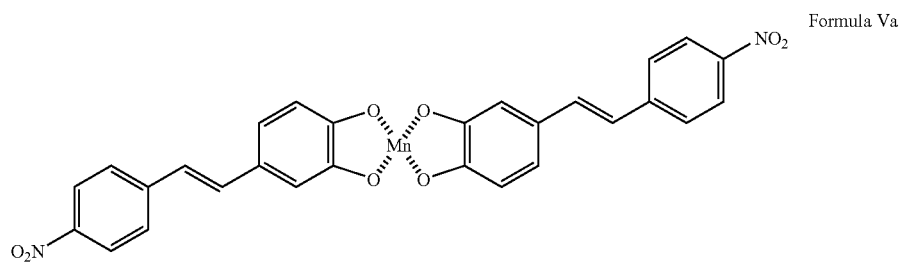

Formula Va

Formula Va represents the compound according to Formula V where M is Mn, $R^4$ and $R^{4*}$ are H, and R and $R^*$ are p-nitro-phenyl, and can be named bis-{4-[2-(4-nitro-phenyl)-vinyl]-benzene-1,2-diol}, manganese(III).

Synthesis of the Compounds of the Invention

The compounds of Formulae I to V can be prepared by solution phase synthesis, as described in greater detail below with reference to the Reaction Schemes. In general, the compounds of Formula I can be prepared using Wittig reaction between a benzaldehyde and a substituted phosphonium salt at room temperature in the presence of a base, preferably lithium ethoxide. An MOM-masking step is performed for OH-masking in those compounds where one or more, but not all of $R^1$ to $R^5$ are OH. Alternatively, the Wittig reaction can also be carried out using reverse intermediates, such as hydroxyl-masked phenyl phosphonium salt and a substituted benzaldehyde. Compounds of Formula II are made by condensation of the R' group with a benzaldehyde. Compounds of Formulae III, IV and V are made by treating a compound of Formula I with the desired metal to be complexed. A compound of Formula I to V is contacted with a pharmaceutically acceptable acid to form the corresponding acid addition salt. A pharmaceutically acceptable acid addition salt of Formula I to V is contacted with a base to form the corresponding free base of Formula I. Representative specific reaction schemes are shown in the Examples.

Synthetic Reaction Parameters

The terms "solvent", "inert organic solvent" or "inert solvent" mean a solvent inert under the conditions of the reaction being described in conjunction therewith. Solvents employed in synthesis of the compounds of the invention include, for example, methanol, acetone, water, acetonitrile, 1,4-dioxane, dimethylformamide ("DMF"), benzene, toluene, tetrahydrofuran ("THF"), chloroform, methylene chloride (or dichloromethane), diethyl ether, pyridine and the like, as well as mixtures thereof. Unless specified to the contrary, the solvents used in the reactions of the present invention are inert organic solvents.

The term "q.s." means adding a quantity sufficient to achieve a stated function, e.g., to bring a solution to the desired volume (i.e., 100%).

Unless specified to the contrary, the reactions described herein take place at atmospheric pressure within a temperature range from −10° C. to 110° C. (preferably from 0° C. to 40° C.; most preferably at "room" or "ambient" temperature, e.g., 20° C.). Further, unless otherwise specified, the reaction times and conditions are intended to be approximate, e.g., taking place at about atmospheric pressure within a temperature range of about −10° C. to about 110° C. (preferably from about 0° C. to about 40° C.; most preferably at about "room" or "ambient" temperature, e.g., approximately 20° C.) over a period of about 1 to about 10 hours (preferably about 5 hours). Parameters given in the Examples are intended to be specific, not approximate.

Isolation and purification of the compounds and intermediates described herein can be effected, if desired, by any suitable separation or purification procedure such as, for example, filtration, extraction, crystallization, column chromatography, thin-layer chromatography or thick-layer chromatography, or a combination of these procedures. Specific illustrations of suitable separation and isolation procedures can be had by reference to the examples hereinbelow. However, other equivalent separation or isolation procedures can, of course, also be used.

Starting Materials

The compounds methyl 4-(bromomethyl)-benzoate, 3,4-dihydroxybenzaldehyde, 4-hydroxy-3-methoxybenzaldehyde, and chloromethylmethyl ether are commercially available, e.g., from Aldrich Chemical Company, Milwaukee, Wis. Other reactants, such as concentrated HCl and triphenylphosphine are likewise commercially available or may be readily prepared by those skilled in the art using commonly employed methodology.

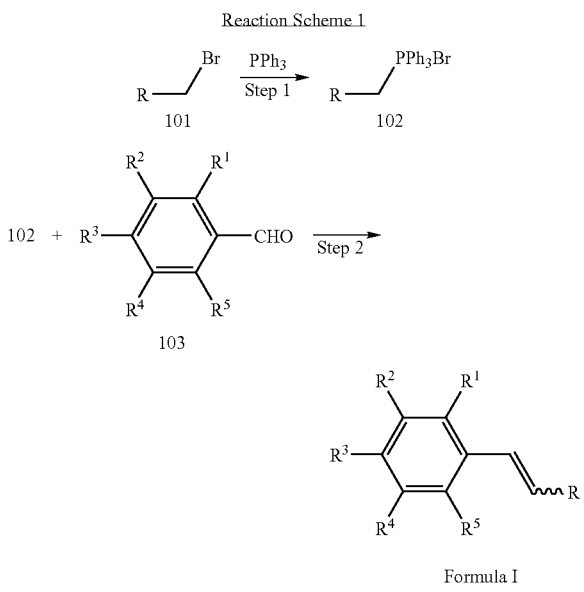

Referring to Reaction Scheme 1, Step 1, a bromomethyl-anthraquinone, -substituted aryl, -optionally substituted heteroaryl or -optionally substituted heterocyclyl compound of Formula 101 is refluxed for 2 hours in an inert organic solvent (such as toluene) with one molar equivalent of triphenylphosphine, to give the corresponding phosphonium salt of Formula 102.

In Step 2, a Wittig reaction is performed with the intermediate of Formula 102 and a benzaldehyde of Formula 103, which are mixed in an inert organic solvent (e.g., methanol) at 0° C. to which a strong base (such as lithium ethoxide) is slowly added, with stirring. The reaction mixture is allowed to warm to room temperature and stirring continued for 2 hours to give the corresponding vinyl conjugate compound of Formula I (where R' is H).

Phenolic conjugates and further derivatized compounds of Formula I (e.g., amidation of compounds where R is a benzoic acid) can be synthesized, for example, as illustrated with reference to a representative di-phenolic derivative in Reaction Scheme 1A.

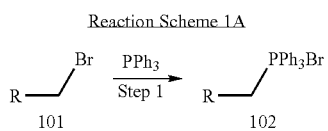

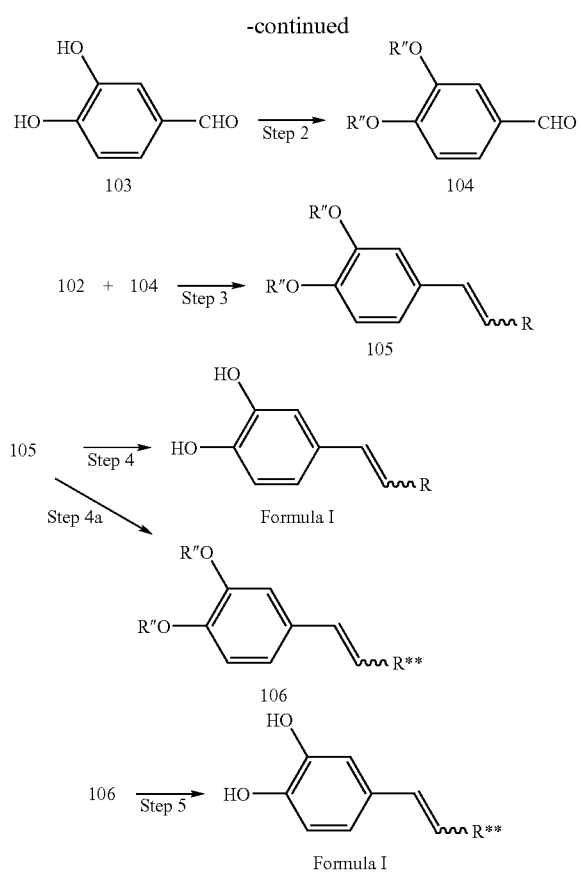

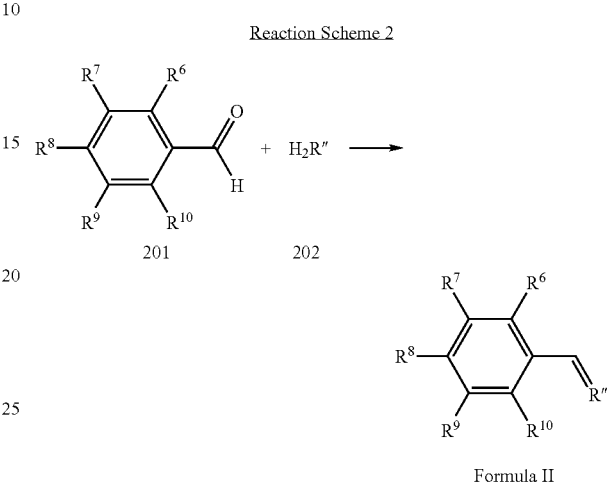

Formula II

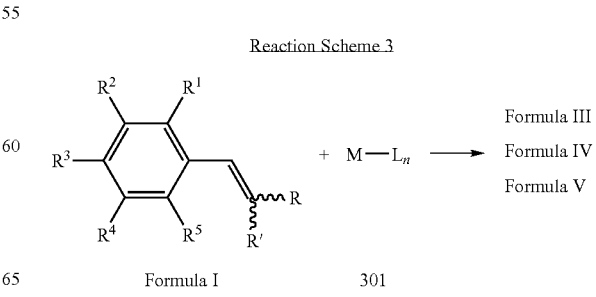

MOM-ether masked compound of Formula 105 can be further derivatized (e.g., a benzoic acid can be amidated by the addition of carbonyldiimidazole and diethanolamine) to give the corresponding compound of Formula 106 (which can also be a compound of Formula I where $R^2$ and $R^3$ are OMOM). As illustrated in Step 5, a further derivatized compound of Formula 106 can be converted to the corresponding phenol of Formula I (e.g., as described with reference to Step 4).

Referring to Reaction Scheme 1A, Step 1, a bromomethyl-anthraquinone, -substituted aryl, -optionally substituted heteroaryl or -optionally substituted heterocyclyl compound of Formula 101 is refluxed for 2 hours in an inert organic solvent (such as toluene) with one molar equivalent of triphenylphosphone, to give the corresponding phosphonium salt of Formula 102.

In Step 2, a hydroxylbenzaldehyde of Formula 103 is dissolved in an inert organic solvent (e.g., DMF) with a 2.2 molar excess of sodium hydride, and then slowly contacted with 4 molar equivalents of a hydroxyl protecting (or masking) reactant, such as chloromethyl methylether, which is added with stirring at a reduced temperature such as 0° C. (e.g., in an ice bath). The reaction mixture is warmed to 50-55° C. for 3 hours, and cooled to give the corresponding MOM-ether masked benzaldehyde of Formula 104.

In Step 3, a Wittig reaction is performed with the intermediates of Formulae 102 and 104, which are mixed in an inert organic solvent (e.g., methanol) at 0° C. to which a strong base (such as lithium ethoxide) is slowly added, with stirring. The reaction mixture is allowed to warm to room temperature and stirring continued for 2 hours to give the corresponding vinyl conjugate compound of Formula 105 (which can be a compound of Formula I where $R^2$ and $R^3$ are OMOM).

In Step 4, a MOM-ether masked compound of Formula 105 dissolved in an inert organic solvent (e.g., methanol) is converted to the corresponding phenol of Formula I by acid catalyzed hydrolysis (e.g., dropwise addition of concentrated HCl) followed by stirring at room temperature for 12 hours.

Alternatively, as illustrated in Step 4a (particularly for the compounds where R is a substituted phenyl group), the MOM-ether masked compound of Formula 105 can be further derivatized (e.g., a benzoic acid can be amidated by the addition of carbonyldiimidazole and diethanolamine) to give the corresponding compound of Formula 106 (which can also be a compound of Formula I where $R^2$ and $R^3$ are OMOM). As illustrated in Step 5, a further derivatized compound of Formula 106 can be converted to the corresponding phenol of Formula I (e.g., as described with reference to Step 4).

As illustrated in Reaction Scheme 2, a benzaldehyde compound of Formula 201 is condensed with malonitrile or an optionally substituted-anthraquinone, -heteroaryl or -heterocyclyl compound of Formula 202 (i.e. a precursor to the R" substituent) to give the corresponding compound of Formula II. The reaction conditions will depend on the nature of Formula 202. For example, where Formula 202 is malonitrile the reaction takes place in an inert organic solvent (e.g., methanol) under basic conditions (e.g., by addition of NaOH) with stirring at room temperature. Where Formula 202 is anthrone or dianthrol, the reaction takes place in an inert organic solvent (e.g., toluene) under acidic conditions (e.g., by addition of camphorsulfonic acid) at reflux. Where Formula 202 is thiazolidine-2,4-dione or 2,4-dihydro-pyrazol-3-one, the reaction takes place in an inert organic solvent (e.g., toluene) in the presence of benzoic acid at reflux.

Similarly, by substituting the compound of Formula 202 with a compound of the formula R—$CH_2$—R' (where R' is alkoxycarbonyl or cyano, and where R is, for example, optionally substituted heteroaryl or cyano) in the condensation reaction described with reference to Reaction Scheme II, the compounds of Formula I where R' is alkoxycarbonyl and the compounds where R' is H and R is di-cyano can be obtained.

As illustrated in Reaction Scheme 3, a compound of Formula I, dissolved in an inert organic solvent (e.g., methanol) is treated with a metal compound of Formula 301, followed by stirring at room temperature for 2 hours. When using a slight molar excess of Formula I, a compound of Formula III results. Alternatively, if a significant molar excess of Formula 301 is employed, the corresponding compound of Formulae IV or V will result (also depending on the starting compound(s) of Formula I).

Compounds of the Present Invention

In one aspect, the present invention provides certain new and useful compounds (including single stereoisomers, mixtures of stereoisomers, and the pharmaceutically acceptable salts thereof) represented by Formula I:

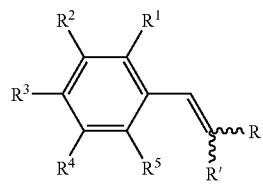

Formula I where:
- R is: anthraquinone, optionally substituted heteroaryl, optionally substituted heterocyclyl, nitro, or substituted phenyl having:
  - a substituent in the para position, selected from: cyano, nitro, alkoxycarbonyl, (nitrogen-containing)-heterocyclyl and (nitrogen-containing)-heteroaryl, and/or
  - a substituent in the meta position selected from: nitro and halo;
- R' is: hydrogen or (optionally substituted alkoxy)-carbonyl; and
- $R^1$ to $R^5$ are independently selected from: optionally substituted alkoxy, optionally substituted alkenyl, optionally substituted alkyl, optionally substituted aryl, (optionally substituted alkoxy)-carbonyl, carboxy, cyano, halo, optionally substituted heteroaryl, hydrogen, hydroxy, nitro, nitrone, sulfonate;

provided that at least one of $R^1$ to $R^5$ is H—[CH$_2$—(CH$_3$)C=CH—CH$_2$]$_n$— or H—[CH$_2$—(CH$_3$)C=CH—CH$_2$]$_n$—O— where n is an integer from 1 to 4, and at least another of $R^1$ to $R^5$ is hydrogen.

In another aspect, the present invention provides certain new and useful compounds (including single stereoisomers, mixtures of stereoisomers, and the pharmaceutically acceptable salts thereof) represented by Formula I, where:
- R is: (substituted phenyl)-alkenyl;
- R' is: hydrogen; and
- $R^1$ to $R^5$ are independently selected from: optionally substituted alkoxy, optionally substituted alkenyl, optionally substituted alkyl, optionally substituted aryl, (optionally substituted alkoxy)-carbonyl, carboxy, cyano, halo, optionally substituted heteroaryl, hydrogen, hydroxy, nitro, nitrone, and sulfonate, provided that (a) at least one of $R^1$ to $R^5$ is methoxymethoxy or H—[CH$_2$—(CH$_3$)C=CH—CH$_2$]$_n$— where n is an integer from 1 to 4, or (b) two adjacent members of $R^1$ to $R^5$ are each O$^-$ and together are complexed with a metal, In still another aspect, the present invention provides certain new and useful compounds (including single stereoisomers, mixtures of stereoisomers, and the pharmaceutically acceptable salts thereof) represented by Formula I, where:
- R is: (optionally substituted heterocyclyl)-alkenyl;
- R' is: hydrogen; and
- $R^1$ to $R^5$ are independently selected from: optionally substituted alkoxy, optionally substituted alkenyl, optionally substituted alkyl, optionally substituted aryl, (optionally substituted alkoxy)-carbonyl, carboxy, cyano, halo, optionally substituted heteroaryl, hydrogen, hydroxy, nitro, nitrone, and sulfonate, with the proviso that at least one of $R^1$ to $R^5$ is hydroxy, methoxymethoxy or H—[CH$_2$—(CH$_3$)C=CH—CH$_2$]$_n$—, where n is an integer from 1 to 4; or
- two adjacent members of $R^1$ to $R^5$ are each O$^-$ and together are complexed with a metal.

In yet another aspect, the present invention provides certain new and useful compounds (including single stereoisomers, mixtures of stereoisomers, and the pharmaceutically acceptable salts thereof) represented by Formula I, where:
- R is: optionally substituted heteroaryl, selected from the group: 1-carboxymethyl-pyridinium-4-yl bromide; 1-(2-carboxy-2-oxo-ethyl)-pyridinium-4-yl bromide; thiazol-2-yl; 6-nitro-benzo[1,3]dioxo-5-yl; and a [2,2']bipyridin-5-yl metal complex;
- R' is: hydrogen; and
- $R^1$ to $R^5$ are independently selected from: optionally substituted alkoxy, optionally substituted alkenyl, optionally substituted alkyl, optionally substituted aryl, (optionally substituted alkoxy)carbonyl, carboxy, cyano, halo, optionally substituted heteroaryl, hydrogen, hydroxy, nitro, nitrone, sulfonate; or
- two adjacent members of $R^1$ to $R^5$ are each O$^-$ and together are complexed with a metal;

provided that where R is a [2,2']bipyridin-5-yl Ru or Pd metal complex, $R^3$ and $R^4$ are not both hydroxy.

Another aspect of the present invention provides certain new and useful compounds (including single stereoisomers, mixtures of stereoisomers, and the pharmaceutically acceptable salts thereof) represented by Formula I, where:
- R is: substituted alkenyl, optionally substituted aryl, (optionally substituted aryl)-carbonyl, optionally substituted heteroaryl, optionally substituted heterocyclyl, or nitro;
- R' is: hydrogen or (optionally substituted alkoxy)-carbonyl;
- three members of $R^1$ to $R^5$ are independently selected from: optionally substituted alkoxy, optionally substituted alkenyl, optionally substituted alkyl, optionally substituted aryl, (optionally substituted alkoxy)-carbonyl, carboxy, cyano, halo, optionally substituted heteroaryl, hydrogen, hydroxy, nitro, nitrone, and sulfonate; and
- two adjacent members of $R^1$ to $R^5$ are each O$^-$ and together are complexed with a metal having one or more apical ligands, said metal optionally being further complexed with a second compound of Formula I.

Still another aspect of the present invention provides certain new and useful compounds (including single stereoisomers, mixtures of stereoisomers, and the pharmaceutically acceptable salts thereof) represented by Formula II:

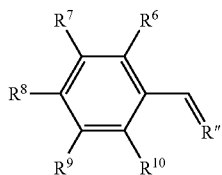

Formula II where:
R″ is: optionally substituted anthracenone, di-cyano, or optionally substituted heterocyclyl selected from: 2,5-(optionally substituted)-2,4-dihydro-pyrazol-3-one; 5-(optionally substituted)-3H-benzofuran-2-one; 2-thioxo-thiazolidin-4-one and thiazolidine-2,4-dione;

$R^6$ to $R^{10}$ are independently selected from: optionally substituted alkenyl, optionally substituted alkoxy, optionally substituted alkyl, optionally substituted aryl, (optionally substituted alkoxy)carbonyl, hydrogen, hydroxy and nitrone; or two adjacent members of $R^6$ to $R^{10}$ are each $O^-$ and together are complexed with a metal;

provided that at least one of $R^6$ to $R^{10}$ is not hydrogen, and further provided that where $R^{10}$ and another of $R^6$ to $R^9$ are hydrogen, at least one of $R^6$ to $R^9$ is methoxymethoxy or H—[CH$_2$—(CH$_3$)C═CH—CH$_2$]$_n$—, where n is an integer from 1 to 4.

Preferred Compounds

In the presently preferred embodiments of the invention, the following combinations and permutations of substituent groups (sub-grouped, respectively, in increasing order of preference, each sub-grouping being intended as combinable with other sub-groupings) define compounds (including single stereoisomers, mixtures of stereoisomers, and pharmaceutically acceptable salts) that are preferred as compositions of matter and/or compounds for use in its methods, and pharmaceutical and cosmetic compositions.

The compounds of Formula I where R′ is hydrogen.
  Especially where R is anthraquinone, optionally substituted heteroaryl, optionally substituted heterocyclyl, nitro, or substituted phenyl having (a) a substituent in the para position selected from: cyano, nitro, alkoxycarbonyl, (nitrogen-containing)-heterocyclyl and (nitrogen-containing)-heteroaryl, and/or (b) a substituent in the meta position selected from: nitro and halo.
    Particularly where R is substituted phenyl.
      Particularly where at least one of $R^1$ to $R^5$ is H—[CH$_2$—(CH$_3$)C═CH—CH$_2$]$_n$— or H—[CH$_2$—(CH$_3$)C═CH—CH$_2$]$_n$—O— where n is an integer from 1 to 4, and at least another of $R^1$ to $R^5$ is hydrogen.
        Preferably where n is 1 or 2.
          More preferably where R is substituted phenyl.
            Most preferably where R is phenyl (a) para-substituted with cyano, nitro or alkoxycarbonyl, and/or (b) meta-substituted with bromo.
      Preferably where $R^1$ to $R^5$ are independently selected from: optionally substituted alkoxy, optionally substituted alkenyl, carboxy, cyano, halo, hydrogen, hydroxy, and nitro.
        More preferably where $R^5$ and another of $R^1$ to $R^4$ are hydrogen, one of $R^1$ to $R^4$ is H—[CH$_2$—(CH$_3$)C═CH—CH$_2$]$_n$— (where n is 1, 2 or 3, especially 1 or 2), and the others of $R^1$ to $R^4$ are selected from hydrogen, hydroxy and lower alkoxy.
        Even more preferably where R is substituted phenyl.
          Most preferably where R is phenyl (a) para-substituted with cyano, nitro or alkoxycarbonyl, and/or (b) meta-substituted with bromo.
    More preferably where R is substituted phenyl.
      Most preferably where R is phenyl (a) para-substituted with cyano, nitro or alkoxycarbonyl, and/or (b) meta-substituted with bromo.
  Preferably where at least two of $R^1$ to $R^5$ are hydrogen.
Especially where R is (substituted phenyl)-alkenyl.
  Particularly where at least one of $R^1$ to $R^5$ is methoxymethoxy or H—[CH$_2$—(CH$_3$)C═CH—CH$_2$]$_n$— where n is an integer from 1 to 4.
    Preferably where R is (substituted phenyl)-vinyl (a) para-substituted with cyano, nitro, alkoxycarbonyl, (nitrogen-containing)-heterocyclyl or (nitrogen-containing)-heteroaryl, and/or (b) meta-substituted with nitro or halo.
      More preferably where R is 1-nitro-4-vinyl-benzene.
Especially where R is (optionally substituted heterocyclyl)-alkenyl.
  Particularly where R is (optionally substituted heterocyclyl)-methene.
    Preferably where at least one of $R^1$ to $R^5$ is hydroxy, methoxymethoxy or H—[CH$_2$—(CH$_3$)C═CH—CH$_2$]$_n$—, where n is an integer from 1 to 4.
      More preferably where R is 5-methyl-4-methylene-2-phenyl-2,4-dihydro-pyrazol-3-one or 5-methylene-thiazolidine-2,4-dione.
        Even more preferably where $R^5$ and another of $R^1$ to $R^4$ are hydrogen, and the others of $R^1$ to $R^4$ are selected from alkoxy, hydrogen, hydroxy, methoxymethoxy, and H—[CH$_2$—(CH$_3$)C═CH—CH$_2$]$_n$— (where n is an integer from 1 to 2).
    Preferably where $R^5$ and another of $R^1$ to $R^4$ are hydrogen, and the others of $R^1$ to $R^4$ are selected from alkoxy, hydrogen, hydroxy, methoxymethoxy, and H—[CH$_2$—(CH$_3$)C═CH—CH$_2$]$_n$—, where n is an integer from 1 to 2.
  Particularly where at least one of $R^1$ to $R^5$ is hydroxy, methoxymethoxy or H—[CH$_2$—(CH$_3$)C═CH—CH$_2$]$_n$—, where n is an integer from 1 to 4.
    Preferably where $R^5$ and another of $R^1$ to $R^4$ are hydrogen, and the others of $R^1$ to $R^4$ are selected from alkoxy, hydrogen, hydroxy, methoxymethoxy, and H—[CH$_2$—(CH$_3$)C═CH—CH$_2$]$_n$—, where n is an integer from 1 to 2.
Especially where R is optionally substituted heteroaryl, selected from the group: 1-carboxymethyl-pyridinium-4-yl bromide; 1-(2-carboxy-2-oxo-ethyl)-pyridinium-4-yl bromide; thiazol-2-yl; 6-nitro-benzo[1,3]dioxo-5-yl; and a [2,2']bipyridin-5-yl metal complex (provided that where R is a [2,2']bipyridin-5-yl Ru or Pd metal complex, $R^3$ and $R^4$ are not both hydroxy).
  Particularly where $R^5$ and another of $R^1$ to $R^4$ are hydrogen, and the others of $R^1$ to $R^4$ are selected from: alkoxy, (optionally substituted alkoxy)carbonyl, hydrogen, hydroxy, and H—[CH$_2$—(CH$_3$)C═CH—CH$_2$]$_n$—, where n is an integer from 1 to 4.

Preferably where $R^1$ is hydrogen, $R^2$ is hydroxy, $R^3$ is hydroxy and $R^4$ is hydrogen.

Preferably where $R^1$ is hydrogen, $R^2$ is methoxymethoxy, $R^3$ is methoxymethoxy, and $R^4$ is hydrogen.

Preferably where $R^1$ is hydrogen, $R^2$ is hydrogen, $R^3$ is methoxycarbonyl and $R^4$ is hydrogen.

Preferably where $R^1$ is hydrogen, $R^2$ is hydrogen, $R^3$ is methoxymethoxy and $R^4$ is methoxymethoxy.

More preferably where R is [2,2']bipyridin-5-yl, the nitrogen atoms of which are complexed to a metal having one or more apical ligands.

Even more preferably where the metal is selected from Zn(II), Mn(III) and Cu(II)

Most preferably where the apical ligand is selected from chloride and acetate.

Particularly where R is [2,2']bipyridin-5-yl, the nitrogen atoms of which are complexed to a metal having one or more apical ligands.

Preferably where the metal is selected from Zn(II), Mn(III) and Cu(II)

More preferably where the apical ligand is selected from chloride and acetate.

Most preferably, a compound selected from the group:

4-(2-[2,2']bipyridinyl-5-yl-vinyl)-1,2-dimethoxymethoxy-benzene, zinc(II) chloride;

4-(2-[2,2']bipyridinyl-5-yl-vinyl)-1,2-dimethoxymethoxy-benzene, copper(II) chloride; and 4-(2-[2,2']bipyridinyl-5-yl-vinyl)-1,2-dimethoxymethoxy-benzene, manganese(III) acetate.

Especially where two adjacent members of $R^1$ to $R^5$ are each $O^-$ and together are complexed with a metal having one or more apical ligands and optionally being further complexed with a second compound of Formula I, Particularly where R is substituted alkenyl, optionally substituted aryl, (optionally substituted aryl)-carbonyl, optionally substituted heteroaryl, optionally substituted heterocyclyl, or nitro.

Preferably where R is substituted phenyl having (a) a substituent in the para position selected from: cyano, nitro, alkoxycarbonyl, (nitrogen-containing)-heterocyclyl and (nitrogen-containing)-heteroaryl, and/or (b) a substituent in the meta position selected from: nitro and halo.

More preferably where R is para-alkoxycarbonyl-phenyl.

Most preferably, a compound selected from the group:

4-[2-(phenyl-1,2-diol)-vinyl]-benzoic acid ethyl ester, zinc(II) chloride;

4-[2-(phenyl-1,2-diol)-vinyl]-benzoic acid ethyl ester, copper(II) chloride;

4-[2-(phenyl-1,2-diol)-vinyl]-benzoic acid ethyl ester, manganese(III) acetate; and bis-{4-[2-(4-methoxycarbonyl-phenyl)-vinyl]-benzene-1,2-diol}, zinc(II) chloride.

More preferably where $R^3$ and $R^4$ are complexed with a metal.

Even more preferably where $R^1$, $R^2$ and $R^5$ are hydrogen.

Still more preferably where the metal is selected from Zn(II), Mn(III) and Cu(II).

Most preferably where the apical ligand is chloride or acetate.

Most preferably where R is para-alkoxycarbonyl-phenyl.

Even more preferably where the metal is selected from Zn(II), Mn(III) and Cu(II).

Still more preferably where the apical ligand is chloride or acetate.

Most preferably where R is para-alkoxycarbonyl-phenyl.

Preferably where $R^3$ and $R^4$ are complexed with a metal.

More preferably where $R^1$, $R^2$ and $R^5$ are hydrogen.

Even more preferably where the metal is selected from Zn(II), Mn(III) and Cu(II).

Most preferably where the apical ligand is chloride or acetate.

More preferably where the metal is selected from Zn(II), Mn(III) and Cu(II).

Even more preferably where the apical ligand is chloride or acetate.

Particularly where $R^3$ and $R^4$ are complexed with a metal.

Preferably where $R^1$, $R^2$ and $R^5$ are hydrogen.

More preferably the metal is selected from Zn(II), Mn(III) and Cu(II).

Even more preferably where the apical ligand is chloride or acetate.

Preferably where the metal is selected from Zn(II), Mn(III) and Cu(II).

More preferably where the apical ligand is chloride or acetate.

Particularly where the compound is selected from Formulae III, IV and V

Preferably where R and R* are independently selected from: optionally substituted anthraquinone, substituted aryl, optionally substituted heteroaryl, optionally substituted heterocyclyl, or nitro.

More preferably where $R^2$, $R^4$ and $R^{4*}$ are independently selected from: optionally substituted alkoxy, hydrogen, or hydroxy.

Preferably where $R^2$, $R^4$ and $R^4$ are independently selected from: optionally substituted alkoxy, hydrogen, or hydroxy.

The compounds of Formula II where at least one of $R^6$ to $R^9$ is methoxymethoxy or H—[CH$_2$—(CH$_3$)C=CH—CH$_2$]$_n$— (where n is an integer from 1 to 4).

Especially where $R^{10}$ and another of $R^6$ to $R^9$ are hydrogen.

Particularly where the rest of $R^6$ to $R^9$ are independently selected from: optionally substituted alkenyl, optionally substituted alkoxy, optionally substituted alkyl, optionally substituted aryl, (optionally substituted alkoxy)carbonyl, hydrogen, hydroxy and nitrone.

Especially where R" is optionally substituted anthracenone, di-cyano, or optionally substituted heterocyclyl selected from: 2,5-(optionally substituted)-2,4-dihydro-pyrazol-3-one; 5-(optionally substituted)-3H-benzofuran-2-one; 2-thioxo-thiazolidin-4-one and thiazolidine-2,4-dione.

Particularly where $R^{10}$ and another of $R^6$ to $R^9$ are hydrogen.

Preferably where the rest of $R^6$ to $R^9$ are independently selected from: optionally substituted alkenyl, optionally substituted alkoxy, optionally substituted alkyl, optionally substituted aryl, (optionally substituted alkoxy)carbonyl, hydrogen, hydroxy and nitrone.

More preferably where the rest of $R^6$ to $R^9$ are selected from: hydrogen, hydroxy, methoxymethoxy, t-butyl and H—[CH$_2$—(CH$_3$)C=CH—CH$_2$]$_n$—, where n is 1 or 2.

Most preferably where $R^6$ is hydrogen and:
$R^7$ is hydrogen, $R^8$ is methoxymethoxy, and $R^9$ is methoxymethoxy; or
$R^7$ is methoxymethoxy, $R^8$ is H—CH$_2$—(CH$_3$)C=CH—CH$_2$—, and $R^9$ is hydroxy; or
$R^7$ is hydroxy, $R^8$ is H—CH$_2$—(CH$_3$)C=CH—CH$_2$—, and $R^9$ is methoxymethoxy, or
$R^7$ is hydroxy, $R^8$ is H—CH$_2$—(CH$_3$)C=CH—CH$_2$—, and $R^9$ is hydroxy; or
$R^7$ is H—CH$_2$—(CH$_3$)C=CH—CH$_2$—, $R^8$ is methoxymethoxy, and $R^9$ is hydrogen; or
$R^7$ is H—CH$_2$—(CH$_3$)C=CH—CH$_2$—, $R^8$ is hydroxy, and $R^9$ is hydrogen; or
$R^7$ is H—[CH$_2$—(CH$_3$)C=CH—CH$_2$]$_2$—, $R^8$ is methoxymethoxy, and $R^9$ is hydrogen; or
$R^7$ is H—[CH$_2$—(CH$_3$)C=CH—CH$_2$]$_2$—, $R^8$ is hydroxy, and $R^9$ is hydrogen; or
$R^7$ is 3-methoxy-4-methoxymethoxy-1-(thiazolidine-2,4-dionyl)-benzylidene-5-yl, $R^8$ is methoxymethoxy, and $R^9$ is methoxy.

Particularly where R" is selected from: anthracenone, dihydroxyanthracenone, di-cyano, 5-methyl-2-phenyl-2,4-dihydro-pyrazol-3-one; 3H-benzofuran-2-one; 5-hydroxy-3H-benzofuran-2-one; 2-thioxo-thiazolidin-4-one and thiazolidine-2,4-dione.

Preferably where $R^{10}$ and another of $R^6$ to $R^9$ are hydrogen.

More preferably where the rest of $R^6$ to $R^9$ are independently selected from: optionally substituted alkenyl, optionally substituted alkoxy, optionally substituted alkyl, optionally substituted aryl, (optionally substituted alkoxy)carbonyl, hydrogen, hydroxy and nitrone.

Even more preferably where the rest of $R^6$ to $R^9$ are selected from: hydrogen, hydroxy, methoxymethoxy, t-butyl and H—[CH$_2$—(CH$_3$)C=CH—CH$_2$]$_n$—, where n is 1 or 2.

Most preferably where $R^6$ is hydrogen and:
$R^7$ is hydrogen, $R^8$ is methoxymethoxy, and $R^9$ is methoxymethoxy; or
$R^7$ is methoxymethoxy, $R^8$ is H—CH$_2$—(CH$_3$)C=CH—CH$_2$—, and $R^9$ is hydroxy; or
$R^7$ is hydroxy, $R^8$ is H—CH$_2$—(CH$_3$)C=CH—CH$_2$—, and $R^9$ is methoxymethoxy; or
$R^7$ is hydroxy, $R^8$ is H—CH$_2$—(CH$_3$)C=CH—CH$_2$—, and $R^9$ is hydroxy; or
$R^7$ is H—CH$_2$—(CH$_3$)C=CH—CH$_2$—, $R^8$ is methoxymethoxy, and $R^9$ is hydrogen; or
$R^7$ is H—CH$_2$—(CH$_3$)C=CH—CH$_2$—, $R^8$ is hydroxy, and $R^9$ is hydrogen; or
$R^7$ is H—[CH$_2$—(CH$_3$)C=CH—CH$_2$]$_2$—, $R^8$ is methoxymethoxy, and $R^9$ is hydrogen; or
$R^7$ is H—[CH$_2$—(CH$_3$)C=CH—CH$_2$]$_2$—, $R^8$ is hydroxy, and $R^9$ is hydrogen; or
$R^7$ is 3-methoxy-4-methoxymethoxy-1-(thiazolidine-2,4-dionyl)-benzylidene-5-yl, $R^8$ is methoxymethoxy, and $R^9$ is methoxy.

Compounds (including single stereoisomers, mixtures of stereoisomers, and pharmaceutically acceptable salts) employed as compositions of matter and/or compounds for use in its the methods, and pharmaceutical and cosmetic compositions of the present invention include:

4-(2-Pentafluorophenyl-vinyl)-benzene-1,2-diol
4-[2-(3,4-Dihydroxy-phenyl)-vinyl]-benzonitrile
1-Benzyl-4-[2-(3,4-dihydroxy-phenyl)-vinyl]-pyridinium; bromide 4-[2-(3,4-Dihydroxy-phenyl)-vinyl]-benzoic acid 3,4,5,6-tetrahydroxy-tetrahydro-pyran-2-ylmethyl ester
4-[2-(3,4-Dihydroxy-phenyl)-vinyl]-benzoic acid 3-hydroxy-13-methyl-7,8,9,11,12,13,14,15,16,17-decahydro-6H-cyclopenta[a]phenanthren-17-yl ester
4-[4-(3-Methoxy-4-methoxymethoxy-phenyl)-buta-1,3-dienyl]-benzoic acid methyl ester
4-[4-(3-Methoxy-4-methoxymethoxy-phenyl)-buta-1,3-dienyl]-benzoic acid methyl ester
4-[4-(3,4-Dihydroxy-phenyl)-buta-1,3-dienyl]-benzoic acid methyl ester
4-[4-(3,4-Bis-methoxymethoxy-phenyl)-buta-1,3-dienyl]-benzoic acid methyl ester
3,4-Bis-[2-(3,4-bis-methoxymethoxy-phenyl)-vinyl]-benzoic acid methyl ester
3-{4-[2-(3,4-Bis-methoxymethoxy-phenyl)-vinyl]-phenyl}-3-oxo-propionic acid ethyl ester
4-{2-[4-(5-Hydroxy-1-phenyl-1H-pyrazol-3-yl)-phenyl]-vinyl}-benzene-1,2-diol
4-[2-(3,4-Bis-methoxymethoxy-phenyl)-vinyl]-phenylamine
N-{4-[2-(3,4-Bis-methoxymethoxy-phenyl)-vinyl]-phenyl}-acetamide
N-{4-[2-(3,4-Dihydroxy-phenyl)-vinyl]-phenyl}-acetamide
N-{4-[2-(3,4-Bis-methoxymethoxy-phenyl)-vinyl]-phenyl}-di-methanesulfonamide
N-{4-[2-(3,4-Bis-methoxymethoxy-phenyl)-vinyl]-phenyl}-methanesulfonamide
{4-[2-(3,4-Bis-methoxymethoxy-phenyl)-vinyl]-phenyl}-ethyl-amine
4-{4-[2-(3,4-Dimethoxy-phenyl)-vinyl]-benzenesulfonyl}-morpholine
4-(3,4-Bis-methoxymethoxy-benzylidene)-5-methyl-2-phenyl-2,4-dihydro-pyrazol-3-one
3,4-Bis-[2-(3-methoxy-4-methoxymethoxy-phenyl)-vinyl]-benzoic acid methyl ester
3-(3,4-Bis-methoxymethoxy-phenyl)-1-[2-hydroxy-3,4-dimethyl-5-(tetrahydro-pyran-2-yloxy)-phenyl]-propenone
5-[2-(3,4-Dimethoxy-phenyl)-vinyl]-2-hydroxy-benzoic acid ethyl ester
4-[2-(3,4-Dimethoxy-phenyl)-vinyl]-benzenesulfonamide
3-(3,5-Bis-methoxymethoxy-benzylidene)-3H-benzofuran-2-one
3-(3,5-Dihydroxy-benzylidene)-3H-benzofuran-2-one
5-[2-(3,4-Dimethoxy-phenyl)-vinyl]-2-methoxymethoxy-benzoic acid ethyl ester
4-{2-[3,4-Bis-(3,7-dimethyl-octa-2,6-dienyloxy)-phenyl]-vinyl}-benzoic acid methyl ester
4-{2-[3,4-Bis-(3,7-dimethyl-octa-2,6-dienyloxy)-phenyl]-vinyl}-benzoic acid methyl ester
5-[2-(4-Nitro-phenyl)-vinyl]-benzene-1,3-diol
2-[2-(3,4-Dimethoxy-phenyl)-vinyl]-5-(4-nitro-phenyl)-furan
4-[2-(3,5-Di-tert-butyl-4-hydroxy-phenyl)-vinyl]-benzoic acid methyl ester
3,3'-Dimethoxy-2,2'-bis-methoxymethoxy-5,5'-bis-[2-(4-nitro-phenyl)-vinyl]-biphenyl
4-[2-(2-Bromo-4,5-dimethoxy-phenyl)-vinyl]-benzoic acid methyl ester 4-[2-(5-Bromo-2,4-dimethoxy-phenyl)-vinyl]-benzoic acid methyl ester
1-Bromo-2,4-dimethoxy-5-[2-(4-nitro-phenyl)-vinyl]-benzene
4-[2-(3-Bromo-5-methoxy-4-methoxymethoxy-phenyl)-vinyl]-benzoic acid methyl ester
4-[2-(3-Bromo-4-hydroxy-5-methoxy-phenyl)-vinyl]-benzoic acid methyl ester
5-[6-Hydroxy-2,7,8-trimethyl-2-(4,8,12-trimethyl-tridecyl)-chroman-5-ylmethylene]-thiazolidine-2,4-dione
1-{4-[2-(3,4-Dimethoxy-phenyl)-vinyl]-benzenesulfonyl}-piperidine
1-{4-[2-(3,4-Dimethoxy-phenyl)-vinyl]-benzenesulfonyl}-pyrrolidine
4-[2-(3,4-Bis-methoxymethoxy-phenyl)-vinyl]-N-dimethylaminomethylene-benzenesulfonamide
4-(2-[2,2']Bipyridinyl-5-yl-vinyl)-benzene-1,2-diol
4-(2-[2,2']Bipyridinyl-5-yl-vinyl)-benzene-1,2-diol, Zn(II)chloride
4-(2-[2,2']Bipyridinyl-5-yl-vinyl)-benzene-1,2-diol, Cu(II)chloride
4-(2-[2,2']Bipyridinyl-5-yl-vinyl)-benzene-1,2-diol, Mn(II)acetate
4-(2-[2,2']Bipyridinyl-5-yl-vinyl)-benzene-1,2-diol, Ru(II) di-[2,2']bipyridine chloride
4(N-t-butiylamino-methyl)benzilidene]thiazolidine-2,4-dione-N-oxide
1-{4-[2-(3,4-Bis-methoxymethoxy-phenyl)-vinyl]-benzenesulfonyl}-piperidine
4-[2-(3,5-Dimethoxy-4-methoxymethoxy-phenyl)-vinyl]-benzoic acid methyl ester
4-[2-(4-Hydroxy-3,5-dimethoxy-phenyl)-vinyl]-benzoic acid methyl ester
1,3-Dimethoxy-2-methoxymethoxy-5-[2-(4-nitro-phenyl)-vinyl]-benzene
4-[2-(2,3,4-Tris-methoxymethoxy-phenyl)-vinyl]-benzoic acid methyl ester
2-Chloro-1-methoxymethoxy-4-[2-(4-nitro-phenyl)-vinyl]-benzene
4-[2-(3,5-Dimethoxy-4-methoxymethoxy-phenyl)-vinyl]-benzonitrile
4-[2-(4-Hydroxy-3,5-dimethoxy-phenyl)-vinyl]-benzonitrile
2,6-Dimethoxy-4-[2-(4-nitro-phenyl)-vinyl]-phenol
1-Methoxymethoxy-2-nitro-4-[2-(4-nitro-phenyl)-vinyl]-benzene
2-Bromo-6-methoxy-4-[2-(4-nitro-phenyl)-vinyl]-phenol
1-Bromo-2-methoxy-4-methoxymethoxy-5-[2-(4-nitro-phenyl)-vinyl]-benzene
1-Bromo-2-methoxy-4-methoxymethoxy-5-[2-(4-nitro-phenyl)-vinyl]-benzene
4-[2-(5-Bromo-4-methoxy-2-methoxymethoxy-phenyl)-vinyl]-benzoic acid methyl ester
4-[2-(3,4-Bis-methoxymethoxy-phenyl)-vinyl]-benzoic acid
1,2,3-Tris-methoxymethoxy-4-[2-(4-nitro-phenyl)-vinyl]-benzene
4-[2-(3-Bromo-4-hydroxy-phenyl)-vinyl]-benzoic acid methyl ester
4-[2-(3,5-Dibromo-4-methoxymethoxy-phenyl)-vinyl]-benzoic acid methyl ester
1,3-Dibromo-2-methoxymethoxy-5-[2-(4-nitro-phenyl)-vinyl]-benzene
4-[2-(3,5-Dibromo-4-methoxymethoxy-phenyl)-vinyl]-benzonitrile
4-[2-(3,5-Dibromo-4-hydroxy-phenyl)-vinyl]-benzoic acid methyl ester
2-{3-[2-(3,4-Dihydroxy-phenyl)-vinyl]-5-hydroxy-phenoxy}-6-hydroxymethyl-tetrahydro-pyran-3,4,5-triol
Astringin
2,3-Bis-(4-acetoxy-3-methoxy-phenyl)-acrylic acid
Acetic acid 4-[2-(4-acetoxy-3-methoxy-phenyl)-vinyl]-2-methoxy-phenyl ester
3,3'-dimethoxy-4,4'-dihydroxy-stilbene
5-[2-(4-Methoxy-phenyl)-vinyl]-benzo[1,3]dioxole
Gnelin
4-(3-Ethoxy-propenyl)-phenol
2-(4-Methoxy-phenyl)-1-(3,4,5-trimethoxy-phenyl)-ethanol
5-[2-(4-Hydroxy-phenyl)-vinyl]-benzene-1,3-diol
1,2-Bis-methoxymethoxy-4-[2-(4-nitro-phenyl)-vinyl]-benzene
1,2,3-Trimethoxy-5-[2-(4-nitro-phenyl)-vinyl]-benzene
4-[2-(3,4,5-Trimethoxy-phenyl)-vinyl]-phenylamine
4-[2-(3,4-Bis-methoxymethoxy-phenyl)-vinyl]-benzoic acid
4-(2-Pyridin-4-yl-vinyl)-benzene-1,2-diol
4-[2-(4-Bromo-phenyl)-vinyl]-benzene-1,2-diol
4-[2-(3,4-Dimethoxy-phenyl)-vinyl]-benzoic acid methyl ester
4-[2-(3,4-Dimethoxy-phenyl)-vinyl]-benzoic acid
4-[2-(4-tert-Butyl-phenyl)-vinyl]-benzene-1,2-diol
4-[2-(4-Trifluoromethyl-phenyl)-vinyl]-benzene-1,2-diol
4-[2-(4-Fluoro-phenyl)-vinyl]-1,2-dimethoxy-benzene
3-{4-[2-(3,4-Dimethoxy-phenyl)-vinyl]-phenyl}-acrylic acid ethyl ester
4-(2-{4-[2-(3,4-Dimethoxy-phenyl)-vinyl]-phenyl}-vinyl)-benzoic acid ethyl ester
4-[2-(3,4-Dimethoxy-phenyl)-vinyl]-benzaldehyde
4-[2-(3,4-Dimethoxy-phenyl)-vinyl]-benzaldehyde
4-[2-(4-Fluoro-phenyl)-vinyl]-benzene-1,2-diol
4-[2-(3,4-Dihydroxy-phenyl)-vinyl]-benzoic acid decyl ester
2-(3,4-Bis-methoxymethoxy-benzylidene)-malononitrile
2-(3,4-Dihydroxy-benzylidene)-malononitrile
4-[2-(4-tert-Butyl-phenyl)-vinyl]-1,2-bis-methoxymethoxy-benzene
1,2-Bis-methoxymethoxy-4-[2-(4-trifluoromethyl-phenyl)-vinyl]-benzene
10-(3,4-Dihydroxy-benzylidene)-10H-anthracen-9-one
2-Methoxy-4-(2-pentafluorophenyl-vinyl)-phenol
2-Methoxy-1-methoxymethoxy-4-[2-(4-nitro-phenyl)-vinyl]-benzene
4-{2-[6-Methoxy-2,7,8-trimethyl-2-(4,8,12-trimethyl-tridecyl)-chroman-5-yl]-vinyl}-benzoic acid ethyl ester
4-[2-(3-Methoxy-4-methoxymethoxy-phenyl)-vinyl]-benzonitrile
4-[2-(3,5-Bis-methoxymethoxy-phenyl)-vinyl]-benzonitrile
2-[2-(3,4-Bis-methoxymethoxy-phenyl)-vinyl]-anthraquinone
4-[2-(3,5-Bis-methoxymethoxy-phenyl)-vinyl]-benzoic acid methyl ester
3-[2-(3,4-Bis-methoxymethoxy-phenyl)-vinyl]-benzoic acid methyl ester
1-[2-(3,4-Dimethoxy-phenyl)-vinyl]4,5-dimethoxy-2-nitro-benzene
4-{2-[3-Iodo-5-methoxy-4-(4-methoxy-benzyloxy)-phenyl]-vinyl}-benzoic acid methyl ester
4-{2-[3-Methoxy-4-(4-methoxy-benzyloxy)-phenyl]-vinyl}-benzoic acid methyl ester
Bis-{4-[2-(3,4-bis-methoxymethoxy-phenyl)-vinyl]-phenyl}-diazene N,N'-dioxide Bis-{4-[2-(3,4-bis-hydroxy-phenyl)-vinyl]-phenyl}-diazene N,N'-dioxide
N-{4-[2-(3,4-Bis-methoxymethoxy-phenyl)-vinyl]-phenyl}-benzamide
2-Bromo-4-methoxy-3-methoxymethoxy-1-[2-(4-nitro-phenyl)-vinyl]-benzene
4-[2-(2-Bromo-4-methoxy-3-methoxymethoxy-phenyl)-vinyl]-benzoic acid methyl ester
1-Bromo-4,5-dimethoxy-2-[2-(4-nitro-phenyl)-vinyl]-benzene
1-Bromo-3-methoxy-2-methoxymethoxy-5-[2-(4-nitro-phenyl)-vinyl]-benzene
2-Nitro-4-[2-(4-nitro-phenyl)-vinyl]-phenol
4-[2-(5-Bromo-4-methoxy-2-methoxymethoxy-phenyl)-vinyl]-benzoic acid methyl ester
4-[2-(3-Bromo-4-methoxymethoxy-phenyl)-vinyl]-benzoic acid methyl ester
Acetic acid 4-(1-acetoxy-allyl)-phenyl ester
Acetoxychavicol.

The compounds (including single stereoisomers, mixtures of stereoisomers, and pharmaceutically acceptable salts) preferred as compositions of matter and/or compounds for use in its the methods, and pharmaceutical and cosmetic compositions of the present invention include:

4-[2-(3,4-Bis-methoxymethoxy-phenyl)-vinyl]-benzoic acid methyl ester
4-[2-(3,4-Dihydroxy-phenyl)-vinyl]-benzoic acid
5-(3,4-Bis-methoxymethoxy-benzylidene)-thiazolidine-2,4-dione
5-(3,4-Dihydroxy-benzylidene)thiazolidine-2,4-dione
4-(2-Nitro-vinyl)-benzene-1,2-diol
4-[2-(3,4-Dihydroxy-phenyl)-vinyl]-N-methyl-N-(2,3,4,5,6-pentahydroxy-hexyl)-benzamide
3-{4-[2-(3,4-Dihydroxy-phenyl)-vinyl]-phenyl}-acrylic acid ethyl ester
4-(2-{4-[2-(3,4-Dihydroxy-phenyl)-vinyl]-phenyl}-vinyl)-benzoic acid methyl ester
4-[2-(3,4-Dihydroxy-phenyl)-vinyl]-benzoic acid decyl ester
(E)-4-[2-(3,4-Dihydroxy-phenyl)-vinyl]-benzoic acid hexyl ester
(Z)-4-[2-(3,4-Dihydroxy-phenyl)-vinyl]-benzoic acid hexyl ester
4-[2-(3,4-Bis-methoxymethoxy-phenyl)-vinyl]-benzoic acid 3,7-dimethyl-octa-2,6-dienyl ester
4-[2-(3,4-Dihydroxy-phenyl)-vinyl]-benzoic acid hex-3-enyl ester
4-[2-(3,4-Bis-methoxymethoxy-phenyl)-vinyl]-benzoic acid hex-3-enyl ester
4-[2-(3,4-Bis-methoxymethoxy-phenyl)-vinyl]-benzoic acid heptadec-12-enyl ester
4-[2-(3-Hydroxy-4-{2-[2-(2-methoxy-ethoxy)-ethoxy]-ethoxy}-phenyl)-vinyl]-benzoic acid ethyl ester
4-[2-(4-Hydroxy-3-methoxy-phenyl)-vinyl]-benzoic acid methyl ester
2-Methoxy-4-[2-(4-nitro-phenyl)-vinyl]-phenol
4-[2-(3,5-Dihydroxy-phenyl)-vinyl]-benzonitrile
4-[2-(4-Methanesulfonyl-phenyl)-vinyl]-1,2-dimethoxybenzene
4-[2-(3,5-Dihydroxy-phenyl)-vinyl]-benzoic acid methyl ester
5-[2-(4-Methoxycarbonyl-phenyl)-vinyl]-2-methoxymethoxy-benzoic acid methoxymethyl ester
2-Hydroxy-5-[2-(4-methoxycarbonyl-phenyl)-vinyl]-benzoic acid
4-[4-(3,4-Dimethoxy-phenyl)-buta-1,3-dienyl]-2-methoxy-phenol
2-Methoxy-1-methoxymethoxy-4-[4-(4-nitro-phenyl)-buta-1,3-dienyl]-benzene
1-[2-(3,4-Dimethoxy-phenyl)-vinyl]-5-methoxymethoxy-2-nitro-benzene
4-[2-(4-Methoxymethoxy-3,5-dimethyl-phenyl)-vinyl]-benzoic acid methyl ester
4-(3,4-Bis-methoxymethoxy-benzylidene)-5-methyl-2-phenyl-2,4-dihydro-pyrazol-3-one
5-[2-(3,4-Dimethoxy-phenyl)-vinyl]-6-nitro-benzo[1,3]dioxole
1-Iodo-3-methoxy-2-methoxymethoxy-5-[2-(4-nitro-phenyl)-vinyl]-benzene
5-[2-(4-Dimethylamino-phenyl)-vinyl]-2-methoxy-phenol
4-{2-[4-(5-Hydroxy-1H-pyrazol-3-yl)-phenyl]-vinyl}-benzene-1,2-diol
{4-[2-(3,4-Bis-methoxymethoxy-phenyl)-vinyl]-phenyl}-dimethyl-amine
{4-[2-(3,4-Bis-methoxymethoxy-phenyl)-vinyl]-phenyl}-methyl-amine
N,N-{4-[2-(3,4-Dihydroxy-phenyl)-vinyl]-phenyl}-dimethanesulfonyl-amide
N{4-[2-(3,4-Dihydroxy-phenyl)-vinyl]-phenyl}-methanesulfonamide
4-[2-(3,4-Bis-methoxymethoxy-phenyl)-vinyl]4'-methyl-[2,2']bipyridinyl
N-{4-[2-(3,4-Bis-methoxymethoxy-phenyl)-vinyl]-phenyl}-benzamide
4-[2-(4'-Methyl-[2,2']bipyridinyl-4-yl)-vinyl]-benzene-1,2-diol
4-{2-[3,5-Bis-methoxymethoxy-2,6-bis-(3-methyl-but-2-enyl)-phenyl]-vinyl}-benzoic acid methyl ester
1,5-Bis-methoxymethoxy-2,4-bis-(3-methyl-but-2-enyl)-3-[2-(4-nitro-phenyl)-vinyl]-benzene
5-[3-(4-Hydroxy-3-methoxy-phenyl)-allylidene]-thiazolidine-2,4-dione
3-(3,4-Bis-methoxymethoxy-benzylidene)-3H-benzofuran-2-one
3-(3,4-Dihydroxy-benzylidene)-3H-benzofuran-2-one
5-[2-(4-Nitro-phenyl)-vinyl]-1H-benzoimidazole
3-(3,4-Dihydroxy-phenyl)-2-(2,5-dihydroxy-phenyl)-acrylic acid methyl ester
3-(3,4-Dihydroxy-benzylidene)-5-hydroxy-3H-benzofuran-2-one
5-Hydroxy-3-(4-hydroxy-3-methoxy-benzylidene)-3H-benzofuran-2-one
1,2-Bis-(3,7-dimethyl-octa-2,6-dienyloxy)-4-[2-(4-nitro-phenyl)-vinyl]-benzene
1,3-Bis-methoxymethoxy-5-[2-(4-nitro-phenyl)-vinyl]-benzene
3,3'-Dimethoxy-2,2'-bis-methoxymethoxy-5,5'-bis-[2-(4-carbomethoxy-phenyl)-vinyl]-biphenyl
5-[3-Methoxy-4-methoxymethoxy-5-(3-methoxy-4-methoxymethoxy-1-(thiazolidine-2,4-dionyl)-benzylidene-5-yl)-benzylidene]-thiazolidine-2,4-dione
4-[2-(2-Bromo-3-hydroxy-4-methoxy-phenyl)-vinyl]-benzoic acid methyl ester
4-(3,5-Di-tert-butyl-4-hydroxy-benzylidene)-5-methyl-2-phenyl-2,4-dihydro-pyrazol-3-one
3-(3,5-Di-tert-butyl-4-hydroxy-benzylidene)-5-hydroxy-3H-benzofuran-2-one
2-{4-[2-(3,4-Dimethoxy-phenyl)-vinyl]-phenyl}-5-methyl-2,4-dihydro-pyrazol-3-one
4-{4-[2-(3,4-Bis-methoxymethoxy-phenyl)-vinyl]-benzenesulfonyl}-morpholine
4-{2-[4-(Morpholine-4-sulfonyl)-phenyl]-vinyl}-benzene-1,2-diol 4-[2-(3,4-Bis-methoxymethoxy-phenyl)-vinyl]-benzene-sulfonamide
4-{2-[4-(Piperidine-1-sulfonyl)-phenyl]-vinyl}-benzene-1,2-diol
5-[2-(3,4-Bis-methoxymethoxy-phenyl)-vinyl]-[2,2']bipyridinyl, Cu(II)chloride
5-[2-(3,4-Bis-methoxymethoxy-phenyl)-vinyl]-[2,2']bipyridinyl, Mn(II)acetate
1-Bromo-3-methoxy-2-methoxymethoxy-5-[2-(4-nitro-phenyl)-vinyl]-benzene
4-[2-(3,4-Bis-methoxymethoxy-phenyl)-vinyl]-phthalic acid dimethyl ester
4-[2-(3,4-Dihydroxy-phenyl)-vinyl]-phthalic acid dimethyl ester
1,2,3-Tris-methoxymethoxy-4-[2-(4-nitro-phenyl)-vinyl]-benzene
4-[2-(2,3,4-Tris-methoxymethoxy-phenyl)-vinyl]-benzonitrile
4-[2-(2,3,4-Trihydroxy-phenyl)-vinyl]-benzonitrile
4-[2-(3-Chloro-4-methoxymethoxy-phenyl)-vinyl]-benzoic acid methyl ester
4-[2-(3-Chloro-4-hydroxy-phenyl)-vinyl]-benzoic acid methyl ester
4-[2-(3-Chloro-4-hydroxy-phenyl)-vinyl]-benzonitrile
4-[2-(3,4-Bis-{2-[2-(2-hydroxy-ethoxy)-ethoxy]-ethoxy}-phenyl)-vinyl]-benzoic acid methyl ester
2-[2-(2-{2-[2-(2-Hydroxy-ethoxy)-ethoxy]-ethoxy}-5-[2-(4-nitro-phenyl)-vinyl]-phenoxy}-ethoxy)-ethoxy]-ethanol
4-[2-(3,4-Bis-{2-[2-(2-methoxy-ethoxy)-ethoxy]-ethoxy}-phenyl)-vinyl]-benzoic acid 2-[2-(2-methoxy-ethoxy)-ethoxy]-ethyl ester
4-[2-(3,4-Bis-{2-[2-(2-methoxy-ethoxy)-ethoxy]-ethoxy}-phenyl)-vinyl]-benzoic acid tetradecyl ester
4-[2-(3,4-Bis-{2-[2-(2-hydroxy-ethoxy)-ethoxy]-ethoxy}-phenyl)-vinyl]-benzoic acid tetradecyl ester
4-[2-(3,4-Bis-2-[2-(2-hydroxy-ethoxy)-ethoxy-ethoxy}-phenyl)-vinyl]-benzoic acid 2-[2-(2-hydroxy-ethoxy)-ethoxy]-ethyl ester
Phosphoric acid 2-methoxy-4-[2-(4-nitro-phenyl)-vinyl]-phenyl ester dimethyl ester
Phosphoric acid 2-methoxy-4-[2-(4-nitro-phenyl)-vinyl]-phenyl ester dimethyl ester, sodium salt
4-[2-(3,4-Bis-2-[2-(2-methoxy-ethoxy)-ethoxy]-ethoxy)-phenyl)-vinyl]-N-(2-hydroxy-1,1-bis-hydroxymethyl-ethyl)-benzamide
Phosphoric acid mono-{4-[2-(4-cyano-phenyl)-vinyl]-2-methoxy-phenyl}ester
Phosphoric acid mono-{3-[2-(4-nitro-phenyl)-vinyl]-5-phosphonooxy-phenyl}ester
4-(4-Methoxy-benzylidene)-5-methyl-2-phenyl-2,4-dihydro-pyrazol-3-one.

The compounds (including single stereoisomers, mixtures of stereoisomers, and pharmaceutically acceptable salts) most preferred as compositions of matter and/or compounds for use in the methods, and pharmaceutical and cosmetic compositions of the present invention include:

4-[2-(4-Nitro-phenyl)-vinyl]-benzene-1,2-diol
4-[2-(3,4-Dihydroxy-phenyl)-vinyl]-benzoic acid methyl ester
4-[2-(3,4-Dihydroxy-phenyl)-vinyl]-N,N-bis-(2-hydroxy-ethyl)-benzamide
4-[2-(3,4-Bis-methoxymethoxy-phenyl)-vinyl]-N,N-bis-(2-hydroxy-ethyl)-benzamide
{4-[2-(3,4-Dihydroxy-phenyl)-vinyl]-phenyl}-morpholin-4-yl-methanone
4-[2-(2,5-Dimethoxy-3,4-dimethyl-phenyl)-vinyl]-benzoic acid methyl ester
4-{2-[4-(2-Nitro-vinyl)-phenyl]-vinyl}-benzene-1,2-diol
1-Carboxymethyl-4-[2-(3,4-dihydroxy-phenyl)-vinyl]-pyridinium; bromide
1-(2-Carboxy-2-oxo-ethyl)-4-[2-(3,4-dihydroxy-phenyl)-vinyl]-pyridinium; bromide
{4-[2-(3,4-Dihydroxy-phenyl)-vinyl]-phenyl}-phosphonic acid diisopropyl ester
4-[2-(3,4-Dihydroxy-phenyl)-vinyl]-benzoic acid 3,4,5,6-tetrahydroxy-tetrahydro-pyran-2-ylmethyl ester
4-[2-(3,4-Dihydroxy-phenyl)-vinyl]-benzoic acid 3,7-dimethyl-octa-2,6-dienyl ester
4-[2-(3,4-Bis-methoxymethoxy-phenyl)-vinyl]-benzoic acid tetradecyl ester
4-[2-(3,4-Bis-2-[2-(2-methoxy-ethoxy)-ethoxy]-ethoxy-phenyl)-vinyl]-benzoic acid ethyl ester
4-[2-(4-Hydroxy-3-methoxy-phenyl)-vinyl]-benzonitrile
4-[2-(5-Methyl-thiophen-2-yl)-vinyl]-benzoic acid methyl ester
4-[2-(phenyl-1,2-diol)vinyl]-benzoic acid methyl ester, zinc(II) chloride
4-[2-(phenyl-1,2-diol)vinyl]-benzoic acid methyl ester, manganese(II) acetate
4-[2-(phenyl-1,2-diol)vinyl]-benzoic acid methyl ester, Copper(II) chloride
bis-{4-[2-(4-methoxycarbonyl-phenyl)-vinyl]-benzene-1,2-diol}, zinc(II) chloride
4-{2-[3-Methoxy-4-methoxymethoxy-5-(3-methyl-but-2-enyl)-phenyl]-vinyl}-benzoic acid methyl ester
4-{2-[4-Hydroxy-3-methoxy-5-(3-methyl-but-2-enyl)-phenyl]-vinyl}-benzoic acid methyl ester
1-Methoxy-2-methoxymethoxy-3-(3-methyl-but-2-enyl)-5-[2-(4-nitro-phenyl)-vinyl]-benzene
2-Methoxy-6-(3-methyl-but-2-enyl)-4-[2-(4-nitro-phenyl)-vinyl]-phenol
2-[2-(3,4-Bis-methoxymethoxy-phenyl)-vinyl]-thiazole
2-[2-(3,4-Dihydroxy-phenyl)-vinyl]-anthraquinone
2-Methoxy-4-[4-(4-nitro-phenyl)-buta-1,3-dienyl]-phenol
3-[2-(3,4-Dimethoxy-phenyl)-vinyl]4-nitro-phenol
2-Methoxymethoxy-1,3-dimethyl-5-[2-(4-nitro-phenyl)-vinyl]-benzene
4-[2-(4-Hydroxy-3,5-dimethyl-phenyl)-vinyl]-benzoic acid methyl ester
2,6-Dimethyl-4-[2-(4-nitro-phenyl)-vinyl]-phenol 2-Hydroxy-5-[2-(4-nitro-phenyl)-vinyl]-benzoic acid
1,2-Bis-methoxymethoxy-4-[4-(4-nitro-phenyl)-buta-1,3-dienyl]-benzene
4-[2-(6-Nitro-benzo[1,3]dioxol-5-yl)-vinyl]-benzoic acid methyl ester
2-Methoxymethoxy-5-[2-(4-nitro-phenyl)-vinyl]-benzoic acid methoxymethyl ester
4-[4-(4-Nitro-phenyl)-buta-1,3-dienyl]-benzene-1,2-diol
4-[2-(3-Iodo-5-methoxy-4-methoxymethoxy-phenyl)-vinyl]-benzoic acid methyl ester
3,4-Bis-[2-(3,4-dihydroxy-phenyl)-vinyl]-benzoic acid methyl ester
4-[3-(3-Methoxy-4-methoxymethoxy-phenyl)-allyidene]-5-methyl-2-phenyl-2,4-dihydro-pyrazol-3-one
4-{2-[3,4-Bis-methoxymethoxy-2-(3-methyl-but-2-enyl)-phenyl]-vinyl}-benzoic acid methyl ester
4-2-[3,4-Dihydroxy-2-(3-methyl-but-2-enyl)-phenyl]-vinyl-benzoic acid methyl ester
4-2-[3,4-Bis-methoxymethoxy-5-(3-methyl-but-2-enyl)-phenyl]-vinyl-benzoic acid methyl ester 1,2-Bis-methoxymethoxy-3-(3-methyl-but-2-enyl)-5-[2-(4-nitro-phenyl)-vinyl]-benzene
4-{2-[3,4-Dihydroxy-5-(3-methyl-but-2-enyl)-phenyl]-vinyl}-benzoic acid methyl ester
4-{2-[4,5-Dihydroxy-2-(3-methyl-but-2-enyl)-phenyl]-vinyl}-benzoic acid methyl ester
3-(3-Methyl-but-2-enyl)-4-[2-(4-nitro-phenyl)-vinyl]-benzene-1,2-diol
3-(3-Methyl-but-2-enyl)-5-[2-(4-nitro-phenyl)-vinyl]-benzene-1,2-diol
5-{4-[2-(3,4-Bis-methoxymethoxy-phenyl)-vinyl]-phenyl}-2-phenyl-2,4-dihydro-pyrazol-3-one
5-{4-[2-(3,4-Dihydroxy-phenyl)-vinyl]-phenyl}-2-phenyl-2,4-dihydro-pyrazol-3-one
2-Iodo-6-methoxy-4-[2-(4-nitro-phenyl)-vinyl]-phenol
3-{4-[2-(3,4-Dihydroxy-phenyl)-vinyl]-phenyl}-4H-isoxazol-5-one
4-{2-[3,5-Bis-methoxymethoxy-2-(3-methyl-but-2-enyl)-phenyl]-vinyl}-benzoic acid methyl ester
4-{2-[3,5-Dihydroxy-2-(3-methyl-but-2-enyl)-phenyl]-vinyl}-benzoic acid methyl ester
1,5-Bis-methoxymethoxy-2-(3-methyl-but-2-enyl)-3-[2-(4-nitro-phenyl)-vinyl]-benzene
4-(3-Methyl-but-2-enyl)-5-[2-(4-nitro-phenyl)-vinyl]-benzene-1,3-diol
4-(3-Methyl-but-2-enyl)-5-[2-(4-nitro-phenyl)-vinyl]-benzene-1,3-diol
4-[2-(4-Hydroxy-3-iodo-5-methoxy-phenyl)-vinyl]-benzoic acid methyl ester
4-(3,4-Dihydroxy-benzylidene)-5-methyl-2-phenyl-2,4-dihydro-pyrazol-3-one
4-[3-(4-Hydroxy-3-methoxy-phenyl)-allylidene]-5-methyl-2-phenyl-2,4-dihydro-pyrazol-3-one
4-[3-(3-Methoxy-4-methoxymethoxy-phenyl)-allylidene]-5-methyl-2-phenyl-2,4-dihydro-pyrazol-3-one
5-[3-(3-Methoxy-4-methoxymethoxy-phenyl)-allylidene]-thiazolidine-2,4-dione
4-{2-[4-(3,7-Dimethyl-octa-2,6-dienyl)-3,5-bis-methoxymethoxy-phenyl]-vinyl}-benzoic acid methyl ester
4-{2-[4-(3,7-Dimethyl-octa-2,6-dienyl)-3,5-dihydroxy-phenyl]-vinyl}-benzoic acid methyl ester
2-(3,7-Dimethyl-octa-2,6-dienyl)-1,3-bis-methoxymethoxy-5-[2-(4-nitro-phenyl)-vinyl]-benzene
2-(3,7-Dimethyl-octa-2,6-dienyl)-5-[2-(4-nitro-phenyl)-vinyl]-benzene-1,3-diol
4-{2-[4-(3,7-Dimethyl-octa-2,6-dienyl)-3,5-bis-methoxymethoxy-phenyl]-vinyl}-benzonitrile
4-{2-[4-(3,7-Dimethyl-octa-2,6-dienyl)-3,5-dihydroxy-phenyl]-vinyl}-benzonitrile
2,6-Di-tert-butyl-4-[2-(4-nitro-phenyl)-vinyl]-phenol
2-(3,7-Dimethyl-octa-2,6-dienyl)-6-methoxy-4-[2-(4-nitro-phenyl)-vinyl]-phenol
5-(3,5-Di-tert-butyl-4-hydroxy-benzylidene)-thiazolidine-2,4-dione
2-Bromo-6-methoxy-4-[2-(4-nitro-phenyl)-vinyl]-phenol
4-{2-[3,5-Bis-methoxymethoxy-4-(3-methyl-but-2-enyl)-phenyl]-vinyl}-benzoic acid methyl ester
4-{2-[3,5-Dihydroxy-4-(3-methyl-but-2-enyl)-phenyl]-vinyl}-benzoic acid methyl ester
4-{2-[3,5-Bis-methoxymethoxy-4-(3-methyl-but-2-enyl)-phenyl]-vinyl}-benzonitrile
4-{2-[3,5-Dihydroxy-4-(3-methyl-but-2-enyl)-phenyl]-vinyl}-benzonitrile
1,3-Bis-methoxymethoxy-2-(3-methyl-but-2-enyl)-5-[2-(4-nitro-phenyl)-vinyl]-benzene
2-(3-Methyl-but-2-enyl)-5-[2-(4-nitro-phenyl)-vinyl]-benzene-1,3-diol
4-{2-[3-(3,7-Dimethyl-octa-2,6-dienyl)-5-methoxy-4-methoxymethoxy-phenyl]-vinyl}-benzoic acid methyl ester
4-{2-[3-(3,7-Dimethyl-octa-2,6-dienyl)-4-hydroxy-5-methoxy-phenyl]-vinyl}-benzoic acid methyl ester
1-(3,7-Dimethyl-octa-2,6-dienyl)-3-methoxy-2-methoxymethoxy-5-[2-(4-nitro-phenyl)-vinyl]-benzene
4-{2-[3-(3,7-Dimethyl-octa-2,6-dienyl)-5-methoxy-4-methoxymethoxy-phenyl]-vinyl}-benzonitrile
4-{2-[3-(3,7-Dimethyl-octa-2,6-dienyl)-4-hydroxy-5-methoxy-phenyl]-vinyl}-benzonitrile
5-Methyl-2-(4-styryl-phenyl)-2,4-dihydro-pyrazol-3-one
2-{4-[2-(3,4-Dihydroxy-phenyl)-vinyl]-phenyl}-5-methyl-2,4-dihydro-pyrazol-3-one
2-{4-[2-(4-Hydroxy-3-methoxy-phenyl)-vinyl]-phenyl}-5-methyl-2,4-dihydro-pyrazol-3-one
2-bromo-4[4-hydroxy-3-(3-methyl-but-2-enyl-phenyl)-vinyl]-phenol
5-{4-[6-Hydroxy-2,7,8-trimethyl-2-(4,8,12-trimethyl-tridecyl)-chroman-5-ylmethoxy]-benzylidene}-thiazolidine-2,4-dione
4-[2-(3,4-Dihydroxy-phenyl)-vinyl]-benzenesulfonamide
4-{2-[4-amino-sulfonyl)-phenyl]-vinyl}-benzene-1,2-diol
5-[2-(3,4-Bis-methoxymethoxy-phenyl)-vinyl]-[2,2']bipyridinyl
5-[2-(3,4-Bis-methoxymethoxy-phenyl)-vinyl]-[2,2']bipyridinyl, Zn(II)chloride
1,3-Bis-methoxymethoxy-5-{2-[4-methoxymethoxy-3-(3-methyl-but-2-enyl)-phenyl]-vinyl}-2-(3-methyl-but-2-enyl)-benzene
5-{2-[4-Hydroxy-3-(3-methyl-but-2-enyl)-phenyl]-vinyl}-2-(3-methyl-but-2-enyl)-benzene-1,3-diol
5-[3,5-Bis-methoxymethoxy-4-(3-methyl-but-2-enyl)-benzylidene]-thiazolidine-2,4-dione
5-[3,5-Dihydroxy-4-(3-methyl-but-2-enyl)-benzylidene]-thiazolidine-2,4-dione
5-[4-Methoxymethoxy-3-(3-methyl-but-2-enyl)-benzylidene]-thiazolidine-2,4-dione
5-[4-Hydroxy-3-(3-methyl-but-2-enyl)-benzylidene]-thiazolidine-2,4-dione
5-[3-(3,7-Dimethyl-octa-2,6-dienyl)-4-hydroxy-benzylidene]-thiazolidine-2,4-dione
5-[3-(3,7-Dimethyl-octa-2,6-dienyl)-4-methoxymethoxy-benzylidene]-thiazolidine-2,4-dione
5-[2-(3,5-dimethoxy-4-methoxymethoxy-phenyl)-vinyl]-2-(3-methyl-but-2-enyl)-1,3-(bis-methoxymethoxy)-benzene
5-[2-(4-Hydroxy-3,5-dimethoxy-phenyl)-vinyl]-2-(3-methyl-but-2-enyl)-benzene-1,3-diol
5-[2-(3-Methoxy-4-methoxymethoxy-5-nitro-phenyl)-vinyl]-2-(3-methyl-but-2-enyl)-1,3-(bis-methoxymethoxy)-benzene
5-[2-(4-Hydroxy-3-methoxy-5-nitro-phenyl)-vinyl]-2-(3-methyl-but-2-enyl)-benzene-1,3-diol
1,3-Bis-methoxymethoxy-5-[2-(4-methoxymethoxy-3-nitro-phenyl)-vinyl]-2-(3-methyl-but-2-enyl)-benzene
5-[2-(4-Hydroxy-3-nitro-phenyl)-vinyl]-2-(3-methyl-but-2-enyl)-benzene-1,3-diol
2-Chloro-4-[2-(4-nitro-phenyl)-vinyl]-phenol
4-[2-(3-Chloro-4-methoxymethoxy-phenyl)-vinyl]-benzonitrile
4-Bromo-5-methoxy-2-[2-(4-nitro-phenyl)-vinyl]-phenol
4-[2-(5-Bromo-2-hydroxy-4-methoxy-phenyl)-vinyl]-benzoic acid methyl ester (E)-4-[2-(4-Nitro-phenyl)-vinyl]-benzene-1,2,3-triol
(Z)-4-[2-(4-Nitro-phenyl)-vinyl]-benzene-1,2,3-triol
5-{3-[3-Methoxy-4-(3-methyl-but-2-enyloxy)-phenyl]-allylidene}-thiazolidine-2,4-dione.

One preferred sub-group of compounds (including single stereoisomers, mixtures of stereoisomers, and pharmaceutically acceptable salts) employed as compositions of matter and/or compounds for use in its the methods, and pharmaceutical and cosmetic compositions of the present invention is:

4-[2-(3,4-dihydroxy-phenyl)-vinyl]-benzoic acid methyl ester;
2-methoxy-6-(3-methyl-but-2-enyl)-4-[2-(4-nitro-phenyl)-vinyl]-phenol;
2-hydroxy-5-[2-(4-nitro-phenyl)-vinyl]-benzoic acid;
3-(3-methyl-but-2-enyl)-4-[2-(4-nitro-phenyl)-vinyl]-benzene-1,2-diol;
4-(3-methyl-but-2-enyl)-5-[2-(4-nitro-phenyl)-vinyl]-benzene-1,3-diol;
5-[2-(4-nitro-phenyl)-vinyl]-benzene-1,3-diol;
2-(3-methyl-but-2-enyl)-5-[2-(4-nitro-phenyl)-vinyl]-benzene-1,3-diol;
2-bromo-4-[4-hydroxy-3-(3-methyl-but-2-enyl-phenyl)-vinyl]-phenol;
2-methoxy-4-[4-(4-nitro-phenyl)-buta-1,3-dienyl]-phenol;
2-methoxymethoxy-5-[2-(4-nitro-phenyl)-vinyl]-benzoic acid methoxymethyl ester;
3-(3-methyl-but-2-enyl)-5-[2-(4-nitro-phenyl)-vinyl]-benzene-1,2-diol;
2-(3,7-dimethyl-octa-2,6-dienyl)-5-[2-(4-nitro-phenyl)-vinyl]-benzene-1,3-diol;
5-{4-[2-(3,4-dihydroxy-phenyl)-vinyl]-phenyl}-2-phenyl-2,4-dihydro-pyrazol-3-one;
4-{2-[3,4-dihydroxy-5-(3-methyl-but-2-enyl)-phenyl]-vinyl}-benzoic acid methyl ester;
4-{2-[3,5-dihydroxy-4-(3-methyl-but-2-enyl)phenyl]-vinyl}-benzonitrile;
4-(3-methyl-but-2-enyl)-5-[2-(4-nitro-phenyl)-vinyl]-benzene-1,3-diol;
4-{2-[4-(5-hydroxy-1H-pyrazol-3-yl)phenyl]-vinyl}-benzene-1,2-diol;
4-{2-[4-(2-nitro-vinyl)-phenyl]-vinyl}-benzene-1,2-diol;
3-[2-(3,4-dimethoxy-phenyl)-vinyl]4-nitro-phenol;
4-[4-(4-nitro-phenyl)-buta-1,3-dienyl]-benzene-1,2-diol;
2-iodo-6-methoxy-4-[2-(4-nitro-phenyl)-vinyl]-phenol;
4-{2-[4-(3,7-dimethyl-octa-2,6-dienyl)-3,5-dihydroxy-phenyl]-vinyl}-benzonitrile;
2-(3,7-dimethyl-octa-2,6-dienyl)-6-methoxy-4-[2-(4-nitro-phenyl)-vinyl]-phenol;
2-bromo-6-methoxy-4-[2-(4-nitro-phenyl)-vinyl]-phenol;
4-{2-[3-(3,7-dimethyl-octa-2,6-dienyl)-4-hydroxy-5-methoxy-phenyl]-vinyl}-benzonitrile; and
2,6-dimethyl-4-[2-(4-nitro-phenyl)-vinyl]-phenol.

Another preferred sub-group of compounds (including single stereoisomers, mixtures of stereoisomers, and pharmaceutically acceptable salts) employed as compositions of matter and/or compounds for use in its the methods, and pharmaceutical and cosmetic compositions of the present invention is:

2-methoxy-6-(3-methyl-but-2-enyl)-4-[2-(4-nitro-phenyl)-vinyl]-phenol;
3-(3-methyl-but-2-enyl)-4-[2-(4-nitro-phenyl)-vinyl]-benzene-1,2-diol;
4-(3-methyl-but-2-enyl)-5-[2-(4-nitro-phenyl)-vinyl]-benzene-1,3-diol;
2-(3-methyl-but-2-enyl)-5-[2-(4-nitro-phenyl)-vinyl]-benzene-1,3-diol;
2-bromo-4-[4-hydroxy-3-(3-methyl-but-2-enyl-phenyl)-vinyl]-phenol;
2-methoxy-4-[4-(4-nitro-phenyl)-buta-1,3-dienyl]-phenol;
2-methoxymethoxy-5-[2-(4-nitro-phenyl)-vinyl]-benzoic acid methoxymethyl ester;
3-(3-methyl-but-2-enyl)-5-[2-(4-nitro-phenyl)-vinyl]-benzene-1,2-diol;
2-(3,7-dimethyl-octa-2,6-dienyl)-5-[2-(4-nitro-phenyl)-vinyl]-benzene-1,3-diol;
5-{4-[2-(3,4-dihydroxy-phenyl)-vinyl]-phenyl}-2-phenyl-2,4-dihydro-pyrazol-3-one;
4-{2-[3,4-dihydroxy-5-(3-methyl-but-2-enyl)-phenyl]-vinyl}-benzoic acid methyl ester;
4-{2-[3,5-dihydroxy-4-(3-methyl-but-2-enyl)phenyl]-vinyl}-benzonitrile;
4-(3-methyl-but-2-enyl)-5-[2-(4-nitro-phenyl)-vinyl]-benzene-1,3-diol;
4-{2-[4-(5-hydroxy-1H-pyrazol-3-yl)phenyl]-vinyl}-benzene-1,2-diol;
4-{2-[4-(2-nitro-vinyl)-phenyl]-vinyl}-benzene-1,2-diol;
4-{2-[4-(3,7-dimethyl-octa-2,6-dienyl)-3,5-dihydroxy-phenyl]-vinyl)-benzonitrile;
2-(3,7-dimethyl-octa-2,6-dienyl)-6-methoxy-4-[2-(4-nitro-phenyl)-vinyl]-phenol; and
4-{2-[3-(3,7-dimethyl-octa-2,6-dienyl)-4-hydroxy-5-methoxy-phenyl]-vinyl}-benzonitrile.

Still another preferred sub-group of compounds (including single stereoisomers, mixtures of stereoisomers, and pharmaceutically acceptable salts) employed as compositions of matter and/or compounds for use in its the methods, and pharmaceutical and cosmetic compositions of the present invention is:

3-(3-methyl-but-2-enyl)-4-[2-(4-nitro-phenyl)-vinyl]-benzene-1,2-diol;
4-[2-(4-nitro-phenyl)-vinyl]-benzene-1,2,3-triol;
2-{4-[2-(4-hydroxy-3-methoxy-phenyl)-vinyl]-phenyl}-5-methyl-2,4-dihydro-pyrazol-3-one;
5-[3-(3,7-dimethyl-octa-2,6-dienyl)-4-hydroxy-benzylidene]-thiazolidine-2,4-dione;
2-(3-methyl-but-2-enyl)-5-[2-(4-nitro-phenyl)-vinyl]-benzene-1,3-diol;
2-bromo-4-[4-hydroxy-3-(3-methyl-but-2-enyl-phenyl)-vinyl]-phenol;
2-bromo-4-[4-hydroxy-3-(3-methyl-but-2-enyl-phenyl)-vinyl]-phenol;
4-[2-(3,4-bis-{2-[2-(2-methoxy-ethoxy)-ethoxy]-ethoxy}-phenyl)-vinyl]-benzoic acid ethyl ester;
2-methoxy-6-(3-methyl-but-2-enyl)-4-[2-(4-nitro-phenyl)-vinyl]-phenol;
4-[3-(3-methoxy-4-methoxymethoxy-phenyl)-allylidene]-5-methyl-2-phenyl-2,4-dihydro-pyrazol-3-one;
4-[2-(3,4-dihydroxy-phenyl)-vinyl]-N,N-bis-(2-hydroxy-ethyl)-benzamide;
4-[2-(3,4-bis-methoxymethoxy-phenyl)-vinyl]-N,N-bis-(2-hydroxy-ethyl)-benzamide;
{4-[2-(3,4-dihydroxy-phenyl)-vinyl]-phenyl}-morpholin-4-yl-methanone;
4-[2-(2,5-dimethoxy-3,4-dimethyl-phenyl)-vinyl]-benzoic acid methyl ester;
3,4-bis-[2-(3,4-dihydroxy-phenyl)-vinyl]-benzoic acid methyl ester;
4-[2-(3,4-dihydroxy-phenyl)-vinyl]-benzenesulfonamide;
4-[2-(3,4-dihydroxy-phenyl)-vinyl]-benzoic acid 3,7-dimethyl-octa-2,6-dienyl ester;
4-[2-(4-hydroxy-3,5-dimethyl-phenyl)-vinyl]-benzoic acid methyl ester;

4-[2-(4-hydroxy-3-iodo-5-methoxy-phenyl)-vinyl]-benzoic acid methyl ester;
4-bromo-5-methoxy-2-[2-(4-nitro-phenyl)-vinyl]-phenol;
4-[2-(5-bromo-2-hydroxy-4-methoxy-phenyl)-vinyl]-benzoic acid methyl ester; and
{4-[2-(3,4-dihydroxy-phenyl)-vinyl]-phenyl}-phosphonic acid diisopropyl ester.

Another preferred sub-group of compounds (including single stereoisomers, mixtures of stereoisomers, and pharmaceutically acceptable salts) employed as compositions of matter and/or compounds for use in its the methods, and pharmaceutical and cosmetic compositions of the present invention is:

5{2-[4-hydroxy-3-(3-methyl-but-2-enyl)-phenyl]-vinyl}-2-(3-methyl-but-2-enyl)-benzene-1,3-diol;
4-(3,4-dihydroxy-benzylidene)-5-methyl-2-phenyl-2,4-dihydro-pyrazol-3-one;
4-(3,5-di-tert-butyl-4-hydroxy-benzylidene)-5-methyl-2-phenyl-2,4-dihydro-pyrazol-3-one;
3-(3,5-di-tert-butyl-4-hydroxy-benzylidene)-5-hydroxy-3H-benzofuran-2-one;
5-{4-[6-hydroxy-2,7,8-trim ethyl-2-(4,8,12-trimethyl-tridecyl)-chroman-5-ylmethoxy]-benzylidene}-thiazolidine-2,4-dione;
4-[2-(3,4-dihydroxy-phenyl)-vinyl]-N,N-bis-(2-hydroxy-ethyl)-benzamide;
4-[2-(3,4-bis-methoxymethoxy-phenyl)-vinyl]-N,N-bis-(2-hydroxy-ethyl)-benzamide;
{4-[2-(3,4-dihydroxy-phenyl)-vinyl]-phenyl}-morpholin-4-yl-methanone;
4-[2-(2,5-dimethoxy-3,4-dimethyl-phenyl)-vinyl]-benzoic acid methyl ester;
3,4-bis-[2-(3,4-dihydroxy-phenyl)-vinyl]-benzoic acid methyl ester;
4-[2-(3,4-dihydroxy-phenyl)-vinyl]-benzenesulfonamide;
4-[2-(3,4-dihydroxy-phenyl)-vinyl]-benzoic acid 3,7-dimethyl-octa-2,6-dienyl ester;
4-[2-(4-hydroxy-3,5-dimethyl-phenyl)-vinyl]-benzoic acid methyl ester;
4-[2-(4-hydroxy-3-iodo-5-methoxy-phenyl)-vinyl]-benzoic acid methyl ester;
4-bromo-5-methoxy-2-[2-(4-nitro-phenyl)-vinyl]-phenol;
4-[2-(5-bromo-2-hydroxy-4-methoxy-phenyl)-vinyl]-benzoic acid methyl ester; and
{4-[2-(3,4-dihydroxy-phenyl)-vinyl]-phenyl}-phosphonic acid diisopropyl ester.

Utility, Testing and Administration

General Utility

Compounds, compositions/formulations and methods of the present invention are useful in treating a number of disorders, particularly those characterized by oxidative stress, e.g., in the treatment of cerebral ischemia ("stroke"), neurodegenerative disorders, myocardial ischemia (myocardial infarction and other forms of heart disease), diabetes, renal disease, pre-menstrual syndrome, asthma, cardiopulmonary inflammatory disorders, chronic heart failure, rheumatoid arthritis, muscle fatigue, irritable bowel syndrome, inflammatory bowel disease, intermittent claudication and for the preservation of allograft tissue for transplantation.

The compounds, formulations and methods of the present invention are useful in treating a number of dermatological conditions, including, but not limited to prevention and protecting skin tissue against age-related damage or damage resulting from insults such as harmful ultraviolet (UV) radiation, stress and fatigue. Such compounds, formulations and methods are likewise useful, e.g., in treating contact dermatitis, acne and psoriasis (including scalp psoriasis), and are amenable to topical application for hair care and treatments of the scalp, for example by incorporation in medicated shampoos, anhydrous hair conditioners and the like.

Compounds Preferred for Certain Groups of Indications

Certain of the conditions characterized by oxidative stress fall within the cardiovascular group, including: myocardial ischemia, myocardial infarction, cardiopulmonary inflammatory disorders; and heart failure (including chronic and congestive heart failure). Preferred for the treatment of such disorders are the compounds of Formula I where R' is hydrogen and R is phenyl substituted in the para position with alkoxycarbonyl or a nitrogen-bearing moiety, such as nitro or cyano, or where R is a nitrogen-containing heteroaryl, particularly a thiazole. Also preferred are the compounds of Formula I where one or more of $R^1$ to $R^5$ is hydroxy, alkoxy (especially methoxy and methoxymethoxy), alkenyl (especially prenyl and geranyl) or halo (especially bromo), especially where R and R' are as defined above. Also preferred are the compounds of Formula II where R" is 2-thioxo-thiazolidin-4-one thiazolidine-2,4-dione (preferably thiazolidine-2,4-dione) and one or more of $R^6$ to $R^{10}$ is hydroxy or alkoxy (especially methoxymethoxy). Particularly preferred for the treatment of such disorders are the following compounds:

5-[2-(4-nitro-phenyl)-vinyl]-benzene-1,3-diol;
4-[2-(4-hydroxy-3,5-dimethyl-phenyl)-vinyl]-benzoic acid methyl ester;
4-[2-(4-hydroxy-3-methoxy-phenyl)-vinyl]-benzonitrile;
4-[2-(3,4-dihydroxy-phenyl)-vinyl]-benzoic acid;
5-(3,4-dihydroxy-benzylidene)-thiazolidine-2,4-dione;
4-(2-nitro-vinyl)-benzene-1,2-diol;
4-[2-(3,4-bis-methoxymethoxy-phenyl)-vinyl]-N,N-bis-(2-hydroxy-ethyl)-benzamide;
4-[2-(3,4-bis-methoxymethoxy-phenyl)-vinyl]-phthalic acid dimethyl ester;
methoxy-2-methoxymethoxy-3-(3-methyl-but-2-enyl)-5-[2-(4-nitro-phenyl)-vinyl]-benzene;
1,3-bis-methoxymethoxy-2-(3-methyl-but-2-enyl)-5-[2-(4-nitro-phenyl)-vinyl]-benzene;
1,3-bis-methoxymethoxy-5-[2-(4-nitro-phenyl)-vinyl]-benzene;
bromo-3-methoxy-2-methoxymethoxy-5-[2-(4-nitro-phenyl)-vinyl]-benzene;
4-{2-[3-(3,7-dimethyl-octa-2,6-dienyl)-4-hydroxy-5-methoxy-phenyl]-vinyl}-benzonitrile;
2-[2-(3,4-bis-methoxymethoxy-phenyl)-vinyl]-thiazole;
5-(3,4-bis-methoxymethoxy-benzylidene)-thiazolidine-2,4-dione; and
4-{2-[3-(3,7-dimethyl-octa-2,6-dienyl)-4-hydroxy-5-methoxy-phenyl]-vinyl}-benzoic acid methyl ester, including single stereoisomers, mixtures of stereoisomers, and the pharmaceutically acceptable salts thereof.

Of the foregoing group, especially preferred for the treatment of cardiovascular conditions are the following compounds:

5-[2-(4-nitro-phenyl)-vinyl]-benzene-1,3-diol;
4-[2-(4-hydroxy-3-methoxy-phenyl)-vinyl]-benzonitrile;
4-[2-(3,4-dihydroxy-phenyl)-vinyl]-benzoic acid;
5-(3,4-dihydroxy-benzylidene)-thiazolidine-2,4-dione;
4-[2-(3,4-bis-methoxymethoxy-phenyl)-vinyl]-N,N-bis-(2-hydroxy-ethyl)-benzamide;
4-[2-(3,4-bis-methoxymethoxy-phenyl)-vinyl]-phthalic acid dimethyl ester;

1-methoxy-2-methoxymethoxy-3-(3-methyl-but-2-enyl)-5-[2-(4-nitro-phenyl)-vinyl]-benzene;
1,3-bis-methoxymethoxy-2-(3-methyl-but-2-enyl)-5-[2-(4-nitro-phenyl)-vinyl]-benzene;
1,3-bis-methoxymethoxy-5-[2-(4-nitro-phenyl)-vinyl]-benzene;
1-bromo-3-methoxy-2-methoxymethoxy-5-[2-(4-nitro-phenyl)-vinyl]-benzene;
4-{2-[3-(3,7-dimethyl-octa-2,6-dienyl)-4-hydroxy-5-methoxy-phenyl]-vinyl}-benzonitrile;
2-[2-(3,4-bis-methoxymethoxy-phenyl)-vinyl]-thiazole;
5-(3,4-bis-methoxymethoxy-benzylidene)-thiazolidine-2,4-dione; and
4-{2-[3-(3,7-dimethyl-octa-2,6-dienyl)-4-hydroxy-5-methoxy-phenyl]-vinyl}-benzoic acid methyl ester, including single stereoisomers, mixtures of stereoisomers, and the pharmaceutically acceptable salts thereof.

Of the foregoing group, most preferred for the treatment of cardiovascular conditions are the following compounds:
5-[2-(4-nitro-phenyl)-vinyl]-benzene-1,3-diol;
4-[2-(4-hydroxy-3-methoxy-phenyl)-vinyl]-benzonitrile;
4-[2-(3,4-dihydroxy-phenyl)-vinyl]-benzoic acid;
5-(3,4-dihydroxy-benzylidene)-thiazolidine-2,4-dione;
1-methoxy-2-methoxymethoxy-3-(3-methyl-but-2-enyl)-5-[2-(4-nitro-phenyl)-vinyl]-benzene;
1,3-bis-methoxymethoxy-5-[2-(4-nitro-phenyl)-vinyl]-benzene;
4-{2-[3-(3,7-dimethyl-octa-2,6-dienyl)-4-hydroxy-5-methoxy-phenyl]-vinyl}-benzonitrile;
2-[2-(3,4-bis-methoxymethoxy-phenyl)-vinyl]-thiazole; and
4-{2-[3-(3,7-dimethyl-octa-2,6-dienyl)-4-hydroxy-5-methoxy-phenyl]-vinyl}-benzoic acid methyl ester, including single stereoisomers, mixtures of stereoisomers, and the pharmaceutically acceptable salts thereof.

Another group of conditions characterized by oxidative stress fall within the cerebrovascular and neurologic group, including: stroke, cerebral ischemia, retinal ischemia, postsurgical cognitive dysfunctions (e.g., following bypass surgery), peripheral neuropathy spinal chord injury, head injury and surgical trauma, and neurodegenerative disorders including Alzheimer's, dementia and Parkinson's disease. Preferred for the treatment of such disorders are the compounds of Formula I where R' is hydrogen and R is phenyl substituted with an alkoxy, alkoxycarbonyl, hydroxy, or a nitrogen-bearing moiety, such as nitro or nitrogen-bearing heterocyclyl (e.g., 2,4-dihydro-pyrazol-3-one); particularly preferred are the compounds where R is phenyl substituted in the para position with nitro or an alkyl ester (especially methyl-, ethyl-, or tetradecyl-ester). Also preferred are the compounds of Formula I where R is a nitrogen-containing heteroaryl (particularly a optionally substituted pyridinium bromide) or vinyl-nitrogen-containing heterocyclyl (particularly vinyl-5-methyl-2-phenyl-2,4-dihydro-pyrazol-3-one). Similarly preferred are the compounds of Formula I where R is tri-substituted phenyl having a nitro and a methoxy substituent at the two meta positions and methoxymethoxy or hydroxy at the para position. Also preferred are the compounds of Formula I where one or more of $R^1$ to $R^5$ is other than hydrogen, selected from hydroxy, alkoxy (especially methoxy and methoxymethoxy), alkenyl (especially prenyl and geranyl) or halo (especially bromo), especially where R and R' are as defined above; particularly where $R^1$ and $R^5$ are hydrogen and two or three of $R^2$, $R^3$ and $R^4$ are selected from hydroxy, methoxymethoxy, and prenyl or geranyl. Also preferred are the compounds of Formula II where R" is 2-thioxo-thiazolidin-4-one or thiazolidine-2,4-dione (preferably thiazolidine-2,4-dione) and one or more of $R^6$ to $R^{10}$ are not hydrogen, selected from hydroxy, alkoxy (especially methoxymethoxy) and alkenyl (especially prenyl and geranyl). Particularly preferred for the treatment of such disorders are the following compounds:
2,6-di-tert-butyl-4-[2-(4-nitro-phenyl)-vinyl]-phenol;
4-{2-[4-(2-nitro-vinyl)-phenyl]-vinyl}-benzene-1,2-diol;
4-[2-(3,4-dihydroxy-phenyl)-vinyl]-benzenesulfonamide-
4-{2-[4-amino-sulfonyl)-phenyl]-vinyl}-benzene-1,2-diol;
3,4-bis-[2-(3,4-dihydroxy-phenyl)-vinyl]-benzoic acid methyl ester;
4-[2-(5-bromo-2-hydroxy-4-methoxy-phenyl)-vinyl]-benzoic acid methyl ester;
4-[2-(2,3,4-trihydroxy-phenyl)-vinyl]-benzonitrile;
2-{4-[2-(4-hydroxy-3-methoxy-phenyl)-vinyl]-phenyl}-5-methyl-2,4-dihydro-pyrazol-3-one;
1-carboxymethyl-4-[2-(3,4-dihydroxy-phenyl)-vinyl]-pyridinium; bromide;
1,3-bis-methoxymethoxy-2-(3-methyl-but-2-enyl)-5-[2-(4-nitro-phenyl)-vinyl]-benzene;
4-[2-(3,4-bis-methoxymethoxy-phenyl)-vinyl]-benzoic acid tetradecyl ester;
4-[2-(3,4-bis-{2-[2-(2-methoxy-ethoxy)-ethoxy]-ethoxy}-phenyl)-vinyl-benzoic acid ethyl ester;
4-{2-[4-(3,7-dimethyl-octa-2,6-dienyl)-3,5-bis-methoxymethoxy-phenyl]-vinyl}-benzoic acid methyl ester;
2-methoxymethoxy-1,3-dimethyl-5-[2-(4-nitro-phenyl)-vinyl]-benzene;
1,2-bis-methoxymethoxy-4-[4-(4-nitro-phenyl)-buta-1,3-dienyl]-benzene;
2-methoxymethoxy-5-[2-(4-nitro-phenyl)-vinyl]-benzoic acid methoxymethyl ester;
1,5-bis-methoxymethoxy-2-(3-methyl-but-2-enyl)-3-[2-(4-nitro-phenyl)-vinyl]-benzene;
1,3-bis-methoxymethoxy-2-(3-methyl-but-2-enyl)-5-[2-(3-nitro-4-methoxymethoxy-5-methoxy-phenyl)-vinyl]-benzene;
1-iodo-3-methoxy-2-methoxymethoxy-5-[2-(4-nitro-phenyl)-vinyl]-benzene;
1-bromo-3-methoxy-2-methoxymethoxy-5-[2-(4-nitro-phenyl)-vinyl]-benzene;
4-[3-(3-methoxy-4-methoxymethoxy-phenyl)-allylidene]-5-methyl-2-phenyl-2,4-dihydro-pyrazol-3-one;
5-[3,5-dihydroxy-4-(3-methyl-but-2-enyl)-benzylidene]-thiazolidine-2,4-dione;
5-[4-methoxymethoxy-3-(3-methyl-but-2-enyl)-benzylidene]-thiazolidine-2,4-dione;
5-[4-hydroxy-3-(3-methyl-but-2-enyl)-benzylidene]-thiazolidine-2,4-dione;
5-[3-(3,7-dimethyl-octa-2,6-dienyl)-4-hydroxy-benzylidene]-thiazolidine-2,4-dione;
5-[3-(3,7-dimethyl-octa-2,6-dienyl)-4-methoxymethoxy-benzylidene]-thiazolidine-2,4-dione;
4-{2-[3,4-dihydroxy-5-(3-methyl-but-2-enyl)-phenyl]-vinyl}-benzoic acid methyl ester;
4-{2-[4,5-dihydroxy-2-(3-methyl-but-2-enyl)-phenyl]-vinyl}-benzoic acid methyl ester;
2-methoxy-6-(3-methyl-but-2-enyl)-4-[2-(4-nitro-phenyl)-vinyl]-phenol;
5-[2-(4-hydroxy-3-methoxy-5-nitro-phenyl)-vinyl]-2-(3-methyl-but-2-enyl)-benzene-1,3-diol; and
4-{2-[4-(3,7-dimethyl-octa-2,6-dienyl)-3,5-bis-methoxymethoxy-phenyl]-vinyl}-benzonitrile including single stereoisomers, mixtures of stereoisomers, and the pharmaceutically acceptable salts thereof.

Of the foregoing group, especially preferred for the treatment of cerebrovascular/neurologic conditions are the following compounds:

4-{2-[4-(2-nitro-vinyl)-phenyl]-vinyl}-benzene-1,2-diol;
3,4-bis-[2-(3,4-dihydroxy-phenyl)-vinyl]-benzoic acid methyl ester;
2-{4-[2-(4-hydroxy-3-methoxy-phenyl)-vinyl]-phenyl}-5-methyl-2,4-dihydro-pyrazol-3-one;
1-carboxymethyl-4-[2-(3,4-dihydroxy-phenyl)-vinyl]-pyridinium; bromide;
1,3-bis-methoxymethoxy-2-(3-methyl-but-2-enyl)-5-[2-(4-nitro-phenyl)-vinyl]-benzene;
4-[2-(3,4-bis-methoxymethoxy-phenyl]-vinyl]-benzoic acid tetradecyl ester;
4-[2-(3,4-bis-{2-[2-(2-methoxy-ethoxy)-ethoxy]-ethoxy)-phenyl]-vinyl}-benzoic acid ethyl ester;
2-methoxymethoxy-1,3-dimethyl-5-[2-(4-nitro-phenyl)-vinyl]-benzene;
5-[3-(3,7-dimethyl-octa-2,6-dienyl)-4-hydroxy-benzylidene]-thiazolidine-2,4-dione;
2-methoxymethoxy-5-[2-(4-nitro-phenyl)-vinyl]-benzoic acid methoxymethyl ester;
1,5-bis-methoxymethoxy-2-(3-methyl-but-2-enyl)-3-[2-(4-nitro-phenyl)-vinyl]-benzene;
1,3-bis-methoxymethoxy-2-(3-methyl-but-2-enyl)-5-[2-(3-nitro-4-methoxymethoxy-5-methoxy-phenyl)-vinyl]-benzene;
1-iodo-3-methoxy-2-methoxymethoxy-5-[2-(4-nitro-phenyl)-vinyl]-benzene;
1-bromo-3-methoxy-2-methoxymethoxy-5-[2-(4-nitro-phenyl)-vinyl]-benzene;
4-[3-(3-methoxy-4-methoxymethoxy-phenyl)-allylidene]-5-methyl-2-phenyl-2,4-dihydro-pyrazol-3-one;
4-{2-[3,4-dihydroxy-5-(3-methyl-but-2-enyl)-phenyl]-vinyl}-benzoic acid methyl ester;
4-{2-[4,5-dihydroxy-2-(3-methyl-but-2-enyl)-phenyl]-vinyl}-benzoic acid methyl ester;
2-methoxy-6-(3-methyl-but-2-enyl)-4-[2-(4-nitro-phenyl)-vinyl]-phenol; and
5-[2-(4-hydroxy-3-methoxy-5-nitro-phenyl)-vinyl]-2-(3-methyl-but-2-enyl)-benzene-1,3-diol, including single stereoisomers, mixtures of stereoisomers, and the pharmaceutically acceptable salts thereof.

Of the foregoing group, most preferred for the treatment of cerebrovascular/neurologic conditions are the following compounds:

4-{2-[4-(2-nitro-vinyl)-phenyl]-vinyl}-benzene-1,2-diol;
3,4-bis-[2-(3,4-dihydroxy-phenyl)-vinyl]-benzoic acid methyl ester;
2-{4-[2-(4-hydroxy-3-methoxy-phenyl)-vinyl]-phenyl}-5-methyl-2,4-dihydro-pyrazol-3-one;
1,3-bis-methoxymethoxy-2-(3-methyl-but-2-enyl)-5-[2-(4-nitro-phenyl)-vinyl]-benzene;
4-[2-(3,4-bis-methoxymethoxy-phenyl)-vinyl]-benzoic acid tetradecyl ester;
4-[2-(3,4-bis-{2-[2-(2-methoxy-ethoxy)-ethoxy]-ethoxy}phenyl)-vinyl]-benzoic acid ethyl ester;
5-[3-(3,7-dimethyl-octa-2,6-dienyl)-4-hydroxy-benzylidene]-thiazolidine-2,4-dione;
1,3-bis-methoxymethoxy-2-(3-methyl-but-2-enyl)-5-[2-(3-nitro-4-methoxymethoxy-5-methoxy-phenyl)-vinyl]-benzene;
1-bromo-3-methoxy-2-methoxymethoxy-5-[2-(4-nitro-phenyl)-vinyl]-benzene;
4-[3-(3-methoxy-4-methoxymethoxy-phenyl)-allylidene]-5-methyl-2-phenyl-2,4-dihydro-pyrazol-3-one;
4-{2-[3,4-dihydroxy-5-(3-methyl-but-2-enyl)-phenyl]-vinyl}-benzoic acid methyl ester;
4-{2-[4,5-dihydroxy-2-(3-methyl-but-2-enyl)-phenyl]-vinyl}-benzoic acid methyl ester;
2-methoxy-6-(3-methyl-but-2-enyl)-4-[2-(4-nitro-phenyl)-vinyl]-phenol; and
5-[2-(4-hydroxy-3-methoxy-5-nitro-phenyl)-vinyl]-2-(3-methyl-but-2-enyl)-benzene-1,3-diol, including single stereoisomers, mixtures of stereoisomers, and the pharmaceutically acceptable salts thereof.

Another group of diseases characterized by oxidative stress and involving inflammatory and/or autoimmune components includes: diabetes; renal disease; pre-menstrual syndrome; asthma; rheumatoid arthritis; osteoarthritis, muscle fatigue; irritable bowel syndrome, inflammatory bowel disease and intermittent claudication. Preferred for the treatment of such disorders are the compounds of Formula I where R' is hydrogen and R is phenyl substituted in the para position with alkoxycarbonyl or a nitrogen-bearing moiety, such as nitro or cyano, or where R is vinyl-nitrogen-containing heteroaryl, particularly vinyl-thiazolidine-2,4-dione or vinyl-nitrogen-containing heterocyclyl, particularly vinyl-5-methyl-2-phenyl-2,4-dihydro-pyrazol-3-one. Also preferred are the compounds of Formula I where one or more of $R^1$ to $R^5$ is hydroxy, alkoxy (especially methoxy and methoxymethoxy), alkoxycarbonyl (especially methoxymethoxycarbonyl) or alkenyl (especially prenyl and geranyl), especially where R and R' are as defined above. Particularly preferred for the treatment of such disorders are the following compounds:

4-[2-(4-nitro-phenyl)-vinyl]-benzene-1,2-diol;
4-[2-(3,4-dihydroxy-phenyl)-vinyl]-benzoic acid methyl ester;
4-[2-(4-nitro-phenyl)-vinyl]-benzene-1,2,3-triol;
5-methyl-2-(4-styryl-phenyl)-2,4-dihydro-pyrazol-3-one;
2-{4-[2-(3,4-dihydroxy-phenyl)-vinyl]-phenyl}-5-methyl-2,4-dihydro-pyrazol-3-one;
4-(3,5-di-tert-butyl-4-hydroxy-benzylidene)-5-methyl-2-phenyl-2,4-dihydro-pyrazol-3-one;
4-[3-(4-hydroxy-3-methoxy-phenyl)-allylidene]-5-methyl-2-phenyl-2,4-dihydro-pyrazol-3-one;
4-{2-[3-methoxy-4-methoxymethoxy-5-(3-methyl-but-2-enyl)-phenyl]-vinyl}-benzoic acid methyl ester;
4-[2-(3-iodo-5-methoxy-4-methoxymethoxy-phenyl)-vinyl]-benzoic acid methyl ester;
2-methoxymethoxy-5-[2-(4-nitro-phenyl)-vinyl]-benzoic acid methoxymethyl ester;
4-[2-(4-methoxymethoxy-3,5-dimethyl-phenyl)-vinyl]-benzoic acid methyl ester;
2-methoxymethoxy-5-[2-(4-nitro-phenyl)-vinyl]-benzoic acid methoxymethyl ester;
N-{4-[2-(3,4-bis-methoxymethoxy-phenyl)vinyl]-phenyl}-benzamide;
4-[3-(3-methoxy-4-methoxymethoxy-phenyl)-allylidene]-5-methyl-2-phenyl-2,4-dihydro-pyrazol-3-one;
5-[3-(3-methoxy-4-methoxymethoxy-phenyl)-allylidene]-thiazolidine-2,4-dione;
3-(3,5-di-tert-butyl-4-hydroxy-benzylidene)-5-hydroxy-3H-benzofuran-2-one;
5-[3,5-bis-methoxymethoxy-4-(3-methyl-but-2-enyl)-benzylidene]-thiazolidine-2,4-dione;

5-[4-methoxymethoxy-3-(3-methyl-but-2-enyl)-benzylidene]-thiazolidine-2,4-dione;
5-[3-(3,7-dimethyl-octa-2,6-dienyl)-4-hydroxy-benzylidene]-thiazolidine-2,4-dione;
5-[3-methoxy-4-methoxymethoxy-5-(3-methoxy-4-methoxymethoxy-1-(thiazolidine-2,4-dionyl)-benzylidene-5-yl)-benzylidene]-thiazolidine-2,4-dione;
4-{2-[3-methoxy-4-methoxymethoxy-5-(3-methyl-but-2-enyl)-phenyl]-vinyl}-benzoic acid methyl ester;
4-{2-[3,4-dihydroxy-2-(3-methyl-but-2-enyl)-phenyl]-vinyl}-benzoic acid methyl ester;
4-{2-[3,4-dihydroxy-5-(3-methyl-but-2-enyl)-phenyl]-vinyl}-benzoic acid methyl ester;
4-{2-[3,5-dihydroxy-2-(3-methyl-but-2-enyl)-phenyl]-vinyl}-benzoic acid methyl ester;
4-{2-[3,5-bis-methoxymethoxy-4-(3-methyl-but-2-enyl)-phenyl]-vinyl}-benzoic acid methyl ester;
4-{2-[3,5-dihydroxy-4-(3-methyl-but-2-enyl)-phenyl]-vinyl}-benzoic acid methyl ester;
3-(3-methyl-but-2-enyl)-4-[2-(4-nitro-phenyl)-vinyl]-benzene-1,2-diol;
3-(3-methyl-but-2-enyl)-5-[2-(4-nitro-phenyl)-vinyl]-benzene-1,2-diol;
4-(3-methyl-but-2-enyl)-5-[2-(4-nitro-phenyl)-vinyl]-benzene-1,3-diol;
4-(3-methyl-but-2-enyl)-5-[2-(4-nitro-phenyl)-vinyl]-benzene-1,3-diol;
2-(3,7-dimethyl-octa-2,6-dienyl)-5-[2-(4-nitro-phenyl)-vinyl]-benzene-1,3-diol;
2-(3-methyl-but-2-enyl)-5-[2-(4-nitro-phenyl)-vinyl]-benzene-1,3-diol;
4-{2-[4-(3,7-dimethyl-octa-2,6-dienyl)-3,5-dihydroxy-phenyl]-vinyl}-benzonitrile;
4-{2-[3,5-dihydroxy-4-(3-methyl-but-2-enyl)-phenyl]-vinyl}-benzonitrile;
2-bromo-4-[4-hydroxy-3-(3-methyl-but-2-enyl-phenyl)-vinyl]-phenol;
5-2-[4-hydroxy-3-(3-methyl-but-2-enyl)-phenyl]-vinyl-2-(3-methyl-but-2-enyl)-benzene-1,3-diol; and
5-{3-[3-methoxy-4-(3-methyl-but-2-enyloxy)-phenyl]-allylidene}-thiazolidine-2,4-dione, including single stereoisomers, mixtures of stereoisomers, and the pharmaceutically acceptable salts thereof.

Of the foregoing group, especially preferred for the treatment of inflammatory/autoimmune conditions are the following compounds:
4-[2-(4-nitro-phenyl)-vinyl]-benzene-1,2,3-triol;
4-[3-(3-methoxy-4-methoxymethoxy-phenyl)-allylidene]-5-methyl-2-phenyl-2,4-dihydro-pyrazol-3-one;
5-[3-(3-methoxy-4-methoxymethoxy-phenyl)-allyidene]-thiazolidine-2,4-dione;
3-(3,5-di-tert-butyl-4-hydroxy-benzylidene)-5-hydroxy-3H-benzofuran-2-one;
4-{2-[3,4-dihydroxy-5-(3-methyl-but-2-enyl)-phenyl]-vinyl}-benzoic acid methyl ester;
3-(3-methyl-but-2-enyl)-4-[2-(4-nitro-phenyl)-vinyl]-benzene-1,2-diol;
3-3-methyl-but-2-enyl)-5-[2-(4-nitro-phenyl)-vinyl]-benzene-1,2-diol;
4-(3-methyl-but-2-enyl)-5-[2-(4-nitro-phenyl)-vinyl]-benzene-1,3-diol;
2-(3-methyl-but-2-enyl)-5-[2-(4-nitro-phenyl)-vinyl]-benzene-1,3-diol;
4-{2-[4-(3,7-dimethyl-octa-2,6-dienyl)-3,5-dihydroxy-phenyl]-vinyl}-benzonitrile;
4-{2-[3,5-dihydroxy-4-(3-methyl-but-2-enyl)-phenyl]-vinyl}-benzonitrile; and
2-bromo-4-[4-hydroxy-3-(3-methyl-but-2-enyl-phenyl)-vinyl]-phenol, including single stereoisomers, mixtures of stereoisomers, and the pharmaceutically acceptable salts thereof.

Of the foregoing group, most preferred for the treatment of inflammatory/autoimmune conditions are the following compounds:
4-[2-(4-nitro-phenyl)-vinyl]-benzene-1,2,3-triol;
3-(3-methyl-but-2-enyl)-4-[2-(4-nitro-phenyl)-vinyl]-benzene-1,2-diol; and
4-(3-methyl-but-2-enyl)-5-[2-(4-nitro-phenyl)-vinyl]-benzene-1,3-diol, including single stereoisomers, mixtures of stereoisomers, and the pharmaceutically acceptable salts thereof.

Another group of diseases characterized by oxidative stress fall within the group dermatologic conditions, including, but not limited to prevention and protecting skin tissue against age-related damage or damage resulting from insults such as harmful ultraviolet (UV) radiation, stress and fatigue. Preferred for the treatment of such disorders are the compounds of Formula I where R' is hydrogen and R is phenyl substituted in the para position with a nitrogen-bearing moiety, such as nitro or cyano. Also preferred are the compounds of Formula I where one or more of $R^1$ to $R^5$ is hydroxy, alkoxy (especially methoxy) or alkenyl (especially prenyl and geranyl), especially where R and R' are as defined above. Particularly preferred are the compounds of Formula I where one or two of $R^2$ to $R^4$ is hydroxy, one of $R^1$ to $R^4$ is prenyl or geranyl, and the remaining substituents of $R^1$ to $R^5$ are hydrogen; especially where R and R' are as defined above. Particularly preferred for the treatment of such disorders are the following compounds:
4-[2-(4-nitro-phenyl)-vinyl]-benzene-1,2-diol;
4-[2-(3,4-dihydroxy-phenyl)-vinyl]-benzoic acid methyl ester;
4-[2-(4-nitro-phenyl)-vinyl]-benzene-1,2,3-triol
2-methoxy-6-(3-methyl-but-2-enyl)-4-[2-(4-nitro-phenyl)-vinyl]-phenol;
2-hydroxy-5-[2-(4-nitro-phenyl)-vinyl]-benzoic acid;
3-(3-methyl-but-2-enyl)-4-[2-(4-nitro-phenyl)-vinyl]-benzene-1,2-diol;
4-(3-methyl-but-2-enyl)-5-[2-(4-nitro-phenyl)-vinyl]-benzene-1,3-diol;
5-[2-(4-nitro-phenyl)-vinyl]-benzene-1,3-diol;
2,6-di-tert-butyl-4-[2-(4-nitro-phenyl)-vinyl]-phenol;
2-(3-methyl-but-2-enyl)-5-[2-(4-nitro-phenyl)-vinyl]-benzene-1,3-diol;
2-bromo-4-[4-hydroxy-3-(3-methyl-but-2-enyl-phenyl)-vinyl]-phenol;
4-(2-nitro-vinyl)-benzene-1,2-diol;
2-methoxy-4-[4-(4-nitro-phenyl)-buta-1,3-dienyl]-phenol;
2-methoxymethoxy-5-[2-(4-nitro-phenyl)-vinyl]-benzoic acid methoxymethyl ester;
3-(3-methyl-but-2-enyl)-5-[2-(4-nitro-phenyl)-vinyl]-benzene-1,2-diol;
2-(3,7-dimethyl-octa-2,6-dienyl)-5-[2-(4-nitro-phenyl)-vinyl]-benzene-1,3-d iol;
5-{4-[2-(3,4-dihydroxy-phenyl)-vinyl]-phenyl}-2-phenyl-2,4-dihydro-pyrazol-3-one;
4-{2-[3,4-dihydroxy-5-(3-methyl-but-2-enyl)-phenyl]-vinyl}-benzoic acid methyl ester;
4-{2-[3,5-dihydroxy-4-(3-methyl-but-2-enyl)-phenyl]-vinyl}-benzonitrile;

4-(3-methyl-but-2-enyl)-5-[2-(4-nitro-phenyl)-vinyl]-benzene-1,3-diol;
4-{2-[4-(5-hydroxy-1H-pyrazol-3-yl)-phenyl]-vinyl}-benzene-1,2-diol;
4-{2-[4-(2-nitro-vinyl)-phenyl]-vinyl}-benzene-1,2-diol;
3-[2-(3,4-dimethoxy-phenyl)-vinyl]4-nitro-phenol;
4-[4-(4-nitro-phenyl)-buta-1,3-dienyl]-benzene-1,2-diol;
4-[3-(3-methoxy-4-methoxymethoxy-phenyl)-allylidene]-5-methyl-2-phenyl-2,4-dihydro-pyrazol-3-one;
5-[3-(3-methoxy-4-methoxymethoxy-phenyl)-allylidene]-thiazolidine-2,4-dione;
3-(3,5-di-tert-butyl-4-hydroxy-benzylidene)-5-hydroxy-3H-benzofuran-2-one;
2-iodo-6-methoxy-4-[2-(4-nitro-phenyl)-vinyl]-phenol;
4-{2-[4-(3,7-dimethyl-octa-2,6-dienyl)-3,5-dihydroxy-phenyl]-vinyl)-benzonitrile;
2-(3,7-dimethyl-octa-2,6-dienyl)-6-methoxy-4-[2-(4-nitro-phenyl)-vinyl]-phenol;
2-bromo-6-methoxy-4-[2-(4-nitro-phenyl)-vinyl]-phenol;
4-{2-[3-(3,7-dimethyl-octa-2,6-dienyl)-4-hydroxy-5-methoxy-phenyl]-vinyl}-benzonitrile;
2,6-dimethyl-4-[2-(4-nitro-phenyl)-vinyl]-phenol;
acetic acid 4-(1-acetoxy-allyl)-phenyl ester;
2-(4-methoxy-phenyl)-1-(3,4,5-trimethoxy-phenyl)-ethanol;
acetic acid 4-[2-(4-acetoxy-3-methoxy-phenyl)-vinyl]-2-methoxy-phenyl ester;
2-{3-[2-(3,4-dihydroxy-phenyl)-vinyl]-5-hydroxy-phenoxy}-6-hydroxymethyl-tetrahydro-pyran-3,4,5-trio;
4-(3-ethoxy-propenyl)-phenol;
2,3-bis-(4-acetoxy-3-methoxy-phenyl)-acrylic acid;
cis-gnetin;
5-[2-(4-methoxy-phenyl)-vinyl]-benzo[1,3]dioxole; and
(4-methoxyphenyl)-(benzo-1,3-dioxol-5-yl)-ethyne, including single stereoisomers, mixtures of stereoisomers, and the pharmaceutically acceptable salts thereof.

Of the foregoing group, especially preferred for the treatment of dermatologic conditions are the following compounds:
4-[2-(4-nitro-phenyl)-vinyl]-benzene-1,2-diol;
4-[2-(3,4-dihydroxy-phenyl)-vinyl]-benzoic acid methyl ester;
4-[2-(4-nitro-phenyl)-vinyl]-benzene-1,2,3-triol;
2-hydroxy-5-[2-(4-nitro-phenyl)-vinyl]-benzoic acid;
3-(3-methyl-but-2-enyl)-4-[2-(4-nitro-phenyl)-vinyl]-benzene-1,2-diol;
4-(3-methyl-but-2-enyl)-5-[2-(4-nitro-phenyl)-vinyl]-benzene-1,3-diol;
2-(3-methyl-but-2-enyl)-5-[2-(4-nitro-phenyl)-vinyl]-benzene-1,3-diol;
2-bromo-4-[4-hydroxy-3-(3-methyl-but-2-enyl-phenyl)-vinyl]-phenol;
3-(3-methyl-but-2-enyl)-5-[2-(4-nitro-phenyl)-vinyl]-benzene-1,2-diol;
2-(3,7-dimethyl-octa-2,6-dienyl)-5-[2-(4-nitro-phenyl)-vinyl]-benzene-1,3-diol;
4-(2-[3,4-dihydroxy-5-(3-methyl-but-2-enyl)-phenyl]-vinyl}-benzoic acid methyl ester;
4-{2-[3,5-dihydroxy-4-(3-methyl-but-2-enyl)-phenyl]-vinyl}-benzonitrile;
4-(3-methyl-but-2-enyl)-5-[2-(4-nitro-phenyl)-vinyl]-benzene-1,3-diol;
4-{2-[4-(2-nitro-vinyl)-phenyl]-vinyl}-benzene-1,2-diol;
3-[2-(3,4-dimethoxy-phenyl)-vinyl]-4-nitro-phenol; and
4-{2-[4-(3,7-dimethyl-octa-2,6-dienyl)-3,5-dihydroxy-phenyl]-vinyl}-benzonitrile, including single stereoisomers, mixtures of stereoisomers, and the pharmaceutically acceptable salts thereof.

Of the foregoing group, most preferred for the treatment of dermatologic conditions are the following compounds:
4-[2-(4-nitro-phenyl)-vinyl]-benzene-1,2,3-triol;
4-(3-methyl-but-2-enyl)-5-[2-(4-nitro-phenyl)-vinyl]-benzene-1,3-diol;
2-(3-methyl-but-2-enyl)-5-[2-(4-nitro-phenyl)-vinyl]-benzene-1,3-diol;
2-bromo-4-[4-hydroxy-3-(3-methyl-but-2-enyl-phenyl)-vinyl]-phenol;
2-(3,7-dimethyl-octa-2,6-dienyl)-5-[2-(4-nitro-phenyl)-vinyl]-benzene-1,3-diol;
4-{2-[3,5-dihydroxy-4-(3-methyl-but-2-enyl)-phenyl]-vinyl}-benzonitrile;
4-(3-methyl-but-2-enyl)-5-[2-(4-nitro-phenyl)-vinyl]-benzene-1,3-diol;
4-{2-[4-(2-nitro-vinyl)-phenyl]-vinyl}-benzene-1,2-diol; and
4-{2-[4-(3,7-dimethyl-octa-2,6-dienyl)-3,5-dihydroxy-phenyl]-vinyl}-benzonitrile, including single stereoisomers, mixtures of stereoisomers, and the pharmaceutically acceptable salts thereof.

With respect to treatment by topical application, e.g., in the treatment of contact dermatitis, psoriasis, acne, signs of skin aging or exposure to harmful levels of UV radiation, particularly preferred are the following compounds:
4-[2-(4-nitro-phenyl)-vinyl]-benzene-1,2-diol;
4-[2-(4-nitro-phenyl)-vinyl]-benzene-1,2,3-triol;
4-(3-methyl-but-2-enyl)-5-[2-(4-nitro-phenyl)-vinyl]-benzene-1,3-diol;
2-bromo-4-[4-hydroxy-3-(3-methyl-but-2-enyl-phenyl)-vinyl]-phenol;
4-{2-[3,5-dihydroxy-4-(3-methyl-but-2-enyl)-phenyl]-vinyl}-benzonitrile;
4-[3-(3-methoxy-4-methoxymethoxy-phenyl)-allylidene]-5-methyl-2-phenyl-2,4-dihydro-pyrazol-3-one;
5-[3-(3-methoxy-4-methoxymethoxy-phenyl)-allylidene]-thiazolidine-2,4-dione;
3-(3,5-di-tert-butyl-4-hydroxy-benzylidene)-5-hydroxy-3H-benzofuran-2-one;
4-{2-[4-(3,7-dimethyl-octa-2,6-dienyl)-3,5-dihydroxy-phenyl]-vinyl}-benzonitrile;
2-(3-methyl-but-2-enyl)-5-[2-(4-nitro-phenyl)-vinyl]-benzene-1,3-diol;
4-[4-(4-nitro-phenyl)-buta-1,3-dienyl]-benzene-1,2-diol;
5-(3,5-di-tert-butyl-4-hydroxy-benzylidene)-thiazolidine-2,4-dione;
4-{2-[3,4-dihydroxy-5-(3-methyl-but-2-enyl)-phenyl]-vinyl}-benzoic acid methyl ester;
3-(3-methyl-but-2-enyl)-4-[2-(4-nitro-phenyl)-vinyl]-benzene-1,2-diol;
3-(3-methyl-but-2-enyl)-5-[2-(4-nitro-phenyl)-vinyl]-benzene-1,2-diol;
4-(3-methyl-but-2-enyl)-5-[2-(4-nitro-phenyl)-vinyl]-benzene-1,3-diol;
2-(3,7-dimethyl-octa-2,6-dienyl)-6-methoxy-4-[2-(4-nitro-phenyl)-vinyl]-phenol;
2-(3,7-dimethyl-octa-2,6-dienyl)-5-[2-(4-nitro-phenyl)-vinyl]-benzene-1,3-diol;
4-{2-[3,5-dihydroxy-4-(3-methyl-but-2-enyl)-phenyl]-vinyl}-benzonitrile; and
2-bromo-4-[4-hydroxy-3-(3-methyl-but-2-enyl-phenyl)-vinyl]-phenol.

including single stereoisomers, mixtures of stereoisomers, and the pharmaceutically acceptable salts thereof.

More preferred for treatment by topical application are the following compounds:

4-[2-(4-nitro-phenyl)-vinyl]-benzene-1,2-diol;
4-[2-(4-nitro-phenyl)-vinyl]-benzene-1,2,3-triol;
4-(3-methyl-but-2-enyl)-5-[2-(4-nitro-phenyl)-vinyl]-benzene-1,3-diol;
2-bromo-4-[4-hydroxy-3-(3-methyl-but-2-enyl-phenyl)-vinyl]-phenol;
4-{2-[3,5-dihydroxy-4-(3-methyl-but-2-enyl)-phenyl]-vinyl}-benzonitrile;
4-[3-(3-methoxy-4-methoxymethoxy-phenyl)-allylidene]-5-methyl-2-phenyl-2,4-dihydro-pyrazol-3-one;
5-[3-(3-methoxy-4-methoxymethoxy-phenyl)-allyidene]-thiazolidine-2,4-dione;
3-(3,5-di-tert-butyl-4-hydroxy-benzylidene)-5-hydroxy-3H-benzofuran-2-one;
4-{2-[4-(3,7-dimethyl-octa-2,6-dienyl)-3,5-dihydroxy-phenyl]-vinyl}-benzonitrile; and
2-(3-methyl-but-2-enyl)-5-[2-(4-nitro-phenyl)-vinyl]-benzene-1,3-diol, including single stereoisomers, mixtures of stereoisomers, and the pharmaceutically acceptable salts thereof.

Most preferred for treatment by topical application are the following compounds:

4-[2-(4-nitro-phenyl)-vinyl]-benzene-1,2-diol;
4-[2-(4-nitro-phenyl)-vinyl]-benzene-1,2,3-triol;
4-(3-methyl-but-2-enyl)-5-[2-(4-nitro-phenyl)-vinyl]-benzene-1,3-diol;
2-bromo-4-[4-hydroxy-3-(3-methyl-but-2-enyl-phenyl) vinyl]-phenol;
4-{2-[3,5-dihydroxy-4-(3-methyl-but-2-enyl)-phenyl]-vinyl}-benzonitrile; and
4-{2-[4-(3,7-dimethyl-octa-2,6-dienyl)-3,5-dihydroxy-phenyl]-vinyl}-benzonitrile, including single stereoisomers, mixtures of stereoisomers, and the pharmaceutically acceptable salts thereof.

For example, exposure to sunlight can pose a number of hazards to the skin. The major short-term hazard of prolonged exposure to sunlight is erythema, i.e., sunburn, which primarily results from UVB radiation having a wavelength of from about 290 nm to about 320 nm. Over the long term, however, such prolonged exposure can often cause malignant changes in the skin surface to occur. Epidemiologic studies demonstrate a strong relationship between sunlight exposure and human skin cancer. Another long-term hazard of ultraviolet radiation is premature aging of the skin, which is primarily caused by UVA radiation having a wavelength of from about 320 nm to about 400 nm. This condition is characterized by wrinkling and pigment changes of the skin, along with other physical changes such as cracking, telangiectasis, solar dermatoses, ecchymoses, and loss of elasticity. Individuals, particularly those having light-skin who burn easily and tan poorly, who have had a great deal sun exposure in childhood can show the following gross cutaneous alterations in later adult life: wrinkling, leatheriness, yellowing, looseness, roughness, dryness, mottling (hyperpigmentation) and various premalignant growths (often subclinical). These cumulative effects of sunlight are often referred to as "photoaging". Although the anatomical degradation of the skin is most advanced in the elderly, the destructive effects of excessive sun exposure are already evident by the second decade. Serious microscopic alterations of the epidermis and dermis occur decades before these become clinically visible. Wrinkling, yellowing, leatheriness and loss of elasticity are very late changes.

Other skin conditions that may benefit from the methods of the present invention include, but are not limited to, diaper rash, a common form of contact dermatitis and irritation occurring in infants, as well as adults, who wear diapers. U.S. Pat. No. 6,211,186, incorporated herein by reference, describes possible etiologies and methods of treating this condition. It is generally thought that one or more fecal and lipolytic enzymes, as well as ammonia, bacteria, urine pH, overhydration and *Candida albicans* may be involved in the onset of skin irritation and inflammation associated with diaper rash. It is also likely that physiological responses of the skin to the irritants, such as production of cytokines by keratinocytes, contribute to the ensuing appearance of erythema, papules, scaling and ulceration characteristic of the condition. In addition, compositions and methods of the present invention may be useful in treating acne, a skin condition characterized by a profound inflammatory component.

The compositions of the present invention are also useful for regulating skin condition, including visible and/or tactile discontinuities in skin (especially the skin surface; such discontinuities are generally undesired). Such discontinuities may be induced or caused by internal and/or external factors, and include the signs of skin aging described herein.

The compositions of the present invention are useful for regulating signs of skin aging, especially visible and/or tactile discontinuities in skin texture associated with aging. It is to be understood that the present invention is not to be limited to regulation of the "signs of skin aging" that arise due to the above-mentioned mechanisms associated with skin aging, but is intended to include regulation of such signs irrespective of their mechanism of origin.

Testing

This section describes how compositions incorporating compositions of the present invention are selected, using in vitro and/or in vivo models, and used as therapeutic interventions in exemplary indications, e.g., stroke, chronic heart failure and myocardial infarction. Those skilled in the art will appreciate that safety and efficacy for use as human therapeutics must typically be demonstrated in randomized, double-blind, placebo- (or active-) controlled, human clinical trials.

Insults to the brain that disrupt its blood supply, as in ischemia, or its oxygen supply, as in hypoxia (low oxygen) or anoxia (no oxygen), rapidly cause neuronal imbalance leading to cell death (Flynn, C. J., et al., 1989, in G. Siegel et al., (Eds), *Basic Neurochemistry*, Raven Press, N.Y.). Investigations into the cellular and molecular mechanisms that lead to neuronal damage and inflammation associated with various types of brain ischemia can be carried out using in vitro model systems, such as primary cell cultures, that retain the metabolic characteristics of neurons in vivo. The use of such cell-based models has led to advances in identification of biochemical mechanisms leading to neuronal death in conditions such as anoxia, hypoglycemia, excitotoxicity, and exposure to reactive oxygen species. Neuronal cell lines such as the pheochromocytoma cell line, PC12, are also useful models for studying the effects of oxidative stress on the structure and function of neuron-specific proteins that are expressed in the cell lines. As many neuronal cell lines do not express all the properties of genuine neurons, primary neuronal cultures are now widely used as in vitro models in which to discern the processes that occur in intact brain.

In vitro models of ischemia approximate oxygen and glucose deprivation that mimic in vivo conditions, for example, by placing neuronal cultures into large anaerobic or hypoxic chambers and exchanging culture medium with de-oxygenated and defined ionic composition media. The toxic overstimulation of neuronal glutamate receptors, especially N-methyl-D-aspartate (NMDA) receptors, contributes to hypoxic-ischemic neuronal injury (Choi, D. M., 1988, *Neuron* 1: 623-634), ischemic induction of reactive oxygen species (ROS) (Watson, B. D., et al., 1988, Ann NY Acad. Sci., 59: 269-281), excessive calcium influx (Grofta, J. C., 1988, *Stroke* 19: 447-454), arachidonic acid increase (Siesjo, B. K., 1981, *J. Cereb. Blood Flow Metab.* 1: 155-186) and DNA damage (MacManus, J. P., et al., 1993, *Neurosci. Lett.*, 164: 89-92), each causing a cascade of neurodegeneration.

Primary embryonic hippocampal neuronal cells are widely recognized as useful in models of neuronal function. The hippocampus is a source of a relatively homogenous population of neurons with well-characterized properties typical of central nervous system (CNS) neurons in general. Pyramidal neurons, the principal cell type in the hippocampus, have been estimated to account for 85% to 90% of the total neuronal population (Banker and Goslin, 1998, *Culturing Nerve Cells*, $2^{nd}$ *edition*. The MIT Press, Cambridge, Mass.). The hippocampus also exhibits a remarkable capacity for activity-dependent changes in synaptic function, such as long-term potentiation (Hawkins R D, Kandel E R, Siegelbaum S A. (1993) Learning to modulate transmitter release: themes and variations in synaptic plasticity [review], *Ann. Rev Neurosci.* 16:625-665.).

In experiments carried out in support of the present invention according to methods detailed in the Examples, anoxia/ischemia was induced in primary cultures of hippocampal neuronal cells, and compounds were tested for their ability to prevent cell death. Compounds found to have activity in such in vitro assays are then further tested in one or more animal models of cerebral ischemia ("stroke"), such as the middle cerebral artery occlusion (MCAO) model in rats.

Briefly, primary cultures of hippocampal neurons are used to test compounds for activity in neuronal protection. Hippocampal cultures are typically prepared from 18- to 19-day fetal rats. At this age, the generation of pyramidal neurons, which begins in the rat at about E15, is essentially complete. The brain tissue at this stage is relatively easy to dissociate, the meninges are removed readily, and the number of glial cells still is relatively modest (Park L C, Calingasan N Y, Uchida K, Zhang H, Gibson G E. (2000) Metabolic impairment elicits brain cell type-selective changes in oxidative stress and cell death in culture. *J Neurochem* 74(1):114-124).

In order to evaluate the activity of compounds of the present invention, a test compound is assessed for its ability to protect cells against one or more standard stressors, including hypoxia, as detailed in the Examples. In general, desirable therapeutic compound candidates are effective in this model at concentrations less than about 10 mM, more preferably at concentrations, less than about 1 mM and even more preferably, less than about 100 µM. By effective, it is meant that such compounds protect at least 20%, preferably 30%, more preferably 40% and even more preferably 50% or more of the cells tested from stressor-induced death. By way of example, compounds that are effective in providing protection over a concentration a range of about 1 to 1000 µM would be expected to provide neuroprotection in vivo. Since precise values may vary depending upon the specific conditions under which the neuroprotective cell assay is carried out, it is the intent of the present disclosure to provide the foregoing criteria as guidance in the form of a benchmark against which to compare subsequently tested compounds, rather than to provide absolute concentrations at which the compounds of the present invention are considered to be effective. Typically, compounds that are found to be neuroprotective in such in vitro cell systems are then further tested in an in vivo animal model of neuroprotection, such as the rat middle cerebral artery occlusion model described below, or other appropriate models such as are well known in the art.

Cerebral ischemic insults are modeled in animals by occluding vessels to, or within, the cranium (Molinari, G. F., 1986, in H. J. M. Barnett, et al., (Eds) *Stroke: Pathophysiology, Diagnosis and Management*, Vol. 1, Churchill Livingstone, N.Y.). The rat middle cerebral artery occlusion (MCAO) model is one of the most widely used techniques to induce transient focal cerebral ischemia approximating cerebral ischemic damage in humans, e.g., those who suffer from a stroke (duration of occlusion and time to treatment in rats can correspond with up to 2 to 5 fold longer periods in humans). The middle cerebral artery used as the ischemic trigger in this model is the most affected vessel in human stroke. The model also entails a period of reperfusion, which typically occurs in human stroke victims. MCAO involving a two-hour occlusion has been found to produce the maximum size of cortical infarction obtainable without increased mortality at twenty-four hours.

Briefly, a nylon filament is implanted into the right carotid artery of the rat. To effect occlusion, the rat is anesthetized, and the filament is advanced into the internal carotid artery 18-20 mm from the point of bifurcation of internal and external arteries and a suture is tightly ligated around the filament for a period of two hours. Two hours post occlusion, animals are re-anesthetized, and the filament is removed, to allow reperfusion for the remainder of the experiment. Test drugs can be administered any time during this process—before, during or after occlusion, and can be administered by one or more of a variety of means, including but not limited to intracerebroventricular (ICV) infusion, intravenous (IV) infusion, intraperitoneal (IP) administration, as well as enteral administration (e.g., gavage). Animals are maintained normothermic during the experiment, as described in the Examples. At a pre-determined time following occlusion and reperfusion, animals are sacrificed and their brains are removed and processed for assessment of damage as measured by infarct volume. In general, compounds are considered to have activity in this model, if they provide a significant reduction in total infarct volume at a dose that is less than about 10 mg/kg, preferably less than 1 mg/kg, more preferably less than 100 µg/kg and even more preferably less than about 1 µg/kg, when administered ICV or IV. By significant reduction of total infarct volume is meant a reduction of at least 20%, preferably at least 30%, more preferably at least 40%, and even more preferably about 50%, compared to control values.

Further validation of efficacy in neuroprotection can be assessed in long term cerebral ischemia (MCAO—7 to 14 days) with the additional sensory motor outcome relief, functional tests, such as the grip strength test or the rotorod test. Animals treated with compounds that show neuroprotection, show a reduction in infarct size and maintain their pre-MCAO grip strength values after MCAO, as compared to untreated animals, who showed a significant reduction in grip strength, indicating loss of sensorimotor function. Likewise, animals treated with compounds that show neuroprotection also maintained their pre-MCAO rotorod activity scores after MCAO, as compared to untreated animals, who showed a significant reduction in rotorod scores, indicating loss of sensorimotor function at higher brain levels.

Similarly, primary cultures of myocytes can be used to test compounds in vitro for ability to provide protection against heart damage, resulting for example from myocardial ischemia or congestive heart failure. Preparation of myocardiocytes from neonatal rats is described in the Examples. Such cells are typically used to study molecular models of myocardial ischemia (Webster, K A, Discher, D J & Bishopric, N H. 1995. J. Mol. Cell Cardiol. 27:453-458; Camilleri, L, Moins, N, Papon, J, Maublant, J, Bailly, P, de Riberolles, C & Veyre, A. 1997. Cell Biol. & Toxicol. 13:435-444; Bielawska, A E, Shapiro, JP, Jiang, L, Melkonyan, H S, Piot, C, Wolfe, C L, Tomei, L D, Hannun, Y A & Umansky, S R. 1997. *Am. J. Pathol.* 151:1257-1263) and are therefore accepted as indicative of myoprotective activity. Exemplary stressor assays for this purpose are provided in the Examples. For example, cardiomyocytes in culture exhibit contractile ("beating") activity; each cardiomyocyte contraction is associated with a rise in intracellular calcium termed a "calcium transient". These calcium transients can be measured using Fluo-4, a fluorescent dye which exhibits large fluorescence intensity increases upon the binding of calcium. This assay is cell-based and tests the ability of potential cytoprotectant molecules to guard against ischemic damage and allow the cells to maintain their contractile function. In vivo testing of therapeutic activity can be demonstrated in the Left Coronary Artery Ligation model of myocardial ischemia Left Coronary Artery Occlusion model of congestive heart failure (Hill, M. et al., Circulation, 2414-2420, 1997), respectively, involving complete blockage over a period of about 30 minutes followed by reperfusion or partial blockage over a period of several weeks. As in the MCAO model, duration of occlusion and time to treatment in rats can correspond with up to 2 to 5 fold longer periods in humans.

In vivo evaluation of anti-inflammatory activity can be determined by well characterized assays measuring Carrageenan-Induced Paw Edema and by Mouse Ear Inflammatory Response to Topical Arachidonic Acid. (Gabor, M., Mouse Ear Inflammation Models and their Pharmacological Applications, 2000.) Carrageenan-Induced Paw Edema is a model of inflammation, which causes time-dependent edema formation following carrageenan administration into the intraplantar surface of a rat paw. The application of arachidonic acid (AA) to the ears of mice produces immediate vasodilatation and erythema, followed by the abrupt development of edema, which is maximal at 40 to 60 min. The onset of edema coincides with the extravasations of protein and leukocytes. After one hour the edema wanes rapidly and the inflammatory cells leave the tissue so that at 6 hours the ears have returned to near normal. These assays, respectively, measure a test compounds ability to treat these inflammatory processes via systemic and topical routes of administration.

Further validation of compounds can be carried out in a whole organ assay, such as the isolated heart (Langendorff) model of cardiac function. Similarly, compounds can be further validated in additional animal models of disease (e.g., diabetes, renal failure, asthma, muscle fatigue, inflammation, arthritis), such as are well known in the art.

Cytoprotective activity for skin can be evaluated in cell culture using the Epiderm Skin Model (EPI-100) from the Mattek Corporation of Ashland, Mass. Cell cultures of neonatal foreskin are cultured in accordance with the manufacturer's directions, and are assayed for percent cellular viability by measuring the amount of 3-(4,5-dimethylthazol-2-yl)-2,5-diphenyltetrazolium bromide (MTT) dye taken up by the cells.

Administration

The compounds of Formula I to V and naturally occurring conjugated phenols are administered at a therapeutically effective dosage, e.g., a dosage sufficient to provide treatment for the disease states previously described. Administration of the compounds of the invention or the pharmaceutically acceptable salts thereof can be via any of the accepted modes of administration for agents that serve similar utilities.

While human dosage levels have yet to be optimized for the compounds of the invention, generally, a daily dose is from about 0.01 to 15.0 mg/kg of body weight, preferably about 0.1 to 7.5 mg/kg of body weight, and most preferably about 0.3 to 1.5 mg/kg of body weight. Thus, for administration to a 70 kg person, the dosage range would be about 0.7 to 1,000 mg per day, preferably about 7.0 to 500 mg per day, and most preferably about 21 to 100 mg per day. The amount of active compound administered will, of course, be dependent on the subject and disease state being treated, the severity of the affliction, the manner and schedule of administration and the judgment of the prescribing physician.

The compositions of the present invention are suitable for providing protection against the harmful effects of ultraviolet radiation, preferably in personal care products. More preferably, the compositions of the present invention are suitable for use as sunscreens to provide protection to human skin from the harmful effects of UV radiation, which include, but are not limited to, sunburn and premature aging of the skin. The present invention therefore also further relates to methods of protecting human skin from the harmful effects of UV radiation. Such methods generally involve attenuating or reducing the amount of UV radiation that reaches the skin's surface. In the case of the present invention, the methods of treatment for the harmful effects of ultraviolet radiation also include administration of a composition of the invention after the exposure to UV radiation has already taken place. To protect the skin from UV radiation, a safe and effective (photoprotective) amount of the composition is topically applied to the skin. "Topical application" refers to application of the present compositions by spreading, spraying, etc. onto the surface of the skin. The exact amount applied may vary depending on the level of UV protection desired. From about 0.5 mg of composition per square centimeter of skin to about 25 mg of composition per square centimeter of skin are typically applied.

Compounds and methods of the invention may be employed in any skin care application where decreased inflammatory response is desirable. For example, compounds and compositions of the invention may be incorporated into leave-on and rinse-off acne preparations, facial milks and conditioners, shower gels, foaming and non-foaming facial cleansers, cosmetics, hand and body lotions, leave-on moisturizers, cosmetic and cleaning wipes, salves for poison ivy, chicken pox, or pruritis, or the like. Generally, for dermal applications, topical administration is preferred; however, systemic administration, as described elsewhere herein, is also possible.

Compositions of the present invention may also be used in cosmetic compositions. Cosmetic compositions of the present invention are ideally suited for use in treating the skin and lips, especially in the form of a lipstick or lip balm for applying to the lips a permanent or semi-permanent color, ideally with a gloss or luster finish. The cosmetic compositions can also be used in treating the skin and/or lips with a skin care agent for protection against exposure to adverse weather, including the wind and rain, dry and/or hot environments, environmental pollutants (e.g., ozone, smoke, and the like), or exposure to excessive doses of sunlight. The compositions are also useful in providing sun protection, moisturizing and/or conditioning for the hair and skin, improved skin feel, regulating skin texture, reducing fine lines and wrinkles, reducing oily shine on hair or skin, skin lightening and reducing skin or hair odor.

The cosmetic compositions can accordingly be applied to the skin and/or lips in the traditional manner with or without a conventional holder or applicator to provide a decorative and/or protective film thereto.

In employing the compounds of this invention for treatment of the above conditions, any pharmaceutically acceptable mode of administration can be used. The compounds of Formula I can be administered either alone or in combination with other pharmaceutically acceptable excipients, including solid, semi-solid, liquid or aerosol dosage forms, such as, for example, tablets, capsules, powders, liquids, suspensions, suppositories, aerosols or the like. The compounds of Formula I can also be administered in sustained or controlled release dosage forms, including depot injections, osmotic pumps, pills, transdermal (including electrotransport) patches, and the like, for the prolonged administration of the compound at a predetermined rate, preferably in unit dosage forms suitable for single administration of precise dosages. The compositions will typically include a conventional pharmaceutical carrier or excipient and a compound of Formula I or a pharmaceutically acceptable salt thereof. In addition, these compositions may include other medicinal agents, pharmaceutical agents, carriers, adjuvants, and the like, including, but not limited to anticoagulants, blood clot dissolvers, permeability enhancers and slow release formulations.

Generally, depending on the intended mode of administration, the pharmaceutically acceptable composition will contain about 0.1% to 90%, preferably about 0.5% to 50%, by weight of a compound or salt of Formula I, the remainder being suitable pharmaceutical excipients, carriers, etc.

One preferred manner of administration for the conditions detailed above is oral, using a convenient daily dosage regimen which can be adjusted according to the degree of affliction. For such oral administration, a pharmaceutically acceptable, non-toxic composition is formed by the incorporation of any of the normally employed excipients, such as, for example, mannitol, lactose, starch, magnesium stearate, sodium saccharine, talcum, cellulose, sodium crosscarmellose, glucose, gelatin, sucrose, magnesium carbonate, and the like. Such compositions take the form of solutions, suspensions, tablets, dispersible tablets, pills, capsules, powders, sustained release formulations and the like.

Preferably the compositions will take the form of a pill or tablet and thus the composition will contain, along with the active ingredient, a diluent such as lactose, sucrose, dicalcium phosphate, or the like; a lubricant such as magnesium stearate or the like; and a binder such as starch, gum acacia, polyvinylpyrrolidine, gelatin, cellulose and derivatives thereof, and the like.

Liquid pharmaceutically administrable compositions can, for example, be prepared by dissolving, dispersing, etc. an active compound as defined above and optional pharmaceutical adjuvants in a carrier, such as, for example, water, saline, aqueous dextrose, glycerol, glycols, ethanol, and the like, to thereby form a solution or suspension. If desired, the pharmaceutical composition to be administered may also contain minor amounts of nontoxic auxiliary substances such as wetting agents, emulsifying agents, or solubilizing agents, pH buffering agents and the like, for example, sodium acetate, sodium citrate, cyclodextrine derivatives, sorbitan monolaurate, triethanolamine acetate, triethanolamine oleate, etc. Actual methods of preparing such dosage forms are known, or will be apparent, to those skilled in this art; for example, see *Remington's Pharmaceutical Sciences*, Mack Publishing Company, Easton, Pa., 15th Edition, 1975. The composition or formulation to be administered will, in any event, contain a quantity of the active compound in an amount effective to alleviate the symptoms of the subject being treated.

Dosage forms or compositions containing active ingredient in the range of 0.005% to 95% with the balance made up from non-toxic carrier may be prepared.

For oral administration, a pharmaceutically acceptable non-toxic composition is formed by the incorporation of any of the normally employed excipients, such as, for example pharmaceutical grades of mannitol, lactose, starch, magnesium stearate, talcum, cellulose derivatives, sodium crosscarmellose, glucose, sucrose, magnesium carbonate, sodium saccharin, talcum and the like. Such compositions take the form of solutions, suspensions, tablets, capsules, powders, sustained release formulations and the like. Such compositions may contain 0.01%-95% active ingredient, preferably 0.1-50%.

For a solid dosage form, the solution or suspension, in for example propylene carbonate, vegetable oils or triglycerides, is preferably encapsulated in a gelatin capsule. Such diester solutions, and the preparation and encapsulation thereof, are disclosed in U.S. Pat. Nos. 4,328,245; 4,409,239; and 4,410,545. For a liquid dosage form, the solution, e.g. in a polyethylene glycol, may be diluted with a sufficient quantity of a pharmaceutically acceptable liquid carrier, e.g. water, to be easily measured for administration.

Alternatively, liquid or semi-solid oral formulations may be prepared by dissolving or dispersing the active compound or salt in vegetable oils, glycols, triglycerides, propylene glycol esters (e.g. propylene carbonate) and the like, and encapsulating these solutions or suspensions in hard or soft gelatin capsule shells.

Other useful formulations include those set forth in U.S. Pat. Nos. Re. 28,819 and 4,358,603.

The formulation can be administered in a single unit dosage form for continuous treatment or in a single unit dosage form ad libitum when relief of symptoms is specifically required. For example, the formulation may be administered as a bolus or as a continuous intravenous infusion after onset of symptoms of stroke, myocardial infarction or chronic heart failure.

Parenteral administration is generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol or the like. In addition, if desired, the pharmaceutical compositions to be administered may also contain minor amounts of non-toxic auxiliary substances such as wetting or emulsifying agents, pH buffering agents, solubility enhancers, and the like, such as for example, sodium acetate, sorbitan monolaurate, triethanolamine oleate, cyclodextrins, etc.

A more recently devised approach for parenteral administration employs the implantation of a slow-release or sustained-release system, such that a constant level of dosage is maintained. See, e.g., U.S. Pat. No. 3,710,795. The percentage of active compound contained in such parenteral compositions is highly dependent on the specific nature thereof, as well as the activity of the compound and the needs of the subject. However, percentages of active ingredient of 0.01% to 10% in solution are employable, and will be higher if the composition is a solid which will be subsequently diluted to the above percentages. Preferably the composition will comprise 0.2-2% of the active agent in solution. Nasal solutions of the active compound alone or in combination with other pharmaceutically acceptable excipients can also be administered.

Formulations of the active compound or a salt may also be administered to the respiratory tract as an aerosol or solution for a nebulizer, or as a microfine powder for insufflation, alone in combination with an inert carrier such as lactose. In such a case, the particles of the formulation have diameters of less than 50 microns, preferably less than 10 microns.

Dermatologic formulations of the present invention typically comprise a cytoprotective derivative of any of Formulae I to V and optionally, a polar solvent. Solvents suitable for use in the formulations of the present invention include any polar solvent capable of dissolving the cytoprotective derivative. Suitable polar solvents include: water; alcohols (such as ethanol, propyl alcohol, isopropyl alcohol, hexanol, and benzyl alcohol); polyols (such as propylene glycol, polypropylene glycol, butylene glycol, hexylene glycol, maltitol, sorbitol, and glycerine); and panthenol dissolved in glycerine, flavor oils and mixtures thereof. Mixtures of these solvents can also be used. Exemplary polar solvents are polyhydric alcohols and water. Examples of preferred solvents include glycerine, panthenol in glycerine, glycols such as propylene glycol and butylene glycol, polyethylene glycols, water and mixtures thereof. Additional preferred polar solvents for use are alcohols, glycerine, panthenol, propylene glycol, butylene glycol, hexylene glycol and mixtures thereof.

Typically, the formulations of the present invention will comprise from about 0.1% to about 80%, preferably from about 0.5% to about 60%, more preferably from about 1% to about 30% and most preferably from about 3% to about 18% polar solvent.

An emollient may also be added to the cosmetic/dermatological compositions of the present invention. The emollient component can comprise fats, oils, fatty alcohols, fatty acids and esters which aid application and adhesion, yield gloss and most importantly provide occlusive moisturization. Suitable emollients for use are isostearic acid derivatives, isopropyl palmitate, lanolin oil, diisopropyl dimerate, maleated soybean oil, octyl palmitate, isopropyl isostearate, cetyl lactate, cetyl ricinoleate, tocopheryl acetate, acetylated lanolin alcohol, cetyl acetate, phenyl trimethicone, glyceryl oleate, tocopheryl linoleate, wheat germ glycerides, arachidyl propionate, myristyl lactate, decyl oleate, propylene glycol ricinoleate, isopropyl lanolate, pentaerythrityl tetrastearate, neopentylglycol dicaprylate/dicaprate, hydrogenated cocoglycerides, isononyl isononanoate, isotridecyl isononanoate, myristal myristate, triisocetyl citrate, cetyl alcohol, octyl dodecanol, oleyl alcohol, panthenol, lanolin alcohol, linoleic acid, linolenic acid, sucrose esters of fatty acids, octyl hydroxystearate and mixtures thereof. Examples of other suitable emollients can be found in the Cosmetic Bench Reference, pp. 1.19-1.22 (1996), incorporated herein by reference. Suitable emollients include polar emollient emulsifiers (such as linear or branched chained polyglycerol esters) and non-polar emollients. The emollient component typically comprises from about 1% to about 90%, preferably from about 10% to about 80%, more preferably from about 20% to about 70%, and most preferably from about 40% to about 60%, of the cosmetic composition.

By "polar emollient," as used herein, is meant any emollient emulsifier having at least one polar moiety and wherein the solubility (at 30 degrees C.) of the cytoprotective derivative compound in the polar emollient is greater than about 1.5%, preferably greater than about 2%, more preferably greater than about 3%. Suitable polar emollients include, but are not limited to, polyol ester and polyol ethers such as linear or branched chained polyglycerol esters and polyglycerol ethers. Nonlimiting examples of such emollients include PG3 diisosterate, polyglyceryl-2-sesquiisostearate, polyglyceryl-5-distearate, polyglyceryl-10-distearate, polyglyceryl-10-diisostearate, acetylated monoglycerides, glycerol esters, glycerol tricaprylate/caprate, glyceryl ricinoleate, glyceryl isostearate, glyceryl myristate, glyceryl linoleate, polyalkylene glycols such as PEG 600, monoglycerides, 2-monolaurin, sorbitan esters and mixtures thereof.

By "non-polar emollient," as used herein, means any emollient emulsifier possessing no permanent electric moments. Suitable non-polar emollients include, but are not limited to, esters and linear or branched chained hydrocarbons. Nonlimiting examples of such emollients isononyl isononanoate, isopropyl isostearate, octyl hydroxystearate, diisopropyl dimerate, lanolin oil, octyl palmitate, isopropyl palmitate, pariffins, isoparrifins, acetylated lanolin, sucrose fatty acid esters, isopropyl myristate, isopropyl stearate, mineral oil, silicone oils, dimethicone, allantoin, isohexadecane, isododecane, petrolatum, and mixtures thereof. The solubility of the conjugated phenol compound in polar or non-polar emollients is determined according to methods known in the art.

Suitable oils include esters, triglycerides, hydrocarbons and silicones. These can be a single material or a mixture of one or more materials. They will normally comprise from 0% to about 100%, preferably from about 5% to about 90%, and most preferably from about 70% to about 90% of the emollient component.

Oils that act as emollients also impart viscosity, tackiness, and drag properties to cosmetic compositions such as lipstick. Examples of suitable oils include caprylic triglycerides; capric triglyceride; isostearic triglyceride; adipic triglyceride; propylene glycol myristyl acetate; lanolin; lanolin oil; polybutene; isopropyl palmitate; isopropyl myristate; isopropyl isostearate; diethyl sebacate; diisopropyl adipate; tocopheryl acetate; tocopheryl linoleate; hexadecyl stearate; ethyl lactate; cetyl oleate; cetyl ricinoleate; oleyl alcohol; hexadecyl alcohol; octyl hyroxystearate; octyl dodecanol; wheat germ oil; hydrogenated vegetable oils; castor oil; petrolatum; modified lanolins; branched-chain hydrocarbons; alcohols and esters; corn oil; cottonseed oil; olive oil; palm kernel oil; rapeseed oil; safflower oil; jojoba oil; evening primrose oil; avocado oil mineral oil, sheabutter, octylpalmitate, maleated soybean oil, glycerol trioctanoate, diisopropyl dimerate, and volatile and non-volatile silicone oils including phenyl trimethicone.

Suitable oils for use herein are acetylglycerides, octanoates, and decanoates of alcohols and polyalcohols, such as those of glycol and glycerol, the ricinoleates of alcohols and polyalcohols such as cetyl ricinoleate, PG-3 diisostearate, polyglycerol ethers, polyglyerol esters, caprylic triglycerides, capric triglycerides, isostearic triglyceride, adipic triglyceride, phenyl trimethicone, lanolin oil, polybutene, isopropyl palmitate, isopropyl isostearate, cetyl ricinoleate, octyl dodecanol, oleyl alcohol, hydrogenated vegetable oils, castor oil, modified lanolins, octyl palmitate, lanolin oil, maleated soybean oil, cetyl ricinoleate, glyceryl trioctanoate, diisopropyl dimerate, synthetic lanolin derivatives and branched chain alcohols, sucrose esters of fatty acids, octyl hydroxystearate and mixtures thereof.

Preferably, the oils used are selected such that the majority (at least about 75%, preferably at least about 80% and most preferably at least about 99%) of the types of oils used have solubility parameters that do not differ by more than from about 1 to about 0.1, preferably from about 0.8 to about 0.1.

A surfactant may also be added to compositions of the invention, in order to confer beneficial cosmetic or application properties. Surfactants suitable for use are those which can form emulsions and/or association structures. Surfactant emulsifier can be from 0% to about 20% of the formulation, preferably from 0% to about 15% and most preferably from about 1% to about 10%. Examples of suitable emulsifiers can be found in U.S. Pat. No. 5,085,856 to Dunphy et al.; and U.S. Pat. No. 5,688,831 to El-Nokaly et al. Examples of other suitable emulsifiers can be found in Cosmetic Bench Reference, pp. 1.22, 1.24-1.26 (1996), all of which are incorporated herein by reference.

Also useful herein are surfactants that form association structures, preferably lamellar or hexagonal liquid crystals, at ambient temperature when mixed with a polar solvent. Ambient temperature/room temperature as used herein typically means about 20° C. Generally ambient temperature can range from about 18° C. to about 27° C., preferably from about 20° C. to about 25° C., depending on such variables as geographical location, i.e. sub-tropical vs. temperature regions. One of ordinary skill in art is readily able to determine if association structures form at ambient temperatures. The surfactants suitable for use generally have a Krafft point at or below about ambient temperature about 20° C. or generally at or below about 18° C. to about 27° C., preferably at or below from about 20° C. to about 25° C.

The definition of Krafft point is well known in the art and one of ordinary skill in the art can readily determine a surfactant's Krafft point. In general terms, Krafft point is the melting point of the hydrocarbon chains of the surfactants. It can also be expressed as the temperature at which the solubility of an association colloid in water suddenly increases because critical micelle concentration is exceeded and micelles form.

In preparing a sample combination of surfactant and polar solvent to demonstrate the ability to form association structures, the surfactant needs to be sufficiently soluble in the polar solvent such that an association structure can form at ambient temperature. One of ordinary skill in the art is capable of determining compatible interactions.

Any surfactant which forms association structures at ambient temperature and is suitable for use in cosmetics is suitable for use herein. Surfactants suitable for use in cosmetics do not present dermatological or toxicological problems. Anionic surfactants, nonionic surfactants, cationic surfactants, amphoteric surfactants and mixtures thereof are suitable for use. Preferably anionic surfactants, nonionic surfactants, cationic surfactants, amphoteric surfactants and mixtures thereof having a Krafft point at or below about ambient temperature are used. More preferably, nonionic surfactants, cationic surfactants, amphoteric surfactants and mixtures thereof having a Krafft point at or below about ambient temperature are used.

The surfactants can be used at levels from about 4% to about 97%, preferably from about 5% to about 95%, more preferably from about 20% to about 90% and most preferably from about 30% to about 70% of the association structure.

The cosmetic compositions of this invention can contain one or more materials, herein singly or collectively referred to as a "solidifying agent", that are effective to solidify the particular liquid base materials to be used in a cosmetic composition. (As used herein, the term "solidify" refers to the physical and/or chemical alteration of the liquid base material so as to form a solid or semi-solid at ambient conditions, i.e., to form a final composition that has a stable physical structure and can be deposited on the skin under normal use conditions.) As is appreciated by those skilled in the art, the selection of the particular solidifying agent for use in the cosmetic compositions will depend upon the particular type of composition desired, i.e., gel or wax-based, the desired rheology, the liquid base material used and the other materials to be used in the composition. The solidifying agent is preferably present at a concentration of from about 0 to about 90%, more preferably from about 1 to about 50%, even more preferably from about 5% to about 40%, most preferably from about 3% to about 20%.

The wax cosmetic stick embodiments of this invention preferably contain from about 5% to about 50% (by weight) of a waxy solidifying agent. By the term "waxy solidifying agent," as used herein, is meant a solidifying material having wax-like characteristics. Such waxy materials may also serve as emollients. Among the waxy materials useful herein are the high melting point waxes, i.e., having a melting point of from about 65° C. to about 125° C., such as beeswax, spermaceti, carnauba, baysberry, candelilla, montan, ozokerite, ceresin, paraffin, synthetic waxes such as Fisher-Tropsch waxes, microcrystalline wax, and mixtures thereof. Ceresin, ozokerite, white beeswax, synthetic waxes, and mixtures thereof, are among those useful herein are disclosed in U.S. Pat. No. 4,049,792, Elsnau, issued Sep. 20, 1977, herein incorporated by reference in its entirety). Low melting waxes, having a melting point of from about 37° C. to about 75° C., are preferred for use in the wax stick embodiments of this invention. Wax stick embodiments of this invention, which contain volatile silicone oils as a liquid base material, preferably contain from about 10% to about 35%, more preferably from about 10% to about 20% (by weight), of a low-melting wax. Such materials include fatty acids, fatty alcohols, fatty acid esters and fatty acid amides, having fatty chains of from about 8 to about 30 carbon atoms, and mixtures thereof. Preferred wax-like materials include cetyl alcohol, palmitic acid, stearyl alcohol, behenamide, sucrose esters of tallow fatty acids, mono and di-fatty acid esters of polyethylene glycol, and mixtures thereof. Stearyl alcohol, cetyl alcohol, and mixtures thereof, are particularly preferred. Additional fatty acids, fatty alcohols, and other wax-like materials useful in this invention are also well known in the art.

EXAMPLES

The following preparations and examples are given to enable those skilled in the art to more clearly understand and to practice the present invention. They should not be considered as limiting the scope of the invention, but merely as being illustrative and representative thereof.

General Characterization Methods

Nuclear Magnetic Resonance (NMR) spectra were recorded on a Bruker DTX 300 spectrometer using, in most cases, tetramethyl silane (TMS) as the internal reference. Mass spectra were obtained on an Agilent 1100 LC/MSD instrument using either electrospray ionization (positive or negative mode) (ESI) or atmospheric pressure chemical ionization (positive or negative mode) (APCI).

Example 1

Preparation of 4-[2-(3,4-bis-methoxymethoxy-phenyl)-vinyl]-benzoic Acid Ethyl Ester

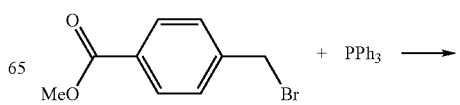

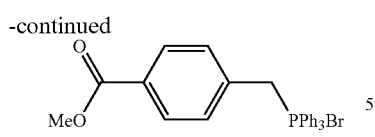

1A.
(4-Methoxycarbonyl-benzyl)-triphenyl-phosphonium bromide

A solution of methyl 4-(bromomethyl)-benzoate (2.29 g, 10 mmol) and triphenylphosphine (2.62 g, 10 mmol) in toluene (40 mL) was refluxed for 2 hours and then cooled down to room temperature. The precipitate was filtered and dried under vacuum, giving 4.71 g (95%) of white solid.

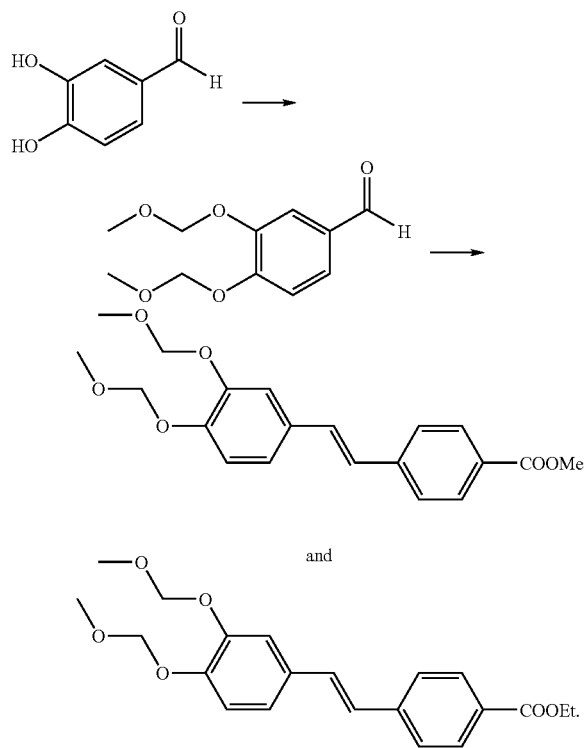

1B. 3,4-Bis-methoxymethoxy-benzaldehyde

To a solution of 3,4-dihydroxbenzaldehyde (2.76 g, 20 mmol, Adrich) in anhydrous N,N-dimethylformamide (DMF, 50 mL, Adrich) was added sodium hydride (1.76 g, 44 mmol, 2.2 eq, 60% in mineral oil, Adrich) portionwise under nitrogen at 0° C. The reaction mixture was stirred at room temperature for 30 min. To the dark blue mixture was added chloromethyl methylether (6.1 mL, 6.44 g, 80 mmol, 4.0 eq, tech, Adrich) dropwise with an ice-water bath and anhydrous potassium carbonate (8.29 g, 60 mmol, 3.0 eq). The brown mixture was heated at 50-55° C. for 3 hours. After the reaction mixture was cooled down, water was added and extracted with ethyl acetate. The organic phase was washed with water, separated, dried over anhydrous magnesium sulfate and chromatographed (silica gel, hexane-methylene chloride 1:1). This gave a pal-yellow liquid as the MOM-ether masked benzaldehyde: 3,4-Bis-methoxymethoxy-benzaldehyde (100% yield).

1C.
4-[2-(3,4-Bis-methoxymethoxy-phenyl)vinyl]-benzoic acid ethyl ester

To a mixture of 3,4-bis-methoxymethoxy-benzaldehyde (100 mmol) and (4-methoxycarbonyl-benzyl)-triphenyl-phosphonium bromide (100 mmol) in of EtOH (300 mL) at 0° C. was added slowly of a lithium ethoxide solution (101 mL, 1 M in EtOH). Upon the completion of the addition, the cold bath was removed and the reaction was allowed to warm to room temperature. The stirring was continued for additional 2 h. The solvent was then removed by rotary evaporation and residue was taken up to 500 mL of EtOAc and washed with ammonium chloride solution (2×100 mL) and water. The organic layer was dried over $Na_2SO_4$ and the crude product was purified on silica (hexane:EtOAc=2:1) to afford a clear sticky solid (yield 99%). NMR indicated the purified product is a mixture of cis/trans isomers containing ethyl and methyl esters. $^1$H-NMR (300 MHz, $CDCl_3$) δ 8.02 (d, J=0.84, 1.5H), 7.93 (d, J=0.84, 0.5H), 7.91 (s, 0.3H), 7.55 (s, 0.75H), 7.52 (s, 0.75H), 7.38-7.33 (m, 1.25H), 7.17-7.12 (m, 2.25H), 7.03-6.98 (m, 1.25H), 6.84 (m, 0.25H), 6.61-6.52 (m, 0.5H), 5.29-5.05 (m, 4H), 4.41-4.25 (m, 1H), 3.90 (s, 1.5H), 3.56-3.39 (m, 6H), 1.40 (q, J=6 Hz, 1.5H).

1D. 4-[2-(3,4-Bis-methoxymethoxy-phenyl)-vinyl]-benzoic acid methyl ester

By following the procedures of Example 1C and substituting the ethanol there used with methanol, the title compound is obtained without the presence of the corresponding ethyl ester.

1E. Other Compounds of Formula I

Similarly, by following the procedures of Example 1A, 1B and 1C and substituting 4-(bromomethyl)-benzoate and 3,4-dihydroxbenzaldehyde accordingly, there are obtained:

- 4-[2-(3,4-Bis-methoxymethoxy-phenyl)-vinyl]-benzoic acid methyl ester
- 4-[2-(3,4-Dihydroxy-phenyl)-vinyl]-benzoic acid methyl ester
- 4-[(2-Pentafluorophenyl-vinyl)-benzene-1,2-diol
- 4-[2-(4-Trifluoromethyl-phenyl)-vinyl]-benzene-1,2-diol
- 4-[2-(4-Fluoro-phenyl)-vinyl]-benzene-1,2-diol
- 4-(2-{4-[2-(3,4-Bis-methoxymethoxy-phenyl)-vinyl]-phenyl}-vinyl)-benzoic acid ethyl ester
- 4-[2-(3,4-Dihydroxy-phenyl)-vinyl]-benzoic acid decyl ester
- 4-[2-(3,4-Dihydroxy-phenyl)-vinyl]-benzoic acid hexyl ester
- 4-[2-(3,4-Bis-methoxymethoxy-phenyl)-vinyl]-benzoic acid 3,7-dimethyl-octa-2,7-dienyl ester
- 4-[2-(3,4-Dihydroxy-phenyl)-vinyl]-benzoic acid 3,7-dimethyl-octa-2,6-dienyl ester
- 4-[2-(3,4-Bis-methoxymethoxy-phenyl)-vinyl]-benzoic acid tetradecyl ester
- 4-[2-(3,4-Bis-methoxymethoxy-phenyl)-vinyl]-benzoic acid heptadec-12-enyl ester
- 4-[2-(3,4-Dihydroxy-phenyl)-vinyl]-benzoic acid hex-3-enyl ester
- 4-[2-(3,4-Bis-methoxymethoxy-phenyl)-vinyl]-benzoic acid hex-3-enyl ester 4-[2-(3-Hydroxy-4-{2-[2-(2-methoxy-ethoxy)-ethoxy]-ethoxy}-phenyl)-vinyl]-benzoic acid ethyl ester 4-[2-(4-Hydroxy-3-methoxy-phenyl)-vinyl]-benzonitrile 4-[2-(4-Hydroxy-3-methoxy-phenyl)-vinyl]-benzoic acid methyl ester 5-[2-(3,4-Dihydroxy-phenyl)-vinyl]-2-hydroxy-benzoic acid ethyl ester 3-[2-(3,4-Dihydroxy-phenyl)-vinyl]-benzoic acid ethyl ester, and 4-[2-(3,5-Dihydroxy-phenyl)-vinyl]-benzoic acid methyl ester;

and, the following compounds of Formula I have been obtained:

2-[2-(3,4-Dihydroxy-phenyl)-vinyl]-anthraquinone, $^1$HNMR (300 MHz, DMSO) δ (ppm) 8.28-7.92 (m, 6H), 7.90-6.47 (m, 5H), 5.74 (s, H). ESI(+)/MS: 343 (M+H)$^+$, 365 (M+Na)$^+$;

4-[2-(1H-Benzoimidazol-5-yl)-vinyl]-benzoic acid methyl ester, $^1$HMNR (300 MHz, CDCL$_3$) δ (ppm) 8.04-7.98 (m, 2H), 7.87-7.84 (d, J=8.43, H), 7.64-7.34 (m, 3H), 7.33-7.12 (m, 2H), 6.86-6.82 (q, H), 3.93-3.82 (m, 3H);

4-[2-(6-Nitro-benzo[1,3]dioxol-5-yl)-vinyl]-benzoic acid methyl ester, $^1$HMNR (300 MHz, CDCL$_3$) δ (ppm) 8.06-7.86 (dd, J=8.4, 2H), 7.78-7.59 (m, 2H), 7.16-7.12 (m, H), 6.99-6.71 (dd, J=12, H), 6.51-6.07 (m, 2H), 3.93-3.89 (d, J=12.6, 2H), 1.56 (s, 3H);

4-[2-(3-Iodo-5-methoxy-4-methoxymethoxy-phenyl)-vinyl]-benzoic acid methyl ester, $^1$H NMR (300 MHz CDCl$_3$) δ (ppm) 7.90-8.02 (dd, J=8.5 2H), 7.50-7.55 (m, H), 7.26-7.34 (m, 2H), 7.0-7.02 (m, H), 6.53-6.68 (m, 2H), 5.13-5.18 (d, 2H), 3.50-3.90 (m, 9H). ESI(+)/MS: 477 (M+Na)$^+$;

4-[2-(4-Hydroxy-3-iodo-5-methoxy-phenyl)-vinyl]-benzoic acid methyl ester, $^1$H NMR (300 MHz CDCl$_3$) δ (ppm) 7.91-8.03 (dd, J=8.4 2H), 7.47-7.53 (m, 2H), 7.32-7.35 (m, H), 6.98-7.02 (m, 2H), 6.53-6.64 (d, H), 3.49-3.94 (m, 6H), ESI(+)/MS: 411 (M+H)$^+$, 433 (M+Na)$^+$;

3,4-Bis-[2-(3,4-dihydroxy-phenyl)-vinyl]-benzoic acid methyl ester, $^1$H NMR (300 MHz CD$_3$OD) δ (ppm) 6.49-8.26 (m, 13H), 4.26-4.46 (m, H), 3.80-3.90 (m, 3H), ESI(+)/MS: 405 (M+H)$^+$; and 4-[2-(5-Bromo-2-hydroxy-4-methoxy-phenyl)-vinyl]-benzoic acid methyl ester, $^1$H NMR (300 MHz CDCl3) δ (ppm), 7.99-7.87 (dd, J=8.5, 2H), 7.31-7.28 (d, J=8.4, 2H), 6.88-6.83 (m, 2H), 6.80 (s, 2H), 5.8 (s, H), 3.90-3.85 (m, 6H). ESI(+)/MS: 364 (M+H)$^+$, 386 (M+Na)$^+$.

Example 2

Preparation of 4-[2-(3,4-Dihydroxy-phenyl)-vinyl]-benzoic acid ethyl ester

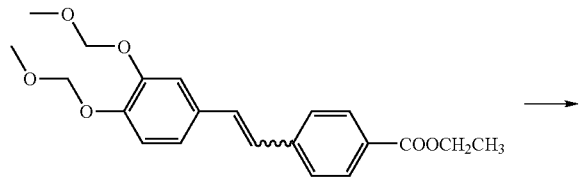

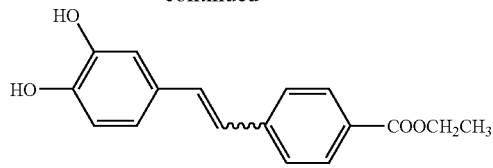

2A

To a solution of 4-[2-(3,4-bis-methoxymethoxy-phenyl)-vinyl]-benzoic acid ethyl ester (1.0 mmol) of 3 in MeOH (100 mL) at room temperature was added slowly 15 drops of a concentrated HCl solution. The resulting solution was stirred for 12 h. The solvent was then evaporated under reduced pressure and the residue was chromatographed (hexane: EtOAc=1:1) to afford the product as a yellow solid (yield 90%). NMR indicated the purified product contains cis/trans isomers and both ethyl and methyl esters. $^1$H-NMR (300 MHz, CD$_3$OD) δ 7.98 (d, J=8.4 Hz, 1.82H), 7.87(d, J=8.4 Hz, 0.18H), 7.54 (d, J=8.4 Hz, 1.82H), 7.37 (d, J=8.4 Hz, 0.18H), 7.16-6.92 (m, 4H), 6.81 (m, 1H), 4.41-4.35 (m, 1.9H), 3.92 (m, 0.5H), 1.41 (m, 2.8H).

2B. Other Compounds of Formula I

Similarly, by following the procedures of Example 2A, there are obtained:

4-[2-(3,4-Bis-{2-[2-(2-methoxy-ethoxy)-ethoxy]-ethoxy}-phenyl)-vinyl]-benzoic acid ethyl ester, $^1$HMNR (300 MHz, CDCL$_3$) δ (ppm) 8.03-7.88 (dd, J=8.5, 2H), 7.55-7.31 (d, J=8.3, 2H), 7.14-6.92 (m, 2H), 6.77 (s, 2H), 6.62-6.53 (q, 1H), 4.22-4.14 (m, 3H), 3.92-3.87 (m, 8H), 3.75-3.68 (m, 4H), 3.66-3.64 (m, 10), 3.56-3.54 (m, 4H), 3.37 (s, 6H);

2-[2-(2-{2-{2-[2-(2-Hydroxy-ethoxy)-ethoxy]-ethoxy)-5-[2-(4-nitro-phenyl)-vinyl]-phenoxy)ethoxy)-ethoxy]-ethanol, $^1$HMNR (300 MHz, CDCL$_3$) δ (ppm) 8.14-8.00 (dd, J=8.9, 2H) 7.55-7.33 (dd, J=8.9, 2H) 7.18-6.86 (m, 1H), 6.86-6.44 (m, 4H), 4.24-4.10 (m, 3H) 3.89-3.72 (m, 4H), 3.68-3.54 (m, 20H). ESI(+)/MS: 522 (M+H)$^+$, 545 (M+Na)$^+$;

4-[2-(3,4-Bis-{2-[2-(2-methoxy-ethoxy)-ethoxy]-ethoxy}-phenyl)-vinyl]-benzoic acid tetradecyl ester, $^1$HMNR (300 MHz, CD$_3$OH) δ (ppm) 7.97-7.95 (d, J=6.0, 2H) 7.62-7.60 (d, J=5.1, 2H) 7.35-6.96 (m, 5H) 4.29-4.34 (m, 6H) 3.99-3.88 (m, 4H), 3.88-3.74 (m, 4H), 3.67-3.45 (m, 8), 3.45-3.32 (m, 4H), 1.19-1.76 (m, 2H), 1.52-1.27 (m, 23H), 0.88-0.86 (m, 3H). ESI(+)/MS: 717 (M+H)$^+$, 739 (M+Na)$^+$;

4-[2-(3,4-Bis-{2-[2-(2-hydroxy-ethoxy)-ethoxy]-ethoxy}-phenyl)-vinyl]-benzoic acid 2-[2-(2-hydroxy-ethoxy)-ethoxy]-ethyl ester, $^1$HMNR (300 MHz, CD$_3$OH) δ (ppm) 8.00-7.97 (dd, 2H) 7.62-7.60 (d, 2H) 7.26-6.97 (m, 5H) 4.35-4.32 (m, 4H) 4.27-4.15 (m, 4H), 3.87-3.76 (m, 6H), 3.75-3.67 (m, 21), 3.08-3.07 (m, 2H). ESI(+)/MS: 653 (M+H)$^+$; and 4-[2-(3,4-Bis-{2-[2-(2-methoxy-ethoxy)-ethoxy]-ethoxy}-phenyl)-vinyl]-N-(2-hydroxy-1,1-bis-hydroxymethyl-ethyl)-benzamide, $^1$HMNR (300 MHz, CDCl$_3$) δ (ppm) 7.99-7.96 (d, J=7.6, 2H), 7.51-7.49 (d, J=7.9, 2H), 7.12-7.02 (m, 3H), 6.95-6.86 (m, 2H), 4.42-4.37 (s, 2H), 4.22-4.18 (m, 4H), 3.88-3.77 (m, 4H), 3.76-3.75 (m, 4H), 3.70-3.67 (m, 12H), 3.57-3.55 (m, 5H), 3.39-3.37 (m, 7H), 3.18 (bs, 6H). ESI(+)/MS: 651 (M+H)$^+$, 674 (M+Na)$^+$.

Example 3

Preparation of 4-[2-(3,4-Dimethoxymethoxy-phenyl)-vinyl]-nitrobenzene

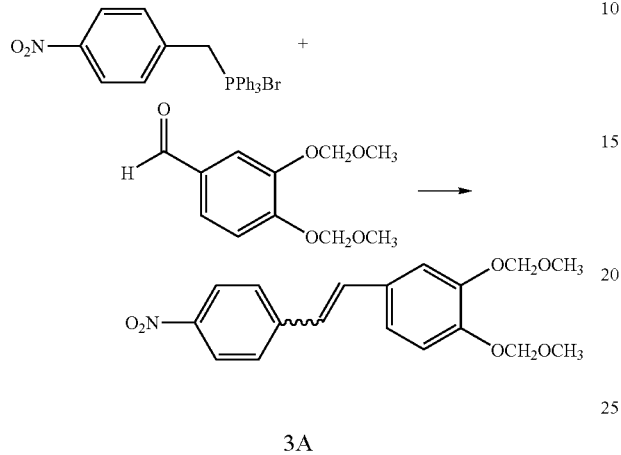

3A

To a solution of (4-nitrobenzyl)-triphenyl-phosphonium bromide (725 mg, 1.51 mmol, prepared in 97% yield in a similar way as described in Example 1) and 3,4-bis-methoxymethoxy-benzaldehyde (299 mg, 1.38 mmol) in ethanol (20 mL) was added lithium ethoxide (1.45 mL, 1.45 mmol, 1 M in tetrahydrofuran) at room temperature over 4 hours. The resulting solution was stirred at room temperature overnight. The solvent was removed under reduced pressure and the residues were chromatographed (silica gel, methylene chloride), affording an orange-red product (214 mg, 41%). $^1$H-NMR (300 Hz, D$_3$CCl) δ (ppm) 8.25-8.05 (m, 2H), 7.65-6.95 (m, 5H), 6.85-6.50 (m, 2H), 5.31 (s, CH$_2$, 40%), 5.28 (s, CH$_2$, 40%), 5.23 (s, CH$_2$, 60%), 5.05 (s, CH2, 60%), 3.56 (s, CH$_3$, 40%), 3.53 (s, CH$_3$, 40%), 3.51 (s, CH$_3$, 60%), 3.38 (s, CH$_3$, 60%).

3B. Other Compounds of Formula I

Similarly, by following the procedures of Example 3A, there are obtained:

2-Methoxymethoxy-1,3-dimethyl-5-[2-(4-nitro-phenyl)-vinyl]-benzene, $^1$H-NMR (CDCl$_3$, 300 MHz) δ (ppm): 8.21-8.18 (d, J=8.8 Hz, 1H), 8.09-8.06 (d, J=8.9 Hz, 1H), 7.61-7.58 (d, J=8.8 Hz, 1H), 7.42-7.39 (d, J=8.8 Hz, 1H), 7.26-7.05 (m, 2H), 6.87 (s, 1H), 6.71-6.67 (d, J=12.2 Hz, 0.5H) 6.53-6.49 (d, J=12.2 Hz, 0.5H); 4.99-4.96 (d, J=8.1, 2H), 3.62-3.61 (d, J=4.2, 3H), 2.33, 2.20 (2s, combined 6H), MS(ESI) m/z: 314 (M+H$^+$, 80), 336 (M+Na$^+$, 100);

2-Methoxymethoxy-5-[2-(4-nitro-phenyl)-vinyl]-benzoic acid methoxymethyl ester, $^1$HMNR (300 MHz, CDCL$_3$) δ (ppm) 8.26-8.11 (dd, J=8.7, 2H), 7.72-7.40 (m, 3H), 7.31-7.07 (m, 3H), 6.73-6.61 (q, H), 5.53-5.27 (m, 4H), 3.96-3.31 (m, 6H), ESI(+)/MS: 386 (M+Na)$^+$;

1,2-Bis-methoxymethoxy-4-[4-(4-nitro-phenyl)-buta-1,3-dienyl]-benzene, $^1$HMNR (300 MHz, CD$_3$OH) δ (ppm) 8.24-8.16 (m, 2H), 7.54-7.50 (m, 2H), 7.26-7.17 (m, 4H), 6.98-6.48 (m, 3H), 5.30-5.23 (m, 4H), 3.55-3.50 (m, 6H), ESI(+)/MS: 394 (M+Na)$^+$;

2-Iodo-6-methoxy-4-[2-(4-nitro-phenyl)-vinyl]-phenol, $^1$H NMR (300 MHz CDCl$_3$) δ 7.43-7.61 (m, 4H), 6.95-7.14 (m, 3H), 6.52-6.63 (m, H), 3.64-3.97 (m, 3H);

2,6-Di-tert-butyl-4-[2-(4-nitro-phenyl)-vinyl]-phenol, $^1$HMNR (300 MHz, CDCL$_3$) δ (ppm) 8.24-8.17 (d, J=8.7, 2H), 7.65-7.62 (d, J=8.6, 2H), 7.41 (s, 2H), 7.28-6.93 (dd, 2H), 1.57-1.51 (m, 18H), ESI(+)/MS: 354 (M+H)$^+$;

2-Bromo-6-methoxy-4-[2-(4-nitro-phenyl)-vinyl]-phenol, $^1$H NMR (300 MHz CD$_3$OD) δ (ppm) 8.04-8.00 (d, J=9.3, 2H), 7.30-7.27 (d, J=9.4, 2H), 6.80-6.77 (d, J=12.0, H), 6.67-6.59 (m, 3H), 6.06 (s, H), 3.88 (s, 3H), ESI(+)/MS: 351 (M+H)$^+$, 431 (M+Na)$^+$;

4-Bromo-5-methoxy-2-[2-(4-nitro-phenyl)-vinyl]-phenol, $^1$H NMR (300 MHz CD$_3$OD) δ (ppm) 8.10-8.07 (d, J=8.8, 2H), 7.40-7.36 (d, J=8.8, 2H), 6.93-6.66 (m, 3H), 5.80 (s, H), 3.92 (s, 3H), ESI(+)/MS: 351 (M+H)$^+$, 373 (M+Na)$^+$;

3-(3,4-Bis-methoxymethoxy-benzylidene)-3H-benzofuran-2-onel ESI(+)/MS: 465 (M+Na)$^+$;

3-(3,4-Dihydroxy-benzylidene)-5-hydroxy-3H-benzofuran-2-one, $^1$H NMR (300 MHz CDCl3) d 8.56-7.79 (m, H), 7.58-7.22 (m, 4H), 7.04-6.70 (m, 2H), 5.33 (s, 2H), 5.21-5.20 (s, H), 4.01-3.55 (m, 6H), 1.83-1.60 (m, 8H), ESI(+)/MS: 413 (M+H)$^+$, 435 (M+Na)+; and 3-(3,5-Bis-methoxymethoxy-benzylidene)-3H-benzofuran-2-one. $^1$H NMR (300 MHz CDCl$_3$) δ 7.83-7.76 (m, H), 7.59-7.51 (m, H), 7.43-6.95 (m, 5H), 6.83-6.82 (m, H), 5.19 (d, 4H), 3.50 (s, 6H), ESI(+)/MS: 343 (M+H)$^+$, 365 (M+Na)$^+$.

Example 4

Preparation of 4-[2-(4-Nitro-phenyl)-vinyl]-benzene-1,2-diol

4A

A solution of 4-[2-(3,4-Dimethoxymethoxy-phenyl)-vinyl]-nitrobenzene (100 mg) in ethanol (20 mL) was added 5 drops of concentrated hydrochloric acid water solution. The resulting solution was stirred at room temperature for two days. Solvents were removed under reduced pressure. The residue was dissolved in methylene chloride and washed with water. The water phase was adjusted to pH 6-7. Organic phase was separated and dried over magnesium sulfate. Evaporation off solvents gave the title compound (which can also be named 4-[2-(3,4-Dihydroxy-phenyl)-vinyl]-nitrobenezene) a dark-brown solid (60 mg, 81%). $^1$H-NMR (300 Hz, D$_3$CCl) δ (ppm) 8.10-7.90 (m, 2H), 7.50-7.25 (m, 2H), 7.10-6.25 (m, 5H).

4B. Other Compounds of Formula I

Similarly, by following the procedures of Example 4A and substituting 4-[2-(3,4-dimethoxymethoxy-phenyl)-vinyl]-nitrobenzene accordingly, there are obtained:

4-[2-(3,4,5-Trimethoxy-phenyl)-vinyl]-nitrobenezene

2-Methoxy-4-[2-(4-nitro-phenyl)-vinyl]-phenol, and

5[2-(4-Nitro-phenyl)-vinyl]benzene-1,3-diol;

and, the following compounds of Formula I have been obtained:

1-{4-[2-(3,4-Dihydroxy-phenyl)-vinyl]-phenyl}-ethanone oxime, $^1$H NMR (MeOD, 300 MHz) δ (ppm): 7.72 (m, 3H), 7.18 (m, 6H). MS (ESI) m/z: 295 (M+H$^+$);

5-{2-[4-Hydroxy-3-(3-meth)-4-but-2-enyl)-phenyl]-vinyl}-2-(3-methyl-but-2-en)-4)-benzene-1,3-diol, $^1$H NMR (CDCl3, 300 MHz) δ (ppm): 7.23 (s, 2H), 6.96 (d, J=16.3, 1H), 6.80 (m, 2H), 6.55 (d, 2H), 5.32 (t, 1H), 5.27 (t, 1H), 5.19 (s, 1H), 5.12 (s, 2H), 3.43 (d, J=7.1, 2H), 3.38 (d, J=7.3, 2H), 1.77 (m, 12H) ppm, MS (ESI) m/z: 364 (M+H$^+$);

4-{2-[3,5-Bis-methoxymethoxy-4-(3-methyl-but-2-enyl)-phenyl]-vinyl}-2,6-dimethoxy-phenol, $^1$H NMR (CDCl$_3$, 300 MHz) δ (ppm): 6.93 (d, J=16.2, 1H), 6.80 (d, J=16.1, 1H), 6.71 (s, 2H), 6.54 (s, 2H), 5.60 (s, 1H), 5.30 (s, 2H), 5.28 (t, 1H), 3.93 (s, 6H), 3.44 (d, J=6.98, 2H), 1.83 (s, 3H), 1.76 (m, 3H), MS (ESI) m/z: 357 (M+H), 379 (M+Na);

5-[2-(4-Hydroxy-3-methoxy-5-nitro-phenyl)-vinyl]-2-(3-methyl-but-2-enyl)-benzene-1,3-diol, $^1$H NMR (CDCl$_3$, 300 MHz) δ (ppm): 7.58 (d, J=1.65, 2H), 7.04 (d, J=1.83, 2H), 6.54 (d, J=16.1, 1H), 6.44 (d, J=16.2, 1H), 6.46 (s, 2H), 5.27 (t, 1H), 3.66 (s, 3H), 3.40 (d, J=3.5, 2H), 1.81 (s, 3H), 1.76 (s, 3H), MS (ESI) m/z: 372 (M+H), 394 (M+Na);

5-[2-(4-Hydroxy-3-nitro-phenyl)-vinyl]-2-(3-methyl-but-2-enyl)-benzene-1,3-diol, $^1$H NMR (CDCl$_3$, 300 MHz) δ (ppm): 8.20 (d, J=2.18, 1H), 8.04 (d, J=2.0, 1H), 7.80 (m, 1H), 7.54 (m, 1H), 7.22 (d, J=8.74, 1H), 7.05 (d, J=8.72, 1H), 6.95 (s, 2H), 6.61 (s, 2H), 6.59 (d, J=12.25, 1H), 6.50 (d, J=12.12, 1H), 6.31 (s, 2H), 5.27 (t, 2H), 5.25 (s, 2H), 5.14 (s, 2H), 3.646 (s, 4H), 1.87(m, 12H), MS (ESI) m/z: 342 (M+H);

2-Chloro-4-[2-(4-nitro-phenyl)-vinyl]-phenol, $^1$H NMR (CDCl$_3$, 300 MHz) δ (ppm): 8.26 (d, J=8.87, 2H), 7.64 (d, J=8.78, 2H), 7.57 (d, J=2.07, 1H), 7.31 (d, J=8.30, 1H), 7.15 (d, J=12.20, 1H), 7.06 (t, 2H), 5.69 (s, 1H), MS (ESI) m/z: 276 (M+H);

Z-4-[2-(4-Nitro-phenyl)-vinyl]-benzene-1,2,3-triol, $^1$H NMR (CDCl$_3$, 300 MHz) δ (ppm): 8.13 (d, J=8.82, 2H), 7.54 (d, J=8.7, 2H), 6.86 (d, J=12.2, 1H), 6.74 (d, J=12.2, 1H), 6.64 (d, J=8.5, 1H), 6.48 (d, J=8.4, 1H), 5.29 (m, 3H), MS (ESI) m/z: 275 (M+H);

E-4-[2-(4-Nitro-phenyl)-vinyl]-benzene-1,2,3-triol, $^1$H NMR (CDCl$_3$, 300 MHz) δ (ppm): 8.35 (d, J=8.82, 2H), 7.64 (d, J=8.7, 2H), 7.49 (d, J=16.2, 1H), 7.17 (d, J=16.2, 1H), 7.04 (d, J=12.09, 1H), 6.50 (d, J=8.6, 2H), 5.72 (s, 1H), 5.30 (s, 1H), 5.22 (s, 1H);

2-Methoxy-4-[4-(4-nitro-phenyl)-buta-1,3-dienyl]-phenol, $^1$H-NMR (CDCl$_3$, 300 MHz) δ (ppm): 8.20-8.18 (d, J=8.9, 2H), 7.55-7.52 (d, J=8.9, 2H), 7.10-6.63 (m, 7H), 5.73 (s, 1H), 3.95 (s, 3H), MS(ESI) m/z: 298 (M+H$^+$, 100);

3-[2-(3,4-Dimethoxy-phenyl)-vinyl]4-nitro-phenol, $^1$H-NMR (CDCl$_3$, 300 MHz) δ (ppm): 8.12-8.15 (d, J=9.0 Hz, 0.4H), 8.05-8.02 (d, J=9.0 Hz, 0.6H), 7.61-7.56 (d, J=16.0 Hz, 0.6H), 7.12-6.55 (m, 6.3H), 3.98-3.59 (4s, combined 6H), MS(ESI) m/z: 302 (M+H$^+$, 25), 319 (M–H$_2$O, 20), 346 (MOM– M+H$^+$);

4-[2-(4-Hydroxy-3,5-dimethyl-phenyl)-vinyl]-benzoic acid methyl ester, $^1$H-NMR (CDCl$_3$, 300 MHz) δ (ppm): 8.03-8.00 (d, J=8.0 Hz, 2H), 7.53-7.50 (d, J=8.0 Hz, 2H), 7.18-6.93 (m, 4H), 5.15 (s, 1H), 3.93 (s, 3H), 2.29, 2.16 (2s, combined 6H), very small amounts of cis isomer, MS(ESI) m/z: 283 (M+H$^+$, 100);

2,6-Dimethyl-4-[2-(4-nitro-phenyl)-vinyl]-phenol, $^1$H-NMR (CDCl$_3$, 300 MHz) δ (ppm): 8.21-8.18 (d, J=8.8 Hz, 2H), 7.59-7.56 (d, J=8.8 Hz, 2H), 7.26-6.95 (m, 4H), 4.84 (s, 1H), 2.29 (s, 6H), very small amounts of cis isomer, MS(ESI) m/z: 270 (M+H$^+$, 100);

2-Hydroxy-5-[2-(4-nitro-phenyl)-vinyl]-benzoic acid, $^1$HMNR (300 MHz, CD$_3$OH) δ (ppm) 8.19-8.04 (m, 2H), 7.79-7.59 (m, 2H), 7.51-7.30 (m, 2H), 7.17-7.09 (m, H), 6.76-6.52 (m, 2H), ESI(+)/MS: 286 (M+H)$^+$;

4-[4-(Nitro-phenyl)-buta-1,3-dienyl]-benzene-1,2-diol, $^1$HMNR (300 MHz, CDCL$_3$) δ (ppm) 8.27-8.08 (m, 2H), 7.71-7.49 (m, 2H), 6.94-6.57 (m, 7H), ESI(+)/MS: 284 (M+H)$^+$, 306 (M+Na)$^+$;

3-(3,4-Dihydroxy-benzylidene)-3H-benzofuran-2-one, $^1$H NMR (300 MHz CD3OD) d 8.12-7.40 (m, H), 7.21-6.98 (m, 2H), 6.95-6.75 (m, 3H), ESI(+)/MS: 271 (M+H)+, 293 (M+Na)$^+$;

5-Hydroxy-3-(4-hydroxy-3-methoxy-benzylidene)-3H-benzofuran-2-one, $^1$H NMR (300 MHz CD3OD) d 8.51-7.70 (m, H), 7.58-7.26 (m, 3H), 7.01-6.74 (m, 3H), 3.95-3.91 (s, 3H), ESI(+)/MS: 285 (M+H)+, 307 (M+Na)$^+$; and 3-(3,5-Dihydroxy-benzylidene)-3H-benzofuran-2-one, $^1$H NMR (300 MHz CD3OD) d 7.91-7.87 (d, H), 7.70 (s, H), 7.43-7.3 (m, H), 7.25-7.12 (m, 2H), 6.64 (s, 2H), 6.41-6.39 (m, H), ESI(+)/MS: 255 (M+H)+, 277 (M+Na)$^+$.

Example 5

Preparation of 10-(3,4-Dihydroxy-benzylidene)-10H-anthracen-9-one

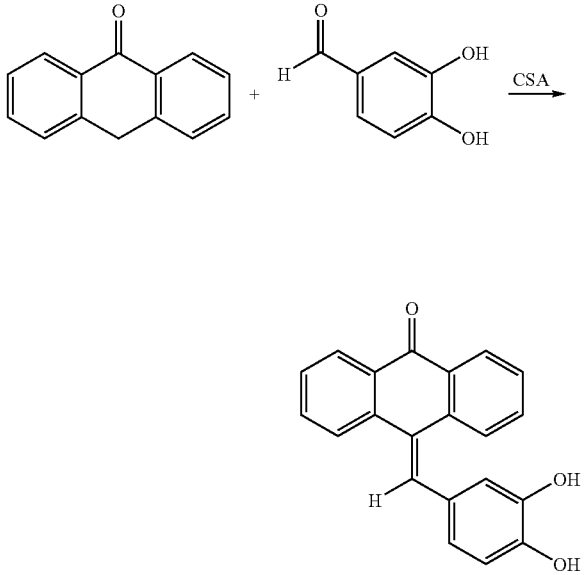

A solution of anthrone (194 mg, 1.0 mmol), 3,4-dihydroxybenzadehyde (138 mg, 1.0 mmol) and camphorsulfonic acid (232 mg, 1.0 mmol) in toluene (5 mL) was refluxed overnight. The solvents were removed under reduced pressure and the residues were chromatographed (silica gel, hexane-ethyl acetate 90:10 to 80:20), resulted in 50 mg of product. $^1$H-NMR (300 Hz, D$_3$COD) δ (ppm) 4.30-4.20 (m, 2H), 3.51 (br. s, 2H), 1.30 (t, J=7.1 Hz, 3H). $^{13}$C-NMR (75 Hz, Cl$_3$CD) δ (ppm) 184.7, 146.7, 146.1, 141.7, 137.5, 135.3, 133.7, 133.2, 131.8, 131.4, 130.2, 129.7, 129.6, 129.1, 128.3, 127.4, 127.2, 124.3, 122.8, 117.1, 116.4. MS (ESI) m/z 315 (M+1, 100).

Example 6

Preparation of 10-(3,4-Dihydroxy-benzylidene)-1,8-dihydroxy-10H-anthracen-9-one

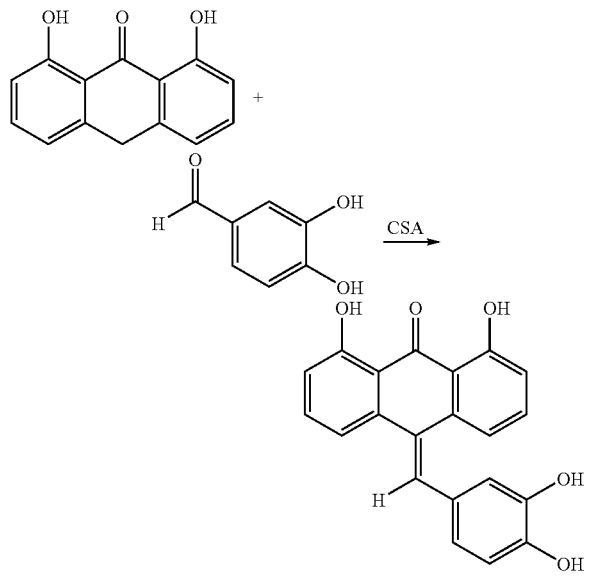

A solution of dithranol (452 mg, 2.0 mmol), 3,4-dihydroxybenzadehyde (276 mg, 2.0 mmol), and camphorsulfonic acid (464 mg, 2.0 mmol) in 10 mL toluene was refluxed overnight The solvents were removed under reduced pressure and the residues were chromatographed (silica gel, methylene chloride-methanol 1:0 to 100:1 to 100:2), yielded 190 mg of product (28%). $^1$H-NMR (300 Hz, D$_3$CCl) δ (ppm) 7.47 (t, J=8.0 Hz, 1H), 7.40-7.30 (m, 2H), 7.27-7.10 (m, 2H), 6.95-6.75 (m, 2H), 6.75-6.60 (m, 3H). $^{13}$C-NMR (75 Hz, Cl$_3$CD) δ (ppm) 192.8, 162.0, 161.5, 145.1, 144.5, 142.7, 137.8, 136.8, 136.8, 136.0, 134.4, 129.2, 128.7, 121.9, 121.0, 116.3, 115.8, 115.7, 115.3, 114.6, 114.0. MS (APCI) m/z 347 (M+1, 100).

Example 7

Preparation of 4-(2-Nitro-vinyl)-benzene-1, 2-diol

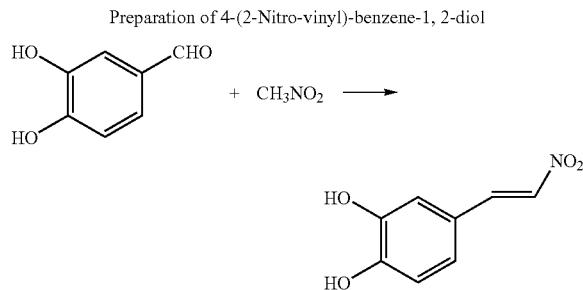

A mixture of aldehyde (500 mg) and ammonium acetate (180 mg) in nitromethane (11 mL) was stirred at 110° C. for 1 h. After cooling to room temperature, the mixture was poured into water and extracted with EtOAc. The EtOAc phase was washed with water and brine and then dried over MgSO$_4$. Removal of solvents under reduced pressure gave an orange solid (530 mg). Further purification by silica gel column eluting with dichloromethane: EtOAc: MeOH (70:30:2) afforded 520 mg of orange solid. $^1$H-NMR (300 MHz, acetone-d with D$_2$O) δ (ppm) 7.93 (d, J=13.5 Hz, 1H), 7.74 (d, J=13.5 Hz, 1H), 7.24 (d, J=2.1 Hz, 1H), 7.15 (dd, J=8.1, 2.0 Hz, 1H), 6.91 (d, J=8.1 Hz, 1H). $^{13}$C-NMR MHz, acetone-d) δ (ppm) 150.06, 146.14, 139.88, 135.39, 124.20, 122.88, 116.25, 115.98.

Example 8

Preparation of 4-{2-[4-(2-Nitro-vinyl)-phenyl]-vinyl}-benzene-1, 2-diol

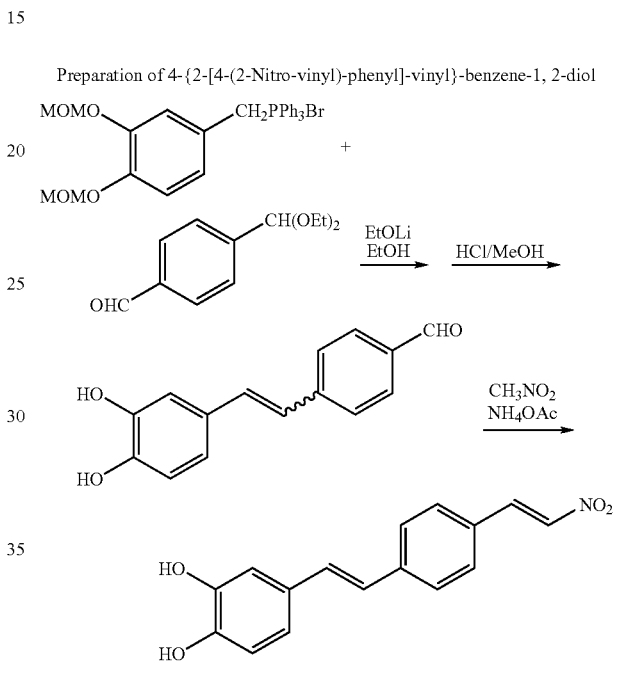

To a solution of (3,4-bis-methoxymethoxy-benzyl)-triphenyl-phosphonium bromide (720 mg) and 4-diethoxymethyl-benzaldehyd (308 mg) in EtOH (20 mL) was added EtOLi (1 M in EtOH solution, 2 mL) slowly over a period of 1 h. After stirring overnight, the solution was diluted with ethyl acetate and washed with water and brine, dried over MgSO$_4$ and then concentrated. The residue was dissolved in MeOH (20 mL) and conc. HCl (10 drops) was added. The solution was stirred at room temperature overnight. The low boiling point materials were stripped off and the residue was purified by silica gel column eluting with 40% EtOAc in hexane to give 190 mg of yellow solid 4-[2-(3,4-dihydroxy-phenyl)-vinyl]-benzaldehyde which was a mixture of cis and trans isomers. This intermediate (180 mg) and NH$_4$OAc (100 mg) were dissolve in nitromethane (10 mL). Then the mixture was stirred at 110° C. for 1 h. The solution was diluted with ethyl acetate and washed with water and brine, dried over MgSO$_4$, and then concentrated. The residue was purified using silica gel column eluting with 5% MeOH in dichloromethane to give a product as a red solid (126 mg). $^1$H-NMR (300 MHz, MeOD-d$_4$) δ (ppm) 8.03 (d, J=13.6 Hz, 1H), 7.86 (d, J=13.6 Hz, 1H), 7.63 (d, J=8.4 Hz, 1H), 7.56 (d, J=8.4 Hz, 1H), 7.15 (d, J=16.3 Hz, 1H), 7.04 (d, J=1.9 Hz, 1H), 6.94-6.87 (m, 2H), 6.77 (d, J=8.2 Hz, 1H). $^{13}$C-NMR (75 MHz, methonal-d$_4$) δ (ppm)

145.51, 144.80, 141.50, 138.02, 135.92, 130.81, 129.18, 128.70, 128.23, 126.05, 123.60, 119.14, 114.68, 112.34.

Example 9

Preparation of 1-Carboxymethyl-4-[2-(3,4-dihydroxy-phenyl)-vinyl-pyridinium bromide

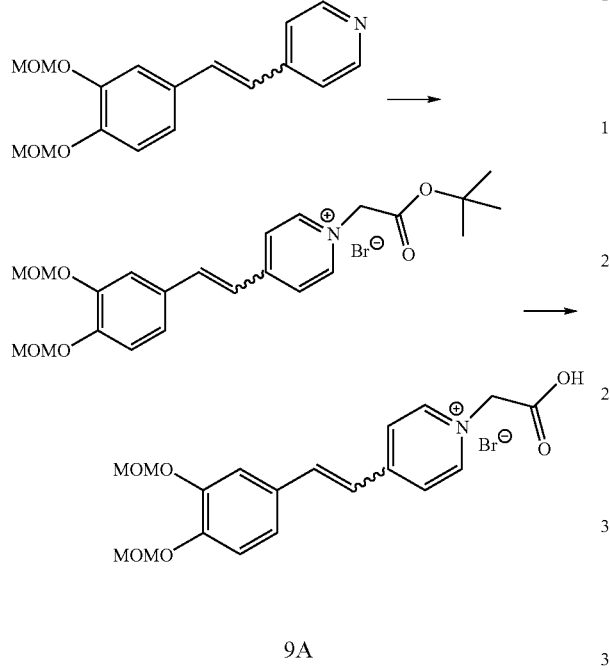

9A

A mixture of MOM-conjugated pyridine (150 mg) and tert-butyl bromoacetate (250 microliter) in 1,4-dioxane (10 mL) was stirred 90-110° C. overnight. The initial colorless solution was turned into brown. And an orange solid was precipitated out. The dioxane was stripped off and the solid was washed with ether extensively. This orange solid was directly used in next step. To a solution of the orange solid and in MeOH-water (18:2 mL) a conc. HBr (48% aqueous solution, 10 drops) was added and the solution was stirred at room temperature overnight. The MeOH was stripped off and the remaining solid was washed with ether, ethyl acetate, and dichloromethane and dried under vacuum to give a brown solid (108 mg). $^1$H-NMR (300 MHz, acetone-$d_6$ with D2O) δ (ppm) 8.70-8.50 (m, 2H), 8.05-7.80 (m, 2H), 7.75-7.50 (m, 1H), 7.20-6.50 (m, 3H), 5.52 and 5.46 (2s, combined 2H). $^{13}$CNMR (75 MHz, acetone-$d_6$ with $D_2O$) δ (ppm) 165.63, 165.14, 151.82, 144.70, 141.69, 141.53, 139.20, 126.03, 124.49, 120.00, 119.88, 116.80, 112.99, 111.53, 56.52, 50.59.

9B. Other Compounds of Formula I

Similarly, by following the procedures of Example 9A and substituting MOM-conjugated pyridine accordingly, there are obtained:

1-Benzyl-4-[2-(3,4-dihydroxy-phenyl)-vinyl]-pyridinium; bromide, and 1-(2-Carboxy-2-oxo-ethyl)-4-[2-(3,4-dihydroxy-phenyl)-vinyl]-pyridinium; bromide.

Example 10

Preparation of {4-[2-(3,4-Dihydroxy-phenyl)-vinyl]-phenyl}-phosphonic acid diisopropyl ester

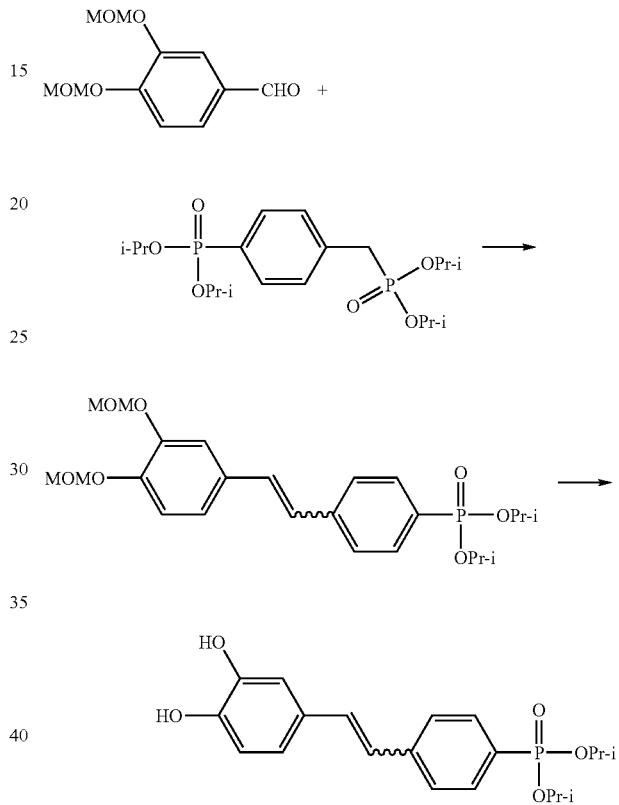

To a solution of 3,4-dimethoxymethoxy-benzaldehyde (500 mg) and phosphonate (1.10 g) in THF (50 mL) was added NaH (60% oil suspension, 170 mg) and the mixture was stirred at 70° C. for 2 h. To this mixture was then added a small amount of MeOH and 50 mL of EtOAc. Washed with water and brine, dried over $MgSO_4$, the EtOAc phase was concentrated. The residue was purified using a SiO2 column, eluting with 2-5% MeOH in $CH_2Cl_2$, leading to the MOMO-phosphonate compound as a clear oil. The intermediate (500 mg) was dissolved in MeOH (30 mL) and conc. HCl (10 drops) was added. The solution was stirred at room temperature overnight, then MeOH was evaporated. The residue was dissolved in EtOAc and washed with water and brine, dried over $MgSO_4$. After the EtOAc layer was concentrated, the residue was purified using $SiO_2$ column, eluting with 2-5% MeOH in $CH_2Cl_2$. A glass solid product (about 340 mg) was obtained. $^1$H-NMR (300 MHz, CDCl$_3$) δ (ppm) 7.80 (m, 2H), 7.48(m, 2H), 7.16-6.70(m, 5H), 4.70(m, 2H), 1.38, 1.26(2d, J=6.2 Hz, 12H). $^{13}$C-NMR (75 MHz, CDCl$_3$) δ (ppm) 145.39, 144.25, 141.83, 141.79, 131.65, 131.51, 128.63, 127.30, 125.86, 125.65, 124.73, 123.89, 119.73, 114.53, 112.44, 71.33, 71.25, 23.62, 23.56, 23.43, 23.37 ppm. $^{31}$PNMR (121 MHz, CDCl$_3$) δ (ppm) 17.18(s).

Example 11

Preparation of 5-(3-,4-Dihydroxy-benzylidene)-thiazolidine-2,4-dione

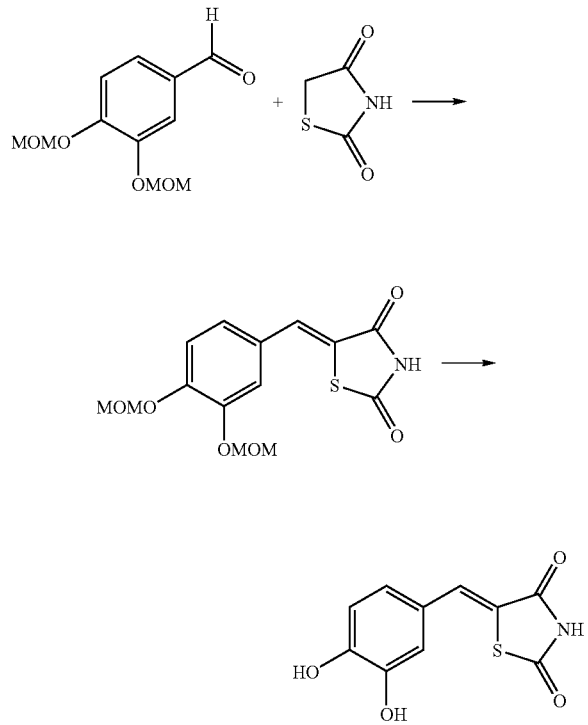

11A

A mixture of 3,4-Bis-methoxymethoxy-benzaldehyde (5 mmol), thiazolidine-2,4-dione (5 mmol), benzoic acid (0.5 mmol), and piperidine (0.5 mmol) in toluene (150 mL) was heated to reflux for 15 h. Upon cooling, to the reaction mixture was added hexane (50 mL). The resulting suspension was gently stirred for 2 min and then allowed to settle. It was then filtered and the solid was washed with cold benzene. 5-(3,4-Bis-methoxymethoxy-benzylidene)-thiazolidine-2,4-dione was obtained as a yellow solid (yield 92%). $^1$H-NMR (300 MHz, CDCl$_3$) δ (ppm) 7.81 (s, 1H), 7.38 (d, J=2.0 Hz, 1H), 7.28-7.25(m, 1H), 7.18-7.15 (m, 1H), 5.32 (s, 2H), 5.63 (s, 2H), 3.57 (s, 3H), 3.54 (s, 3H). $^{13}$C-NMR (75 MHz) δ (ppm) 168.1, 167.6, 149.8, 147.9, 134.6, 127.7, 126.1, 121.0, 118.8, 116.8, 96.0, 95.5, 56.9, 56.8.

5-(3,4-Dihydroxy-benzylidene)-thiazolidine-2,4-dione was prepared from 5-(3,4-bis-methoxymethoxy-benzylidene)-thiazolidine-2,4-dione after treatment with HCl as described for synthesis of Example 2. $^1$H-NMR (300 MHz, CD$_3$OD) δ (ppm) 7.65 (s, 1H), 7.01-6.93 (m, 2H), 6.88-6.85 (m, 1H).

11B. Other Compounds of Formula II

Similarly, by following the procedures of Example 11A, there are obtained:

5-[3,5-Bis-methoxymethoxy-4-(3-methyl-but-2-enyl)-benzylidene]-thiazolidine-2,4-dione, $^1$H NMR (CDCl$_3$, 300 MHz) δ (ppm): 8.43 (s, 1H), 7.79 (s, 1H), 6.97 (s, 2H), 5.23 (s, 4H), 5.14 (t, 1H), 3.50 (s, 6H), 3.42 (d, J=7.1, 2H), 1.79 (s, 3H), 1.66 (s, 3H), MS (ESI) m/z: 394 (M+H$^+$), 416 (M+Na)$^+$;

5-[3,5-Dihydroxy-4-(3-methyl-but-2-enyl)-benzylidene]-thiazolidine-2,4-dione, $^1$H NMR (CDCl$_3$, 300 MHz) δ (ppm): 7.48 (s, 1H), 6.45 (s, 3H), 5.13 (t, 1H), 3.24 (d, J=7.1, 2H), 1.79 (s, 3H), 1.66 (s, 3H), MS (ESI) m/z: 306 (M+H)$^+$;

5-[4-Methoxymethoxy-3-(3-methyl-but-2-enyl)-benzylidene]-thiazolidine-2,4-dione, $^1$H NMR (CDCl$_3$, 300 MHz) δ (ppm): 7.82 (s, 1H), 7.33 (s, 2H), 7.23 (s, 1H), 5.33 (t, 1H), 5.27 (s, 2H), 3.48 (s, 3H), 3.36 (d, J=7.4, 2H), 1.79 (s, 3H), 1.66 (s, 3H), MS (ESI) m/z: 334 (M+H$^+$), 356 (M+Na)$^+$;

5-[4-Hydroxy-3-(3-methyl-but-2-enyl)-benzylidene]-thiazolidine-2,4-dione, 3H NMR (CDCl$_3$, 300 MHz) δ (ppm): 7.77 (s, 1H), 7.29 (m, 3H), 6.95 (d, J=8.3, 1H), 5.33 (t, 1H), 3.37 (d, J=7.1, 2H), 1.79 (s, 3H), 1.66 (s, 3H), MS (ESI) m/z: 290 (M+H)$^+$, 312 (M+Na)$^+$;

5-[3-(3,7-Dimethyl-octa-2,6-dienyl)-4-hydroxy-benzylidene]-thiazolidine-2,4-dione. $^1$H NMR (CDCl$_3$, 300 MHz) δ (ppm): 7.77 (s, 1H), 7.27 (s, 3H), 6.95 (d, J=8.2, 1H), 5.36 (t, 1H), 5.11 (t, 1H), 3.42 (d, J=7.4, 2H), 2.15 (m, 2H), 1.75 (s, 3H), 1.68 (s, 3H), 1.60 (s, 3H). MS (ESI) m/z: 358 (M+H)$^+$, 380 (M+Na)$^+$;

5-[3-(3,7-Dimethyl-octa-2,6-dienyl)-4-methoxymethoxy-benzylidene]-thiazolidine-2,4-dione, $^1$H NMR (CDCl$_3$, 300 MHz) δ (ppm): 7.77 (s, 1H), 7.27 (s, 3H), 6.95 (d, J=8.2, 1H), 5.36 (t, 1H), 5.11 (t, 1H), 5.27 (s, 2H), 3.50 (s, 3H), 3.38 (d, J=7.4, 2H), 2.15 (m, 2H), 1.75 (s, 3H), 1.68 (s, 3H), 1.60 (s, 3H), MS (ESI) m/z: 358 (M+H)$^+$, 380 (M+Na)$^+$;

5-{3-[3-Methoxy-4-(3-methyl-but-2-enyloxy)-phenyl]-allylidene}-thiazolidine-2,4-dione, The compound obtained as a yellow solid (>45% yield), $^1$H NMR (CDCl$_3$, 300 MHz) δ (ppm): 7.55 (d, J=11.5, 1H), 7.00 (m, 4H), 6.54 (m, 1H), 5.51 (t, 1H), 5.30 (s, 1H), 4.64 (d, J=6.39, 2H), 3.93 (s, 3H), 1.78 (s, 3H), 1.75 (s, 3H), MS (ESI) m/z: 346 (M+H), 368 (M+Na);

4-(3,4-Dihydroxy-benzylidene)-5-methyl-2-phenyl-2,4-dihydro-pyrazol-3-one, $^1$H NMR (300 MHz CDCl$_3$) δ (ppm) 8.46 (s, H), 7.81-7.88 (m, 3H), 7.36-7.44 (m, 3H), 7.14-7.20 (t, H), 6.84-6.87 (d, J=8.3, H), 2.27 (s, 3H);

4-[3-(4-Hydroxy-3-methoxy-phenyl)-allylidene]-5-methyl-2-phenyl-2,4-dihydro-pyrazol-3-one, $^1$H NMR (300 MHz CDCl$_3$) δ (ppm) 8.36-8.40 (q, H), 7.94-7.97 (d, J=9.8, 2H), 7.38-7.43 (m, 3H), 7.11-7.19 (m, 5H), 6.90-6.94 (d, 2H), 3.92 (s, 3H), 2.26 (s, 3H), ESI(+)/MS: 335 (M+H)$^+$, 357 (M+Na)$^+$;

5-[3-(3-Methoxy-4-methoxymethoxy-phenyl)-allylidene]-thiazolidine-2,4-dione, $^1$H NMR (300 MHz CDCl$_3$) δ (ppm) 8.21-7.46 (m, H), 6.54-7.15 (m, 5H), 5.25-5.28 (d, 2H), 3.90-3.97 (s, 3H), 3.50-3.51 (s, 3H), ESI(+)/MS: 322 (M+H)$^+$, 344 (M+Na)$^+$; and 5-(3,5-Di-tert-butyl-4-hydroxy-benzylidene)-thiazolidine-2,4-dione, $^1$HMNR (300 MHz, CDCL$_3$ & CDCL$_3$)

δ (ppm) 7.82 (s, H), 7.36 (s, 2H), 5.71 (s, H) 1.47 (s, 18H), ESI(+)/MS: 334 (M+H)⁺, 356 (M+Na)⁺.

Example 12

Preparation of 2-(3,4-Dihydroxy-benzlidene)-malononitrile

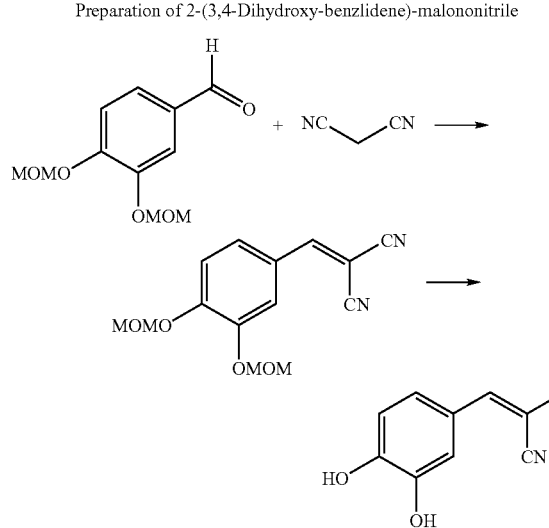

A mixture of 3,4-Bis-methoxymethoxy-benzaldehyde (1.0 mmol), malononitrile (1.0 mmol), and NaOH (2 mg) in 5 mL of MeOH was stirred for 24 at room temperature. After solvent removal, the residue was dissolved in EtOAc and filtered through a silica pad. Solvent was evaporated to afford condensation product, 2-(3,4-bis-methoxymethoxy-benzylidene)-malononitrile, as a yellow solid (yield 94%). ¹H-NMR (300 MHz, CDCl₃) δ (ppm) 7.86 (s, 1H), 7.68 (s, 1H), 7.53 (d, J=9 Hz, 1H), 7.29 (d, J=9 Hz, 1H), 5.35 (s, 2H), 5.28 (s, 2H), 3.54 (s, 3H), 3.53 (s, 3H). ¹³C-NMR (75 MHz) δ (ppm) 168.1, 167.6, 149.8, 147.9, 134.6, 127.7, 126.1, 121.0, 118.8, 116.8, 96.0, 95.5, 56.9, 56.8.

Treatment of 2-(3,4-bis-methoxymethoxy-benzylidene)malononitrile with HCl as described in Example 2 to remove MOM protecting group and chromatography afforded the product as a light brown solid (yield 85%). ¹H-NMR (300 MHz, aceton-d₆) δ (ppm) 9.79 (bs, 0.3H), 8.01 (s, 1H), 7.75 (s, 1H), 7.43 (d, J=8.2 Hz, 1H), 7.04 (d, J=8.2 Hz, 1H); ¹³C-NMR (75 MHz) δ (ppm) 159.5, 151.8, 145.1, 126.9, 123.6, 115.5, 115.3, 114.4, 113.4, 75.9.

Example 13

Preparation of 4-[2-(3,4-Bis-methoxymethoxy-phenyl)-vinyl]-benzoic Acid

To a solution of 4-[2-(3,4-bis-methoxymethoxy-phenyl)-vinyl]-benzoic acid ethyl ester (1.0 mmol) in MeOH (20 mL) was added 10% NaOH solution (3 eq). The resulting suspension was vigorously stirred for 8 h at room temperature. The mixture was then quenched by adding saturated NaH₂PO₄ (50 mL). The mixture was extracted with EtOAc (3×50 mL) and the combined organic layers were dried over Na₂SO₄. The crude product was purified on a short silica gel column.

Example 14

Preparation of 4-[2-(3,4-Dihydroxy-phenyl)-vinyl]-N, N-bis-(2-hydroxyethyl)-benzamide

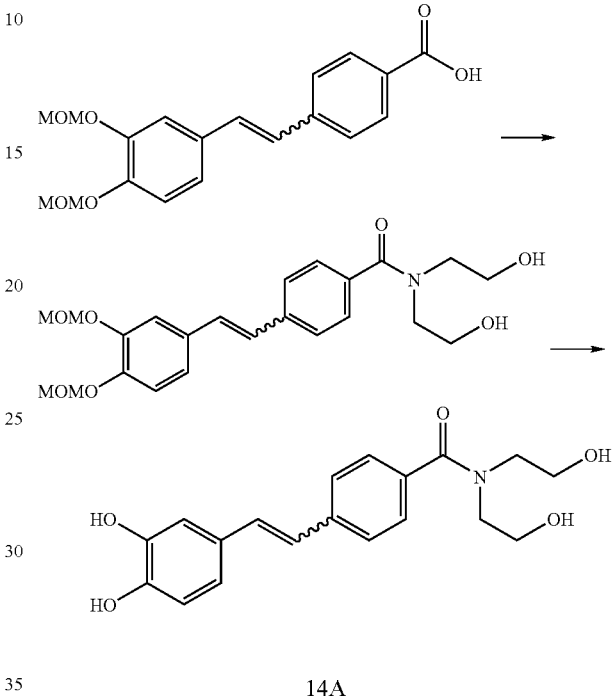

14A

A mixture of 4-[2-(3,4-bis-methoxymethoxy-phenyl)-vinyl]-benzoic acid (1.0 mmol) and carbonyldiimidazole (1.0 mmol) in dry THF (20 mL) was stirred at room temperature for 3 h. Diethanolamine (1.0 mmol) was added dropwise and the mixture was stirred for additional 3 days at room temperature. Solvent was then removed under reduced pressure and the residue was chromatographed on a silica gel column (EtOAc/hexanes) to afford MOMO-phenyl-vinyl-benzamide-as a clear oil. ¹H-NMR (300 MHz, CDCl₃) δ (ppm) 7.97 (m, 2.5H), 7.45 (m, 2H), 7.30-6.96 (m, 4H), 6.50 (m, 0.5H), 5.27-5.03 (m, 4H), 3.89 (s, 2H), 3.66 (s, 4H), 3.54-3.37 (m, 8H).

To a solution of the obtained compound (0.5 mmol) in MeOH (50 mL) was added 10 drops of concentrated HCl. The solution was stirred at room temperature for 24 h followed by solvent evaporation. The residue was chromatographed on a silica gel column (DCM/hexanes) to afford the product as a pale yellow solid (50% overall yield). ¹H-NMR (300 MHz, CD₃OD) δ 7.96-7.33 (m, 4H), 7.05-6.40 (m, 5H), 3.88 (s, 2H), 3.66 (m, 4H), 3.52 (s, 2H).

14B. Other Compounds of Formula I

Similarly, by following the procedures of Example 14A, there is obtained:

{4-[2-(3,4-Dihydroxy-phenyl)-vinyl]-phenyl}-morpholin-4-yl-methanone, ¹HNMR (300 MHz, DMSO) δ 7.61-7.58 (d, J=8.3 Hz, 2H), 7.39-7.36 (d, J=8.1 Hz, 2H), 7.17-7.12 (d, J=16.3 Hz, H), 6.98 (s, H), 6.93-6.88 (d, J=15.1 Hz, H), 6.92-6.89 (m, H), 6.75-6.72 (d, J=8 Hz, H), 5.74 (s, H) 3.45-3.65 (m, 8H).

Example 15

Preparation of 4-[2-(3-,4-Dihydroxy-phenyl)-vinyl]-benzoic acid 3,4,5,6-tetrahydroxy-tetrahydro-pyran-2-yl methyl ester

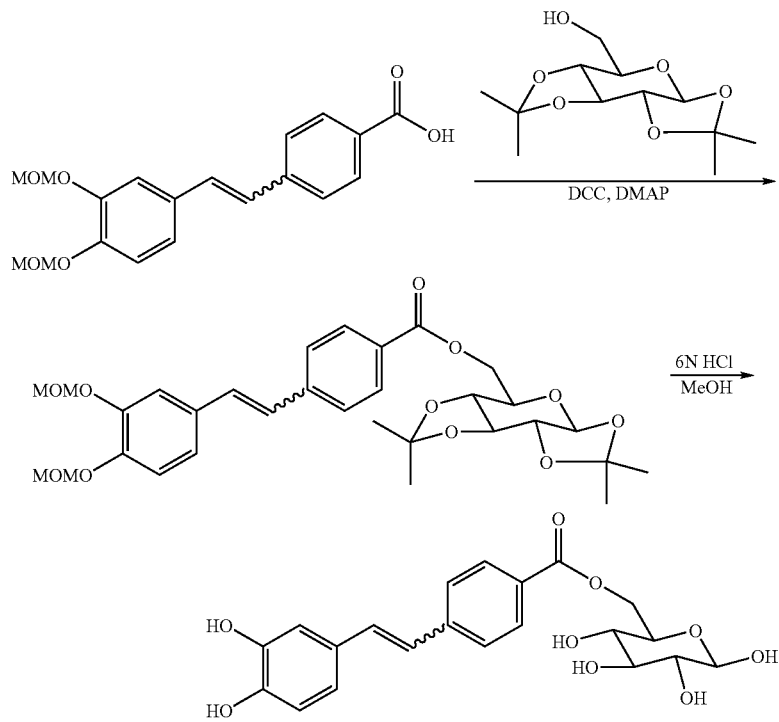

A mixture of 4-[2-(3,4-bis-methoxymethoxy-phenyl)-vinyl]-benzoic acid (1.0 mmol), a protected glucose (1.5 mmol), DCC (1.2 mmol), DMAP (1.0 mmol), and 10 mL dichloromethane was stirred for 24 h at room temperature. The reaction was then quenched by adding 50 mL of EtOAc and pouring into a saturated NH4Cl solution (aq). The organic layer was washed with 0.5 N HCl (3×20 mL) and dried over $Na_2SO_4$. Solvent removal followed by chromatography on a silica gel column afforded the conjugate illustrated as an intermediate as a pale yellow oil. To the solution of the obtained compound in MeOH (50 mL) was added 5 mL of 6 N HCl. The resulting suspension was stirred for 72 h at room temperature. The solvent was then evaporated under reduced pressure and residue was chromatographed (silica gel, DCM/MeOH) to afford product as a yellow solid (overall yield 68%). $^1$H-NMR (300 MHz, $CD_3OD$) δ (ppm) 8.02-7.94 (m, 2H), 7.56 (m, 2H), 7.20-6.78 (m, 5H), 5.25 (m, 0.5H), 4.56-4.38 (m, 2.5H), 4.15-3.80 (m, 3H), 3.62-3.51 (m, 1H).

Example 16

Preparation of 4-[2-(3,4-Dihydroxy-phenyl)-vinyl]-N-methyl-N-(2,3,4,5,6-pentahydroxy-hexyl)-benzamide

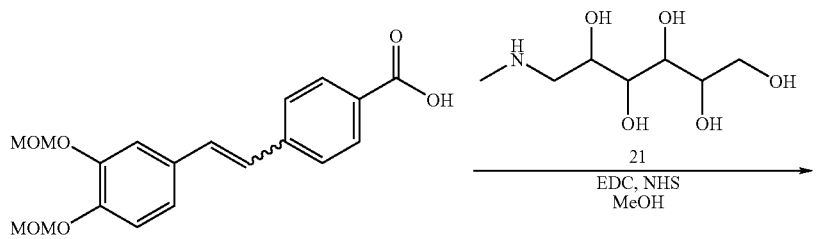

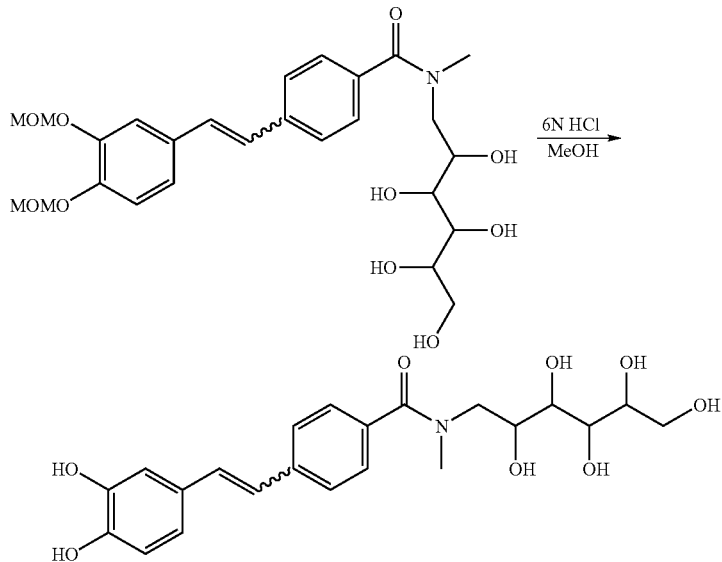

To a solution of 4-[2-(3,4-bis-methoxymethoxy-phenyl)-vinyl]-benzoic acid (1.0 mmol) and N-hydroxysuccinamide (1.1 mmol) in MeOH (10 mL) was added dimethylaminopropyl-3-ethylcarbodiimide hydrochloride (1.2 mmol) in small portions. The mixture was stirred for 1 h followed by addition of amine (1.2 mmol). The resulting mixture was stirred for 10 h at room temperature. The solvent was removed under reduced pressure and the residue was chromatographed on a silica gel column (DCM/MeOH) to afford a yellow solid compound illustrated as an intermediate. To this compound in 50 mL MeOH was added 12 drops of concentrated HCl and stirred was continued for 24 h. After solvent evaporation, the residue was again chromatographed (silica gel, DCM/MeOH) to afford final product as a yellow solid. $^1$H-NMR (300 MHz, CD$_3$OD) δ (ppm) 7.72-7.62 (m, 2H), 7.46-7.22 (m, 4H), 6.94-6.63 (m, 2H), 6.50-6.28 (m, 1H), 3.95-3.20 (m, 8H), 2.99-2.89 (m, 3H).

Example 17

Preparation of 4-{2-[6-Methoxy-2, 7, 8-trimethyl-2-(4,8,12-trimethyl-tridecyl)-chroman-5-yl]-vinyl}-benzoic acid methyl ester

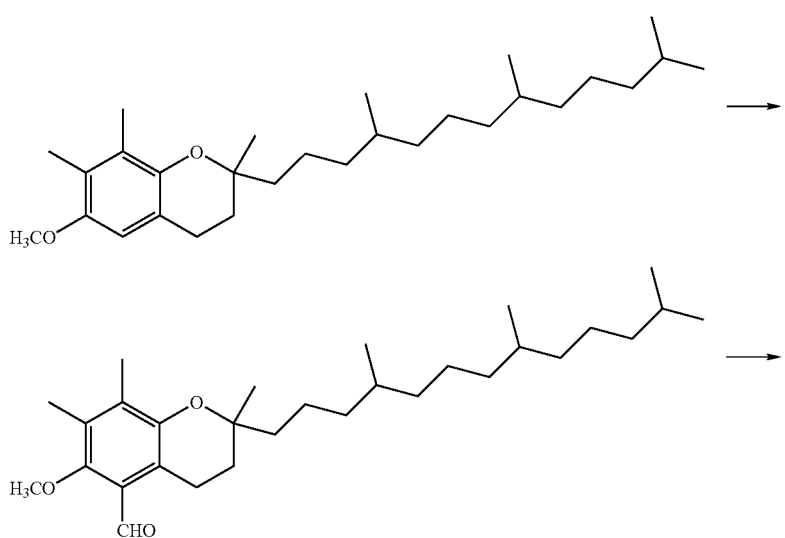

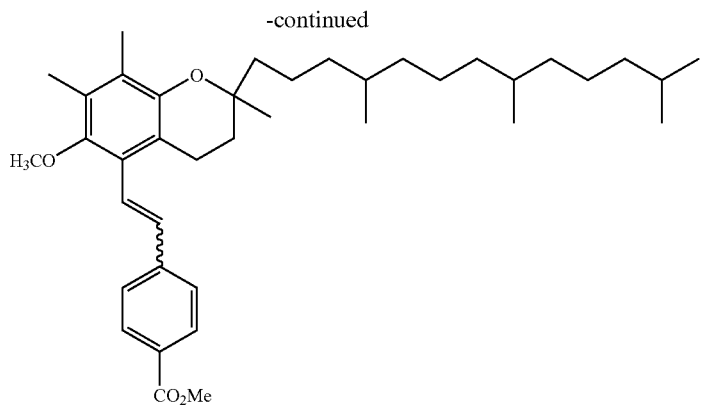

6-Methoxy-2, 7, 8-trimethyl-2-(4,8,12-trimethyl-tridecyl)-chroman-5-carbaldehyde. To a solution of 6-methoxy-2, 7,8-trimethyl-2-(4,8,12-trimethyl-tridecyl)-chroman (1.0 g, 2.32 mmol) in methylene chloride (4 mL) at 0° C. was added titanium tetrachloride (0.528 mL, 308 mg, 2.78 mmol). The solution turned into black. To this solution was added α,α-dichloromethyl methyl ether tetrachloride (0.252 mL, 320 mg, 2.78 mmol). After 5 min the ice-water bath was removed. The solution was stirred at 20° C. for 1 hour, then poured into ice-water. The mixture was extracted with methylene chloride, dried over magnesium sulfate. Evaporation off solvents and chromatography of the obtained residues (silica gel, hexane-ethyl acetate 95:5) gave 1.0 g (94%) of aldehyde. $^1$H-NMR (300 Hz, D$_3$CCl) δ (ppm) 10.5 (s, 1H), 3.77 (s, 3H), 3.08 (t, J=7.2 Hz, 2H), 2.21 (s, 3H), 2.17 (s, 3H), 1.78-1.00 (m, 23H), 0.88-0.80 (m, 15H).

4-{2-[6-Methoxy-2, 7, 8-trimethyl-tridecyl)-chroman-5-yl]-vinyl}-benzoic acid methyl ester. To a solution of the intermediate aldehyde (100 mg, 0.218 mmol) and (4-methoxycarbonyl-benzyl)-triphenyl-phosphonium bromide (128 mg, 0.262 mmol) in ethanol (4 mL) was added lithium ethoxide (1 M in ethanol, 0.262 mL, 0.262 mmol) dropwise. The resulted solution was stirred at 20° C. overnight. Ethanol was removed under reduced pressure, and the residue was chromatographed (silica gel, hexane-ethyl acetate 95:5), affording 95 mg of products, which was a mixture of 50%-50% of cis-, trans-isomers. $^1$H-NMR (300 Hz, D$_3$CCl) δ (ppm) 8.05-8.00 (m, 1H), 7.90-7.80 (m, 1H), 7.60-7.50 (m, 1H), 7.35-7.10 (m, 2H), 6.80-6.60 (m, 1H), 4.38 (s, CH$_3$, 50%), 4.32 (s, CH$_3$, 50%), 3.61 (s, CH$_3$, 50%), 3.60 (s, CH$_3$, 50%), 2.81 (t, J=6.6 Hz, 2H), 2.30-2.10 (m, 6H), 1.78-1.00 (m, 23H), 0.88-0.80 (m, 15H). MS (APCI) m/z 591 (M+1, 46).

Example 18

Preparation of 2-[2-(3,4-Bis-methoxymethoxy-phenyl)-vinyl]-thiazole

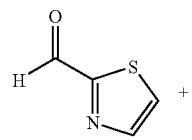

+

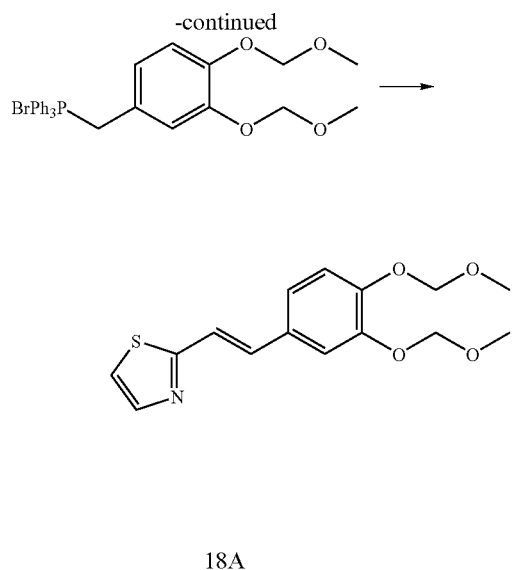

18A

To a solution of the (3,4-bis-methoxymethoxy-benzyl)-triphenyl-phosphonium bromide (0.731 g, 1.32 mmoles) and 2-thiazolecarbox-aldehyde (0.134 g, 1.2 mmoles) in ethanol was added lithium ethoxide (1.32 ml, 1.32 mmol). The solution turned into a brown color. It was allowed to stir for about two hours at room temperature. The reaction mixture was then added to 100 ml of concentrated NaH$_2$PO$_4$ and was extracted with ethyl acetate. The organic layer was dried over sodium sulfate and concentrated. The crude product was purified using a silica gel column (hexanes:EtOAc 3:1), resulting 26 mg of product. NMR spectrum indicated that it is a mixture of cis/trans isomers. $^1$H-NMR (300 Hz, D$_3$CCl) δ (ppm) 7.76 (dd, 1H), 7.40 (m, 1.4H), 7.09-7.24 (m, 3.2H), 6.8 (dd, 1.3H), 5.2-5.28 (ss, 4H), 3.4-3.5 (ss, 6H). MS (ESI) m/z: 308 (M+H, 100).

18B. Other Compounds of Formula I

Similarly, by following the procedures of Example 18A and substituting 2-thiazolecarbox-aldehyde accordingly, there are obtained:

2-[2-(3,4-Dihydroxy-phenyl)-vinyl]-3-methyl-thiazol-3-ium iodide, and

4-[2-(5-Methyl-thiophen-2-yl)-vinyl]-benzene-1,2-diol.

Example 19

Preparation of 4-[2-(3,4-Dimethoxy-phenyl)-vinyl]-methanesulfonyl-benzene

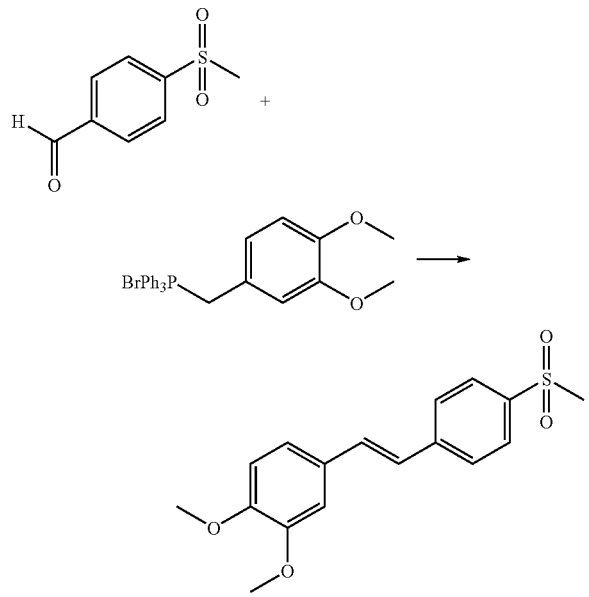

To a solution of the 4-methanesulfonyl-benzaldehyde (0.53 g, 2.71 mmoles) and (3,4-dimethoxy-benzyl)-triphenyl-phosphonium bromide (1.47 g, 2.99 mmoles) in ethanol was added lithium ethoxide (2.99 ml, 2.99 mmoles) dropwise to give a brown colored solution. The reaction was complete within two hours. The reaction was quenched by adding 100 ml of concentrated $NaH_2PO_4$, followed by the extraction with ethyl acetate. The organic layer was dried over sodium sulfate and concentrated. The crude product was purified using a silica gel column (hexanes:EtOAc 3:1), resulting 26 mg of product. NMR spectrum indicated that it is a mixture of cis/trans isomers. $^1$H-NMR (300 Hz, $D_3CCl$) δ (ppm) 7.92-7.79 (m, 2H), 7.48-7.45 (m, 2.2H), 7.27-6.68 (m, 4.6H), 6.55 (d, 0.4H), 3.96-3.92 (d, 2.6H), 3.87-3.66 (d, 2.6H), 3.07-3.04 (d, 3H). MS (ESI) m/z: 319 (M+H. 100), 341 (M+Na, 30).

Example 20

Preparation of 4-(2-Thiazol-2-yl-vinyl)-benzoic acid methyl ester

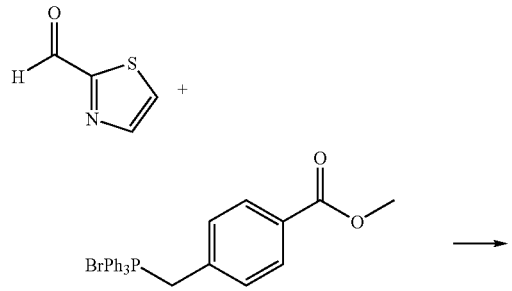

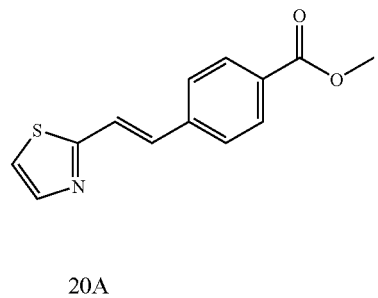

20A

To a solution of (4-methoxycarbonyl-benzyl)-triphenyl-phosphonium bromide and 2-thiazolcarbox-aldehyde (0.50 g, 4.42 mmoles) in ethanol (10 mL) was added lithium ethoxide (4.86 mL, 4.86 mmol) drop-wise and the solution became orange in color quickly. The reaction was allowed to stir for about one hour. The volume was reduced and a concentrated $NaH_2PO_4$ aqueous solution (100 mL) was added and followed by EtOAc extraction. The organic layer was dried over sodium sulfate and concentrated. The crude product was purified using a silica gel column (DCM as the eluent), affording 1.0 g of product. NMR spectrum indicated that it is a mixture of methyl and ethyl esters. $^1$H-NMR (300 Hz, $D_3CCl$) δ (ppm) 8.05 (d, J=6 Hz, 2H), 7.75 (d, J=3.26 Hz, 1H), 7.52 (d, J=6.5 Hz, 2H), 7.16 (d, J=3.26 Hz, 1H), 6.92 (s, 2H), 4.40 (q, J=7.12 Hz, 1.32H), 3.92 (s, 1.5H), 1.40 (t, J=7.12 Hz, 2H).

20B. Other Compounds of Formula I

Similarly, by following the procedures of Example 20A and substituting (4-methoxycarbonyl-benzyl)-triphenyl-phosphonium bromide and 2-thiazolcarbox-aldehyde accordingly, there are obtained:

4-[2-(1H-Benzoimidazol-5-yl)-vinyl]-benzoic acid ethyl ester, and 4-(5-Methyl-thiophen-2-yl-vinyl)-benzoic acid ethyl ester

Example 21

Preparation of 4-[2-(2,5-Dimethoxy-3,4-dimethyl-phenyl)-vinyl]-benzoic acid ethyl ester

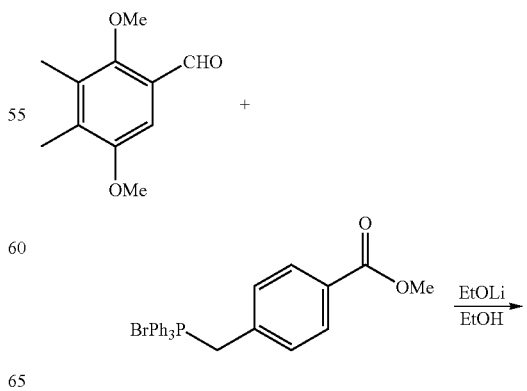

-continued

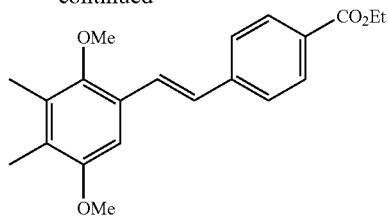

The compound was prepared in a similar way described in Example 1. The crude product was purified on a silica gel column (hexane:EtOAc=3:1) to afford a clear oil (yield 99%). NMR spectrum indicated the purified product is a mixture of cis/trans isomers containing ethyl and methyl esters. $^1$H-NMR (300 MHz, CDCl$_3$) δ (ppm) 7.95-7.88 (m, 2H), 7.38-7.23 (m, 2H), 7.00-6.60 (m, 3H), 4.75-4.63 (m, 1.4H), 3.94-3.64 (m, 6.9H), 2.22-2.12 (m, 6H), 1.27-1.24 (m, 2.1H).

Example 22

Preparation of 4-[2-(3,4-Dihydroxy-phenyl)-vinyl]-benzoic acid ethyl ester, zinc (II) chloride

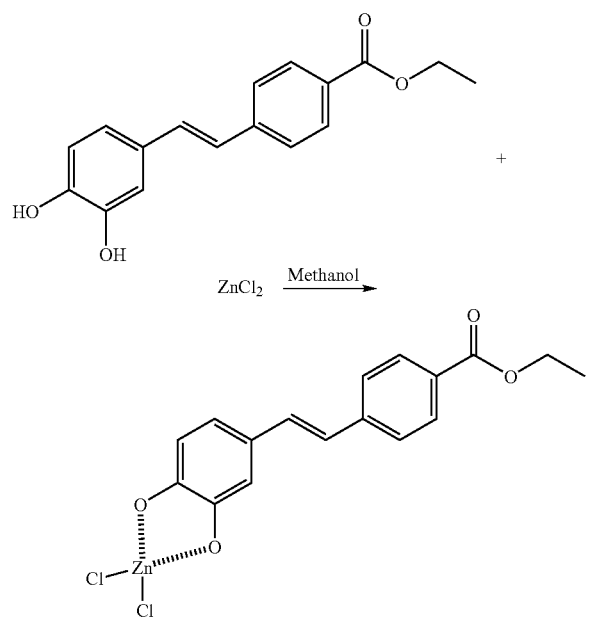

To a solution of 4-[2-(3,4-Dihydroxy-phenyl)-vinyl]-benzoic acid ethyl ester (0.023 g, 0.08 mmol) in methanol (5 mL) was added zinc (II) chloride (0.011 g, 0.080 mmol) portionwise. The reaction was allowed to stir for two hours before it was evaporated to dryness. This afforded 0.030 g of product as a brownish solid. $^1$H-NMR (300 Hz, D$_3$COD) δ (ppm) 7.97 (d, J=8.4 Hz, 2H), 7.60 (d, J=8.37 Hz, 2H), 7.15 (d, J=16.2 Hz, 1H), 7.05 (s, 1H), 6.99 (d, J=16.4 Hz, 1H), 6.94 (d, 2H), 6.77 (d, J=8.1 Hz, 1H), 4.37 (q, J=7.12 Hz, 2H), 1.39 (t, J=7.12 Hz, 3H). MS (ESI) m/z: 419 (M+H, 100), 441 (M+Na, 80).

22B. Other Compounds of Formula III

Similarly, by following the procedures of Example 22A and substituting zinc (II) chloride accordingly, there are obtained:

4-[2-(phenyl-1,2-diol)-vinyl]-benzoic acid ethyl ester, manganese(III) acetate, and 4-[2-(phenyl-1,2-diol)-vinyl]-benzoic acid ethyl ester, copper(II) chloride.

Example 23

Preparation of prenylated and geranylated, MOM-vanillin intermediates

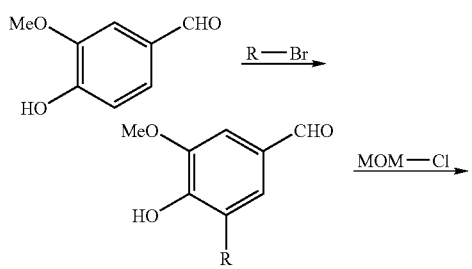

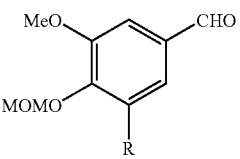

R = prenyl or geranyl

23A

A mixture of vanillin (12 g) and prenyl bromide was stirred in 1N NaOH aqueous solution (1 eq.) at 0° C. with the aid of an ice-water bath. With vigorously stirring, prenyl bromide was added dropwise in 45 min. The solution was stirred at this temperature for 3 h. After acidfied with aqueous HCl, the solution was extracted with DCM. The DCM phase was washed with brine and then dried over anhydrous sodium sulfate. A crude product was obtained as a clear oil (1.5 g) after evaporation. Column chromatography purification (silica gel, 20-30% EtOAc in hexane the eluents) gave the prenylated vanillin 4-hydroxy-3-methoxy-5-(3-methyl-but-2-enyl)-benzaldehyde. $^1$H-NMR (CDCl$_3$, 300 MHz) δ (ppm) 9.79 (s, 1H), 7.27 (m, 2H), 6.43(br., s, 1H), 5.31 (m, 1H), 3.90 (s, 3H), 3.37 (d, J=7.3 Hz, 2H), 1.74, 1.71 (2s, 6H). $^{13}$C-NMR (CDCl$_3$, 75 MHz) δ (ppm) 191.76, 149.81, 147.26, 134.13, 129.32, 128.11, 128.05, 121.57, 107.15, 56.62, 28.16, 26.23, 18.24.

Similarly, a geranyled vanillin was made using the described procedure. $^1$H-NMR (CDCl$_3$, 300 MHz) δ (ppm) 9.80 (s, H, CHO), 7.30 (s, 2H, ArH), 6.26 (s, H, OH), 5.42 (t, H, vinyl H), 5.10 (t, H, vinylH), 3.96 (s, 3H, OCH$_3$), 3.42 (d, J=7.26, 2H, allylicH), 2.05 (s, 3H, CH$_3$), 1.60 (s, 2H, CH$_2$). MS (ESI) m/z: 289 (M+H)$^+$, 311 (M+Na)$^+$.

23B

A solution of prenylated vanillin (220 mg), MOM-Cl (0.12 mL) and DIPEA (0.2 mL) in DCM (20 mL) was stirred for 2 h. The reaction was quenched by adding water and saturated aqueous K$_2$CO$_3$ solution. DCM extraction followed by evaporation to dryness gave a crude product. The title compound 3-methoxy-4-methoxymethoxy-5-(3-methyl-but-2-enyl)-benzaldehyde was obtained as an oil (250 mg) after column chromatography purification. $^1$H-NMR (CDCl$_3$, 300 MHz) δ (ppm) 9.87 (s, 1H), 7.31 (m, 2H), 5.31 (m, 1H), 5.20

(s, 2H), 3.89 (s, 3H), 3.58 (s, 3H), 3.46 (d, J=7.3 Hz, 2H), 1.76, 1.73 (2s, 6H) ppm. $^{13}$C-NMR (CDCl$_3$, 75 MHz) δ (ppm) 191.92, 152.99, 149.95, 136.70, 134.07, 132.85, 126.66, 122.08, 108.91, 99.26, 58.08, 56.32, 28.74, 26.22, 18.30.

Similarly, a geranyled MOM-vanillin intermediate was made using the described procedure with the exception of using NaH and DMF in lieu of DIPEA and DCM, respectively. $^1$H-NMR (CDCl$_3$, 300 MHz) δ (ppm) 9.86 (s, H, CHO), 7.31 (s, 2H, ArH), 5.42 (t, H, vinylH), 5.20 (s, 2H, OCH$_2$O), 5.10 (t, H, vinylH), 3.90 (s, 3H, OCH$_3$), 3.59 (s, 3H, OCH$_3$), 3.49 (d, J=7.26, 2H, allylicH), 2.05 (s, 3H, CH$_3$), 1.60 (s, 2H, CH$_2$). MS (ESI) m/z: 333 (M+H)$^+$, 355 (M+Na)$^+$.

Example 24

Preparation of prenyl-substituted, MOM-3, 4-dihydroxybenzaldehyde intermediates

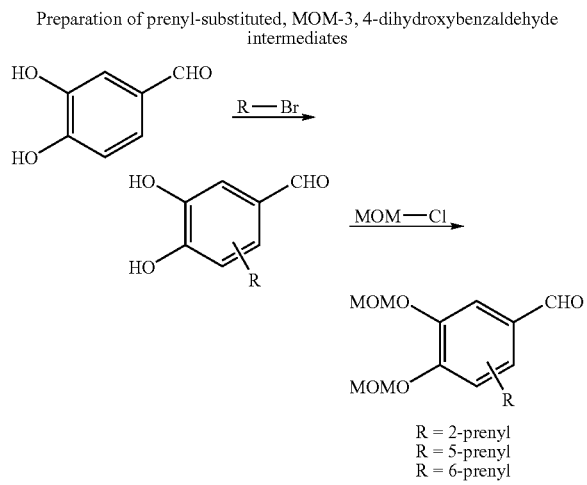

24A

By following a procedure corresponding to the one described in Example 23A, the prenyl-substituted 3,4-dihydroxylbenzaldehydes were prepared. For 2-prenyl-3,4-dihydroxylbenzaldehyde: $^1$H-NMR (CDCl$_3$, 300 MHz) δ (ppm) 10.00 (s, 1H, CHO), 7.37 (d, J=8.3 Hz, 1H), 6.69 (d, J=8.3 Hz, 1H), 5.8 (br., 2H, OH), 5.20 (m, 1H), 3.89 (d, J=6.7 Hz, 2H), 1.83, 1.76 (2s, 6H). For 5-prenyl-3,4-dihydroxylbenzaldehyde: $^1$H-NMR (CDCl$_3$, 300 MHz) δ (ppm) 9.77(s, 1H, CHO), 7.35(d, J=3.1 Hz, 1H), 7.26 (d, J=3.1 Hz, 1H), 5.8 (br., 2H, OH), 5.30 (m, 1H), 3.42 (d, J=7.3 Hz, 2H), 1.78, 1.73 (2s, 6H).

24B

The corresponding MOM-prenyl-substitituted benzaldehydes were prepared following a procedure corresponding to the one described in Example 23B. For 2-prenyl-3,4-bis-methoxymethoxy-benzaldehyde: $^1$H-NMR (CDCl$_3$, 300 MHz) δ (ppm) 10.12(s, 1H, CHO), 7.64(d, J=8.7 Hz, 1H), 7.12(d, J=8.3 Hz, 1H), 5.28 (s, 2H), 5.15 (m, 1H), 5.11 (s, 2H), 3.84(d, J=6.5 Hz, 2H), 3.61 (s, 3H), 3.51 (s, 3H), 1.79, 1.54 (2s, 6H). For 5-prenyl-3,4-bis-methoxymethoxy-benzaldehyde: $^1$H-NMR (CDCl$_3$, 300 MHz) δ (ppm) 9.86 (s, 1H, CHO), 7.52(d, J=1.9 Hz, 1H), 7.38 (d, J=1.9 Hz, 1H), 5.25 (m, 5H), 3.60 (s, 3H), 3.51 (s, 3H), 3.46 (d, J=7.3 Hz, 2H), 1.77, 1.73 (2s, 6H). $^{13}$C-NMR (CDCl$_3$, 75 MHz) δ (ppm) 191.67, 150.57, 150.41, 137.08, 134.06, 132.87, 126.25, 122.00, 114.22, 99.38, 95.41, 58.02, 56.78, 28.84, 26.17, 18.26. For 6-prenyl-3,4-bi-methoxymethoxy-benzaldehyde): $^1$H NMR (CDCl$_3$, 300 MHz) δ (ppm) 10.14 (s, 1H, CHO), 7.63(s, 1H), 7.03(s, 1H), 5.24 (m, 5H), 3.66 (d, J=6.9 Hz, 2H), 3.50 (s, 6H), 1.71, 1.70 (2s, 6H).

Example 25

Preparation of prenyl-substituted, MOM-3,5-dihydroxybenzaldehyde intermediates

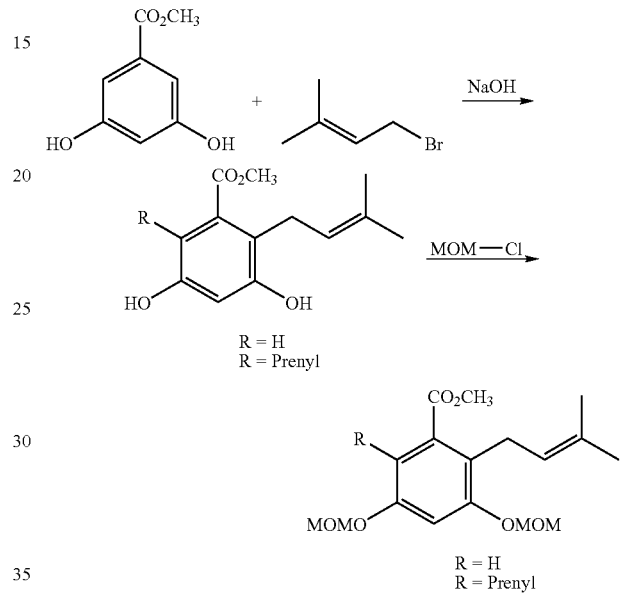

25A

To a solution of methyl 3,5-hydroxybenzoate (500 mg, 2.97 mmol) in deionized water (2.97 mL) placed in an ice-bath, NaOH (118.8 mg, 2.97 mmol) pellets were added and allowed to dissolve. Bromo-3-methyl-2-butene (prenyl bromide) (590 mg, 1.3 mmol) was added dropwise. This solution was stirred at 0° C. and after 30 minutes white solid started to appear. After an hour of stirring, workup was carried out with water and the pH of the aqueous layer was tested to be acidic, indicating the completion of reaction. Extraction with EtOAc followed by column chromatography purification (silica gel, 30% EtOAc in hexane as the eluents) gave two major fractions. Fraction 1: methyl 2-(3-methyl-2-butene)-3,5-hydroxybenzoate (26% yield). $^1$H-NMR (CDCl$_3$, 300 MHz) δ (ppm) 6.85 (d, J=2.6, H, ArH), 6.51, (d, J=2.6, H, ArH), 6.13 (s, H, OH), 5.81 (s, H, OH), 5.18 (t, J=6.7, H, vinyl H), 3.57 (d, J=6.7, 2H, allylic H), 1.78 (s, 3H, CH$_3$), 1.71 (s, 3H, CH$_3$). $^{13}$C-NMR (CDCl$_3$, 75 MHz) δ (ppm) 169.43, 156.68, 154.84, 134.95, 132.34, 122.73, 120.68, 109.87, 107.40, 52.82, 26.17, 18.32. MS (ESI) m/z: 237 (MH$^+$). Fraction 2: methyl 2,6-di-(3-methyl-2-butene)-3,5-hydroxybenzoate (23% yield). $^1$H-NMR (CDCl$_3$, 300 MHz) δ (ppm) 6.35 (s, H, ArH), 5.19 (t, 6.8, 2H, vinyl H), 3.87 (s, 3H, OCH$_3$), 3.20 (d, J=6.8, 2H, allylic H), 1.70 (s, 3H, CH$_3$), 1.64 (s, 3H, CH$_3$). $^{13}$C-NMR (CDCl$_3$, 75 MHz) δ (ppm) 174.66, 157.85, 139.20, 138.20, 126.18, 120.29, 109.21, 64.83, 56.35, 31.00, 29.82, 21.93, 18.24. MS (ESI) m/z: 305 (MH+).

25B

MOM-addition to methyl 2-(3-methyl-2-butene)-3,5-hydroxybenzoate and methyl 2,6-di-(3-methyl-2-butene)-3,5-hydroxybenzoate were carried out following a procedure corresponding to the one described in Example 23B. For methyl 2-(3-methyl-2-butene)-3,5-bis-methoxymethoxybenzoate: $^1$H-NMR (CDCl$_3$, 300 MHz) δ: (ppm) 7.10 (d, J=3.0, H, ArH), 6.93 (d, J=3.0, H, ArH), 5.18 (s, 2H, OCH$_2$O), 5.16 (s, 2H, OCH$_2$O), 5.15 (t, H, vinylH), 3.87 (d, J=6.9, 2H, allylicH), 3.86 (s, 3H, OCH$_3$), 3.47 (s, 6H, OCH$_3$), 1.75 (s, 3H, CH$_3$), 1.66 (s, 3H, CH$_3$). For methyl 2,6-di-(3-methyl-2-butene)-3,5-bis-methoxymethoxybenzoate: $^1$H NMR (CDCl$_3$, 300 MHz) δ (ppm) 7.27 (s, 2H, ArH), 6.93 (d, J=3.0, H, ArH), 5.18 (s, 2H, OCH$_2$O), 5.16 (s, 2H, OCH$_2$O), 5.15 (t, H, vinylH), 3.87 (d, J=6.9, 2H, allylicH), 3.86 (s, 3H, OCH$_3$), 3.47 (s, 6H, OCH$_3$), 1.75 (s, 3H, CH$_3$), 1.66 (s, 3H, CH$_3$).

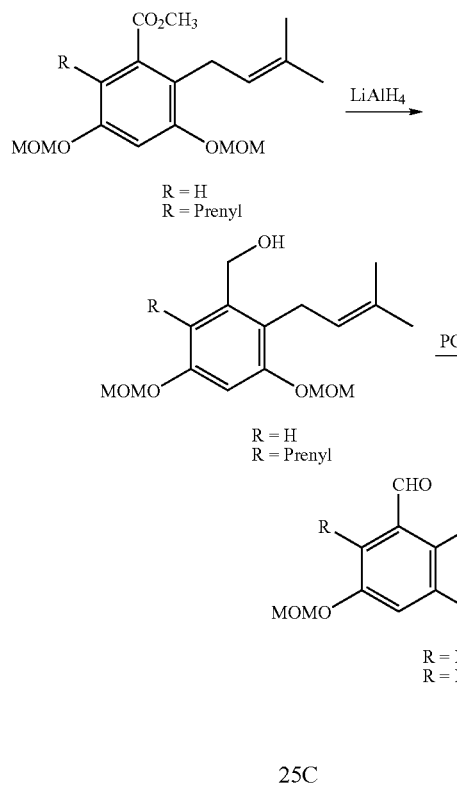

25C

To a solution of methyl 2-(3-methyl-2-butene)-3,5-bis-methoxymethoxybenzoate (1.62 g, 5.0 mmol) in THF was added LAH (227 mg, 6.0 mmol) slowly with stirring. Stirred at room temperature for an hour, the reaction mixture was then heated up to reflux (60° C.) for an additional hour. It was worked up by quenching with aqueous HCl solution, extracting with EtOAc and drying over anhydrous MgSO$_4$. Upon filtration and evaporation to dryness, it afforded the alcohol intermediate. $^1$H-NMR (CDCl$_3$, 300 MHz) δ (ppm) 6.80 (d, J=2.4, 2H, ArH), 6.77 (d, J=1.2, 2H, ArH), 5.18 (s, 2H, OCH$_2$O), 5.16 (s, 2H, OCH$_2$O), 5.15 (t, H, vinylH), 4.65 (s, 2H, CH$_2$OH), 3.87 (d, J=6.9, 2H, allylicH), 3.48 (s, 6H, OCH$_3$), 1.78 (s, 3H, CH$_3$), 1.70 (s, 3H, CH$_3$). MS (ESI) m/z: 297 (MH+), 319 (M+Na)+.

25D

A solution of this alcohol intermediate (200 mg, 0.68 mmol) was dissolved in dry CH$_2$Cl$_2$, while stirring added molecular sieves. After 2 minutes, PCC (218 mg, 1.03 mmol) was added slowly. The reaction mixture was stirred for 2 hours and its color turned from a bright orange to dark brown. A dry silica gel was used to filter out the impurities leaving the desired product 3,5-bis-methoxymethoxy-2-(3-methyl-but-2-enyl)-benzaldehyde. $^1$H-NMR (CDCl$_3$, 300 MHz) δ (ppm) 10.26 (s, H, CHO), 7.20 (d, J=2.7, 2H, ArH), 7.03 (d, J=1.2, 2H, ArH), 5.21 (s, 2H, OCH$_2$O), 5.16 (s, 2H, OCH$_2$O), 5.15 (t, H, vinylH), 3.71 (d, J=6.9, 2H, allylicH), 3.48 (s, 6H, OCH$_3$), 1.78 (s, 3H, CH$_3$), 1.66 (s, 3H, CH$_3$). MS (ESI) m/z: 295 (M+H)+, 317 (M+Na)+.

25E

By following a synthetic sequence corresponding to the one described in Example 25C and 25D, 3,5-bis-methoxymethoxy-2,6-di-(3-methyl-but-2-enyl)-benzaldehyde was prepared, starting from 2,6-di-(3-methyl-2-butene)-3,5-bis-methoxymethoxybenzoate. $^1$H NMR (CDCl$_3$, 300 MHz) δ (ppm) 10.44 (s, H, CHO), 7.13 (s, H, ArH), 5.26 (s, 4H, OCH$_2$O), 5.18 (t, 2H, vinylH), 3.59 (d, J=6.9, 4H, allylicH), 3.48 (s, 12H, OCH$_3$), 1.78 (s, 6H, CH$_3$), 1.66 (s, 6H, CH$_3$). MS (ESI) m/z: 363 (M+H)+, 385 (M+Na)+.

Example 26

Preparation of 4-prenyl- and 4-geranyl-substituted, MOM-3, 5-bis-methoxymethoxybenzaldehyde 26A. MOM-Addition to Methyl-3, 5-dihydroxybenzonate

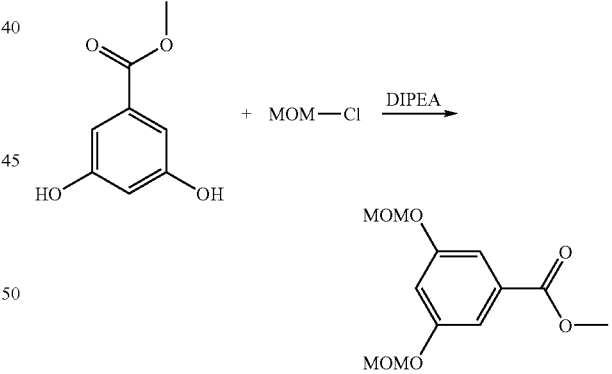

To a solution of methyl-3,5-dihydroxybenzonate (5.0 g, 29.7 mmol), DIPEA (16.63 ml, 95.2 mmol), and a catalytic amount of DMAP in CH$_2$Cl$_2$ was added MOM-Cl (6.78 ml, 89.9 mmol) dropwise over 30 minutes with stirring. The reaction mixture was allowed to stir at room temperature overnight. It was worked up by adding dilute aqueous HCl solution and followed by extraction with DCM. Removal of most mono-protected side product was achieved by washing with aqueous NaOH solution. This solution was then evaporated to dryness and afforded the product as yellow oil. $^1$H-NMR (CDCl$_3$, 300 MHz) δ (ppm) 7.36 (d, J=2.31, 2H, ArH), 6.92 (d, J=2.31, H, ArH), 5.19 (s, 4H, OCH$_2$), 3.90 (s, 3H, OCH$_3$), 3.49 (s, 6H, OCH$_3$). MS (ESI) m/z: 257 (M+H)+.

26B. Reduction of methyl-3, 5-dihydroxybenzonate to the alcohol intermediate

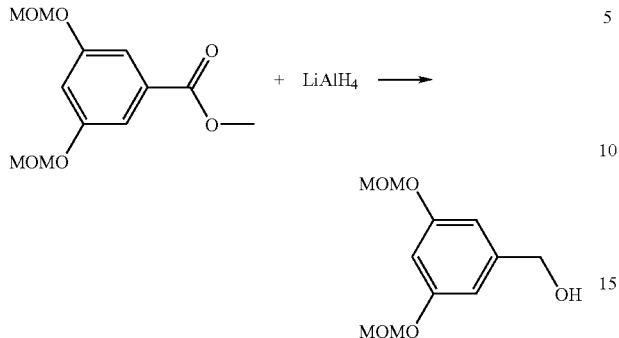

The alcohol intermediate was prepared from methyl-3, 5-dihydroxybenzonate by employing a reduction procedure corresponding to the one described in Example 25. The product obtained was a yellow oil. $^1$H-NMR (CDCl$_3$, 300 MHz) δ (ppm) 6.69 (d, J=4.29, 2H, ArH), 6.64 (d, J=1.87, H, ArH), 5.14 (s, 4H, OCH$_2$), 4.60 (s, 2H, CH$_2$OH), 3.49 (s, 6H, OCH$_3$). MS (ESI) m/z: 229 (M+H)$^+$, 251 (M+Na)$^+$.

26C. TBDMS Protection of (3,4-bis-methoxymethoxy-phenyl)-methanol

A solution of (3,4-bis-methoxymethoxy-phenyl)-methanol (4.2 g, 18.4 mmol), imidazole, and TBDMS-Cl (3.33 g, 22.1 mmol) in a minimum amount of DMF (5 ml) was stirred at room temperature for 2 hours. It was worked up by adding water to the mixture and followed with extraction with EtOAc. Column chromatography purification on silica gel using 30% EtOAc in hexanes as the eluents afforded the product (3,5-bis-methoxymethoxy-benzyloxy)-tert-butyl-dimethyl-silane as a clear oil. $^1$H-NMR (CDCl$_3$, 300 MHz) δ (ppm) 6.69 (d, J=4.29, 2H, ArH), 6.62 (d, J=1.87, H, ArH), 5.14 (s, 4H, OCH$_2$), 4.68 (s, 2H, CH$_2$OTBDMS), 4.13 (s, 6H, OCH$_3$), 0.95 (s, 9H, t-butyl CH$_3$), 0.099 (s, 6H, Si—CH$_3$). MS (ESI) m/z: 343 (M+H)$^+$, 365 (M+Na)$^+$.

26D. Prenylation and Geranylation of (3,5-bis-methoxymethoxy-benzyloxy)-tert-butyl-dimethyl-silane To cold solution (−20° C.) of (3,5-bis-methoxymethoxy-benzyloxy)-tert-butyl-dimethyl-silane (1.80 g, 5.26 mmol) and TMEDA (1.27 g, 10.89 mmol) in THF was added n-BuLi (2.31 ml, 5.79 mmol) dropwise under nitrogen atmosphere. It was allowed to stir at this temperature for 50 minutes and followed by addition of CuCN (480 mg, 5.37 mmol). After stirring for additional 50 minutes at −20° C., the mixture was then transferred via a cannula to a solution of prenyl bromide in THF and allowed to stir for 2 hours at −78° C. under nitrogen. The reaction mixture was warmed up to room temperature ant then quenched with water. After extraction with EtOAc, the organic solution was evaporated to dryness, yielding a yellow oil. This crude product was purified using column chromatography (silica gel, 20% EtOAc in hexanes as the eluents). This gave a 3-prenyl-substituted product as a clear oil. $^1$H-NMR (CDCl$_3$, 300 MHz) δ (ppm) 6.75 (s, 2H, ArH), 5.18 (s, 4H, OCH$_2$), 4.67 (s, 2H, CH$_2$OTBDMS), 3.46 (s, 6H, OCH$_3$), 3.35 (d, 2H, allylicH) 1.78 (s, 3H, CH$_3$), 1.65 (s, 3H, CH$_3$), 0.95 (s, 9H, t-butyl CH$_3$), 0.099 (s, 6H, Si—CH$_3$). MS (ESI) m/z: 411 (M+H)$^+$, 433 (M+Na)$^+$.

Similarly, the corresponding 3-geranyl-substituted derivative was made using the same starting material along with geranyl bromide. $^1$H NMR (CDCl$_3$, 300 MHz) δ (ppm) 6.79 (d, J=4.29, 2H, ArH), 5.22 (t, H, vinylH), 5.15 (s, 4H, OCH$_2$), 5.08 (t, H, vinylH), 4.68 (s, 2H, CH$_2$OTBDMS), 3.46 (s, 6H, OCH$_3$), 3.39 (d, J=6.96, 2H, ArCH$_2$), 2.00 (q, 2H, geranylCH$_2$), 1.95 (q, 2H, geranylCH$_2$), 1.77 (s, 3H, geranylCH$_3$), 1.64 (s, 3H, geranylCH$_3$), 1.56 (s, 3H, geranylCH$_3$), 0.95 (s, 9H, t-butyl CH$_3$), 0.099 (s, 6H, Si—CH$_3$). MS (ESI) m/z: 479 (M+H)$^+$, 501 (M+Na)$^+$.

26E. Hydrolysis of [3,5-bis-methoxymethoxy-4-(3-methyl-but-2-enyl)-benzyloxy]-tert-butyl-dimethyl-silane and tert-butyl-[4-(3,7-dimethyl-octa-2,6-dienyl)-3,5-bis-methoxymethoxy-benzyloxy]-dimethyl-silane To a solution of [3,5-bis-methoxymethoxy-4-(3-methyl-but-2-enyl)-benzyloxy]-tert-butyl-dimethyl-silane (1.6 g, 3.9 mmol) in THF was added TBAF solution in THF (4.68 ml, 4.68 mmol) dropwise with stirring. It was stirred for 2 hours at room temperature until TLC indicated the completion of reaction. The mixture was partitioned between water and EtOAc. The solvent removal of organic layer gave a clean product as a clear oil that was characterized without further purification. $^1$H-NMR (CDCl$_3$, 300 MHz) δ (ppm) 6.78 (s, 2H, ArH), 5.20 (s, 4H, OCH$_2$), 5.16 (t, H, vinylH), 4.63 (s, 2H, CH$_2$OH), 3.48 (s, 6H, OCH$_3$), 3.39 (d, 2H, allylicH) 1.78 (s, 3H, CH$_3$), 1.65 (s, 3H, CH$_3$). MS (ESI) m/z: 297 (M+H)$^+$, 319 (M+Na)$^+$.

Similarly, tert-butyl-[4-(3,7-dimethyl-octa-2,6-dienyl)-3,5-bis-methoxymethoxy-benzyloxy]-dimethyl-silane was made using the same procedure starting from the corresponding TBDMS-protected precursor. $^1$H-NMR (CDCl$_3$, 300 MHz) δ (ppm) 6.79 (d, J=4.29, 2H, ArH), 5.22 (t, H, vinylH), 5.15 (s, 4H, OCH$_2$), 5.08 (t, H, vinylH), 4.63 (s, 2H, CH$_2$OH), 3.46 (s, 6H, OCH$_3$), 3.39 (d, J=6.96, 2H, ArCH$_2$), 2.00 (q, 2H, geranylCH$_2$), 1.95 (q, 2H, geranylCH$_2$), 1.77 (s, 3H, geranylCH$_3$), 1.64 (s, 3H, geranylCH$_3$), 1.56 (s, 3H, geranylCH$_3$). MS (ESI) m/z: 365 (M+H)$^+$, 387 (M+Na)$^+$.

26F. Preparation of 3,5-bis-methoxymethoxy-4-(3-methyl-but-2-enyl)-benzaldehyde and 4-(3,7-dimethyl-octa-2,6-dienyl)-3,5-bis-methoxymethoxy-benzaldehyde

[3,5-Bis-methoxymethoxy-4-(3-methyl-but-2-enyl)-phenyl]-methanol (1.3 g, 4.39 mmol) was prepared by employing the an oxidation procedure corresponding to the one described in Example 25. $^1$H-NMR (CDCl$_3$, 300 MHz) δ (ppm) 9.88 (s, H, CHO), 7.28 (s, 2H, ArH), 5.30 (s, 4H, OCH$_2$), 5.17 (t, H, vinylH), 3.49 (s, 6H, OCH$_3$), 3.43 (d, 2H, allylicH), 1.79 (s, 3H, CH$_3$), 1.67 (s, 3H, CH$_3$). MS (ESI) m/z: 295 (M+H)$^+$, 317 (M+Na)$^+$.

4-(3,7-Dimethyl-octa-2,6-dienyl)-3,5-bis-methoxymethoxy-benzaldehyde was also prepared in the same way. $^1$H-NMR (CDCl$_3$, 300 MHz) δ (ppm) 9.88 (s, H, CHO), 7.31 (d, J=6.69, 2H, ArH), 5.26 (s, 4H, OCH$_2$), 5.16 (t, H, vinylH), 5.08 (t, H, vinylH), 3.46 (s, 6H, OCH$_3$), 3.39 (d, J=6.96, 2H, ArCH$_2$), 2.00 (q, 2H, geranylCH$_2$), 1.95 (q, 2H, geranylCH$_2$), 1.77 (s, 3H, geranylCH$_3$), 1.64(s, 3H, geranylCH$_3$), 1.56 (s, 3H, geranylCH$_3$). MS (ESI) m/z: 363 (M+H)$^+$, 385 (M+Na)$^+$.

Example 27

Preparation of Prenyl-/geranyl-substituted, MOM-compounds of Formula I

A mixture of the aldehyde (1.0 eq.), phosphonium salt (1.2 eq.), and EtOLi (1.2 eq.) was stirred at room temperature for 1.5 h. Workup and purification was carried out following a procedure corresponding to the one described in Example 3. As such, the following compounds were made:

4-{2-[3-Methoxy-4-methoxymethoxy-5-(3-methyl-but-2-enyl)-phenyl]-vinyl}-benzoic acid methyl ester. The compound was obtained as an oil (>95% yield). $^1$H-NMR (CDCl$_3$, 300 MHz) δ (ppm) 8.00 (m, 2H), 7.56-7.34 (m, 2H), 7.20-6.94 (m, 2H), 6.60 (m, 2H), 5.16-5.07(m, 1H), 5.08, 5.07 (2s, 2H), 3.91, 3.90 (2s, 3H), 3.60, 3.58 (2s, 3H), 3.40 (m, 2H), 1.62, 1.60, 1.56, 1.50 (4s, 3H). $^{13}$C-NMR (CDCl$_3$, 75 MHz) δ (ppm) 167.32, 152.75, 152.10, 142.87, 142.37, 136.49, 136.03, 133.24, 133.07, 132.70, 132.42, 131.62, 130.43, 129.88, 129.34 128.82, 127.01, 126.59, 123.15, 122.77, 121.48, 110.88, 108.10, 99.07, 99.29, 57.97, 57.90, 56.12, 55.93, 52.48, 28.93, 28.64, 26.24, 26.07, 18.34, 18.14. MS (ESI) m/z: 397 (M+H)$^+$.

4-[2-(3-methoxy-4-methoxymethoxy-5-(3-methyl-but-2-enyl)-phenyl)-vinyl]-nitrobenzene. The compound was obtained as a yellow thick oil (yield 69%). $^1$H-NMR (CDCl$_3$, 300 MHz) δ(ppm) 8.20, 8.08 (2d, J=8.8 Hz, 2H), 7.63, 7.43 (2d, J=8.8 Hz, 2H), 6.96-6.52 (m, 4H), 5.20, 5.13, 5.08(m+2s, 3H), 3.91, 3.60 (m, 6H), 3.44, 3.30 (2d, J=7.3 Hz, 2H), 1.77-1.57 (m, 6H). $^{13}$C-NMR (CDCl$_3$, 75 MHz): 152.82, 152.33, 144.98, 144.44, 144.20, 136.65, 136.30, 134.15, 133.74, 133.25, 132.64, 132.13, 130.17, 127.57, 127.10, 125.70, 124.57, 123.87, 123.05, 122.59, 121.85, 110.88, 108.27, 99.37, 99.30, 58.00, 57.92, 56.24, 56.02, 28.92, 28.61, 26.25, 26.07, 18.34, 18.11. MS (ESI) m/z: 384 (M+H)$^+$, 406 (M+Na)$^+$.

4-{2-[3,4-Bis-methoxymethoxy-2-(3-methyl-but-2-enyl)-phenyl]-vinyl}-benzoic acid methyl ester. Yield 91%. $^1$H-NMR (CDCl$_3$, 300 MHz) δ(ppm) 8.02, 7.91 (2d, J=8.4 Hz, 2H), 7.53, 7.36(2d, J=8.4 Hz, 2H), 7.17-6.93 (m, 2H), 6.80-6.60(m, 2H), 5.22-5.11 (m, 5H), 3.92, 3.88 (2s, 3 μl, COOMe), 3.60-3.45 (m, 8H), 1.75, 1.67, 1.63, 1.56 (4s, 6H). $^{13}$C-NMR (CDCl$_3$, 75 MHz) δ(ppm) 167.35, 149.76, 142.82, 142.21, 135.08, 132.22, 132.08, 131.58, 130.44, 129.76, 129.54, 129.33, 128.65, 126.59, 125.72, 122.85, 114.19, 99.66, 99.61, 95.44, 58.05, 57.98, 56.70, 52.50, 27.23, 26.12, 26.07, 18.61, 18.53. MS (ESI) m/z: 449 (M+Na)$^+$.

4-{2-[3,4-Bis-methoxymethoxy-5-(3-methyl-but-2-enyl)-phenyl]-vinyl}-benzoic acid methyl ester. Yield 96%. $^1$H-NMR (CDCl$_3$, 300 MHz) δ(ppm) 8.02, 7.91 (2d, J=8.4 Hz, 2H), 7.53, 7.36(2d, J=8.4 Hz, 2H), 7.17-6.93 (m, 2H), 6.80-6.60(m, 2H), 5.24-4.99 (m, 5H), 3.90 (s, 3H, COOMe), 3.60-3.29 (m, 8H), 1.75, 1.67, 1.63, 1.56 (4s, 6H). $^{13}$C-NMR (CDCl$_3$, 75 MHz) δ(ppm) 167.31, 150.46, 149.82, 144.61, 142.73, 136.18, 132.86, 132.22, 130.41, 129.89, 129.29, 129.08, 129.01, 128.80, 126.62, 124.82, 122.66, 115.19, 99.53, 99.46, 95.44, 57.88, 56.47, 52.44, 29.01, 28.68, 26.24, 26.04, 18.34, 18.11. MS (ESI) m/z: 449 (M+Na)$^+$.

4-[2-(3,4-Dimethoxymethoxy-5-(3-methyl-but-2-enyl)-phenyl)vinyl]-nitrobenzene. $^1$H-NMR (CDCl$_3$, 300 MHz) δ(ppm) 8.10, 8.08 (2d, J=8.4 Hz, 2H), 7.53, 7.36 (2d, J=8.4 Hz, 2H), 7.17-6.93(m, 2H), 6.80-6.60(m, 2H), 5.25-5.10 (m, 5H), 3.60-3.29 (m, 6H), 1.75, 1.67, 1.63, 1.56 (4s, 6H). $^{13}$C-NMR (CDCl$_3$, 75 MHz) δ(ppm) 150.53, 149.97, 144.91, 136.44, 133.92, 133.51, 132.79, 132.22, 130.12, 127.70, 127.13, 124.55, 124.26, 123.90, 122.49, 115.06, 99.53, 99.47, 95.38, 57.92, 56.73, 56.51, 28.99, 28.66, 26.25, 26.07, 18.35, 18.11. MS (ESI) m/z: 436 (M+Na)$^+$.

4-{2-[3-(3,7-Dimethyl-octa-2,6-dienyl)-5-methoxy-4-methoxymethoxy-phenyl]-vinyl}-benzoic acid methyl ester. $^1$H-NMR (CDCl$_3$, 300 MHz) δ (ppm) 8.02 (d, J=8.46, H, ArH), 7.92 (d, J=8.37, H, ArH), 7.56 (d, J=8.28, H, ArH), 7.36 (d, J=8.25, 2H, ArH), 6.95 (m, J=2H, ArH), 6.62 (m, H, ArH), 5.25 (t, H, vinylH), 5.20 (s, 2H, OCH$_2$O), 5.10 (t, H, vinylH), 3.90 (s, 3H, OCH$_3$), 3.59 (s, 3H, OCH$_3$), 3.49 (d, J=7.26, 2H, allylicH), 2.05 (s, 3H, CH$_3$), 1.60 (s, 2H, CH$_2$). MS (ESI) m/z: 465 (M+H)$^+$, 487 (M+Na)$^+$.

4-{2-[3-(3,7-Dimethyl-octa-2,6-dienyl)-5-methoxy-4-methoxymethoxy-phenyl]-vinyl}-nitrobenzene. $^1$H-NMR (CDCl$_3$, 300 MHz) δ (ppm) 8.22 (d, J=8.85 Hz, 2H, ArH), 8.10 (d, J=8.82 Hz, H, ArH), 7.62 (d, J=8.82 Hz, H, ArH), 7.17 (m, 2H, ArH), 7.04 (m, ArH), 6.62 (m, H, ArH), 5.15 (t, H, vinylH), 5.08 (s, 2H, OCH$_2$O), 5.10 (t, H, vinylH), 3.90 (s, 3H, OCH$_3$), 3.59 (s, 3H, OCH$_3$), 3.49 (d, J=7.26 Hz, 2H, allylicH), 2.05 (s, 3H, CH$_3$), 1.60 (s, 2H, CH$_2$). MS (ESI) m/z: 452 (M+H)$^+$, 474 (M+Na)$^+$.

4-{2-[3-(3,7-Dimethyl-octa-2,6-dienyl)-5-methoxy-4-methoxymethoxy-phenyl]-vinyl}-benzonitrile. $^1$H NMR (CDCl$_3$, 300 MHz) δ (ppm) 7.56 (m, 3H, ArH), 7.55 (d, J=8.82, H, ArH), 7.28 (m, 3H, ArH), 6.64 (m, 2H, ArH), 5.15 (t, H, vinylH), 5.08 (s, 2H, OCH$_2$O), 5.10 (t, H, vinylH), 3.90 (s, 3H, OCH$_3$), 3.59 (s, 3H, OCH$_3$), 3.49 (d, J=7.26, 2H, allylicH), 2.05 (s, 3H, CH$_3$), 1.60 (s, 2H, CH$_2$). MS: 432 (M+H)$^+$, 454 (M+Na)$^+$.

1-(3,7-Dimethyl-octa-2,6-dienyl)-3-methoxy-2-methoxymethoxy-5-[2-(4-nitro-phenyl)-vinyl]-benzene. $^1$H NMR (CDCl$_3$, 300 MHz) δ (ppm): 8.22 (d, J=8.8, 2H), 8.10 (d, J=8.8, 1H), 7.62 (d, J=8.8, 1H), 7.17 (m, 2H), 7.04 (m, 2H), 6.62 (m, 1H), 5.15 (t, 1H), 5.08 (s, 2H), 5.10 (t, 1H), 3.90 (s, 3H), 3.59 (s, 3H), 3.49 (d, J=7.26, 2H), 2.05 (s, 3H), 1.60 (s, 2H). MS (ESI) m/z: 452 (M+H$^+$), 474 (M+Na)$^+$.

4-{2-[3,5-Bis-methoxymethoxy-4-(3-methyl-but-2-enyl)-phenyl]-vinyl}-benzonitrile. $^1$H NMR (CDCl$_3$, 300 MHz) δ (ppm): 7.54 (m, 3H), 7.38 (d, J=8.9, 2H), 7.36 (m, 1H), 6.64 (m, 2H), 5.25 (s, 4H), 5.22 (t, 1H), 3.51 (s, 6H), 3.42 (d, 2H), 1.77 (s, 3H), 1.71 (s, 3H). MS (ESI) m/z: 394 (M+H$^+$), 416 (M+Na)$^+$.

4-[2-(3-Chloro-4-methoxymethoxy-phenyl)-vinyl]-benzonitrile. $^1$H NMR (CDCl$_3$, 300 MHz) δ (ppm): 7.57 (m, 5.2H), 7.33 (t, 2.6H), 7.02 (m, 5.6H), 6.64 (d, J=12.18, 1H), 6.56 (d, J=12.20, 1H), 5.28 (s, 1.3H), 5.24 (2H), 3.54 (s, 1.7H), 3.52 (s, 3.5H). MS (ESI) m/z: 300 (M+H), 322 (M+Na).

Example 28

Preparation of Prenyl-/geranyl-substituted, Phenolic Compounds of Formula I

MOM-hydrolysisreaction was carried out by following a procedure corresponding to the one described in Example 4. As such the following compounds were made:

4-{2-[4-Hydroxy-3-methoxy-5-(3-methyl-but-2-enyl)-phenyl]-vinyl}-benzoic acid methyl ester. Yield 90%. $^1$H NMR (CDCl$_3$, 300 MHz): 8.01, 7.91 (2d, J=8.4 Hz, 2H), 7.53, 7.36(2d, J=8.4 Hz, 2H), 7.17-6.93(m, 2H), 6.60-6.45(m, 2H), 5.80, 5.69(2s, 1H, OH), 5.34, 5.15 (2m, 1H), 3.95, 3.92 (2s, 6H, OMe), 3.37, 3.25 (2d, J=7.1 Hz, 2H), 1.75, 1.67, 1.63, 1.56 (4s, 6H) ppm. $^{13}$C NMR (CDCl$_3$, 75 MHz): 167.40, 167.37, 147.03, 147.34, 144.38, 132.77, 130.43, 129.88, 129.34, 128.68, 128.10, 128.06, 127.59, 126.38, 122.10, 109.32, 106.44, 56.44, 56.22, 28.28, 26.28, 26.14, 18.28, 18.11 ppm. MS (ESI) m/z: 353 (M+H)$^+$.

4-{2-[4-Hydroxy-3-methoxy-5-(3-methyl-but-2-enyl)-phenyl]-vinyl}-nitrobenzene. $^1$H NMR (CDCl$_3$, 300 MHz): 8.20, 8.08 (2d, J=8.8 Hz, 2H), 7.63, 7.43 (2d, J=8.8 Hz, 2H), 6.96-6.52 (m, 4H), 5.87, 5.74 (2s, 1H, OH), 5.20-5.13, 5.08(m, 1H), 3.95, 3.68 (2s, 3H), 3.44, 3.30 (2d, J=7.3 Hz, 2H), 1.77-1.57 (m, 6H) ppm. $^{13}$C NMR (CDCl$_3$, 75 MHz): 147.04, 144.87, 144.79, 13415, 133.58, 130.13, 128.12, 126.41, 124.59, 124.06, 123.87, 122.52, 122.24, 109.22, 106.54, 56.51, 28.48, 28.18, 26.28, 26.13, 18.29, 18.09 ppm. MS (ESI) m/z: 340 (M+H)$^+$, 362 (M+Na)$^+$.

4-{2-[4,5-Dihydroxy-2-(3-methyl-but-2-enyl)-phenyl]-vinyl}-benzoic acid methyl ester. $^1$H NMR (CDCl$_3$, 300 MHz): 8.01, 7.98 (2d, J=8.4 Hz, 2H), 7.53, 7.36(2d, J=8.4 Hz, 2H), 7.17-6.93(m, 2H), 6.80-6.60(m, 2H), 5.80 (br., 2H, OH), 5.20 (m, 1H), 3.92, 3.86 (2s, 3H, COOMe), 3.35, 3.19 (2d, J=7.14 Hz, 2H), 1.75, 1.67, 1.63, 1.56 (4s, 6H) ppm. $^{13}$C NMR (CDCl$_3$, 75 MHz): 168.02, 167.97, 144.12, 143.15, 142.63, 142.44, 133.47, 132.87, 132.72, 131.96, 130.48, 129.84, 129.34, 129.17, 128.25, 126.57, 123.17, 116.41, 52.69, 31.97, 26.17, 18.38, 18.28 ppm. MS (ESI) m/z: 339 (M+H)$^+$, 361(M+Na)$^+$.

4-{2-[3,4-Dihydroxy-5-(3-methyl-but-2-enyl)-phenyl]-vinyl}-benzoic acid methyl ester. $^1$H NMR (CDCl$_3$, 300 MHz): 8.01, 7.88 (2d, J=8.4 Hz, 2H), 7.53, 7.36(2d, J=8.4 Hz, 2H), 7.17-6.93(m, 2H), 6.80-6.60(m, 2H), 5.80 (br., 2H, OH), 5.34-5.15 (m, 1H), 3.89, 3.88 (2s, 3H, COOMe), 3.40, 3.25 (2d, J=6.36 Hz, 2H), 1.75, 1.67, 1.63, 1.56 (4s, 6H) ppm. $^{13}$C NMR (CDCl$_3$, 75 MHz): 167.67, 143.77, 443.16, 142.24, 132.35, 130.48, 129.79, 129.58, 129.54, 129.41, 126.55, 122.35, 121.89, 121.83, 113.60, 113.47, 52.65, 52.61, 27.25, 26.21, 26.17, 26.08, 18.36, 18.23 ppm. MS (ESI) m/z: 339 (M+H)$^+$, 361(M+Na)$^+$.

4-{2-[3,4-Dihydroxy-2-(3-methyl-but-2-enyl)-phenyl]-vinyl}-benzoic acid methyl ester. $^1$H NMR (CDCl$_3$, 300 MHz): 8.02, 7.91 (2d, J=8.4 Hz, 2H), 7.53, 7.36(2d, J=8.4 Hz, 2H), 7.17-6.93(m, 2H), 6.80-6.60(m, 2H), 5.80 (br., 2H, OH), 5.22-5.11 (m, 1H), 3.92, 3.88 (2s, 3H, COOMe), 3.53, 3.38 (2d, J=6.36 Hz, 2H), 1.75, 1.67, 1.63, 1.56 (4s, 6H) ppm. $^{13}$C NMR (CDCl$_3$, 75 MHz): 167.76, 144.43, 443.94, 142.60, 132.35, 130.48, 129.79, 129.58, 129.54, 129.41, 126.55, 122.35, 121.89, 121.83, 113.60, 113.47, 52.65, 52.61, 27.25, 26.21, 26.17, 26.08, 18.51, 18.40 ppm. MS (ESI) m/z: 339 (M+H)$^+$, 361(M+Na)$^+$.

4-{2-[3,4-Dihydroxy-5-(3-methyl-but-2-enyl)-phenyl]-vinyl}-nitrobenzene. $^1$H NMR (CDCl$_3$, 300 MHz): 8.16, 8.06 (2d, J=8.8 Hz, 2H), 7.70, 7.58(2d, J=8.8 Hz, 2H), 7.17-6.93(m, 2H), 6.80-6.60(m, 2H), 5.50 (br., 2H, OH), 5.34 (m, 1H), 3.33 (2d, J=6.74 Hz, 2H), 1.75, 1.67, 1.63, 1.56 (4s, 6H) ppm. $^{13}$C NMR (CDCl$_3$, 75 MHz): 146.69, 144.75, 144.60, 142.59, 131.55, 130.07, 128.94, 128.85, 127.04, 124.60, 123.83, 122.10, 121.82, 119.26, 113.74, 113.67, 27.29, 26.21, 26.12, 18.53, 18.23 ppm. MS (ESI) m/z: 326 (M+H)$^+$.

4-{2-[3,4-Dihydroxy-2-(3-methyl-but-2-enyl)-phenyl]-vinyl}-nitrobenzene. $^1$H NMR (CDCl$_3$, 300 MHz): 8.33, 8.14 (2d, J=8.8 Hz, 2H), 7.70, 7.58(2d, J=8.8 Hz, 2H), 7.17-6.93(m, 2H), 6.80-6.60(m, 2H), 5.50 (br., 2H, OH), 5.34 (m, 1H), 3.67, 3.52 (2d, J=6.74 Hz, 2H), 1.75, 1.67, 1.63, 1.56 (4s, 6H) ppm. $^{13}$C NMR (CDCl$_3$, 75 MHz): 146.81, 144.83, 144.20, 142.59, 131.55, 130.07, 128.94, 128.85, 127.04, 124.60, 123.83, 122.10, 121.82, 119.26, 113.74, 113.67, 27.29, 26.21, 26.12, 18.53, 18.42 ppm. MS (ESI) m/z: 326 (M+H)$^+$.

4-{2-[3-(3,7-Dimethyl-octa-2,6-dienyl)-4-hydroxy-5-methoxy-phenyl]-vinyl}-benzoic acid methyl ester. $^1$H NMR (CDCl$_3$, 300 MHz) $^1$H NMR (CDCl$_3$, 300 MHz) δ (ppm) 7.56 (m, 3H, ArH), 7.55 (d, J=8.82, H, ArH), 7.28 (m, 3H, ArH), 6.64 (m, 2H, ArH), 5.15 (t, H, vinylH), 5.10 (t, H, vinylH), 3.90 (s, 3H, OCH$_3$), 3.49 (d, J=7.26, 2H, allylicH), 2.05 (s, 3H, CH$_3$), 1.60 (s, 2H, CH$_2$). MS (ESI) m/z: 388 (M+H)$^+$, 442 (M+Na)$^+$.

4-{2-[3-(3,7-Dimethyl-octa-2,6-dienyl)-4-hydroxy-5-methoxy-phenyl]-vinyl}-benzoic acid methyl ester. $^1$H NMR (CDCl$_3$, 300 MHz) δ (ppm) 8.02 (d, J=8.46, H, ArH), 7.92 (d, J=8.37, H, ArH), 7.56 (d, J=8.28, H, ArH), 7.36 (d, J=8.25, 2H, ArH), 6.95 (m, J=2H, ArH), 6.62 (m, H, ArH), 5.25 (t, H, vinylH), 5.10 (t, H, vinylH), 3.90 (s, 3H, OCH$_3$), 3.49 (d, J=7.26, 2H, allylicH), 2.05 (s, 3H, CH$_3$), 1.60 (s, 2H, CH$_2$). MS (ESI) m/z: 421(M+H)$^+$, 443 (M+Na)$^+$.

4-{2-[3-(3,7-Dimethyl-octa-2,6-dienyl)-4-hydroxy-5-methoxy-phenyl]-vinyl}-nitrobenzene. $^1$H NMR (CDC$_3$, 300 MHz) δ (ppm) 8.22 (d, J=8.85, 2H, ArH), 8.10 (d, J=8.82, H, ArH), 7.62 (d, J=8.82, H, ArH), 7.17 (m, 2H, ArH), 7.04 (m, J=2H, ArH), 6.62 (m, H, ArH), 5.15 (t, H, vinylH), 5.10 (t, H, vinylH), 3.90 (s, 3H, OCH$_3$), 3.49 (d, J=7.26, 2H, allylicH), 2.05 (s, 3H, CH$_3$), 1.60 (s, 2H, CH$_2$). MS (ESI) m/z: 407 (M+H)$^+$, 430 (M+Na)$^+$.

4-{2-[3-(3,7-Dimethyl-octa-2,6-dienyl)-4-hydroxy-5-methoxy-phenyl]-vinyl}-benzonitrile. $^1$H NMR (CDCl$_3$, 300 MHz) δ (ppm) 7.56 (m, 3H, ArH), 7.55 (d, J=8.82, H, ArH), 7.28 (m, 3H, ArH), 6.64 (m, 2H, ArH), 5.15 (t, H, vinylH), 5.10 (t, H, vinylH), 3.90 (s, 3H, OCH$_3$), 3.49 (d, J=7.26, 2H, allylicH), 2.05 (s, 3H, CH$_3$), 1.60 (s, 2H, CH$_2$). MS (ESI) m/z: 388 (M+H)$^+$, 442 (M+Na)$^+$.

2-{4-[2-(3,4-Dihydroxy-phenyl)-vinyl]-phenyl}-5-methyl-2,4-dihydro-pyrazol-3-one: 2 HNMR (CDCl$_3$—CD$_3$OD, 300 MHz): 7.63-7.31 (m, 4H), 7.20-5.30 (m, 5H), 3.36 (s, 2H), 2.20 (s, 3H) ppm. $^{13}$CNMR (CDCl$_3$—CD$_3$OD, 75 MHz): 175.20, 161.55, 152.88, 147.94, 140.15, 134.77, 134.25, 133.35, 133.23, 132.72, 131.24, 130.74, 125.51, 125.12, 123.06, 119.49, 119.87, 118.87, 118.79, 20.56, 16.29 ppm. MS (m/z): 309 (MH$^+$).

Example 29

Preparation of Prenyl-/geranyl-substituted, MOM Compounds of Formula I

A mixture of the aldehyde (1.0 eq.), phosphonium salt (1.2 eq.), and EtOLi (1.2 eq.) was stirred at room temperature for 1.5 h. Workup and purification was carried out following a procedure corresponding to the one described in Example 3. As such, the following compounds were made:

4-{2-[3,5-Bis-methoxymethoxy-2-(3-methyl-but-2-enyl)-phenyl]-vinyl}-benzoic acid methyl ester. $^1$H NMR (CDCl$_3$, 300 MHz) δ (ppm) 8.04 (d, J=8.37, H, ArH), 7.85 (d, J=8.40, H, ArH), 7.47 (d, J=16.11, 2H, ArH), 7.20 (d, J=8.4, H, ArH), 6.99 (d, J=2.34, H, ArH), 6.78 (d, J=2.34, H, ArH), 6.71 (d, J=2.37, H, ArH), 5.21 (s, 4H, OCH$_2$O), 4.93 (s, H, vinylH), 3.93 (d, J=15.9, 2H, allylicH), 3.50 (s, 3H, OCH$_3$), 3.48 (s, 3H, OCH$_3$), 1.68 (s, 3H, CH$_3$), 1.60 (s, 3H, CH$_3$).

4-{2-[3,5-Bis-methoxymethoxy-2-(3-methyl-but-2-enyl)-phenyl]-vinyl}-nitrobenzene. $^1$H NMR (CDCl$_3$, 300 MHz) δ (ppm) 8.24 (d, J=8.82, H, ArH), 8.14 (d, J=8.7, H, ArH), 8.04 (d, J=8.91, H, ArH), 7.62 (d, J=8.76, H, ArH), 7.34 (d, J=8.4, H, ArH), 7.28 (d, J=2.34, H, ArH), 7.25 (d, J=2.34, H, ArH) 6.99 (d, J=2.37, H, ArH) 5.21 (s, 4H, OCH$_2$O), 4.93 (s, H, vinylH), 3.93 (d, J=15.9, 2H, allylicH), 3.50 (s, 3H, OCH$_3$), 3.48 (s, 3H, OCH$_3$), 1.68 (s, 3H, CH$_3$), 1.60 (s, 3H, CH$_3$).

4-{2-[4-(3,7-Dimethyl-octa-2,6-dienyl)-3,5-bis-methoxymethoxy-phenyl]-vinyl}-benzoic acid methyl ester. $^1$H NMR (CDCl$_3$, 300 MHz) δ (ppm) 8.03 (d, J=8.37, 2H, ArH), 7.92 (d, J=8.34, 2H, ArH) 7.57 (d, J=8.4, 2H, ArH), 7.37 (d, J=8.28, 2H, ArH), 7.13 (d, J=14.52, 2H, ArH), 6.64 (d, J=8.37, H, ArH), 6.59 (d, J=6.69, 2H, ArH), 5.24 (s, 4H, OCH$_2$), 5.16 (t, H, vinylH), 5.08 (t, H, vinylH), 4.13 (s, 3H, OCH$_3$), 3.42 (s, 6H, OCH$_3$), 3.39 (d, J=6.96, 2H, ArCH$_2$), 2.00 (q, 2H, geranylCH$_2$), 1.95 (q, 2H, geranylCH$_2$), 1.77 (s, 3H, geranylCH$_3$), 1.64(s, 3H, geranylCH$_3$), 1.56 (s, 3H, geranylCH$_3$). MS (ESI) m/z: 495 (M+H)$^+$, 517 (M+Na)$^+$.

4-{2-[4-(3,7-Dimethyl-octa-2,6-dienyl)-3,5-bis-methoxymethoxy-phenyl]-vinyl}-nitrobenzene. $^1$H NMR (CDCl$_3$, 300 MHz) δ (ppm) 8.21 (d, J=8.37, 2H, ArH), 8.10 (d, J=8.34, 2H, ArH) 7.62 (d, J=8.4, 2H, ArH), 7.44 (d, J=8.28, 2H, ArH), 7.41 (d, J=14.52, 2H, ArH), 6.99 (d, J=8.37, H, ArH), 6.62 (d, J=6.69, 2H, ArH), 5.24 (s, 4H, OCH$_2$), 5.16 (t, H, vinylH), 5.08 (t, H, vinylH), 3.42 (s, 6H, OCH$_3$), 3.39 (d, J=6.96, 2H, ArCH$_2$), 2.00 (q, 2H, geranylCH$_2$), 1.95 (q, 2H, geranylCH$_2$), 1.77 (s, 3H, geranylCH$_3$), 1.64(s, 3H, geranylCH$_3$), 1.56 (s, 3H, geranylCH$_3$). MS (ESI) m/z: 482 (M+H)$^+$, 504 (M+Na)$^+$.

4-{2-[4-(3,7-Dimethyl-octa-2,6-dienyl)-3,5-bis-methoxymethoxy-phenyl]-vinyl}-benzonitrile. $^1$H NMR (CDCl$_3$, 300 MHz) δ: 8.21 (d, J=8.37, 2H, ArH), 8.10 (d, J=8.34, 2H, ArH) 7.62 (d, J=8.4, 2H, ArH), 7.44 (d, J=8.28, 2H, ArH), 7.41 (d, J=14.52, 2H, ArH), 6.99 (d, J=8.37, H, ArH), 6.62 (d, J=6.69, 2H, ArH), 5.24 (s, 4H, OCH$_2$), 5.16 (t, H, vinylH), 5.08 (t, H, vinylH), 3.42 (s, 6H, OCH$_3$), 3.39 (d, J=6.96, 2H, ArCH$_2$), 2.00 (q, 2H, geranylCH$_2$), 1.95 (q, 2H, geranylCH$_2$), 1.77 (s, 3H, geranylCH$_3$), 1.64(s, 3H, geranylCH$_3$), 1.56 (s, 3H, geranylCH$_3$). MS (ESI) m/z: 462 (M+H)$^+$, 484 (M+Na)$^+$.

4-{2-[3,5-Bis-methoxymethoxy-2,6-bis-(3-methyl-but-2-enyl)-phenyl]-vinyl}-benzoic acid methyl ester. $^1$H NMR (CDCl$_3$, 300 MHz) δ (ppm) 8.04 (d, J=8.37, 2H, ArH), 8.01 (d, J=8.40, H, ArH), 7.54 (d, J=16.11, 2H, ArH), 7.34 (d, J=8.4, H, ArH), 7.08 (d, J=2.34, H, ArH), 6.64 (d, J=2.34, H, ArH), 6.60 (d, J=2.37, H, ArH), 5.24 (s, 4H, OCH$_2$O), 4.99 (s, 2H, vinylH), 3.90 (d, J=15.9, 4H, allylicH), 3.57 (s, 3H, OCH$_3$), 3.49 (s, 3H, OCH$_3$), 1.76 (s, 6H, CH$_3$), 1.60 (s, 6H, CH$_3$).

4-{2-[3,5-Bis-methoxymethoxy-2,6-bis-(3-methyl-but-2-enyl)-phenyl]-vinyl}-nitrobenzene. $^1$H NMR (CDCl$_3$, 300 MHz) δ: 8.13 (d, J=8.82, 2H, ArH), 7.08 (d, J=8.7, 2H, ArH), 6.95 (d, J=8.91, H, ArH), 6.62 (d, J=8.76, 4H, ArH), 5.23 (s, 4H, OCH$_2$O), 5.11 (s, 2H, vinylH), 3.59 (d, J=15.9, 4H, allylicH), 3.50 (s, 3H, OCH$_3$), 3.48 (s, 3H, OCH$_3$), 1.76 (s, 6H, CH$_3$), 1.67 (s, 6H, CH$_3$).

4-{2-[3,5-Bis-methoxymethoxy-4-(3-methyl-but-2-enyl)-phenyl]-vinyl}-benzoic acid methyl ester. $^1$H NMR (CDCl$_3$, 300 MHz) δ (ppm) 8.03 (d, J=8.41, H, ArH), 7.92 (d, J=6.67, H, ArH), 7.57 (d, J=8.43, H, ArH), 7.37 (d, J=8.28, H, ArH), 6.97 (s, H, ArH), 6.57 (s, 2H, ArH), 6.64 (s, 1H, ArH), 5.25 (s, 4H, OCH$_2$), 5.22 (t, H, vinylH), 4.99 (s, 3H, OCH$_3$), 3.91 (d, 2H, allylicH), 3.40 (s, 6H, OCH$_3$), 1.77 (s, 3H, CH$_3$), 1.71 (s, 3H, CH$_3$). MS (ESI) m/z: 427 (M+H)$^+$, 449 (M+Na)$^+$.

4-{2-[3,5-Bis-methoxymethoxy-4-(3-methyl-but-2-en)-4)-phenyl]-vinyl}-nitrobenzene. $^1$H NMR (CDCl$_3$, 300 MHz) δ (ppm) 8.22 (d, J=8.79, H, ArH), 8.10 (d, J=8.85, H, ArH), 7.59 (d, J=8.82, H, ArH), 7.44 (d, J=8.82, H, ArH), 6.98 (s, 2H, ArH), 6.62 (s, 2H, ArH), 6.59 (s, 1H, ArH), 5.25 (s, 4H, OCH$_2$), 5.22 (t, H, vinylH), 3.51 (s, 6H, OCH$_3$), 3.42 (d, 2H, allylicH), 1.77 (s, 3H, CH$_3$), 1.71 (s, 3H, CH$_3$). MS (ESI) m/z: 414 (M+H)$^+$, 436 (M+Na)$^+$.

4-{2-[3,5-Bis-methoxymethoxy-4-(3-methyl-but-2-enyl)-phenyl]-vinyl}-benzonitrile. $^1$H NMR (CDCl$_3$, 300 MHz) δ (ppm) 7.54 (m, 3H, ArH), 7.38 (d, J=8.85, 2H, ArH), 7.36 (m, H, ArH), 6.64 (m, 2H, ArH), 5.25 (s, 4H, OCH$_2$), 5.22 (t, H, vinylH), 3.51 (s, 6H, OCH$_3$), 3.42 (d, 2H, allylicH), 1.77 (s, 3H, CH$_3$), 1.71 (s, 3H, CH$_3$). MS (ESI) m/z: 394 (M+H)$^+$, 416 (M+Na)$^+$.

Example 30

Preparation of Prenyl-/geranyl-substituted, Phenolic Compounds of Formula I

MOM-hydrolysis reaction was carried out by following a procedure corresponding to the one described in Example 4. As such the following compounds were made:

4-{2-[3,5-Dihydroxy-2-(3-methyl-but-2-enyl)-phenyl]-vinyl}-benzoic acid methyl ester. $^1$H NMR (CDCl$_3$, 300 MHz) δ (ppm) 8.04 (d, J=8.37, H, ArH), 7.85 (d, J=8.40, H, ArH), 7.47 (d, J=16.11, 2H, ArH), 7.20 (d, J=8.4, H, ArH), 6.99 (d, J=2.34, H, ArH), 6.78 (d, J=2.34, H, ArH) 6.71 (d, J=2.37, H, ArH) 4.93 (t, H, vinylH), 3.93 (d, J=15.9, 2H, allylicH), 1.68 (s, 3H, CH$_3$), 1.60 (s, 3H, CH$_3$). MS (ESI) m/z: 339 (M+H)$^+$.

4-{2-[3,5-Dihydroxy-2-(3-methyl-but-2-enyl)-phenyl]-vinyl}-nitrobenzene. Cis-isomer: $^1$H NMR (CDCl$_3$, 300 MHz) δ (ppm) 8.03 (d, J=1.83, 2H, ArH), 8.01 (d, J=1.8, H, ArH), 7.27 (d, J=8.76, 2H, ArH), 6.87 (d, J=12.09, H, ArH), 6.66 (d, J=12.09, H, ArH), 6.32 (d, J=2.4, H, ArH) 6.15 (d, J=2.4, H, ArH) 5.05 (t, H, vinylH), 3.30 (d, J=15.9, 2H, allylicH), 1.78 (s, 3H, CH$_3$), 1.67 (s, 3H, CH$_3$).). MS (ESI) m/z: 326 (M+H)$^+$, 348 (M+Na)$^+$. Trans-isomer: $^1$H NMR (CDCl$_3$, 300 MHz) δ (ppm)

8.24 (d, J=8.76, 2H, ArH), 7.61 (d, J=7.76, 2H, ArH), 7.49 (d, J=16.05, 2H, ArH), 6.99 (d, J=16.02, H, ArH), 6.37 (d, J=2.37, H, ArH), 5.21 (t, H, vinylH), 3.45 (d, J=6.63, 2H, allylicH), 1.83 (s, 3H, CH$_3$), 1.75 (s, 3H, CH$_3$). MS (ESI) m/z: 326 (M+H)$^+$, 348 (M+Na)$^+$.

4-{2-[4-(3,7-Dimethyl-octa-2,6-dienyl)-3,5-dihydroxy-phenyl]-vinyl}-benzoic acid methyl ester. $^1$H NMR (CDCl$_3$, 300 MHz) δ (ppm) 8.03 (d, J=8.37, 2H, ArH), 7.92 (d, J=8.34, 2H, ArH) 7.57 (d, J=8.4, 2H, ArH), 7.37 (d, J=8.28, 2H, ArH), 7.13 (d, J=14.52, 2H, ArH), 6.64 (d, J=8.37, H, ArH), 6.59 (d, J=6.69, 2H, ArH), 5.16 (t, H, vinylH), 5.08 (t, H, vinylH), 4.13 (s, 3H, OCH$_3$), 3.39 (d, J=6.96, 2H, ArCH$_2$), 2.00 (q, 2H, geranylCH$_2$), 1.95 (q, 2H, geranylCH$_2$), 1.77 (s, 3H, geranylCH$_3$), 1.64(s, 3H, geranylCH$_3$), 1.56 (s, 3H, geranylCH$_3$). MS (ESI) m/z: 407 (M+H)$^+$, 429 (M+Na)$^+$.

4-2-[4-(3,7-Dimethyl-octa-2,6-dienyl)-3,5-dihydroxy-phenyl]-vinyl-nitrobenzene. $^1$H NMR (CDCl$_3$, 300 MHz) δ (ppm) 8.21 (d, J=8.37, 2H, ArH), 8.10 (d, J=8.34, 2H, ArH) 7.62 (d, J=8.4, 2H, ArH), 7.44 (d, J=8.28, 2H, ArH), 7.41 (d, J=14.52, 2H, ArH), 6.99 (d, J=8.37, H, ArH), 6.62 (d, J=6.69, 2H, ArH), 5.16 (t, H, vinylH), 5.08 (t, H, vinylH), 3.39 (d, J=6.96, 2H, ArCH$_2$), 2.00 (q, 2H, geranylCH$_2$), 1.95 (q, 2H, geranylCH$_2$), 1.77 (s, 3H, geranylCH$_3$), 1.64(s, 3H, geranylCH$_3$), 1.56 (s, 3H, geranylCH$_3$). MS (ESI) m/z: 394 (M+H$^+$), 416 (M+Na$^+$).

4-{2-[4-(3,7-Dimethyl-octa-2,6-dienyl)-3,5-dihydroxy-phenyl]-vinyl}-benzonitrile. $^1$H NMR (CDCl$_3$, 300 MHz) δ (ppm) 8.21 (d, J=8.37, 2H, ArH), 8.10 (d, J=8.34, 2H, ArH) 7.62 (d, J=8.4, 2H, ArH), 7.44 (d, J=8.28, 2H, ArH), 7.41 (d, J=14.52, 2H, ArH), 6.99 (d, J=8.37, H, ArH), 6.62 (d, J=6.69, 2H, ArH), 5.16 (t, H, vinylH), 5.08 (t, H, vinylH), 3.39 (d, J=6.96, 2H, ArCH$_2$), 2.00 (q, 2H, geranylCH$_2$), 1.95 (q, 2H, geranylCH$_2$), 1.77 (s, 3H, geranylCH$_3$), 1.64(s, 3H, geranylCH$_3$), 1.56 (s, 3H, geranylCH$_3$). MS (ESI) m/z: 374 (M+H)$^+$, 396 (M+Na)$^+$.

4-{2-[3,5-Dihydroxy-4-(3-methyl-but-2-enyl)-phenyl]-vinyl}-benzoic acid methyl ester. $^1$H NMR (CDCl$_3$, 300 MHz) δ (ppm) 8.03 (d, J=8.41, H, ArH), 7.92 (d, J=6.67, H, ArH), 7.57 (d, J=8.43, H, ArH), 7.37 (d, J=8.28, H, ArH), 6.97 (s, H, ArH), 6.57 (s, 2H, ArH), 6.64 (s, $_1$H, ArH), 5.22 (t, H, vinylH), 4.99 (s, 3H, OCH$_3$), 3.91 (d, 2H, allylicH), 1.77 (s, 3H, CH$_3$), 1.71 (s, 3H, CH$_3$). MS (ESI) m/z: 338 (M+H)$^+$, 361 (M+Na)$^+$.

4-{2-[3,5-Dihydroxy-4-(3-methyl-but-2-enyl)-phenyl]-vinyl}-nitrobenzene. $^1$H NMR (CDCl$_3$, 300 MHz) δ (ppm) 8.22 (d, J=8.76, H, ArH), 8.19 (d, J=8.85, H, ArH), 7.60 (d, J=8.82, H, ArH), 7.43 (d, J=8.82, H, ArH), 7.07 (s, 2H, ArH), 6.63 (s, 2H, ArH), 6.26 (s, 1H, ArH), 5.22 (t, H, vinylH), 3.42 (d, 2H, allylicH), 1.77 (s, 3H, CH$_3$), 1.71 (s, 3H, CH$_3$). MS (ESI) m/z: 326 (M+H)$^+$, 348 (M+Na)$^+$.

4-{2-[3,5-Dihydroxy-4-(3-methyl-but-2-enyl)-phenyl]-vinyl}-benzonitrile. $^1$H NMR (CDCl$_3$, 300 MHz) δ (ppm) 7.54 (m, 3H, ArH), 7.38 (d, J=8.85, 2H, ArH), 7.36 (m, H, ArH), 6.64 (m, 2H, ArH), 5.22 (t, H, vinylH), 3.42 (d, 2H, allylicH), 1.77 (s, 3H, CH$_3$), 1.71 (s, 3H, CH$_3$). MS (ESI) m/z: 306 (M+H)$^+$, 328 (M+Na)$^+$.

Example 31

2-Bromo-4-[4-hydroxy-3-(3-methyl-but-2-enyl-phenyl)-vinyl]-phenol

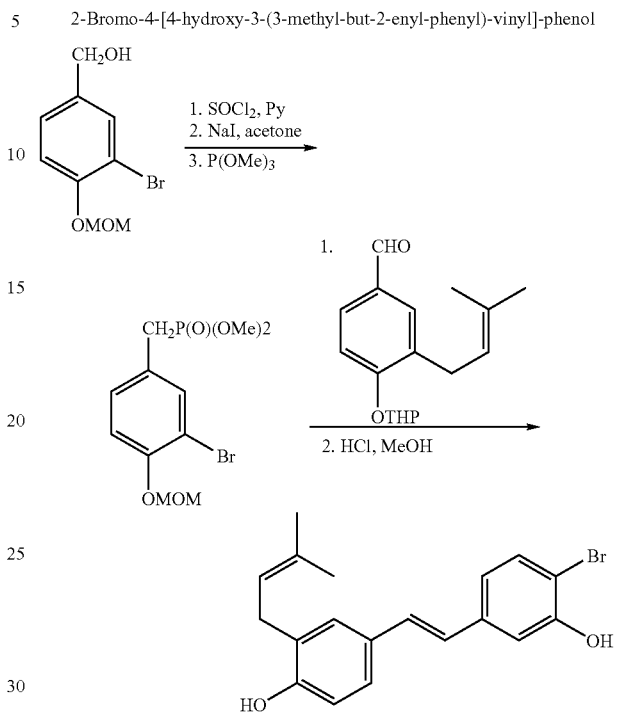

(3-Bromo-4-methoxymethoxy-phenyl)-methanol (250 mg) was dissolved in DCM (20 mL), pyridine (0.15 mL) was added followed by thionyl chloride (0.15 mL), and the mixture was stirred for 1 hour. The mixture was partitioned with water and ethyl acetate. The solvent removal gave 2-bromo-4-chloromethyl-1-methoxymethoxy-benzene as a clear oil, which was used directly in next step. The oil was dissolved in acetone, and sodium iodide (300 mg) was added. The mixture was stirred overnight and a yellow precipitate was formed. Extraction with ethyl acetate and water gave 2-iodo-4-chloromethyl-1-methoxymethoxy-benzene as a brown oil that turned into solid after standing. $^1$HNMR (CDCl$_3$, 300 MHz): 7.58 (d, J=2.0 Hz, 1H), 7.25 (dd, J=2.0, 8.5 Hz, 1H), 7.07 (d, J=8.5 Hz, 1H), 5.25 (s, 2H), 4.39(s, 2H), 3.51 (s, 3H) ppm. The iodide (170 mg) and trimethylphosphate (0.1 mL) were mixed and stirred at 120° C. for 1 hour. After cooling to room temperature, the reaction mixture was directly applied to silica gel column eluting with 5% MeOH in DCM to yield 150 mg of the corresponding phosphonate.

To a mixture of phosphonate (200 mg) and 3-(3-methyl-but-2-enyl)-4-(tetrahydro-pyran-2-yloxy)-benzaldehyde (200 mg) in DMF (10 mL) was added NaH (80 mg). The mixture was stirred at room temperature for 2 hours, and partitioned with ethyl acetate and water. After evaporation of the solvent, purification by flash chromatography eluted with 20% EtOAc in hexane, gave 2-[4-[2-(4-bromo-3-methoxymethoxy-phenyl)-vinyl]-2-(3-methyl-but-2-enyl)-phenoxy]-tetrahydro-pyran as an oil (200 mg). MS (m/z): 509, 511 (MNa$^+$).

The above MOM ether was stirred overnight in MeOH with several drops of conc. HCl. After evaporation of the solvent and purification by flash chromatography (hexane:EtOAc=1:

1), 2-bromo-4-[4-hydroxy-3-(3-methyl-but-2-enyl-phenyl)-vinyl]-phenol (40 mg) was obtained. ¹HNMR (CDCl₃, 300 MHz): 7.60-6.80 (m, 8H, aromatic), 5.53 (s, 1H, OH), 5.33 (m, 1H, vinyl), 5.25 (s, 1H, OH), 3.35 (d, J=3.1 Hz, 2H), 1.08 (s, 6H, 2Me) ppm. ¹³CNMR (CDCl₃, 75 MHz): 154.16, 151.30, 135.13, 132.18, 129.98, 129.43, 128.16, 127.72, 125.63, 124.41, 121.54, 116.15, 116.07, 29.89, 25.84, 17.94 ppm. MS (m/z): 359, 361 (MH⁺).

Example 32

5-{4-[2-(3,4-Bis-methoxymethoxy-phenyl)-vinyl]-pheny}-2-phenyl-2,4-dihydro-pyrazol-3-one

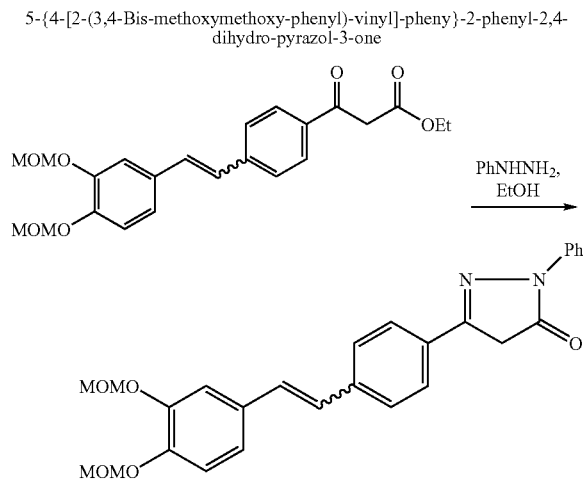

A solution of 3-{4-[2-(3,4-bis-methoxymethoxy-phenyl)-vinyl]-phenyl}-3-oxo-propionic acid ethyl ester (400 mg) and hydrazine (excess) in EtOH (30 mL) was stirred at 90° C. for 5 hours. Evaporation and purification by flash chromatography eluted with 5-10% MeOH in DCM gave 5-{4-[2-(3,4-bis-methoxymethoxy-phenyl)-vinyl]-phenyl}-2-phenyl-2,4-dihydro-pyrazol-3-one as a yellow oil (260 mg). ¹H NMR (CDCl₃, 300 MHz): 7.95 (d, J=8.7 Hz, 2H), 7.62 (d, J=8.7 Hz, 2H), 7.40-7.00(m, 7H), 6.90 (d, 1H), 6.58 (d, J=12.0 Hz, 1H), 6.50 (d, J=12.0 Hz, 1H) 5.21, 5.07(2s, 4H, MOM), 3.78(s, 2H), 33.51, 3.41 (2s, 6H, MOM) ppm. ¹³C NMR (CDCl₃, 75 MHz 170.65, 154.82, 147.23, 147.15, 140.38, 138.53, 131.56, 129.84, 129.68, 129.29, 128.88, 126.17, 125.69, 123.72, 119.42, 117.83, 116.67, 56.69, 56.52, 40.03 ppm. MS: 459 (MH⁺).

Example 33

5-{4-[2-(3,4-Dihydroxy-phenyl)-vinyl]-phenyl}-2-phenyl-2,4-dihydro-pyrazol-3-one A solution of 5-{4-[2-(3,4-bis-methoxymethoxy-phenyl)-vinyl]-phenyl}-2-phenyl-2,4-dihydro-pyrazol-3-one (the cruce reaction product from Example 32) and conc. HCl in MeOH was stirred at room temperature for overnight. Evaporation of the solvent and purification by flash chromatography eluting with 10-15% MeOH in DCM, gave 5-{4-[2-(3,4-dihydroxy-phenyl)-vinyl]-phenyl}-2-phenyl-2,4-dihydro-pyrazol-3-one. ¹H NMR (CD₃OD+CDCl₃, 300 MHz): 7.75-6.45(m, all aromatic peaks). ¹³C NMR (CD₃OD+CDCl₃, 75 MHz): 168.65, 148.27, 144.57, 144.36, 142.01, 132.16, 130.44, 129.07, 128.75, 126.94, 121.37, 120.82, 115.66, 115.08, 113.49. MS: 347 and 371 (MH⁺).

Example 34

2-{4-[2-(4-Hydroxy-3-methoxy-phenyl)-vinyl]-phenyl}-5-methyl-2,4-dihydro-pyrazol-3-one

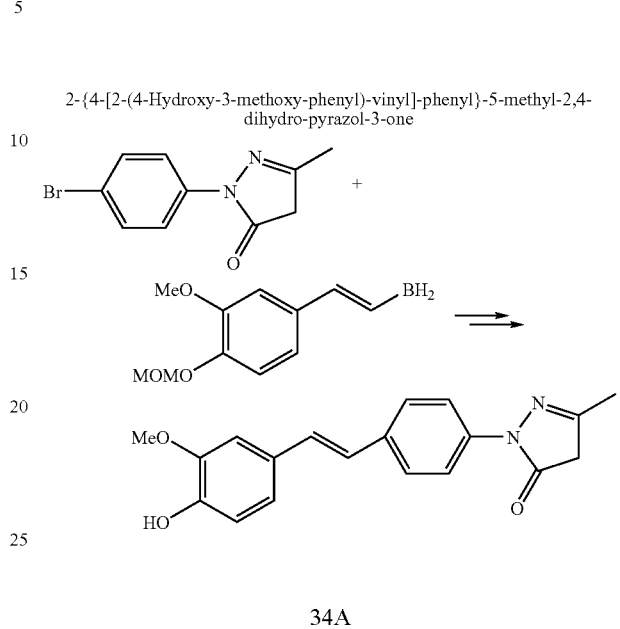

34A 2-(4-Bromo-phenyl)-5-methyl-2,4-dihydro-pyrazol-3-one (105 mg) was dissolved in DME (ethylene glycol dimethyl ether, 2 mL), then Pd(PPh₃)₄ (15 mg, 3% mol) was added. The air was exchanged with argon and the mixture was stirred for 10 min. A solution of 2-(3-methoxy-4-methoxymethoxy-phenyl)-vinyl-boronic acid (90 mg) in DME (1 mL) was added followed by sodium carbonate solution (2M, 0.75 mL). The mixture was stirred for 1 hour at 110° C. After partitioning with ethyl acetate and water and purification over silica gel eluting with 50% EtOAc in hexane gave 140 mg of 2-{4-[2-(3-methoxy-4-methoxymethoxy-phenyl)-vinyl]-phenyl}-5-methyl-2,4-dihydro-pyrazol-3-one as an oily product, which was then hydrolyzed with conc. HCl in methanol. Evaporation of the solvent and purification over silica gel gave 2-{4-[2-(4-hydroxy-3-methoxy-phenyl)-vinyl]-phenyl}-5-methyl-2,4-dihydro -pyrazol-3-one as a light yellow solid (90 mg). ¹HNMR (CDCl₃, 300 MHz): 7.74 (d, J=8.6 Hz, 2H), 7.30 (d, J=8.6 Hz, 2H), 6.77 (s, 3H), 6.48 (s 2H), 5.66 (s, 1H), 3.63 (s, 3H), 3.42 (s, 2H), 2.19(s, 3H) ppm. ¹³CNMR (CDCl₃—CD₃OD, 75 MHz): 170.48, 156.45, 146.04, 144.89, 136.70, 134.28, 129.97, 129.41, 128.00, 122.47, 118.46, 114.21, 111.14, 55.72, 43.10, 17.05 ppm. MS (m/z): 323 (MH⁺).

34B

Similarly, by following the procedure of Example 34A, 5-methyl-2-(4-styryl-phenyl)-2,4-dihydro-pyrazol-3-one was made. ¹HNMR (DMSO-d₆, 300 MHz): 8.10-7.00 (m, 11H), 5.5 (br., 0.45H, contributed from enol form), 3.55(s, 1.55H, contributed from amide form), 2.25 and 2.21 (2s, 3H, Me) ppm. ¹³CNMR (DMSO-d₆, 75 MHz): 137.95, 134.32, 129.59, 128.72, 128.59, 128.42, 127.81, 127.27, 120.89, 14.84 ppm. MS (m/z): 277 (MH$^+$).

Example 35

N-{4-[2-(3,4-Dihydroxyphenyl)-trans-vinyl]-benzenesulfonyl}-morpholine

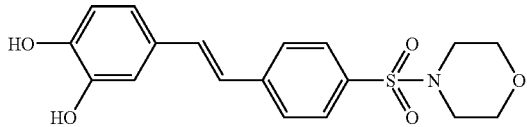

35A. Preparation of N-(4-bromobenzenesulfonyl)morpholine

To a solution of 4-bromobenzenesulfonylchloride (2.555 g, 10 mmol) in CH$_2$Cl$_2$ (40 mL) was added a solution of triethylamine (1.53 mL, 11 mmol) and morpholine (0.96 mL, 11 mmol) at room temperature under argon atmosphere. The solution was stirred for 2 h and the mixture was purified by flash chromatography eluted with mixed solvent of EtOAc: hexanes (1:2, v/v) to provide 3.028 g (9.89 mmol, yield 98.9%) of N-(4-bromobenzenesulfonyl)morpholine as a white solid.

35B. Preparation of N-(4-bromobenzenesulfonyl)piperidine

Similarly, following the procedure of Example 35A and employing commercially available 4-bromobenzenesulfonamide, N-(4-bromobenzenesulfonyl)piperidine was prepared in 99.3% yield. MS (ESI) m/z: 304 and 306 (M+1)$^+$, and 326 and 328 (M+23)$^+$.

35C. Preparation of 3,4-di(methoxymethoxy)styrene

A solution of CH$_3$PPh$_3$Br (10.72 g, 30 mmol) in anhydrous DMF (50 mL) under argon atmosphere was cooled to 0-5° C. Sodium hydride (2.0 g, 60% suspension in mineral oil, 50 mmol, 1.66 eq.) was added in portions. The mixture was stirred at room temperature for 1 hour and then 3,4-di-(methoxymethoxy)-benzaldehyde (6 g, 26.52 mmol) was added in portions. The resulting mixture was stirred at room temperature until completion of the reaction (about 2 hours). The mixture was cooled again to 0-5° C. and water (5 mL) was slowly injected to decompose the excess NaH. After an additional 10 min, the mixture was mixed with water (200 mL) and extracted with CH$_2$Cl$_2$ (2×200 mL). The organic layer was washed with water (200 mL), dried over anhydrous sodium sulfate, filtered and evaporated. The residue was mixed with hexanes and loaded to a silica gel column that was eluted with a mixed solvent of hexane and EtOAc to afford, after evaporation, 3.974 g of 3,4-di(methoxymethoxy)styrene as a yellowish oil (17.72 mmol, yield 66.8%). MS (ESI) m/z: 225 (M+1)$^+$ and 247 (M+23)$^+$.

35D. Preparation of N-{4-[2-(3,4-di(methoxymethoxy)phenyl)-trans-vinyl]benzenesulfonyl}morpholine N-(4-bromobenzenesulfonyl)morpholine (1.0 g, 3.266 mmol) was mixed with (n-Bu)$_4$NBr (TBAB, 1.05 g, 3.266 mmol), K$_2$CO$_3$ (0.451 g, 3.266 mmol) and LiCl (0.1384 g, 3.266 mmol) under argon atmosphere. Then dry DMF (25 mL) and 3,4-di(methoxymethoxy)styrene (0.7324 g, 3.226 mmol) were added, followed by the catalyst Pd(OAc)$_2$ (73 mg, 0.3266 mmol). The mixture was heated between 80-90° C. under argon atmosphere for 24 hours. After removal of the DMF solvent, the residue obtained was loaded to a silica gel column with CH$_2$Cl$_2$ as solvent. The column was eluted with CH$_2$Cl$_2$/EtOAc (2:1, v/v) to yield 1.205 g of N-{4-[2-(3,4-di(methoxymethoxy)phenyl)-trans-vinyl]benzenesulfonyl}morpholine as a yellowish solid (2.6805 mmol, yield 82.1%). $^1$H NMR (CDCl$_3$, 300.16 MHz) δ (ppm) 7.72 (d, J=8.5 Hz, 2H), 7.64 (d, J=8.5 Hz, 2H), 7.38 (d, J=1.7 Hz, 1H), 7.20-7.13 (m, 3H), 7.00 (d, J=16.2 Hz, 1H), 5.30 (s, 2H), 5.27 (s, 2H), 3.77-3.74 (m, 4H), 3.56 (s, 3H), 3.53 (s, 3H) and 3.04-3.01 (m, 4H). MS (ESI) m/z: 450 (M+1)$^+$ and 472 (M+23)$^+$.

35E

Similarly, by following the procedure described in Example 35D and substituting the sulfonamide accordingly, the following compounds were obtained:

N-{4-[2-(3,4-Di(methoxymethoxy)phenyl)-trans-vinyl]benzenesulfonyl}piperidine. $^1$H NMR (CDCl$_3$, 300.16 MHz) δ (ppm) 7.72 (d, J=8.5 Hz, 2H), 7.61 (d, J=8.5 Hz, 2H), 7.37 (d, J=1.7 Hz, 1H), 7.20-7.13 (m, 3H), 7.00 (d, J=16.3 Hz, 1H), 5.30 (s, 2H), 5.27 (s, 2H), 3.56 (s, 3H), 3.53 (s, 3H), 3.00 (m, 4H), 1.67-1.61 (m, 4H) and 1.44-1.42 (m, 2H). MS (ESI) m/z: 448 (M+1)$^+$ and 470 (M+23)$^+$.

4-[2-(3,4-Di(methoxymethoxy)phenyl)-trans-vinyl]benzenesulfonamide. $^1$H NMR (DMSO-d$_6$, 300.16 MHz) δ (ppm) 7.78 (d, J=8.7 Hz, 2H), 7.73 (d, J=8.7 Hz, 2H), 7.39 (d, J=1.9 Hz, 1H), 7.33 (s, 2H), 7.32 (d, J=16.4 Hz, 1H), 7.22 (dd, J=8.4 & 2.0 Hz, 1H), 7.17 (d, J=16.4 Hz, 1H), 7.10 (d, J=8.4 Hz, 1H), 5.24 (s, 2H), 5.20 (s, 2H), 3.42 (s, 3H) and 3.39 (s, 3H). MS (ESI) m/z: 380(M+1)$^+$, 397 (M+18)$^+$ and 402 (M+23)$^+$.

35F. Preparation of N-{4-[2-(3,4-Dihydroxyphenyl)-trans-vinyl]benzenesulfonyl}-morpholine N{4-[2-(3,4-Di(methoxymethoxy)phenyl)-trans-vinyl]benzenesulfonyl} morpholine (0.6 g, 1.3347 mmol) was dissolved in a mixed solvent of MeOH (100 mL) and CH$_2$Cl$_2$ (60 mL). The homogeneous solution was bubbled with argon gas. Water (0.2 g, 11.11 mmol) and concentrated hydrochloric acid (0.9 mL, 10.8 mmol) were added and stirred for 45 hours. The solvents were removed by evaporation and the solid residue was washed with water for several times. The solid was dried under high vacuum in the presence of Drierite providing 0.4388 g of N-{4-[2-(3,4-dihydroxyphenyl)-trans-vinyl]benzenesulfonyl}-morpholine as a yellowish solid (1.214 mmol, yield 91.0%). $^1$H NMR (Acetone-D$_6$ and DMSO-d$_6$, 300.16 MHz) δ (ppm) 9.05 & 9.03 (2s, 0.64H), 8.81 & 8.79 (2s, 0.65H), 7.81 (d, J=8.5 Hz, 2H), 7.71 (d, J=8.3 Hz, 2H), 7.32 (d, J=16.3 Hz, 1H), 7.13-7.04 (m, 2H), 6.96 (dd, J=8.2 & 1.9 Hz, 1H), 6.80 (d, J=8.3 Hz, 1H), 3.68-3.65 (m, 4H) and 2.94-2.91 (m, 4H). MS (ESI) m/z: 362 (M+1)$^+$, 384 (M+23)$^+$ and 745 (2M+23)$^+$.

35G

Similarly, by following the procedure described in 35F and substituting the sulfonamide accordingly, the following compounds were obtained:

N-{4-[2-(3,4-Dihydroxyphenyl)-trans-vinyl]
benzenesulfonyl}piperidine. $^1$H NMR (DMSO-d$_6$, 300.16 MHz) δ (ppm) 9.27 (s, 1H), 9.01 (s, 1H), 7.75 (d, J=8.5 Hz, 2H), 7.64 (d, J=8.5 Hz, 2H), 7.25 (d, J=16.4 Hz, 1H), 7.03 (s, 1H), 7.00 (d, J=16.4 Hz, 1H), 6.92 (dd, J=8.2 & 1.9 Hz, 1H), 6.78 (d, J=8.2 Hz, 1H), 2.88-2.84 (m, 4H), 1.60-1.45 (m, 4H) and 1.40-1.30 (m, 4H). MS (ESI) m/z: 360 (M+1)$^+$, 382 (M+23)$^+$ and 741 (2M+23)$^+$.

4-[2-(3,4-Dihydroxyphenyl)-trans-vinyl]benzenesulfonamide. $^1$H NMR (DMSO-d$_6$, 300.16 MHz) δ (ppm) 9.24 (s, 1H), 9.01 (s, 1H), 7.75 (d, J=8.6 Hz, 2H), 7.69 (d, J=8.6 Hz, 2H), 7.31 (s, 2H), 7.22 (d, J=16.3 Hz, 1H), 7.01 (d, J=1.9 Hz, 1H), 6.97 (d, J=16.3 Hz, 1H), 6.90 (dd, J=8.2 & 1.9 Hz, 1H) and 6.73 (d, J=8.2 Hz, 1H). MS (ESI) m/z: 275 (M−16)+, 292 (M+1)$^+$, 314 (M+23)$^+$ and 605 (2M+23)$^+$.

Example 36

5-[2-(3,4-Bis-methoxymethoxy-phenyl)-vinyl]-[2,2′]bipyridinyl

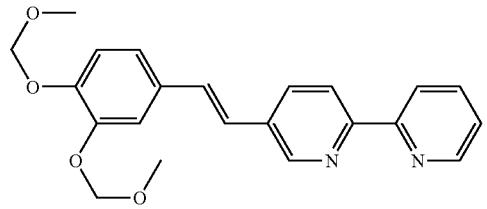

36A. Preparation of 2-(tributyltin)pyridine

A solution of 2-bromopyridine (9.48 g, 60 mmol) in absolute THF (100 mL) was cooled to −78° C. During 25 minutes, n-BuLi (25 mL, 2.5 M hexanes solution, 62.5 mmol) was added slowly. The mixture was stirred for additional 30 minutes and. n-Bu$_3$SnCl (18.6 mL with 96% purity, 66 mmol) was added dropwise. The reaction mixture was stirred at −78° C. for an additional 1 hour and was slowly warmed to room temperature during 1 hour, then stirred at room temperarture for 30 minutes. The solution was poured onto ice (200 g) and extracted with CH$_2$Cl$_2$ (2×200 mL). The organic layer was washed with water, dried over anhydrous sodium sulfate, filtered and evaporated. The residue was purified by chromatography eluted with hexanes:EtOAc (4:1, v/v) to afford 2-(tributyltin)pyridine as a yellowish liquid (18.35 g, 49.85 mmol, yield 83.1%). $^1$H NMR (CDCl3, 300.16 MHz) δ (ppm) 8.74-8.72 (m, 1H), 7.49-7.46 (m, 1H), 7.42-7.38 (m, 1H), 7.13-7.09 (m, 1H), 1.59-1.51 (m, 6H), 1.39-1.27 (m, 6H), 1.15-1.09 (m, 6H) and 0.88 (t, J=7.4 Hz, 9H). MS (ESI) m/z=366, 368 and 370 (M+1)$^+$.

36B. Preparation of 5-methyl-[2.2]bipyridinyl

A solution of 2-(tributyltin)pyridine (9.20 g, 25 mmol) and 2-bromo-5-methylpyridine (4.3 g, 25 mmol) in toluene was bubbled with argon gas for 10 min. The catalyst Pd(PPh$_3$)$_4$ (0.29 g, 0.25 mmol, 1 mol %) was added and the mixture was refluxed under argon atmosphere for 3 days. Removal of solvent gave an oil that was purified by chromatography over silica gel eluted with CH$_2$Cl$_2$ and then EtOAc. The brown liquid obtained was dried overnight under high vacuum providing 4.1073 g of 5-methyl-[2,2′]bipyridinyl as a brown liquid (24.13 mmol, yield 96.5%). $^1$H NMR (CDCl3, 300.16 MHz) δ (ppm) 8.66 (ddd, J=4.8, 1.8 & 0.9 Hz, 1H), 8.51 (dt, J=2.9 & 0.7 Hz, 1H), 8.35 (dt, J=8.0 & 1.1 Hz, 1H), 8.28 (d, J=8.1 Hz, 1H), 7.80 (td, J=7.7 & 1.8 Hz, 1H), 7.63 (ddd, J=8.1, 1.5 & 0.7 Hz, 1H), 7.28 (ddd, J=7.5, 4.8 & 1.2 Hz, 1H) and 2.39 (s, 3H). MS (ESI) m/z: 171 (M+1)$^+$ and (2M+23)$^+$.

36C. Preparation of 5-(bromomethyl)-[2,2′]bipyridinyl

A solution of 5-methyl-[2,2′]bipyridinyl (3.96 g, 23.264 mmol) in CCl4 (80 mL) was bubbled with argon gas. NBS (5.507 g, 30.94 mmol, 1.33 eq) and (PhCOO)$_2$ (0.2922 g, 1.21 mmol, 5 mol %) were added. The mixture was refluxed under argon atmosphere for 2 days. After being cooled to room temperature, the solid was removed by filtration, the filtrate was evaporated, and the residue chromatographed on a silica gel column eluted with a mixed solvent of CH$_2$Cl$_2$ and EtOAc (1:1, v/v). A mixture of three components was obtained (3.88 g). The mixture contained the desired monobromide of 5-(bromomethyl)-[2,2′]bipyridinyl (69.8 wt. %, 10.87 mmol, yield 46.7%), a dibromo by-product (20.2 wt. %, yield 10.3%) and the unreacted starting methylbipyridine (10 wt. %, 9.8% of starting amount). $^1$H NMR (CDCl3, 300.16 MHz) for the monobromide δ (ppm) 8.71-8.67 (m, 2H), 8.40 (d, J=8.0 Hz, 2H), 7.87-7.80 (m, 2H), 7.35-7.26 (m, 1H) and 4.54 (s, 2H) ppm. MS for the monobromide (ESI) m/z: 249 and 251 (M$^+$).

36D. Preparation of (5-[2,2′]bipyridinyl)methyl triphenylphosphine bromide

The mixture obtained in Example 36C above (3.88 g, 10.87 mmol of the monobromide) was mixed with toluene (100 mL) and filtered to remove insoluble solid. To the filtrate was added triphenylphosphine (4.08 g, 15.55 mmol) and the mixture was refluxed under argon atmosphere for 5.5 hours. After being cooled to room temperature, the solid was collected by filtration and washed with hexanes. The lightly brown solid was pumped under high vacuum to afford 4.761 g of (5-[2,2′]bipyridinyl)methyl triphenylphosphine bromide (9.31 mmol, yield 85.6%). MS (ESI) m/z: 431 (M$^+$ without Br$^−$).

36E, Preparation of 5-{2-[3,4-bis(methoxymethoxy)phenyl]vinyl}-[2,2′]bipyridinyl (5-[2,2]Bipyridinyl)methyl triphenylphosphine bromide (2.00 g, 3.91 mmol) and 3,4-di(methoxymethoxy)-benzaldehyde (0.8847 g, 3.91 mmol) were mixed into absolute ethanol (50 mL) under argon atmosphere. To this heterogenerous solution was added dropwise 5.5 mL of 1.0 M EtOLi solution in EtOH (5.5 mmol). The mixture became homogeneous brown solution after the completion of the addition. The reaction solution was stirred at room temperature for 6 hours. Removal of the solvent gave oil that was flashed through a short silica gel column to remove dark color and salts with EtOAc as solvent. Ph$_3$PO was yesprecipitated from a mixed solvent of EtOAc and hexanes. The filtrate was concentrated and the resulting oil was purified by chromatography over silica gel eluted with a mixed solvent of EtOAc and hexanes (1:1, v/v). The resulting yellow oil was pumped overnight under high vacuum to provide 1.29 g of 5-{2-[3,4-bis(methoxymethoxy)phenyl]vinyl}-[2,2′]bipyridinyl (3.409 mmol, yield 87.2%) as a Z/E mixture with the ratio of about 2:1. $^1$H NMR (CDCl$_3$, 300.16 MHz) δ (ppm) 8.75 (d, 0.45H), 8.70-8.67 (m, 0.37H), 8.66 (ddd, J=4.8, 1.8 & 0.9 Hz, 1H), 8.56 (dt, J=2.2 & 0.7 Hz, 1H), 8.42-8.37 (m, 0.92H), 8.35 (dt, J=8.0 &

1.1 Hz, 1H), 8.26 (dd, J=8.2 & 0.4 Hz, 1H), 7.96 (dd, 0.47H), 7.83-7.77 (m, 1.44H), 7.72 (ddd, J=8.7, 2.2 & 0.5 Hz, 1H), 7.39 (d, 0.47H), 7.31-7.26 (m, 1.39H), 7.17-7.14 (m, 1.43H), 7.07 (d, J=2.0 Hz, 1H), 7.04 (d, J=8.4 Hz, 1H), 7.01 (d, 0.5H), 6.89 (ddd, J=2.0 & 0.5 Hz, 1H), 6.69 (d, J=12.1 Hz, 1H), 6.53 (d, J=12.1 Hz, 1H), 5.31 (s, 0.9H), 5.27 (s, 0.96H), 5.22 (s, 2H), 5.07 (s, 1.98H), 3.57 (s, 1.35H), 3.53 (s, 10.38H), 3.51 (s, 3.0H) and 3.37 (s, 2.91H). MS (ESI) m/z: 379 (M+1)$^+$.

Example 37

5-{2-[3,4-Dihydroxyphenyl]vinyl}-[2,2']bipyridinyl

A solution of 5-{2-[3,4-bis(methoxymethoxy)phenyl]vinyl}-[2,2']bipyridinyl (0.85 g, 2.246 mmol), concentrated hydrochloric acid (5 mL) and water (2 mL) in methanol (100 mL) was stirred under argon atmosphere at room temperature for 15 hoursw. Water (50 mL) was added to the mixture and methanol was rotary evaporated. More water (100 mL) was added and the resulting mixture was neutralized to pH 7 with sodium hydroxide solution. The solid precipitate was collected by filtration and washed with water and a mixed solvent of hexane and EtOAc (3:1, v/v). The resulting orange solid was dried under high vacuum giving 0.5559 g of 5-{2-[3,4-dihydroxyphenyl]vinyl}-[2,2']bipyridinyl (1.915 mmol, yield 85.3%) as a Z/E mixture. $^1$H NMR (MeOH, 300.16 MHz): 8.71 (d, J=1.7 Hz, 0.70H), 8.65-8.62 (m, 1.56H), 8.51 (d, J=1.4 Hz, 1.03H), 8.31-8.23 (m, 2.29H), 8.16 (d, J=8.3 Hz, 1.00H), 8.0 (dd, J=2.0 Hz, 0.78H), 7.94-7.89 (m, 1.63H), 7.80 (dd, J=8.2 & 2.0 Hz, 1.04H), 7.44-7.40 (m, 1.52H), 7.23 (d, J=16.4 Hz, 0.74H), 7.08 (d, J=1.8 Hz, 0.71H), 7.00 (d, J=16.4 Hz, 0.74H), 6.95 (dd, J=8.2 & 1.8 Hz, 0.70H), 6.77 (d, J=8.2 Hz, 0.74H), 6.72-6.67 (m, 2.80H), 6.61 (dd, J=8.1 & 1.5 Hz, 1.01H), 6.47 (d, J=12.1 Hz, 1.00H). UV-Vis (MeOH): $E_{max}$=252 nm, 288 nm and 352 nm. MS (ESI) m/z: 291 (M+1)$^+$.

Example 38

5-{2-(3,4-Bis(methoxymethoxy)phenyl]vinyl}-[2,2']Bipyridinyl, Zn(II) Chloride

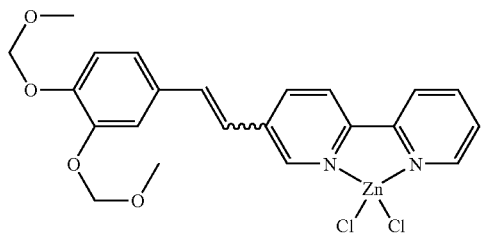

38A

To a solution of zinc(II) chloride (25.57 mg, 0.1876 mmol) in acetone (3 mL) was added a solution of 5-{2-[3,4-bis(methoxymethoxy)phenyl]vinyl}-[2,2']bipyridinyl (71 mg, 0.1876 mmol), as prepared above, in methylene chloride (6 mL). The mixture was stirred at room temperature in a sealed tube for 1 hour. Removal of solvents gave the title product as a bright yellow solid that was pumped overnight under high vacuum. MS (ESI) m/z: 379 ($M_{ligand}$+1)$^+$ and 539 ($M_{complex}$+23)$^+$. UV-Vis (CH$_2$Cl$_2$): $E_{max}$=291 nm and 374 nm (for the ligand, $E_{max}$=248 nm and 336 nm in CH$_2$Cl$_2$).

38B

Similarly, by following the procedure of Example 38A and substituting zinc(II) chloride accordingly, there were obtained:
- 5-{2-[3,4-Bis(methoxymethoxy)phenyl]vinyl}-[2,2']bipyridinyl, copper(II) chloride. MS (ESI) m/z=379 ($M_{ligand}$+1)$^+$ and 500 ($M_{complex}$+23-Cl)$^+$. UV-Vis (CH$_2$Cl$_2$): $E_{max}$=275 nm and 385 nm.
- 5-{2-[3,4-Bis(methoxymethoxy)phenyl]vinyl}-[2,2']bipyridinyl, manganese(III) acetate. MS (ESI) m/z=379 ($M_{ligand}$+1)$^+$. UV-Vis (CH$_2$Cl$_2$): $E_{max}$=248 nm and 335 nm.

38C

Similarly by following the procedure of Example 38A and substituting 5-{2-[3,4-bis(methoxymethoxy)phenyl]vinyl}-[2,2']bipyridinyl with 5-{2-[3,4-dihydroxyphenyl]vinyl}-[2,2']bipyridinyl, and optionally substituting zinc(II) chloride with the appropriate metal salts, the following compounds were obtained:
- {2-[3,4-Dihydroxyphenyl]vinyl}-[2,2']bipyridinyl, zinc (II) chloride. MS (ESI) m/z: 291 ($M_{ligand}$+1)$^+$ and 413 ($M_{complex}$-Cl+Na)$^+$. UV-Vis (MeOH): $E_{max}$=295 nm and 382 nm (for the ligand, $E_{max}$=252 nm, 288 nm and 352 nm in MeOH).
- 5-[2-(3,4-Dihydroxyphenyl)vinyl]-[2,2']bipyridinyl, copper(II) chloride. MS (ESI) m/z: 291 ($M_{ligand}$+1)$^+$. UV-Vis (MeOH): $E_{max}$=245 nm, 293 nm, 316 nm, 360 nm and 485 nm.
- 5-[2-(3,4-Dihydroxyphenyl)vinyl]-[2,2']bipyridinyl, manganese(III) acetate. MS (ESI) m/z: 291 ($M_{ligand}$+1)$^+$ from positive ESI; m/z=521 ($M_{complex}$-1) from negative ESI. UV-Vis (MeOH): $E_{max}$=245 nm, 288 nm and 345 nm.

Example 39

1,3-Bis-methoxymethoxy-5-{2-[4-methoxymethoxy-3-(3-methyl-but-2-enyl)-phenyl]-vinyl}-2-(3-methyl-but-2-enyl)-benzene

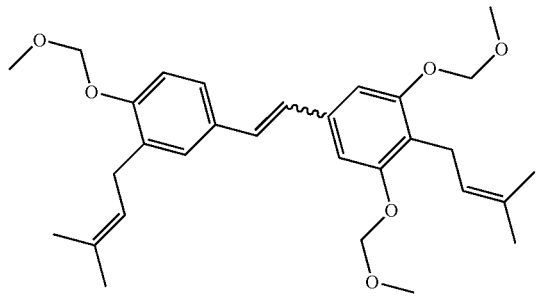

39A. 4-Methoxymethoxy-3-(3-methyl-but-2-enyl)-benzaldehyde

To an ice cold solution of 1 M NaOH (4.1 mmol) was added 4-hydroxy-benzaldehyde (500 mg, 4.1 mmol). After 5 minutes, prenyl bromide (626 ul, 4.9 mmol) was added dropwise and the solution was allowed to slowly come to room temperature for another two hours. The pH was adjusted to 10 and the impurities were extracted out with EtOAc, leaving the product and starting material in the aqueous layer. The aqueous layer was made slightly acidic, and then extracted with EtOAc, washed with $H_2O$ and brine, dried with $MgSO_4$ and evaporated yielding a yellow oil. After a quick silica gel column (eluting with EtOAc:9Hexane and increased up to 8EtOAc:2Hexane) and evaporation, the prenylated benzaldehyde was obtained as a thick yellow oil. $^1H$ NMR ($CDC_3$, 300 MHz) δ (ppm): 9.81 (s, 1H), 7.66 (m, 2H), 6.97 (d, J=8.1, 1H), 5.33 (t, 1H), 3.41 (d, J=7.2, 2H), 1.77 (s, 6H). MS (ESI) m/z: 191 $(M+H^+)$, 213 $(M+Na^+)$. Prenylated benzaldehyde (1.2 g, 6.32) was dissolved in DMF, allowed to cool in an ice bath and stirred. After slow addition of NaH (303 mg, 7.58 mmol), methoxymethoxy chloride (576 ul, 7.58 mmol) was added dropwise. This was left stirring at room temperature for 2 hours. Work up with water, brine, extraction with EtOAc, and evaporation yielded 4-methoxymethoxy-3-(3-methyl-but-2-enyl)-benzaldehyde as a clear dark yellow liquid. $^1H$ NMR ($CDCl_3$, 300 MHz) δ (ppm): 9.81 (s, H), 7.16 (m, 2H), 7.05 (d, J=8.2, 1H), 5.30 (t, 1H), 5.20 (s, 2H) 3.48 (s, 3H), 3.36 (d, J=7.2, 2H), 1.77 (s, 6H) ppm. MS (ESI) m/z: 234 $(M+H)^+$, 261 $(M+Na)^+$.

39B. Methanesulfonic acid 3,5-bis-methoxymethoxy-4-(3-methyl-but-2-enyl)-benzyl ester

[3,5-Bis-methoxymethoxy-4-(3-methyl-but-2-enyl)-phenyl]-methanol (2.0 g, 6.75 mmol) was dissolved in $CH_2Cl_2$ and placed in an ice bath. Triethylamine (1.2 ml, 8.92 mmol) was added and stirred until the reaction solution was at 0° C., followed by the dropwise addition of mesylate chloride (900 ul, 8.92 mmol). After stirring in the ice bath for 1 hour, the reaction was quenched with water, extracted with EtOAc, washed with brine, dried with $MgSO_4$, filtered and evaporated yielding methanesulfonic acid 3,5-bis-methoxymethoxy-4-(3-methyl-but-2-enyl)-benzyl ester as a yellow oil. $^1H$ NMR ($CDCl_3$, 300 MHz) δ (ppm): 6.82 (s, 2H), 5.20 (t, 1H), 5.16 (s, 4H), 4.13 (s, 2H), 3.48 (s, 6H), 3.39 (d, 2H) 2.96 (s, 3H), 1.78 (s, 3H), 1.65 (s, 3H). MS (ESI) m/z: 375 $(M+H)^+$, 397 $(M+Na)^+$.

39C. 1,3-bis-methoxymethoxy-2-(3-methyl-but-2-enyl)-benzyl)-triphenyl-phosphonium bromide Methanesulfonic acid 3,5-bis-methoxymethoxy-4-(3-methyl-but-2-enyl)-benzyl ester (100 mg, 0.27 mmol) was allowed to dissolve in acetone and stir as NaBr (83 mg, 0.81 mmol) was added. The solvent was evaporated to dry and the residue was washed with dichloro methane and filtered. The solvents were evaporated to dry yielding yellow oil. $^1H$ NMR ($CDCl_3$, 300 MHz) δ (ppm): 6.81 (s, 2H), 5.20 (t, 1H), 5.16 (s, 4H), 4.44 (s, 2H), 3.48 (s, 6H), 3.39 (d, 2H), 1.78 (s, 3H), 1.65 (s, 3H). The bromide was converted to the triphenyl phosphomium bromide following the procedure of Example 1.

39D. 1,3-Bis-methoxymethoxy-5-{2-[4-methoxymethoxy-3-(3-methyl-but-2-enyl)-phenyl]-vinyl}-2-(3-methyl-but-2-enyl)-benzene To a solution of 1,3-Bis-methoxymethoxy-2-(3-methyl-but-2-enyl)-benzyl)-triphenyl-phosphonium bromide (500 mg, 0.81 mmol) in DMF was added 4-methoxymethoxy-3-(3-methyl-but-2-enyl)-benzaldehyde (157 mg, 0.67 mmol) followed by stirring. NaH (32.4 mg, 1.2 mmol) was slowly added and after 30 minutes of stirring at room temperature, it was worked up with water, brine and EtOAc. This was dried with $MgSO_4$, filtered, and evaporated yielding a green oil. Column purification yielded 1,3-bis-methoxymethoxy-5-{2-[4-methoxymethoxy-3-(3-methyl-but-2-enyl)-phenyl]-vinyl}-2-(3-methyl-but-2-enyl)-benzene as a yellow oil. $^1H$ NMR ($CDCl_3$, 300 MHz) δ (ppm): 7.28 (d, J=6.7, 1H), 7.01 (m, 2H), 6.95 (m, 3H, ArH), 6.65 (d, J=17.7, 1H), 6.45 (d, J=8.9, 1H), 5.32 (t, 1H), 5.24 (s, 2H), 5.17 (m, 4H), 3.48 (m, 6H), 3.37 (m, 3H), 3.39 (d, 2H), 3.22 (d, 2H), 1.78 (s, 6H), 1.65 (s, 6H). MS (ESI) m/z: 497 $(M+H)^+$, 519 $(M+Na)^+$.

39E

Similarly the following compounds were prepared:

1,3-Bis-methoxymethoxy-5-[2-(4-methoxymethoxy-3,5-dimethoxy-phenyl)-vinyl]-2-(3-methyl-but-2-enyl) benzene $^1H$ NMR ($CDCl_3$, 300 MHz) δ (ppm): 6.96 (d, J=4.65, 2H), 6.74 (s, 1H), 6.68 (s, 1H), 6.49 (m, 2H), 5.25 (s, 2H), 5.21 (t, 1H), 5.14 (s, 2H), 5.03 (s, 2H) 3.93 (s, 3H), 3.69 (s, 3H), 3.61 (s, 3H), 3.58 (s, 3H), 3.39 (s, 3H), 3.35 (d, J=6.88, 2H), 1.76 (m, 3H), 1.67 (m, 3H). MS (ESI) m/z: 489 (M+H), 511 (M+Na).

1,3-Bis-methoxymethoxy-5-[2-(4-methoxymethoxy-3-methoxy-5-nitro-phenyl)-vinyl]-2-(3-methyl-but-2-enyl)-benzene. $^1H$ NMR ($CDCl_3$, 300 MHz) δ (ppm): 7.46 (s, 0.5H), 7.21 (s, 0.5H), 6.97 (m, 2H), 6.64 (m, 1.5H), 6.45 (m, 1.5H), 5.24 (s, 2H), 5.20 (s, 2H), 5.05 (s, 2H), 3.98 (s, 3H), 3.64 (s, 3H), 3.53 (s, 3H), 3.41 (s, 3H), 1.79 (m, 3H), 1.63 (m 3H). MS (ESI) m/z: 504 (M+H), 526 (M+Na).

1,3-Bis-methoxymethoxy-5-[2-(4-methoxymethoxy-3-nitro-phenyl)-vinyl]-2-(3-methyl-but-2-enyl)-benzene $^1H$ NMR ($CDCl_3$, 300 MHz) δ (ppm): 7.76 (m, 3H), 6.97 (m, 4H), 5.31 (s, 2H), 5.26 (t, 1H) 5.24 (s, 2H), 5.04 (s, 2H), 3.54 (s, 3H), 3.50 (s, 3H), 3.38 (s, 3H), 1.79 (m, 3H), 1.66 (m 3H). MS (ESI) m/z: 474 (M+H), 496 (M+Na).

Example 40

4-[3-(3-Methoxy-4-methoxymethoxy-phenyl)-allylidene]-5-methyl-2-phenyl-2,4-dihydro-pyrazol-3-one

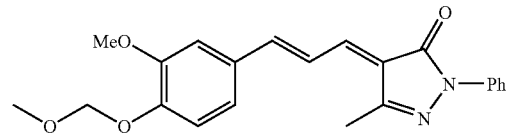

To a solution of bis-(3,4-dimethoxy methyl oxy) benzaldehyde (502 mg, 2.26 mmol—prepared from 3-(4-hydroxy-3-methoxy-phenyl)-propenal in a procedure as described in Example 23B), 3-methyl-1-phenyl-2-pyrazolin-5-one (392 mg, 2.25 mmol) and benzoic acid (26 mg, 0.21 mmol) in toluene (75 mL) was added piperidine (19 mg, 0.22 mmol). The solution was refluxed under nitrogen at 120° C. with water-jacketed condensing for 9 hours. The solvent volume was reduced under reduced pressure and EtOAc was added. The mixture was washed 3 times with aqueous NaCl and 0.5 M HCl and dried over sodium sulfate for 2 hours. The solvent was removed under reduced pressure and the residues were chromatographed (silica gel, hexanes:EtOAc=5:2) to afford a dark red product (372 mg, 44%). $^1H$-NMR ($CDCl_3$, 300 MHz) δ (ppm): 9.90 (s, 0.03H), 8.45-8.10 (m, 1H), 7.96-7.93 (d, J=9.9 Hz, 2H) 3-7.16 (m, 8H), 5.34-5.27 (2d, J=6.2 Hz, combined 2H), 4.05-3.94 (2s, combined 3H), 3.53 (s, 3H), 2.54-2.26 (m, 3H). MS (ESI) m/z: 379 (M+H$^+$, 100), 779 (M+M+Na$^+$, 65).

Example 41

Determination of Activity Utilizing Neuronal Cell Stress Assay

A. Isolation and Culture of Primary Hippocampal Neuronal Cells.

The following materials are employed:

Neurobasal/B27i: Neurobasal medium (available from Invitrogen, San Diego, Calif.) with 1×B27 supplement (Invitrogen), 0.5 µM L-glutamine, 25 µM L-glutamic acid, and 1× Penicillin/Streptomycin.

Hank's Basic Salt Solution (HBSS, Ca/Mg-free) is prepared by preparing 1× Hanks CMF (Gibco) supplemented with HEPES (10 mM, pH 7.3), sodium bicarbonate (0.35%), 1× Penicillin/Streptomycin, and 1 mM MEM sodium pyruvate.

Poly-D-lysine (Sigma, St. Louis, Mo.), 50 µg/ml solution.

Sigmacote (Sigma, St. Louis, Mo.).

Plastic Culture Flasks (T75 cm$^2$) or 24-well cell culture plates treated with Poly-D-Lysine (Sigma, St. Louis, Mo.).

A pregnant female mouse (E18-E19) is euthanized with $CO_2$ followed by removal of the uterus, which is then placed in a sterile plastic petri dish. The embryos are removed from the sac, and the embryonic brains removed and immersed in cold (4° C.) Buffered Salt Solution (HBSS; Ca/Mg free; Life Technologies) in a small petri dish. Hippocampi are then removed from the brains under a dissecting microscope and placed on a paraffin-covered dish. The meninges are stripped away and the dissected hippocampi are collected in a small petri dish in HBSS. The hippocampi are transferred to a 15-ml centrifuge tube (normally 10-12 brains) filled with HBSS. The tube containing the brains is centrifuged at 1000 rpm for 2 min in a tabletop centrifuge. The supernatant is removed, 2 ml of HBSS is added to the hippocampi in the tube, and the resulting suspension is triturated 2 times each with long-tipped siliconized glass pipettes having progressively smaller apertures, starting with a pipette with a standard size opening (approximately 1.0 mm diameter), following with one having an aperture of half standard size (approximately 0.5 mm diameter), then with one having an aperture about one-half that size (0.25 mm diameter). The suspension is then centrifuged again at 1000 rpm for 2 min in a tabletop centrifuge, the supernatant is discarded, and 2 ml of Neurobasal/B27i (with antibiotics) is added to the tube. The trituration procedure described above is then repeated on this suspension.

The density of cells is determined on a small aliquot of cells using standard counting procedures and correcting for cell viability by trypan blue stain exclusion. Using this procedure, the expected yield is 3×10$^5$-6×10$^5$ cells/brain. Cells are then added to PDL-coated 24 well plates, flasks or MetTek dishes in Neurobasal/B271 at a density of about 1.5×10$^6$ cells (T75 flask) or about 100,000 cells/well of a 24-well plate. Plated cells are incubated at 37° C. in an atmosphere of 5% $CO_2$/95% $O_2$-Media is renewed after 34 days by replacing half of it with fresh Neurobasal/B27m medium, containing 5 µM cytosine arabinoside (Ara-C). Seven to eight days from the initial culture, the media is renewed again, by removing one-half or it and replacing with an equal amount of fresh Neurobasal/B27m medium (without Ara-C).

B. Hippocampal Anoxia-Reoxygenation Cell Death Assay.

This assay is used to induce ischemia by anoxia-reoxygenation in cultured hippocampal neuronal cells. Test compounds are added to assess potency and efficacy against ischemia-induced neuronal cell injury and cell death.

The following materials are employed:

Neurobasal media, NoG neurobasal media, B27 supplement and B27 Supplement minus AO (Invitrogen).

Neurobasal/B27 medium is prepared with 2× B27 minus AO supplement, 0.5 mM L-glutamine and 0.25× penicillin/streptomycin.

Cell Tracker Green was obtained from Molecular Probes and a fresh 51M solution was prepared from 10 mM stock just before use.

NoG-Neurobasal contains NoG neurobasal medium plus 0.5 mM glucose, 0.1 mM L-glutamine and 0.25× Penicillin/Streptomycin.

Primary hippocampal neuronal cells were prepared according to the methods described above and were cultured in poly-D-lysine coated 24 well plates for 10-11 days prior to use.

Deoxygenated LoG-Neurobasal medium (100 ml) is prepared by pre-equilibrating the medium in a Ti 50 cm$^2$ flask in a hypoxic chamber overnight. Following pre-incubation under hypoxic conditions, the LoG-Neurobasal media is lightly bubbled with 100% $N_2$ for 30 min to completely deoxygenate the media. An additional 20 ml LoG-Neurobasal is pre-equilibrated in a T75 cm$^2$ flask and 100 ml Neurobasal/B27AO is incubated in a normal incubator (5% $CO_2$) overnight. Reoxygenated medium is prepared by placing medium overnight in the culture incubator (5% $CO_2$/95% $O_2$) prior to use.

Existing culture medium (Neurobasal/B27m) is removed from the cells by aspiration. Cells are washed once with 2 ml/well (24-well culture plates) of glucose free-BSS. Neurons are replenished 10-11 days after initial culture with deoxygenated LoG-Neurobasal (1 ml per well for each well of a 24-well plate). Test compounds are added directly to each well (3 concentrations of the compound plus positive control, each in triplicate). Most test compounds are dissolved in 100% DMSO; concentrations are adjusted such that the final concentration of DMSO in the cell media never exceeded 0.5%. Plates containing cells with test compounds are placed in a hypoxic chamber for 5 hr with plate lids ajar. For normoxia controls, pre-equilibrated normoxic LoG-Neurobasal medium is added to each well of cells, and the plate is replaced in the normal culture incubator for 5 hr. After 5 hr of hypoxia, the existing media is carefully aspirated off, and 2 mL of new, reoxygenated (pre-equilibrated) Neurobasal/B27AO is added to each well. The same test compounds (in the same the concentrations) are added back into the corresponding wells. Plates are placed in the cell culture incubator (5% $CO_2$/95% $O_2$) and reoxygenated for 20-24 hr. After reoxygenation for 20-24 hr, live neurons are quantitated using the cell tracker green fluorescence method, described below.

To test for cell viability, existing culture medium is aspirated from each well of the 24 well plates, and neurons are washed once with 2 ml of HBSS (pH 7.4, prewarmed to 30-37° C.). To each well is added one milliliter of 5 µM Cell Tracker Green fluorescent dye dissolved in HBSS. Plates are placed in the dark at room temperature for 15 minutes, and are then washed with two milliliters of HBSS. One milliliter of HBSS is then added to each well, and fluorescent cells are counted using a fluorescent microscope. Significantly increased cell viability compared to control cells is indicative of a protective compound.

Results

When tested as described above, compounds of the present invention, such as:

2,6-di-tert-butyl-4-[2-(4-nitro-phenyl)-vinyl]-phenol;
4-{2-[4-(2-nitro-vinyl)-phenyl]-vinyl}-benzene-1,2-diol;
4-[2-(3,4-dihydroxy-phenyl)-vinyl]-benzenesulfonamide4-{2-[4-amino-sulfonyl)-phenyl]-vinyl}-benzene-1,2-diol;
3,4-bis-[2-(3,4-dihydroxy-phenyl)-vinyl]-benzoic acid methyl ester;
4-[2-(5-bromo-2-hydroxy-4-methoxy-phenyl)-vinyl]-benzoic acid methyl ester;
4-[2-(2,3,4-trihydroxy-phenyl)-vinyl]-benzonitrile;
2-{4-[2-(4-hydroxy-3-methoxy-phenyl)-vinyl]-phenyl}-5-methyl-2,4-dihydro-pyrazol-3-one;
1-carboxymethyl-4-[2-(3,4-dihydroxy-phenyl)-vinyl]-pyridinium; bromide;
1,3-bis-methoxymethoxy-2-(3-methyl-but-2-enyl)-5-[2-(4-nitro-phenyl)-vinyl]-benzene;
4-[2-(3,4-bis-methoxymethoxy-phenyl)-vinyl]-benzoic acid tetradecyl ester;
4-[2-(3,4-bis-{2-[2-(2-methoxy-ethoxy)-ethoxy]-ethoxy}-phenyl)-vinyl]-benzoic acid ethyl ester;
4-{2-[4-(3,7-dimethyl-octa-2,6-dienyl)-3,5-bis-methoxymethoxy-phenyl]-vinyl}-benzoic acid methyl ester;
2-methoxymethoxy-1,3-dimethyl-5-[2-(4-nitro-phenyl)-vinyl]-benzene;
1,2-bis-methoxymethoxy-4-[4-(4-nitro-phenyl)-buta-1,3-dienyl]-benzene;
2-methoxymethoxy-5-[2-(4-nitro-phenyl)-vinyl]-benzoic acid methoxymethyl ester;
1,5-bis-methoxymethoxy-2-(3-methyl-but-2-enyl)-3-[2-(4-nitro-phenyl)-vinyl]-benzene;
1,3-bis-methoxymethoxy-2-(3-methyl-but-2-enyl)-5-[2-(3-nitro-4-methoxymethoxy-5-methoxy-phenyl)-vinyl]-benzene;
1-iodo-3-methoxy-2-methoxymethoxy-5-[2-(4-nitro-phenyl)-vinyl]-benzene;
1-bromo-3-methoxy-2-methoxymethoxy-5-[2-(4-nitro-phenyl)-vinyl]-benzene;
4-[3-(3-methoxy-4-methoxymethoxy-phenyl)-allylidene]-5-methyl-2-phenyl-2,4-dihydro-pyrazol-3-one;
5-[3,5-dihydroxy-4-(3-methyl-but-2-enyl)-benzylidene]-thiazolidine-2,4-dione;
5-[4-methoxymethoxy-3-(3-methyl-but-2-enyl)-benzylidene]-thiazolidine-2,4-dione;
5-[4-hydroxy-3-(3-methyl-but-2-enyl)-benzylidene]-thiazolidine-2,4-dione;
5-[3-(3,7-dimethyl-octa-2,6-dienyl)-4-hydroxy-benzylidene]-thiazolidine-2,4-dione;
5-[3-(3,7-dimethyl-octa-2,6-dienyl)-4-methoxymethoxy-benzylidene]-thiazolidine-2,4-dione;
4-{2-[3,4-dihydroxy-5-(3-methyl-but-2-enyl)phenyl]-vinyl}-benzoic acid methyl ester;
4(2-[4,5-dihydroxy-2-(3-methyl-but-2-enyl)-phenyl]-vinyl)benzoic acid methyl ester;
2-methoxy-6-(3-methyl-but-2-enyl)-4-[2-(4-nitro-phenyl)vinyl]-phenol;
5-[2-(4-hydroxy-3-methoxy-5-nitro-phenyl)-vinyl]-2-(3-methyl-but-2-enyl)benzene-1,3-diol;
4(2-[4-(3,7-dimethyl-octa-2,6-dienyl)-3,5-bis-methoxymethoxy-phenyl]-vinyl)-benzonitrile;
4-[2-(4-nitro-phenyl)vinyl]benzene-1,2-diol;
2-hydroxy-5-[2-(4-nitro-phenyl)vinyl]-benzoic acid;
2-bromo-6-methoxy-4-[2-(4-nitro-phenyl)-vinyl]-phenol;
2-chloro-4-[2-(4-nitro-phenyl)-vinyl]-phenol;
4-[2-(3,4-dihydroxy-phenyl)-vinyl]-benzoic acid methyl ester;
4-[2-(2,5-dimethoxy-3,4-dimethyl-phenyl)-vinyl]-benzoic acid methyl ester;
3-{4-[2-(3,4-dihydroxy-phenyl)-vinyl]-phenyl}4H-isoxazol-5-one;
2-{4-[2-(3,4-dihydroxy-phenyl)-vinyl]-phenyl}-5-methyl-2,4-dihydro-pyrazol-3-one;
4-[2-(6-nitro-benzo[1,3]dioxol-5-yl)-vinyl]-benzoic acid methyl ester;
4-[2-(3,4-bis-methoxymethoxy-phenyl)-vinyl]-N,N-bis-(2-hydroxy-ethyl)-benzamide;
4-[2-(3-iodo-5-methoxy-4-methoxymethoxy-phenyl)-vinyl]-benzoic acid methyl ester;
4-{2-[3-(3,7-dimethyl-octa-2,6-dienyl)-5-methoxy-4-methoxymethoxy-phenyl]-vinyl}-benzoic acid methyl ester;
4-[2-(3,4-bis-methoxymethoxy-phenyl)-vinyl]-phthalic acid dimethyl ester;
4-[2-(3,4-bis-methoxymethoxy-phenyl)-vinyl]-benzoic acid 3,7-dimethyl-octa-2,6-dienyl ester;
1,3-bis-methoxymethoxy-2-(3-methyl-but-2-enyl)-5-[2-(4-nitro-phenyl)-vinyl]-benzene;
1,5-bis-methoxymethoxy-2,4-bis-(3-methyl-but-2-enyl)-3-[2-(4-nitro-phenyl)-vinyl]-benzene;
4-[2-(3-chloro-4-methoxymethoxy-phenyl)-vinyl]-benzonitrile;
5-[2-(3,4-bis-methoxymethoxy-phenyl)-vinyl]-[2,2']bipyridinyl;
4-(3,4-bis-methoxymethoxy-benzylidene)-5-meth-2-phenyl-2,4-dihydro-pyrazol-3-one;
5-[2-(3,4-bis-methoxymethoxy-phenyl)-vinyl]-[2,2']bipyridinyl, Zn(II)chloride;
4-{2-[4-hydroxy-3-methoxy-5-(3-methyl-but-2-enyl)-phenyl]-vinyl}-benzoic acid methyl ester;
4-{2-[4-(3,7-dimethyl-octa-2,6-dienyl)-3,5-dihydroxy-phenyl]-vinyl}-benzoic acid methyl ester;
4-(3-methyl-but-2-enyl)-5-[2-(4-nitro-phenyl)-vinyl]-benzene-1,3-diol;
2-(3,7-dimethyl-octa-2,6-dienyl)-6-methoxy-4-[2-(4-nitro-phenyl)-vinyl]-phenol;
4-{2-[3,5-dihydroxy-4-(3-methyl-but-2-enyl)-phenyl]-vinyl}-benzonitrile; and
5-{3-[3-methoxy-4-(3-methyl-but-2-enyloxy)-phenyl]-allylidene}-thiazolidine-2,4-dione, provided protection against stressor-induced cell death in at least about 20% of the cells tested, at concentrations ranging from about 1 to 1000 μM.

Example 42

Myocyte Calcium-Contractility Assay

A. Isolation and Culture of Primary Neonate Myocytes.
The following materials are employed:
10× Heart Dissection Solution (HDS) contains the following components (g/l) in tissue grade water: NaCl, 68; HEPES, 47.6; $NaH_2PO_4$, 2; Glucose, 10; KCl, 4; $MgSO_4$, 1, pH adjusted to 7.4. Prior to filter sterilization of diluted (1×HDS) solution, 10 mg phenol red is added to each 500 milliliters of medium.
Transferrin and Bovine Insulin (available from Life Technologies) are resuspended at a concentration of 4 mg/ml in tissue culture grade water.
DMEM-F12—DMEM/F12, powder, 1:1 containing glutamine and pyridoxine hydrochloride (available from Life Technologies). To one liter equivalent of the powder is added 2.43 g of sodium bicarbonate and 10 ml of 100× Penicillin/Streptomycin in 950 ml of tissue culture grade water with stirring. The pH is adjusted to 7.2 with 1M HCl and volume adjusted to 1 liter. The solution is filter sterilized, followed by the addition of 2.5 ml of 4 mg/ml Transferrin, 250 µl 4 mg/ml Insulin and 30.7 mg of bromodeoxyuridine.

DMEM-F12-5% FBS is also prepared for pre-coating the tissue culture plates and initial suspension of the cardiomyocyte pellet.

Collagenase solution-57.1 mg of collagenase is resuspended in 140 ml 1×HDS.

Tissue culture ware is pre-coated with DMEM-F12-5% FBS by incubating 501 µl per well of a 96-well plate and 0.5 ml per 24-well plate at 37° C.

Two-day old rat pups are removed from their mothers and placed in a sterile container. Pups are dipped quickly into 70% alcohol, then decapitated and the body placed in an empty sterile tissue culture dish. An incision is made starting at the neck and progressing towards the belly, cutting through the sternum. The heart is removed and placed in a tissue culture dishes containing 1×HDS. The atria are trimmed, and the remaining ventricles are placed into a separate tissue culture dish containing 1×HDS, where they are sectioned into 3-4 pieces each. Ventricles are then transferred to a sterile 250 ml glass flask and the 1×HDS is removed. Twenty milliliters of pre-warmed collagenase solution is added to the ventricles, followed by incubation at 37° C. with shaking. After 20 minutes, the collagenase solution is removed and replaced with 20 ml fresh pre-warmed collagenase. Incubation is continued for an additional 20 minutes. At the end of the incubation, any tissue chunks are allowed to settle prior to removing the collagenase (containing the isolated cardiomyocytes) from the disrupted tissue pieces. The isolated myocytes are added to a 50 ml Falcon tube containing 2 ml Fetal Bovine Serum (FBS). The remaining tissue pieces are subjected to a second digestion by adding 20 ml fresh pre-warmed collagenase and incubating as above for 20 minutes. This second digest is then centrifuged at 1000 rpm for 5 minutes (tabletop centrifuge). The resulting supernatant is discarded, and the cell pellet is suspended with 4 ml FBS. The resulting cell suspension is placed in the incubator at 37° C. This step is repeated several additional times to harvest additional material.

Percoll gradients are prepared by adding 2.5 ml of 10×HDS to 22.5 ml of Percoll (Life Technologies) with mixing (Percoll Stock). Top Gradient solution (11 ml Percoll Stock and 14 ml 1×HDS) and Bottom Gradient solution (13 ml Percoll Stock and 7 ml 1×HDS) are prepared. Four milliliters of the Top Gradient solution is transferred into 6×15 ml sterile Falcon tubes. Three milliliters of the Bottom Gradient solution is placed in each tube by inserting a serological pipette to the bottom of the tube and slowly adding the liquid.

All the digests (6) are pooled in one 50 ml Falcon tube and centrifuged on a tabletop centrifuge at 1000 rpm for 10 minutes. The supernatant is discarded, and the cell pellet is resuspended in 12 ml of 1×HDS. Two milliliters of the cell suspension is added to the top of each gradient. The gradient tubes are then centrifuged at 3000 rpm for 30 minutes without braking in a Beckman Allegra 6 centrifuge (GH 3.8A rotor). Following centrifugation, the cells segregate into two sharp bands at the two interfaces. The lower band of the two bands is enriched for cardiomyocytes; there is also a cardiomyocyte pellet at the bottom of the tube. The upper band is enriched for fibroblasts and other non-cardiomyocytes. The upper portion of the gradient is aspirated down to just above the cardiomyocyte layer. The cardiomyocyte layer is then carefully removed along with the pellet, and the two fractions are pooled in a sterile 50 ml Falcon tube, along with corresponding fractions from additional gradient tube; then 1×HDS is added to a total volume of about 50 ml. The tube is centrifuged at 1000 rpm for 10 minutes. The supernatant is discarded and resuspended in 10 ml 1×HDS. A further 40 ml of 1×HDS is added and the centrifugation step is repeated. The cell pellet is resuspended carefully but thoroughly in 50 ml of DMEMF12-5% FBS.

A small aliquot of the cell suspension is counted in a hemocytometer. The DMEM/F12-FBS coating medium is aspirated from the tissue culture dishes. The cardiomyocytes are added to the dishes at a plating density of $7.5 \times 10^4$/well per 96-well in 200 µL and $6 \times 10^4$/well per 24-well in 1 ml. The cultures are incubated at 37° C. with 5% $CO_2$ overnight. The original medium is removed, and add fresh DMEM/F12-5% FBS is added to each culture, prior to incubation at 37° C. with 5% $CO_2$ for a further 48 hours, before use.

B. Contractility Assay

The following materials are employed:

Complete DMEM-F12: DMEM/F12, powder, 1:1 containing glutamine and pyridoxine hydrochloride (available from Life Technologies—Invitrogen Life Technologies, Carlsbad, Calif.). Powder sufficient to prepare one liter of buffer and 2.43 g of sodium bicarbonate is mixed into 950 ml of tissue culture grade water. The pH is adjusted to 7.2 with 1M HCl and the remaining water added to make 1 liter. Following filter sterilization, 10 ml of 100× Penicillin/Streptomycin, 2.5 ml of 4 mg/ml Transferrin, 250 µl 4 mg/ml Insulin and 30.7 mg of bromodeoxyuridine are added, and the mixture is incubated at 37° C. prior to use.

1 mM glucose in DMEM is made from DMEM without L-glutamine, without glucose, without sodium pyruvate (available from Life Technologies).

20 µM Fluo-4: Cell permanent AM ester of Fluo-4 (available as a dry powder to be stored at −20° C., from Molecular Probes—Eugene, Oreg.). This fluorescent dye is light sensitive and should be made up fresh at 1 mM in DMSO prior to use to prevent light degradation.

Neonatal cardiomyocytes are isolated as described above. The cardiomyocytes are plated in 96-well format (black clear-bottomed plates) at a density of $7.5 \times 10^4$ per well and grown for 2 days in the presence of 5% FBS prior to use in the assay.

Physiological ischemia is simulated by placing the cardiomyocytes in an anaerobic chamber (0% $O_2$, 85% $N_2$, 5% $CO_2$ & 10% $H_2$) in DMEM containing 1 mM glucose. Positive control cells are treated with DMEM-F12 containing 25 mM Glucose, which protects against the anoxia.

The test compounds are made up in DMEM-1 mM glucose in 96 deep-well mother plates and appropriately diluted for use in the assay. The media is removed from the cells and replaced with 2001 µl of either DMEM-F12 or 1 mM DMEM with or without test compounds. The plates are then placed inside a 37° C. incubator in the anaerobic chamber and incubated for 16 hours. The plates are then removed and reoxygenated by the addition of pre-warmed DMEM-F12 containing 5% FBS. Since the anoxic treatment may damage and/or kill the cells, causing them to dislodge from the bottom of the wells gentle aspiration of media is required at this step. The cells are then placed in a normal incubator at 37° C. and incubated for two hours to allow the cells to reoxygenate.

A working solution of 20 µM Fluo-4 is added to pre-warmed 1×HBSS. The cells are loaded with Fluo-4 by first removing media from the cells and replacing with 100 µl of 20 µM Fluo-4. Unloaded control cells are treated in parallel with 1×HBSS alone. All cells are then incubated at 37° C. for 30 minutes. Before fluorescence measurements are made, the cells are washed in indicator-free medium (HBSS) to remove any dye that is non-specifically associated with the cell surface. Cells are then incubated for an additional 20 minutes at room temperature. Basal Fluo-4 fluorescence is measured using the 485 nm excitation and 538 nm emission filter pair on a microplate flourometer (Fluorskan™, Thermo Labsystems Oy, Helsinki, Finland). Each well is read for 60 ms to obtain a baseline reading, then removed from the fluorimeter and stimulated to contract by addition of 1×HBSS (which contains 1.3 mM $CaCl_2$), followed by incubation at 37° C. for 90 minutes. A second fluorescence reading is then taken. Difference in pre vs. post stimulation fluorescence readings is indicative of activity.

Results

When tested as described above, compounds of the present invention, such as:

- 5-[2-(4-nitro-phenyl)-vinyl]-benzene-1,3-diol;
- 4-[2-(4-hydroxy-3,5-dimethyl-phenyl)-vinyl]-benzoic acid methyl ester;
- 4-[2-(4-hydroxy-3-methoxy-phenyl)-vinyl]-benzonitrile;
- 4-[2-(3,4-dihydroxy-phenyl)vinyl]-benzoic acid;
- 5-(3,4-dihydroxy-benzylidene)-thiazolidine-2,4-dione;
- 4-(2-nitro-vinyl)-benzene-1,2-diol;
- 4-[2-(3,4-bis-methoxymethoxy-phenyl)-vinyl]-N,N-bis-(2-hydroxy-ethyl)-benzamide;
- 4-[2-(3,4-bis-methoxymethoxy-phenyl)-vinyl]-phthalic acid dimethyl ester;
- 1-methoxy-2-methoxymethoxy-3-(3-methyl-but-2-enyl)-5-[2-(4-nitro-phenyl)-vinyl]-benzene;
- 1,3-bis-methoxymethoxy-2-(3-methyl-but-2-enyl)-5-[2-(4-nitro-phenyl)-vinyl]-benzene;
- 1,3-bis-methoxymethoxy-5-[2-(4-nitro-phenyl)vinyl]-benzene;
- 1-bromo-3-methoxy-2-methoxymethoxy-5-[2-(4-nitro-phenyl)vinyl]-benzene;
- 4-{2-[3-(3,7-dimethyl-octa-2,6-dienyl)-4-hydroxy-5-methoxy-phenyl]-vinyl}-benzonitrile;
- 2-[2-(3,4-bis-methoxymethoxy-phenyl)-vinyl]-thiazole;
- 5-(3,4-bis-methoxymethoxy-benzylidene)-thiazolidine-2,4-dione;
- 4-{2-[3-(3,7-dimethyl-octa-2,6-dienyl)-4-hydroxy-5-methoxy-phenyl]-vinyl}-benzoic acid methyl ester;
- 2,6-dimethyl-4-[2-(4-nitro-phenyl)-vinyl]-phenol;
- 2-bromo-6-methoxy-4-[2-(4-nitro-phenyl)-vinyl]-phenol;
- 4-[2-(4-hydroxy-3-iodo-5-methoxy-phenyl)-vinyl]-benzoic acid methyl ester;
- 4-[2-(3,4-dihydroxy-phenyl)-vinyl]-N,N-bis-(2-hydroxyethyl)-benzamide;
- 4-{2-[4-(5-hydroxy-1H-pyrazol-3-yl)-phenyl]-vinyl}-benzene-1,2-diol;
- 1-carboxymethyl-4-[2-(3,4-dihydroxy-phenyl)-vinyl]-pyridinium, bromide;
- 1-(2-carboxy-2-oxo-ethyl)-4-[2-(3,4-dihydroxy-phenyl)-vinyl]-pyridinium, bromide;
- 4-[2-(5-methyl-thiophen-2-yl)-vinyl]-benzoic acid methyl ester;
- 2-[2-(3,4-dihydroxy-phenyl)-vinyl]-anthraquinone;
- 4-[2-(1H-benzoimidazol-5-yl)-vinyl]-benzoic acid methyl ester;
- 2-methoxy-4-[4-(4-nitro-phenyl)-buta-1,3-dienyl]-phenol;
- 4-{2-[3-methoxy-4-methoxymethoxy-5-(3-methyl-but-2-enyl)-phenyl]-vinyl}-benzoic acid methyl ester;
- 4-{2-[3,4-bis-methoxymethoxy-5-(3-methyl-but-2-enyl)-phenyl]-vinyl}-benzoic acid methyl ester;
- 4-{2-[4-(3,7-dimethyl-octa-2,6-dienyl)-3,5-bis-methoxymethoxy-phenyl]-vinyl}-benzoic acid methyl ester;
- 5-[2-(4-methoxycarbonyl-phenyl)-vinyl]-2-methoxymethoxy-benzoic acid methoxymethyl ester;
- 1,2-bis-methoxymethoxy-3-(3-methyl-but-2-enyl)-5-[2-(4-nitro-phenyl)-vinyl]-benzene;
- 2-(3,7-dimethyl-octa-2,6-dienyl)-1,3-bis-methoxymethoxy-5-[2-(4-nitro-phenyl)-vinyl]-benzene;
- 1-(3,7-dimethyl-octa-2,6-dienyl)-3-methoxy-2-methoxymethoxy-5-[2-(4-nitro-phenyl)-4)-vinyl]-benzene;
- 4-{2-[3,5-bis-methoxymethoxy-4-(3-methyl-but-2-enyl)-phenyl]-vinyl}-benzonitrile;
- {4-[2-(3,4-bis-methoxymethoxy-phenyl)-vinyl]-phenyl}-dimethyl-amine;
- {4-[2-(3,4-bis-methoxymethoxy-phenyl)-vinyl]-phenyl}-methyl-amine;
- 4-[2-(3,4-bis-methoxymethoxy-phenyl)-vinyl]-4'-methyl-[2,2']bipyridinyl;
- 2-methoxy-1-methoxymethoxy-4-[4-(4-nitro-phenyl)-buta-1,3-dienyl]-benzene;
- 4-(3,4-dihydroxy-benzylidene)-5-methyl-2-phenyl-2,4-dihydro-pyrazol-3-one;
- 3-(3,4-bis-methoxymethoxy-benzylidene)-3H-benzofuran-2-one;
- 3-(3,5-di-tert-butyl-4-hydroxy-benzylidene)-5-hydroxy-3H-benzofuran-2-one;
- 5-{4-[6-hydroxy-2,7,8-trimethyl-2-(4,8,12-trimethyl-tridecyl)-chroman-5-ylmethoxy]-benzylidene}-thiazolidine-2,4-dione;
- 4-{2-[3,4-bis-methoxymethoxy-5-(3-methyl-but-2-enyl)-phenyl]-vinyl}-benzoic acid methyl ester;
- 1,2-bis-methoxymethoxy-3-(3-methyl-but-2-enyl-5-[2-(4-nitro-phenyl)vinyl]-benzene;
- 1,5-bis-methoxymethoxy-2-(3-methyl-but-2-enyl)-3-[2-(4-nitro-phenyl)-vinyl]-benzene;
- 2-(3,7-dimethyl-octa-2,6-dienyl)-1,3-bis-methoxymethoxy-5-[2-(4-nitro-phenyl)-vinyl]-benzene;
- 1-(3,7-dimethyl-octa-2,6-dienyl)-3-methoxy-2-methoxymethoxy-5-[2-(4-nitro-phenyl)-vinyl]-benzene;
- 4-{2-[4-(3,7-dimethyl-octa-2,6-dienyl)-3,5-bis-methoxymethoxy-phenyl]-vinyl}-benzonitrile;
- 4-{2-[3,5-bis-methoxymethoxy-4-(3-methyl-but-2-enyl)-phenyl]-vinyl}-benzonitrile;
- 4-{2-[3-(3,7-dimethyl-octa-2,6-dienyl)-5-methoxy-4-methoxymethoxy-phenyl]-vinyl}-benzonitrile; and
- 5-[2-(3,5-dimethoxy-4-methoxymethoxy-phenyl)-vinyl]-2-(3-methyl-but-2-enyl)-1,3-(bis-methoxymethoxy)-benzene, showed the presence of calcium transients in amounts indicative of ability guard against ischemic damage and allow the cells to maintain their contractile function.

Example 43

Rat Middle Cerebral Artery Occlusion (MCAO) Model of Cerebral Ischemia

A. Animal Preparation

Male Wistar rats (Harlan, Ind.) weighing 300-350 g are commonly used in these experiments. Animals are allowed free access to water and commercial rodent diet under standard laboratory conditions. Room temperature is maintained at 20-23° C. and room illumination is on a 12/12-hour light/dark cycle. Animals are acclimatized to the laboratory environment 5 to 7 days prior to the study, and fasted (with free access to water) overnight before surgery.

B. Middle Cerebral Artery Occlusion (MCAO)

Anesthesia is maintained by inhalation of 3.0% isoflurane (Aerrane, Front Dodge, Iowa) in 0.8% oxygen. The animal's neck is shaved and sterilized before operation. Body temperatures are controlled and maintained at 37.5° C.+/−1 degree via external heating and cooling devices. To lower the body temperature, animals are placed in a cooling chamber that uses ice to cool circulating air. Throughout the study the body temperature is recorded using a temperature transponder (BMDS Inc., Seaford, DL) implanted subcutaneously at the time of MCAO between the rat shoulder blades, which allows the user to read the body temperature via a pocket scanner (BMDS Inc., Seaford, DL). The body temperature can also be taken by inserting the temperature probe into the animal's rectum. Body temperature is recorded every hour for 6 hours post-occlusion, but temperature is measured more frequently to facilitate maintaining the animals' normothermic temperature.

Animals are subjected to two hours MCAO using a modified intraluminal filament technique, as follows. A midline incision on the ventral part of the neck is made to expose external and internal carotid arteries. The right external and common carotid arteries are ligated by a suture (silk 5/0, Carlisle Laboratories, Farmers Branch, Tex.) and the right internal artery is temporarily ligated using a microvascular clip (Fine Science Tool Inc., Foster City, Calif.). A small incision is made in the common carotid artery. A nylon filament, its tip rounded by heating, is prepared from a fishing line (Stren Fishing Lines, Wilmington, Del.) and is inserted from the right common carotid artery. The filament is advanced into the internal carotid artery 18-20 mm from the point of bifurcation of internal and external arteries and a suture is tightly ligated around the filament. Two hours post occlusion, animals are re-anesthetized to allow reperfusion for the remaining of the experiment by removal of the filament.

C. Drug Administration

Test compounds can be administered by any of a number of routes, such as those described below. Compounds can be administered before, during or after occlusion, as appropriate to the protocol.

a) Intracerebroventricular (ICV) Infusion

The anesthetized animal is placed on a stereotaxic apparatus (Harvard Apparatus, S. Natick, Mass.). Anesthesia is maintained by inhalation of 3.0% isoflurane (Aerrane, Front Dodge, Iowa) in 0.8% oxygen throughout the entire procedure. The scalp is shaved and sterilized prior to surgery. A midline sagittal incision about 3 cm long is made slightly behind the eyes to expose the skull. The skull is scraped with a rounded end spatula to remove periosteal connective tissue. A bur hole is placed 1.5 mm lateral, 1 mm posterior to the left of the bregma to mark the left lateral ventricle. A brain infusion cannula (ALZET—Alza, Palo Alto, Calif.) is inserted 4 mm deep into the hole. The desired depth is adjusted by attaching spacers to the cannula. The cannula, attached to a 4-cm silastic catheter (*Helix* Medical Inc., Carpinteria, Calif.), is fixed in place with dental cement (Ketac-cement, Norristown, Pa.). The catheter is either attached to a primed osmotic pump placed subcutaneously between the shoulder blades for permanent infusion or to a syringe for a short infusion.

b) Intravenous (IV) Osmotic Pump Implantation into the Jugular Vein

Anesthesia is maintained by inhalation of 3.0% isoflurane (Aerrane, Front Dodge, Iowa) in 0.8% oxygen throughout the entire procedure. The animal's neck is shaved and sterilized before operation. A midline incision is made on the ventral part of the neck to exposes the jugular vein. The vein is isolated and ligated with a suture (silk 5/0, Carlisle Laboratories, Farmers Branch, Tex.) rostral to the point of the incision and a microvascular clip (Fine Science Tool Inc., Foster City, Calif.) is placed close to the heart. A small incision is made between the two ligations. A 2-cm silastic catheter (*Helix* Medical Inc.) attached to a PE-60 tube (Becton. Dickinson and Co. Sparks, Md.) connected to an ALZET (Alza, Palo Alto, Calif.) pump is introduced and advanced 2 mm into the jugular vein toward the heart. The microvascular clip is removed and the catheter is secured in place with a suture (silk 5/0, Carlisle Laboratories, Farmers Branch, Tex.). The pump is placed into a pocket made subcutaneously between the shoulder blades, allowing the catheter to reach over neck to the jugular vein with sufficient slack to permit free movement of neck and head.

c) IV Infusion via Femoral Vein

Anesthesia is maintained by inhalation of 3.0% isoflurane (Aerrane, Front Dodge, Iowa) in 0.8% oxygen throughout the entire procedure. The exterior site of the right femoral vein is shaved and sterilized prior to surgery. A 3-cm incision is made in the right groin region and the femoral vein is isolated: A small incision is made on the femoral vein, temporarily ligated with a microvascular clip, to introduce and advance a polyethylene (PE-50) catheter (Becton Dickinson and Co. Sparks, Md.). The catheter is secured in place with suture (silk 5/0, Carlisle Laboratories, Farmers Branch, Tex.). The other end of the catheter is attached to a syringe filled with the heparinized saline for the bolus injection. Using a hemostat, a pocket is made subcutaneously on the back of the animal so the PE catheter can be brought up to the exteriorization point at the nape of the neck for either a bolus injection or a continuous injection by an osmotic pump.

d) Intraperitoneal (IP) Injection

An awake rat is held in a standard hand hold position, a 23 3/4G needle is injected into the lower right quarter of the abdomen past the peritoneum, slightly off the midline. To avoid organ injection, the plunger of the syringe is slightly pulled back. If no fluid is withdrawn, the content of the syringe is delivered into the abdominal cavity.

e) Gavage Feeding

A standard rat gavage tube (Popper & Sons Inc., NY) is attached to a 3-cc hypodermic syringe. The animal is held by the shoulder in a vertical position. The feeding tube is placed into the mouth then advanced until it reaches the stomach (the approximate insertion length of the tube was measured prior to the feeding). The content of the syringe is slowly delivered, and then the tube is withdrawn.

D. Behavioral Assessment

One hour after MCAO, the animal is gently held by its tail and observed for forelimb flexion. Then the animal is placed on the floor to be observed for walking pattern; only the animals that score 3 on the Bederson grading system (Table 1) are included in the study.

TABLE 1

Bederson Grading System for Neurological Evaluation

| Neurological deficit | Grading | Behavioral observation |
|---|---|---|
| Normal | grade 0: | No observable deficit |
| Moderate | grade 1: | forelimb flexion |
| Severe | grade 2: | forelimb flexion, decreased resistance to lateral push |
|  | grade 3: | forelimb flexion, decreased resistance to lateral push, circle to paretic side |

E. Evaluation of Ischemic Damage

Twenty-four hours post-MCAO, or longer in some experiments, animals are sacrificed by $CO_2$ asphyxiation (dry ice). The brain is quickly removed from the skull, using standard procedures, rinsed in chilled saline solution, and placed on a rat brain tissue slicer (ASI instrument, MI). Seven 2-mm thick coronal slices are cut from each brain using razor blades. The slices are immersed in 0.9% saline containing 1.0% 2,3,5-triphenyltetrazolume chloride (TTC) (Sigma Chemical Co., St. Louis, Mo.) and incubated in a 37° C. water bath for 30 minutes.

After staining, each 2-mm slice is photographed with a TMC-7 camera (JH Technologies, Ca) which is directly connected to a desktop PC to capture and save the image of each brain slice. This image is used for the measurements of the regions of interest using a computer-based image processing system (Metamorph).

To measure each area, the region of interest is selected using a freehand selection tool, the area is automatically computed by selecting the measure command. The measurements for primary regions of interest are right hemisphere, left hemisphere, total infarct, subcortical infarct, total penumbra and subcortical penumbra. After all regions of interest are measured for all seven slices of the brain, they are sorted by slice number and the corresponding regions of interest using an Excell macro called statistic final. This macro also calculates the cortical penumbra, cortical infarct and total ischemic damage for each slice; the corresponding areas of each rat brain are added together to produce a single measurement for each area. Since the ipsilateral hemisphere is swollen following MCAO, edema volume is calculated and reported as the volumetric differences between the right and left hemispheres of each brain slice. Using the % of hemispheric swelling all the volumes are corrected for the edema.

The volume of the damage is determined using the calculations below for each rat's brain.

| Measurement | Equation | Corrected Value(s) |
|---|---|---|
| Cortical Penumbra (C.P.) | Total Penumbra − Subcortical Penumbra | Total Penumbra (T.P.$_{corr.}$) = (T.P. × % H.S./100)<br>C.P.$_{corr.}$ = C.P. − (C.P. × % H.S./100)<br>S.P.$_{corr.}$ = S.P. − (S.P. × % H.S./100) |
| Cortical Infarct | Total Infarct − Subcortical Infarct | T.I.$_{corr.}$ = T.I. − (T.I. × % H.S./100)<br>S.I.$_{corr.}$ = S.I. − (S.I. × % H.S./100)<br>C.I.$_{corr.}$ = C.I. − (C.I. × % H.S./100) |
| Total Ischemic Damage (T.I.D.) | Total Penumbra + Total Infarct | T.I.D.$_{corrected}$ = T.I.D. − (T.I.D. × % H.S./100) |
| Total Volume ($mm^3$) | Each value is multiplied by 2 (the thickness of the tissue). | |
| Edema Volume | The volumetric differences between the sum of right and left hemispheres determines the edema volume. | |
| % Hemispheric swelling (H.S.) | Edema × 100/left hemisphere | |

F. Statistical Analysis

Sample size is chosen to achieve a 90% probability of significant results. The measurements representing the same region of interest in seven slices of each rat's brain are added together to yield a single measurement for total infarct, subcortical infarct, cortical infarct, total penumbra, subcortical penumbra, cortical penumbra, total ischemic damage and edema in each animal. Group data are presented as means+/− SEM. Differences at the level of $p<0.05$ are considered statistically significant. Between groups, comparisons of each region of interest are carried out by unpaired student t test (between two groups) or one way ANOVA followed by post hoc Bonferroni's multiple comparisons or by the nonparametric Dunnett's test (between control and the drug treated groups).

Results

When tested as described above, compounds of the present invention, such as:

4-[2-(3,4-Bis-methoxymethoxy-phenyl)-vinyl]-benzoic acid tetradecyl ester;

4-[2-(phenyl-1,2-diol)vinyl]-benzoic acid methyl ester, zinc(II)chloride; and

2-Methoxy-6-(3-methyl-but-2-enyl)-4-[2-(4-nitro-phenyl)-vinyl]-phenol, provided a reduction in total infarct volume of at least about 20% at doses in the range of less than about 1 µg/kg to about 10 mg/kg that is less than about 10 mg/kg.

Example 44

Model of Myocardial Infarction: Left Coronary Ligation (Rat)

Animal Preparation:

Male Sprague-Dawley weighing 250-320 g are allowed free access to water and commercial rodent diet under standard laboratory conditions. Room temperature is maintained at 20-23° C. and room illumination is on a 12/12-hour light/dark cycle. Animals are acclimatized to the laboratory environment 5 to 7 days prior to the study and are fasted overnight prior to surgery.

Surgical Procedure for Acute Studies:

Rats are anaesthetized with Urethane (1.2-1.5 gm/kg). Core body temperature is maintained at 37° C. by using a heating blanket. The surgical area is shaved, and a ventral midline incision is made to expose the trachea and jugular area. A catheter (PE50) is placed in the jugular for administration of compound and maintenance anesthesia. The trachea is incised and a 14-16-gauge modified intravenous catheter is inserted and tied in place as an endotracheal tube. The animal is placed in right lateral recumbency and initially placed on a Harvard ventilator with a tidal volume of 5-10 ml/kg. 100%

$O_2$ is delivered to the animals by the ventilator. ECG electrodes are placed to record a standard Lead II ECG. The surgical site is cleaned with alcohol swab, and a skin incision is made over the rib cage over the $4^{th}$-$5^{th}$ intercostal space. The underlying muscles are dissected with care to avoid the lateral thoracic vein, to expose the intercostal muscles. The chest cavity is entered through the $4^{th}$-$5^{th}$ intercostal space, and the incision expanded to allow visualization of the heart. The pericardium is opened to expose the heart. A 6-0 silk suture with a taper needle is passed around the left coronary artery near its origin, which lies in contact with the left margin of the pulmonary cone, at about 1 mm from the insertion of the left auricular appendage. A piece of tubing is placed over the suture to form an occluder. The coronary artery is occluded for 30 minutes by sliding the tube towards the heart until resistance is felt and holding it in place with a vascular clamp. The ECG is monitored for S-T changes indicative of ischemia. After 30 minutes, the occluder is removed, leaving the suture in place. The ECG is monitored for the first 10 minutes of reperfusion. The rat is transferred to the pressure control ventilator for the remainder of the protocol. The rats are ventilated by a small animal ventilator with a peak inspiratory pressure of 10-15 cm $H_2O$ and respiratory rate 60-110 breaths/min. The heart is allowed to reperfuse for 90 minutes.

Surgical Procedure for 24 Hour Study:

Rats are anaesthetized with Ketamine/Xyiazine IP (95 and 5 mg/kg) and intubated with a 14-16-gauge modified intravenous catheter. Anesthesia level is checked every 15 minutes by toe pinch. Core body temperature is maintained at 37° C. by using a heating blanket. The surgical area is shaved and scrubbed. A ventral midline incision is made to expose the jugular vein. A catheter (PE50) is placed in the jugular for administration of compound and maintenance anesthesia. The animal is placed in right lateral recumbency and initially placed on a ventilator with a tidal volume of 5-10 ml/kg $H_2O$ or a pressure controlled ventilator with a peak inspiratory pressure of 8-15 cm $H_2O$ and respiratory rate 60-110 breaths/min. 100% $O_2$ is delivered to the animals by the ventilator. ECG electrodes are placed to record a standard Lead II ECG. The surgical site is cleaned with surgical scrub and alcohol. A skin incision is made over the rib cage over the $4^{th}$-5th intercostal space. The underlying muscles are dissected with care to avoid the lateral thoracic vein, to expose the intercostal muscles. The chest cavity is entered through $4^{th}$-5th intercostal space, and the incision expanded to allow visualization of the heart. The pericardium is opened to expose the heart. A 6-0 silk suture with a taper needle is passed around the left coronary artery near its origin, which lies in contact with the left margin of the pulmonary cone, at about 1 mm from the insertion of the left auricular appendage. A piece of tubing is placed over the suture to form an occluder. The coronary artery is occluded for 30 minutes by sliding the tube towards the heart until resistance is felt and holding it in place with a vascular clamp. The ECG is monitored for S-T changes indicative of ischemia. After 30 minutes, the occluder is removed, leaving the suture in place. The ECG is monitored for the first 10 minutes of reperfusion. The incision is closed in three layers. The IV catheter is removed or tunneled under the skin and exteriorized between the shoulder blades to allow for blood withdrawal or further drug therapy. The rat is ventilated until able to ventilate on its own. The rats are extubated and recovered on a heating pad. Once awake, they are returned to their cage(s). Animals may receive Buprenorphine (0.01-0.05 mg/kg SQ) for post-operative analgesia. After the designated reperfusion time (24 hours) the animals are anesthetized and the hearts removed under deep anesthesia.

Treatment Protocols

Diet

Animals are fed a custom diet prior to or after coronary ligation. The length of treatment varies with the study. Doses are calculated based on the average consumption of 15 gms of feed per day for a 300 gm rat. Rat weights are monitored during the study. Feed not consumed is weighed to estimate consumption rates.

Gavage

Animals are dosed orally by gavage. Length and frequency of treatment vary with the study. A standard rat gavage tube (Popper & Sons Inc, NY) is attached to a 3-cc hypodermic syringe. The animal is held by the shoulder in a vertical position. The feeding tube is placed into the mouth then advanced until it reaches the stomach (the approximate insertion length of the tube is measured prior to the feeding). The content of the syringe is slowly delivered, and then the tube is withdrawn.

IV Treatment

A ventral incision is made to expose the jugular area. A catheter (PE50) is placed in the jugular vein for administration of compound. Animals are dosed by bolus injection and/or continuous infusion. The time and duration of treatment varies with the protocol.

Tissue Processing

After reperfusion, each animal receives 200 units of heparin IV under general anesthesia and the heart is removed and placed in cold saline. After removal the coronary artery is ligated with the suture that is already in place. The heart is placed on a perfusion apparatus and Evans Blue dyed is infused delineate the area at risk. The heart is then cut into five 2-mm thick transverse slices from apex to base. The slices are incubated in 1% triphenyltetrazolium chloride (TTC) in 0.9% saline for 20 minutes at 37° C. Tetrazolium reacts with NADH in the presence of dehydrogenase enzymes causing viable tissue to stain a deep red color and that is easily distinguished from the infarcted pale-unstained necrotic tissue. The slices are placed apex side down in the lid of a small petri dish for the staining procedure. The bottom of the dish is placed over the slices to keep them flat. The slices are photographed in order from apex to base, with the base side up. The areas of infarcted tissue, area at risk and the whole left ventricle are determined using a computerized image analysis system. The total area for each region is added together to give a total for the entire heart. Infarct size is expressed both as a percentage of the total ventricle and the area at risk.

Statistical Analysis

Group data is represented as means+/−SEM. Comparisons between treatment groups are made using ANOVA with $p<0.05$ considered significant. Post hoc comparisons may be made using either Dunnelt's test or Tukey's test.

Results

The compounds of the present invention show activity when tested by this method.

Example 45

Evaluations of Sensorimotor Behavior

A. Fore and Hindlimb Grip Strength Test in Rats

Animals with cerebral infarction induced by transient or permanent unilateral occlusion of the middle cerebral artery (MCA) and sham-operated rats are tested for grip strength, a standard model of neuromuscular function and sensorimotor integration, using a Computerized Grip Strength Meter for Rats (Dual Stand Model, Columbus Instruments, Columbus, Ohio).

Animals are moved into the testing room for 30 minutes before testing. Prior to testing, each gauge is calibrated with a set of known weights and the apparatus is adjusted for the size of animal, according to manufacturer's instructions. The forelimb measurements are carried out with the meter in the tension peak mode to freeze the reading as the subject is pulled away from the grip bar. The hindlimb measurements are carried out with the meter in the compression peak mode to freeze the reading as the subject's hindlimbs are pulled over the bar toward the meter. Each animal is hand-held by the investigator as pulled past the grip bars, using a consistent technique, leaving the fore and hind limbs free to grasp the grip bars.

Testing is carried out on postoperative day 2 and repeated, in a blind-randomized fashion, twice weekly for a defined interval. Typically, three successive readings are taken for each animal with an intertrial interval long enough to record the data and zero both meters for the next trail.

B. Rota-Rod Test in Rats

Apparatus:

Rota-Rod Treadmill for Rats (7750 Accelerating Model, from UGO BASILE, COMERIO-ITALY).

Procedure:

Animals with cerebral infarction induced by transient or permanent unilateral occlusion of the middle cerebral artery (MCA) and sham-operated rats are tested in this study, using a Rota-Rod Treadmill for Rats (7750 Accelerating Model, UGO Basile, Comerio, Italy). The animals are moved into the testing room 30 minutes before testing. Every rat receives 2-3 training runs of 1-2 minutes at intervals of 2-3 hours before testing.

The cylinder on the apparatus is set in motion before placing the rats in position. The motor is set at a constant selected speed in 7700 on RESET mode, and the rats are placed, one by one, in their sections.

Testing is carried out on postoperative day 2 and repeated, in a blind-randomized fashion, twice weekly for a defined interval. Typically, three successive readings are taken for each animal with an intertrial interval long enough to record the data and zero both meters for the next trail.

The compounds of the present invention show activity when tested by this method.

Example 46

Left Coronary Artery Occlusion Model of Congestive Heart Failure

Experimental Preparation 225-275 g male Sprague-Dawley CD (Charles River) rats are used for this experiment. Animals are allowed free access to water and commercial rodent diet under standard laboratory conditions. Room temperature is maintained at 20-23° C. and room illumination is on a 12/12-hour light/dark cycle. Animals are acclimatized to the laboratory environment 5 to 7 days prior to the study. The animals are fasted overnight prior to surgery.

Animals are anaesthetized with ketamine/xylazine (95 mg/kg and 5 mg/kg) and intubated with a 14-16-gauge modified intravenous catheter. Anesthesia level is checked by toe pinch. Core body temperature is maintained at 37° C. by using a heating blanket. The surgical area is clipped and scrubbed. The animal is placed in right lateral recumbency and initially placed on a ventilator with a peak inspiratory pressure of 10-15 cm $H_2O$ and respiratory rate 60-110 breaths/min. 100% $O_2$ is delivered to the animals by the ventilator. ECG electrodes are placed to record a standard Lead II ECG. The surgical site is scrubbed with surgical scrub and alcohol. An incision is made over rib cage over the $4^{th}$-$5^{th}$ intercostal space. The underlying muscles are dissected with care to avoid the lateral thoracic vein, to expose the intercostal muscles. The chest cavity is entered through $4^{th}$-$5^{th}$ intercostal space, and the incision expanded to allow visualization of the heart. The pericardium is opened to expose the heart. A 6-0 silk suture with a taper needle is passed around the left coronary artery near its origin, which lies in contact with the left margin of the pulmonary cone, at about 1 mm from the insertion of the left auricular appendage. The coronary artery is occluded by tying the suture around the artery. The ECG is monitored for S-T changes indicative of ischemia. If the animal develops ventricular fibrillation, gentle cardiac massage is used to convert the animal to a normal rhythm. The incision is closed in three layers. The rat is ventilated until are able to ventilate on their own. The rats are extubated and recovered on a heating pad. Animals receive buprenorphine (0.01-0.05 mg/kg SQ) for post operative analgesia. Once awake, they are returned to their cage. Animals are monitored daily for signs of infection or distress. Infected or moribund animals are euthanized. Animals are weighed once a week.

Treatment Protocols

Diet

Animals are fed a custom diet prior to or after coronary ligation. The length of treatment will vary with the study. Doses are calculated based on the average consumption of feed per day. Rat weights are monitored during the study. Feed not consumed is weighed to estimate consumption rates.

Gavage

Animals are dosed orally by gavage. Length and frequency of treatment will vary with the study. A standard rat gavage tube (Popper & Sons Inc, NY) is attached to a 3-cc hypodermic syringe. The animal is held by the shoulder in a vertical position. The feeding tube is placed into the mouth then advanced until it reaches the stomach (the approximate insertion length of the tube is measured prior to the feeding). The content of the syringe is slowly delivered, and then the tube is withdrawn.

Drinking Water

Compound can also be dissolved in the drinking water. Water consumption is monitored. In the case of a bitter tasting compound, flavoring agents may be added to the water of both vehicle and treated groups. In the case of insoluble compounds, solubilizing agents may be used (i.e. 0.015% cremophor.0.015% alcohol).

Alzet Pumps

Alzet pumps can be implanted using aseptic techniques into the peritoneum or subcutaneously behind the shoulder blades. Pumps are implanted using Isoflurane anesthesia. Serial implantation can be used for extended studies.

Measurements

In vivo

After 6-12 weeks the animals are anesthetized with Ketamine/Xylazine (95 mg/kg and 5 mg/kg), and a catheter is placed in the right carotid artery and advanced into the left ventricle for hemodynamic measurements. The catheter is attached to a pressure transducer calibrated against a mercury manometer immediately prior to use. Recordings are made by a DATAQ data analysis system. Pressure traces are recorded and analyzed for heart rate, left ventricular systolic and diastolic pressure, left ventricular developed pressure, and dP/dt max and min. An average of at least five peaks is used to determine values for left ventricular systolic and end diastolic pressure. Left ventricular developed pressure is determined by subtracting end diastolic pressure from left ventricular systolic pressure. Heart rate is determined from the frequency spectrum of a 5 second sample. After measurements are taken, 2 ml blood is removed and placed in serum and plasma tubes for possible analysis.

Ex Vivo

After removal, the heart is placed in cold saline to stop the beating, then trimmed and weighed. Heart weight is presented as total weight and as a percentage of total body weight. After removal of the heart, lungs and liver are weighed and dried overnight for determination of wet to dry ratios.

The heart is sliced and slice #3 is incubated in 1% triphenyltetrazolium chloride (TTC) in 0.9% saline for 20 minutes at 37° C. Tetrazolium reacts with NADH in the presence of dehydrogenase enzymes causing viable tissue to stain a deep red color that is easily distinguished from the infarcted pale-unstained necrotic tissue. The slice is placed apex side down in the lid of a small petri dish for the staining procedure. The bottom of the dish is placed over the slice to keep it flat. The slice is photographed. The areas of infarcted tissue, left and right ventricle are determined using a computerized image analysis system. Infarct size is expressed as a percentage of the total ventricle. Total areas of the left and right ventricle are measured. The remaining sections are divided into right and left ventricle and frozen for TBARS and glutathione assays.

Statistical Analysis

Group data is presented as means+/−SEM. Comparisons between treatment groups are made using ANOVA with $p<0.05$ considered significant. Post hoc comparisons use either Dunnett's test or Tukey's test. Survival curves are generated using Graph Pad Prism. For each X value (time) Prism shows the fraction still alive. It also shows standard error. Prism calculates survival fractions using the product limit or Kaplan-Meier method.

The compounds of the present invention show activity when tested by this method.

Example 47

Skin Protection Assay

Cytoprotective activity for skin can be evaluated in cell culture using the Epiderm Skin Model (EPI-100) from the Mattek Corporation of Ashland, Mass. Cell cultures of neonatal foreskin are cultured in accordance with the manufacturer's directions, and are assayed for percent cellular viability by measuring the amount of 3-(4,5-dimethylthazol-2-yl)-2,5-diphenyltetrazolium bromide (MTT) dye taken up by the cells. Viable cells take up this dye and convert it to insoluble formazin crystals that resides in the mitochondria of the cells until extracted with alcohol. The amount of MTT converted to extractable formazin crystals is directly proportional to the viability of the cell culture. MTT is measured spectrophotometrically.

Cells are exposed to UV light at a rate of 1.5 Minimal Erythemal Dose (MED) per hour per square centimeter, for a total dose of about 31.5 $mJ/cm^2$, from a solar simulator (filtered to yield wavelengths in the region of 290-400 nm) in the presence of the cytoprotective compound or mixtures thereof to measure the effect of test compounds to protect the cell culture from the generation of free radicals resulting from the ultraviolet light.

The controls for this study are cell cultures without added test compound (positive control). All cell cultures are also compared to cultures that are not exposed to UV light and do not include the cytoprotective agents or blends in order to determine percent cellular viability (negative control). This latter measurement is assumed to be equal to 100% viability.

Cell cultures treated with the cytoprotective compounds of the invention show greater survival than do positive control cell cultures, when tested as described above.

Example 48

Rat Paw Edema Assay

Animal Preparation:

Male Sprague-Dawley rats weighing between 175 to 200 g are used in this study. Animals are allowed free access to water and commercial rodent diet under standard laboratory conditions. Room temperature is maintained at 20-23° C. and room illumination is on a 12/12-hour light/dark cycle. Animals are acclimatized to the laboratory environment 5 to 7 days prior to the study.

Experimental Procedure:

Each animal is treated by administration of vehicle, reference or test substance one hour prior to carrageenan injection, as follows:

I.V. Infusion via Femoral Vein:

Anesthesia is maintained by inhalation of 3.0% isoflurane (Aerrane, Front Dodge, Iowa) in oxygen throughout the entire procedure. The exterior site of the right femoral vein is shaved and sterilized prior to surgery. A 3-cm incision is made in the right groin region and the femoral vein is isolated. The femoral vein is temporarily ligated with a micro-vascular clip, and a small incision is made on the femoral vein to introduce and advance a polyethylene (PE-50) catheter (Becton. Dickinson and Co., Sparks, Md.). The catheter is secured in place with suture (silk 5/0, Carlisle Laboratories, Farmers Branch, Tex.). The other end of the catheter is attached to a syringe filled with the saline for the bolus injection. Using a hemostat, a pocket is made subcutaneously on the back of the animal so the PE catheter can be brought up to the exteriorization point between the shoulder blade for either a bolus injection or a continuous injection by an osmotic pump.

I.P. Injection:

An awake rat is held in a standard hand held position. A 23 3/4G needle is injected into the lower right quarter of the abdomen pass the peritoneum, slightly off the midline. To avoid organ injection, the plunger of the syringe is slightly pulled back. If no fluid is withdrawn, the content of the syringe is delivered into the abdominal cavity.

Gavage Feeding:

A standard rat gavage tube (Popper & Sons Inc, NY) is attached to a 3-cc hypodermic syringe. The animal is held in a vertical position. The feeding tube is placed into the mouth and then gently advanced until it reaches the stomach (the approximate insertion length of the tube should be measured prior to feeding). The content of the syringe is slowly delivered, and then the tube is withdrawn.

One hour post treatment each animal is anesthetized with 3.0% isoflurane (Aerrane, Front Dodge, Iowa) in oxygen and administered 100 μl of 1% Carrageenan Lambda type IV (Sigma Chemical Company, St. Louis, Mo.) suspension in saline, into the intraplantar surface of the right hind paw. Paw edema is measured four hours after carrageenan injection, either by measuring the increase in paw volume using a plethysmometer or the increase in paw weight using a fine scale. Immediately prior to edema measurement, the animals are euthanized via $CO_2$ asphyxiation and 500 µl blood is withdrawn by cardiac puncture for later analysis. Paw volume is determined by the extent to which water is displaced by the paw from a pre-calibrated chamber. The volume of the left hind paw (control) is subtracted from the volume of the right hind paw (carrageenan-treated) to determine the volume of carrageenan-induced edema. To measure the weight difference between paws, both hind paws were removed and weighed separately.

To minimize the variation in the model following steps are taken:

Carrageenan is made fresh every day prior to the study (2-3 hours before injection).

The plethysmometer is calibrated each day prior to the study.

If carrageenan injection causes significant bleeding or a hematoma on the treated foot, the animal is excluded from the study.

Each paw is marked at the tibio-tarsal joint across the ankle prior to measurements, to ensure each paw is submerged at the same level.

If reading on the volume needs to be repeated, the paw must be dried off completely.

Statistical Analysis

The difference of the weight or the volume between right and left paw is calculated for each animal for the analysis. Group data are presented as means+/−SEM and $p<0.05$ are considered significant. Inter-group comparisons are carried out by unpaired student t test (between two groups) or one-way ANOVA followed by post hoc Bonferroni's multiple comparisons.

Results

The compounds of the present invention, such as:
4-[2-(4-nitro-phenyl)-vinyl]-benzene-1,2-diol;
4-{2-[4-(2-nitro-vinyl)-phenyl]-vinyl}benzene-1,2-diol;
4-[2-(3,4-dihydroxy-phenyl)vinyl]-benzoic acid methyl ester;
4-[2-(3,4-Bis-methoxymethoxy-phenyl)vinyl]-benzoic acid tetradecyl ester;
4-[2-(3,4-Bis-{2-[2-(2-methoxy-ethoxy)ethoxy]-ethoxy}-phenyl)vinyl]-benzoic acid ethyl ester;
4-{2-[3,4-dihydroxy-5-(3-methyl-but-2-enyl)-phenyl]-vinyl}-benzoic acid methyl ester;
2-methoxy-6-(3-methyl-but-2-enyl)-4-[2-(4-nitro-phenyl)-vinyl]-phenol;
3-(3-methyl-but-2-enyl)-4-[2-(4-nitro-phenyl)-vinyl]-benzene-1,2-diol; and
4-(3-methyl-but-2-enyl)-5-[2-(4-nitro-phenyl)-vinyl]-benzene-1,3-diol, showed significant reduction in edema (10 to 70%, $p<0.05$) when tested by this method.

Example 49

Mouse Ear Inflammatory Response to Topical Arachidonic Acid

Animals:
Balb C Mice 23-28 gms, from Simonsen Labs, Gilroy, Calif.
Materials:
Arachidonic Acid, 99% pure from Porcine Liver (Sigma Aldrich) reconstituted in acetone 2 mg/20 ul (200 mg/ml).
Inhalation anesthesia: Isoflurane 3% (Baxter).
Blood Sample tubes: Microtainer tubes w/ heparin (Becton Dickinson).
TNFa Elisa assay (R&D Science).

Experimental Procedure

Test compounds, positive control (arachidonic acid only) and standard (Dexamethasone @ 0.1 mg/kg) prepared in solutions of acetone, ethanol or aqueous ethanol, are applied to both sides of the right ear with an Eppendorf repipettor pipette, in a volume of 10 µl each side (20 µl total). 30 Minutes later, 10 µl of arachidonic acid is applied to both sides of the right ear (20 µl total). One hour after the application of arachidonic acid, the mice are deeply anesthetized with isoflurane and a blood sample is taken via the orbital sinuses and placed in Microtainer tubes. The animals are then euthanized by $CO_2$ inhalation and the right ears removed at the base. A uniform plug of ear tissue is obtained using a 8 mm dermal punch. The earplugs are quickly weighed to the nearest 0.1 mg and then flash frozen for TNFa determination.

The earplugs are thawed and placed in 1 ml PBS, and homogenized using a mortar and pestle. The homogenates are placed in 15 ml centrifuge tubes and spun at 5000 g for 10 minutes. The supernatant of each sample is aspirated and placed in 1.5 ml centrifuge tubes and flash frozen. The samples are stored at −70° C. until assayed for TNFα.

Statistical Analysis:

Group data are presented as means+/−SEM and $p<0.05$ is considered significant. Inter-group comparisons are carried out by unpaired student t tests (between two groups) or ANOVA (three or more groups) followed by post hoc Dunnet's test.

Results

The compounds of the present invention, such as:
4-[2-(4-nitro-phenyl)-vinyl]-benzene-1,2-diol;
4-[2-(4-nitro-phenyl)-vinyl]-benzene-1,2,3-triol;
4-(3-methyl-but-2-enyl)-5-[2-(4-nitro-phenyl)-vinyl]-benzene-1,3-diol;
2-bromo-4-[4-hydroxy-3-(3-methyl-but-2-enyl-phenyl)-vinyl]-phenol;
4-{2-[3,5-dihydroxy-4-(3-methyl-but-2-enyl)-phenyl]-vinyl}-benzonitrile;
4-[3-(3-methoxy-4-methoxymethoxy-phenyl)-allylidene]-5-methyl-2-phenyl-2,4-dihydro-pyrazol-3-one;
5-[3-(3-methoxy-4-methoxymethoxy-phenyl)-allylidene]-thiazolidine-2,4-dione;
3-(3,5-di-tert-butyl-4-hydroxy-benzylidene)-5-hydroxy-3H-benzofuran-2-one;
4-{2-[4-(3,7-dimethyl-octa-2,6-dienyl)-3,5-dihydroxy-phenyl]-vinyl}-benzonitrile;
2-hydroxy-5-[2-(4-nitro-phenyl)-vinyl]-benzoic acid;
3-[2-(3,4-dimethoxy-phenyl)-vinyl]-4-nitro-phenol;
2-iodo-6-methoxy-4-[2-(4-nitro-phenyl)-vinyl]-phenol;
5-[2-(4-nitro-phenyl)-vinyl]-benzene-1,3-diol;
4-[2-(3,4-dihydroxy-phenyl)-vinyl]-benzoic acid methyl ester;
4-[2-(4-hydroxy-3,5-dimethyl-phenyl)-vinyl]-benzoic acid methyl ester;
5-{4-[2-(3,4-dihydroxy-phenyl)-vinyl]-phenyl}-2-phenyl-2,4-dihydro-pyrazol-3-one;
5-methyl-2-(4-styryl-phenyl)-2,4-dihydro-pyrazol-3-one;
2-{4-[2-(3,4-dihydroxy-phenyl)-vinyl]-phenyl}-5-methyl-2,4-dihydro-pyrazol-3-one
4-{2-[4-(5-hydroxy-1H-pyrazol-3-yl)-phenyl]-vinyl}-benzene-1,2-diol;

4-[3-(4-hydroxy-3-methoxy-phenyl)-allyidene]-5-methyl-2-phenyl-2,4-dihydro-pyrazol-3-one;

4-[4-(4-nitro-phenyl)-buta-1,3-dienyl]-benzene-1,2-diol;

4-{2-[3-methoxy-4-methoxymethoxy-5-(3-methyl-but-2-enyl)-phenyl]-vinyl}-benzoic acid methyl ester;

2-methoxymethoxy-5-[2-(4-nitro-phenyl)-vinyl]-benzoic acid methoxymethyl ester;

1-bromo-3-methoxy-2-methoxymethoxy-5-[2-(4-nitrophenyl)-vinyl]-benzene;

5-{4-[2-(3,4-bis-methoxymethoxy-phenyl)-vinyl]-phenyl}-2-phenyl-2,4-dihydro-pyrazol-3-one 4{2-[3-(3,7-dimethyl-octa-2,6-dienyl)-4-hydroxy-5-methoxy-phenyl]-vinyl}-benzonitrile;

4-(3,4-dihydroxy-benzylidene)-5-methyl-2-phenyl-2,4-dihydro-pyrazol-3-one;

5-(3,5-di-tert-butyl-4-hydroxy-benzylidene)-thiazolidine-2,4-dione;

5-[3-(3,7-dimethyl-octa-2,6-dienyl)-4-hydroxy-benzylidene]-thiazolidine-2,4-dione;

5-[3-methoxy-4-methoxymethoxy-5-(3-methoxy-4-methoxymethoxy-1-(thiazolidine-2,4-dionyl)-benzylidene-5-yl)-benzylidene]-thiazolidine-2,4-dione;

4-{2-[3,4-dihydroxy-5-(3-methyl-but-2-enyl)-phenyl]-vinyl}-benzoic acid methyl ester;

4-{2-[3,5-dihydroxy-4-(3-methyl-but-2-enyl)-phenyl]-vinyl}-benzoic acid methyl ester;

2-methoxy-6-(3-methyl-but-2-enyl)-4-[2-(4-nitro-phenyl)-vinyl]-phenol;

3-(3-methyl-but-2-enyl)-4-[2-(4-nitro-phenyl)-vinyl]-benzene-1,2-diol;

3-(3-methyl-but-2-enyl)-5-[2-(4-nitro-phenyl)vinyl]-benzene-1,2-diol;

4-(3-methyl-but-2-enyl)-5-[2-(4-nitro-phenyl)vinyl]-benzene-1,3-diol;

2-(3,7-dimethyl-octa-2,6-dienyl)-6-methoxy-4-[2-(4-nitro-phenyl)-vinyl]-phenol;

2-(3,7-dimethyl-octa-2,6-dienyl)-5-[2-(4-nitro-phenyl)-vinyl]-benzene-1,3-diol;

2-(3-methyl-but-2-enyl)-5-[2-(4-nitro-phenyl)-vinyl]-benzene-1,3-diol;

4-{2-[3,5-dihydroxy-4-(3-methyl-but-2-enyl)-phenyl]-vinyl}-benzonitrile; and 2-bromo-4-[4-hydroxy-3<3-methyl-but-2-enyl-phenyl)-vinyl]-phenol, showed significant reduction in edema (15 to 80%, $p<0.05$) when tested by this method.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto. All patents and publications cited above are hereby incorporated by reference.

We claim:
1. A compound of formula A

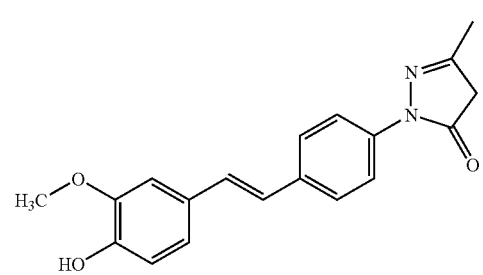

or formula B

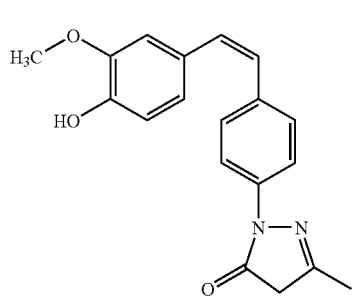

or mixtures and pharmaceutically acceptable salts thereof.

2. A compound as in claim 1, wherein the compound is of formula A:

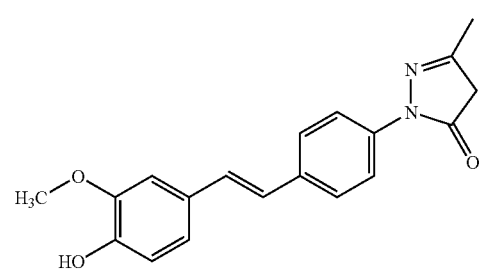

and pharmaceutically acceptable salts thereof.

3. A compound as in claim 1, wherein the compound is of formula B:

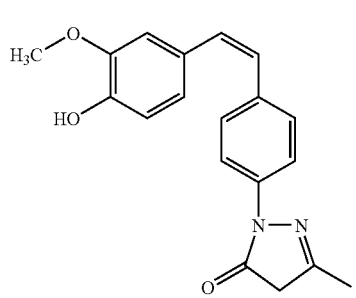

and pharmaceutically acceptable salts thereof.

4. A skin care composition comprising a therapeutically effective amount of one or more compounds of claim 1, further optionally comprising a pharmaceutically or cosmetically acceptable carrier or excipient.

5. The skin care composition of claim 4, formulated for topical administration to the skin of a mammalian subject.

6. The skin care composition of claim 5, wherein said composition is included in a topical cosmetic formulation.

7. The skin care composition of claim 5, wherein said composition is included in a topical pharmaceutical formulation.

8. The skin care composition of claim 4, formulated for transdermal administration to a mammalian subject.

9. The skin care composition of claim 5, formulated for oral administration to a mammalian subject.

* * * * *

UNITED STATES PATENT AND TRADEMARK OFFICE
CERTIFICATE OF CORRECTION

PATENT NO. : 7,629,375 B2  Page 1 of 1
APPLICATION NO. : 11/015198
DATED : December 8, 2009
INVENTOR(S) : Wang et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1203 days.

Signed and Sealed this

Twenty-first Day of December, 2010

David J. Kappos
*Director of the United States Patent and Trademark Office*